United States Patent
Nugent et al.

(10) Patent No.: US 11,332,740 B2
(45) Date of Patent: *May 17, 2022

(54) METHODS FOR SEAMLESS NUCLEIC ACID ASSEMBLY

(71) Applicant: TWIST BIOSCIENCE CORPORATION, South San Francisco, CA (US)

(72) Inventors: Rebecca Nugent, San Francisco, CA (US); Siyuan Chen, San Mateo, CA (US); Elian Lee, Union City, CA (US); Nathan Raynard, San Mateo, CA (US)

(73) Assignee: Twist Bioscience Corporation, South San Francisco, CA (US)

( * ) Notice: Subject to any disclaimer, the term of this patent is extended or adjusted under 35 U.S.C. 154(b) by 12 days.

This patent is subject to a terminal disclaimer.

(21) Appl. No.: 16/879,705

(22) Filed: May 20, 2020

(65) Prior Publication Data

US 2020/0283760 A1    Sep. 10, 2020

Related U.S. Application Data

(63) Continuation of application No. 16/006,581, filed on Jun. 12, 2018, now Pat. No. 10,696,965.

(60) Provisional application No. 62/663,089, filed on Apr. 26, 2018, provisional application No. 62/518,496, filed on Jun. 12, 2017.

(51) Int. Cl.
| | |
|---|---|
| *C12N 15/10* | (2006.01) |
| *C12N 9/00* | (2006.01) |
| *C12N 9/12* | (2006.01) |
| *C12P 19/34* | (2006.01) |
| *C12Q 1/6869* | (2018.01) |
| *C12Q 1/6855* | (2018.01) |
| *C12Q 1/6811* | (2018.01) |

(52) U.S. Cl.
CPC ....... *C12N 15/1096* (2013.01); *C12N 9/1252* (2013.01); *C12N 9/93* (2013.01); *C12N 15/1031* (2013.01); *C12N 15/1093* (2013.01); *C12P 19/34* (2013.01); *C12Q 1/6811* (2013.01); *C12Q 1/6855* (2013.01); *C12Q 1/6869* (2013.01); *C12Q 2531/101* (2013.01); *C12Y 207/07007* (2013.01); *C12Y 301/11002* (2013.01)

(58) Field of Classification Search
CPC ............ C12N 15/1096; C12N 15/1031; C12N 15/1093; C12N 9/93; C12N 9/1252; C12Q 1/6811; C12Q 1/6869; C12Q 1/6855; C12Q 2531/101; C12P 19/34; C12Y 301/11002; C12Y 207/07007
See application file for complete search history.

(56) References Cited

U.S. PATENT DOCUMENTS

| | | | |
|---|---|---|---|
| 3,549,368 | A | 12/1970 | Robert et al. |
| 3,920,714 | A | 11/1975 | Streck |
| 4,123,661 | A | 10/1978 | Wolf et al. |
| 4,415,732 | A | 11/1983 | Caruthers et al. |
| 4,613,398 | A | 9/1986 | Chiong et al. |
| 4,726,877 | A | 2/1988 | Fryd et al. |
| 4,808,511 | A | 2/1989 | Holmes |
| 4,837,401 | A | 6/1989 | Hirose et al. |
| 4,863,557 | A | 9/1989 | Kokaku et al. |
| 4,981,797 | A | 1/1991 | Jessee et al. |
| 4,988,617 | A | 1/1991 | Landegren et al. |
| 5,102,797 | A | 4/1992 | Tucker et al. |
| 5,118,605 | A | 6/1992 | Urdea |
| 5,137,814 | A | 8/1992 | Rashtchian et al. |
| 5,143,854 | A | 9/1992 | Pirrung et al. |
| 5,242,794 | A | 9/1993 | Whiteley et al. |
| 5,242,974 | A | 9/1993 | Holmes |
| 5,288,514 | A | 2/1994 | Ellman |
| 5,299,491 | A | 4/1994 | Kawada |
| 5,368,823 | A | 11/1994 | McGraw et al. |
| 5,384,261 | A | 1/1995 | Winkler et al. |
| 5,387,541 | A | 2/1995 | Hodge et al. |
| 5,395,753 | A | 3/1995 | Prakash |
| 5,431,720 | A | 7/1995 | Nagai et al. |
| 5,445,934 | A | 8/1995 | Fodor et al. |
| 5,449,754 | A | 9/1995 | Nishioka |
| 5,459,039 | A | 10/1995 | Modrich et al. |
| 5,474,796 | A | 12/1995 | Brennan |

(Continued)

FOREIGN PATENT DOCUMENTS

| | | |
|---|---|---|
| AU | 3157000 A | 9/2000 |
| CA | 2362939 A1 | 8/2000 |

(Continued)

OTHER PUBLICATIONS

Abudayyeh et al.: C2c2 is a single-component programmable RNA-guided RNA-targeting CRISPR effector. Science, available on line, Jun. 13, 2016, at: http://zlab.mit.edu/assets/reprints/Abudayyeh_OO_Science_2016.pdf, 17 pages.

Acevedo-Rocha et al.: Directed evolution of stereoselective enzymes based on genetic selection as opposed to screening systems. J. Biotechnol. 191:3-10 (2014).

Adessi et al.: Solid phase DNA amplification: characterisation of primer attachment and amplification mechanisms. Nucleic Acids Res. 28(20):E87, 2000.

(Continued)

*Primary Examiner* — Narayan K Bhat

(74) *Attorney, Agent, or Firm* — Wilson Sonsini Goodrich & Rosati

(57) ABSTRACT

Provided herein are methods, systems, and compositions for seamless nucleic acid assembly. Methods, systems, and compositions as provided herein provide for efficient assembly of nucleic acids without primer removal. Methods, systems, and compositions for seamless nucleic acid assembly comprise use of an endonuclease or exonuclease, optionally in conjunction with additional enzymes to assemble nucleic acids or polynucleotides.

17 Claims, 37 Drawing Sheets
(7 of 37 Drawing Sheet(s) Filed in Color)

Specification includes a Sequence Listing.

(56) References Cited

U.S. PATENT DOCUMENTS

| | | |
|---|---|---|
| 5,476,930 A | 12/1995 | Letsinger et al. |
| 5,487,993 A | 1/1996 | Herrnstadt et al. |
| 5,494,810 A | 2/1996 | Barany et al. |
| 5,501,893 A | 3/1996 | Laermer et al. |
| 5,508,169 A | 4/1996 | Deugau et al. |
| 5,510,270 A | 4/1996 | Fodor et al. |
| 5,514,789 A | 5/1996 | Kempe |
| 5,527,681 A | 6/1996 | Holmes |
| 5,530,516 A | 6/1996 | Sheets |
| 5,556,750 A | 9/1996 | Modrich et al. |
| 5,586,211 A | 12/1996 | Dumitrou et al. |
| 5,641,658 A | 6/1997 | Adams et al. |
| 5,677,195 A | 10/1997 | Winkler et al. |
| 5,679,522 A | 10/1997 | Modrich et al. |
| 5,683,879 A | 11/1997 | Laney et al. |
| 5,688,642 A | 11/1997 | Chrisey et al. |
| 5,700,637 A | 12/1997 | Southern |
| 5,700,642 A | 12/1997 | Monforte et al. |
| 5,702,894 A | 12/1997 | Modrich et al. |
| 5,707,806 A | 1/1998 | Shuber |
| 5,712,124 A | 1/1998 | Walker |
| 5,712,126 A | 1/1998 | Weissman et al. |
| 5,739,386 A | 4/1998 | Holmes |
| 5,750,672 A | 5/1998 | Kempe |
| 5,780,613 A | 7/1998 | Letsinger et al. |
| 5,830,643 A | 11/1998 | Yamamoto et al. |
| 5,830,655 A | 11/1998 | Monforte et al. |
| 5,830,662 A | 11/1998 | Soares et al. |
| 5,834,252 A | 11/1998 | Stemmer et al. |
| 5,843,669 A | 12/1998 | Kaiser et al. |
| 5,843,767 A | 12/1998 | Beattie |
| 5,846,717 A | 12/1998 | Brow et al. |
| 5,854,033 A | 12/1998 | Lizardi |
| 5,858,754 A | 1/1999 | Modrich et al. |
| 5,861,482 A | 1/1999 | Modrich et al. |
| 5,863,801 A | 1/1999 | Southgate et al. |
| 5,869,245 A | 2/1999 | Yeung |
| 5,877,280 A | 3/1999 | Wetmur |
| 5,882,496 A | 3/1999 | Northrup et al. |
| 5,922,539 A | 7/1999 | Modrich et al. |
| 5,922,593 A | 7/1999 | Livingston |
| 5,928,907 A | 7/1999 | Woudenberg et al. |
| 5,962,272 A | 10/1999 | Chenchik et al. |
| 5,976,842 A | 11/1999 | Wurst |
| 5,976,846 A | 11/1999 | Passmore et al. |
| 5,989,872 A | 11/1999 | Luo et al. |
| 5,994,069 A | 11/1999 | Hall et al. |
| 6,001,567 A | 12/1999 | Brow et al. |
| 6,008,031 A | 12/1999 | Modrich et al. |
| 6,013,440 A | 1/2000 | Lipshutz et al. |
| 6,015,674 A | 1/2000 | Woudenberg et al. |
| 6,017,434 A | 1/2000 | Simpson et al. |
| 6,020,481 A | 2/2000 | Benson et al. |
| 6,027,898 A | 2/2000 | Gjerde et al. |
| 6,028,189 A | 2/2000 | Blanchard |
| 6,028,198 A | 2/2000 | Liu et al. |
| 6,040,138 A | 3/2000 | Lockhart et al. |
| 6,077,674 A | 6/2000 | Schleifer et al. |
| 6,087,482 A | 7/2000 | Teng et al. |
| 6,090,543 A | 7/2000 | Prudent et al. |
| 6,090,606 A | 7/2000 | Kaiser et al. |
| 6,103,474 A | 8/2000 | Dellinger et al. |
| 6,107,038 A | 8/2000 | Choudhary et al. |
| 6,110,682 A | 8/2000 | Dellinger et al. |
| 6,114,115 A | 9/2000 | Wagner, Jr. |
| 6,130,045 A | 10/2000 | Wurst et al. |
| 6,132,997 A | 10/2000 | Shannon |
| 6,136,568 A | 10/2000 | Hiatt et al. |
| 6,171,797 B1 | 1/2001 | Perbost |
| 6,180,351 B1 | 1/2001 | Cattell |
| 6,201,112 B1 | 3/2001 | Ach |
| 6,218,118 B1 | 4/2001 | Sampson et al. |
| 6,221,653 B1 | 4/2001 | Caren et al. |
| 6,222,030 B1 | 4/2001 | Dellinger et al. |
| 6,232,072 B1 | 5/2001 | Fisher |
| 6,235,483 B1 | 5/2001 | Wolber et al. |
| 6,242,266 B1 | 6/2001 | Schleifer et al. |
| 6,251,588 B1 | 6/2001 | Shannon et al. |
| 6,251,595 B1 | 6/2001 | Gordon et al. |
| 6,251,685 B1 | 6/2001 | Dorsel et al. |
| 6,258,454 B1 | 7/2001 | Lefkowitz et al. |
| 6,262,490 B1 | 7/2001 | Hsu et al. |
| 6,274,725 B1 | 8/2001 | Sanghvi et al. |
| 6,284,465 B1 | 9/2001 | Wolber |
| 6,287,776 B1 | 9/2001 | Hefti |
| 6,287,824 B1 | 9/2001 | Lizardi |
| 6,297,017 B1 | 10/2001 | Schmidt et al. |
| 6,300,137 B1 | 10/2001 | Earhart et al. |
| 6,306,599 B1 | 10/2001 | Perbost |
| 6,309,822 B1 | 10/2001 | Fodor et al. |
| 6,309,828 B1 | 10/2001 | Schleifer et al. |
| 6,312,911 B1 | 11/2001 | Bancroft et al. |
| 6,319,674 B1 | 11/2001 | Fulcrand et al. |
| 6,323,043 B1 | 11/2001 | Caren et al. |
| 6,329,210 B1 | 12/2001 | Schleifer |
| 6,346,423 B1 | 2/2002 | Schembri |
| 6,365,355 B1 | 4/2002 | McCutchen-Maloney |
| 6,372,483 B2 | 4/2002 | Schleifer et al. |
| 6,375,903 B1 | 4/2002 | Cerrina et al. |
| 6,376,285 B1 | 4/2002 | Joyner et al. |
| 6,384,210 B1 | 5/2002 | Blanchard |
| 6,387,636 B1 | 5/2002 | Perbost et al. |
| 6,399,394 B1 | 6/2002 | Dahm et al. |
| 6,399,516 B1 | 6/2002 | Ayon |
| 6,403,314 B1 | 6/2002 | Lange et al. |
| 6,406,849 B1 | 6/2002 | Dorsel et al. |
| 6,406,851 B1 | 6/2002 | Bass |
| 6,408,308 B1 | 6/2002 | Maslyn et al. |
| 6,419,883 B1 | 7/2002 | Blanchard |
| 6,428,957 B1 | 8/2002 | Delenstarr |
| 6,440,669 B1 | 8/2002 | Bass et al. |
| 6,444,268 B2 | 9/2002 | Lefkowitz et al. |
| 6,446,642 B1 | 9/2002 | Caren et al. |
| 6,446,682 B1 | 9/2002 | Viken |
| 6,451,998 B1 | 9/2002 | Perbost |
| 6,458,526 B1 | 10/2002 | Schembri et al. |
| 6,458,535 B1 | 10/2002 | Hall et al. |
| 6,458,583 B1 | 10/2002 | Bruhn et al. |
| 6,461,812 B2 | 10/2002 | Barth et al. |
| 6,461,816 B1 | 10/2002 | Wolber et al. |
| 6,469,156 B1 | 10/2002 | Schafer et al. |
| 6,472,147 B1 | 10/2002 | Janda et al. |
| 6,492,107 B1 | 12/2002 | Kauffman et al. |
| 6,518,056 B2 | 2/2003 | Schembri et al. |
| 6,521,427 B1 | 2/2003 | Evans |
| 6,521,453 B1 | 2/2003 | Crameri et al. |
| 6,555,357 B1 | 4/2003 | Kaiser et al. |
| 6,558,908 B2 | 5/2003 | Wolber et al. |
| 6,562,611 B1 | 5/2003 | Kaiser et al. |
| 6,566,495 B1 | 5/2003 | Fodor et al. |
| 6,582,908 B2 | 6/2003 | Fodor et al. |
| 6,582,938 B1 | 6/2003 | Su et al. |
| 6,586,211 B1 | 7/2003 | Staehler et al. |
| 6,587,579 B1 | 7/2003 | Bass |
| 6,589,739 B2 | 7/2003 | Fisher |
| 6,599,693 B1 | 7/2003 | Webb |
| 6,602,472 B1 | 8/2003 | Zimmermann et al. |
| 6,610,978 B2 | 8/2003 | Yin et al. |
| 6,613,513 B1 | 9/2003 | Parce et al. |
| 6,613,523 B2 | 9/2003 | Fischer |
| 6,613,560 B1 | 9/2003 | Tso et al. |
| 6,613,893 B1 | 9/2003 | Webb |
| 6,621,076 B1 | 9/2003 | Van De Goor et al. |
| 6,630,581 B2 | 10/2003 | Dellinger et al. |
| 6,632,641 B1 | 10/2003 | Brennan et al. |
| 6,635,226 B1 | 10/2003 | Tso et al. |
| 6,642,373 B2 | 11/2003 | Manoharan et al. |
| 6,649,348 B2 | 11/2003 | Bass et al. |
| 6,660,338 B1 | 12/2003 | Hargreaves |
| 6,664,112 B2 | 12/2003 | Mulligan et al. |
| 6,670,127 B2 | 12/2003 | Evans |
| 6,670,461 B2 | 12/2003 | Wengel et al. |
| 6,673,552 B2 | 1/2004 | Frey |
| 6,682,702 B2 | 1/2004 | Barth et al. |

(56) References Cited

U.S. PATENT DOCUMENTS

| | | |
|---|---|---|
| 6,689,319 B1 | 2/2004 | Fisher et al. |
| 6,692,917 B2 | 2/2004 | Neri et al. |
| 6,702,256 B2 | 3/2004 | Killeen et al. |
| 6,706,471 B1 | 3/2004 | Brow et al. |
| 6,706,875 B1 | 3/2004 | Goldberg et al. |
| 6,709,841 B2 | 3/2004 | Short |
| 6,709,852 B1 | 3/2004 | Bloom et al. |
| 6,709,854 B2 | 3/2004 | Donahue et al. |
| 6,713,262 B2 | 3/2004 | Gillibolian et al. |
| 6,716,629 B2 | 4/2004 | Hess et al. |
| 6,716,634 B1 | 4/2004 | Myerson |
| 6,723,509 B2 | 4/2004 | Ach |
| 6,728,129 B2 | 4/2004 | Lindsey et al. |
| 6,743,585 B2 | 6/2004 | Dellinger et al. |
| 6,753,145 B2 | 6/2004 | Holcomb et al. |
| 6,768,005 B2 | 7/2004 | Mellor et al. |
| 6,770,748 B2 | 8/2004 | Imanishi et al. |
| 6,770,892 B2 | 8/2004 | Corson et al. |
| 6,773,676 B2 | 8/2004 | Schembri |
| 6,773,888 B2 | 8/2004 | Li et al. |
| 6,780,982 B2 | 8/2004 | Lyamichev et al. |
| 6,787,308 B2 | 9/2004 | Balasubramanian et al. |
| 6,789,965 B2 | 9/2004 | Barth et al. |
| 6,790,620 B2 | 9/2004 | Bass et al. |
| 6,794,499 B2 | 9/2004 | Wengel et al. |
| 6,796,634 B2 | 9/2004 | Caren et al. |
| 6,800,439 B1 | 10/2004 | McGall et al. |
| 6,814,846 B1 | 11/2004 | Berndt |
| 6,815,218 B1 | 11/2004 | Jacobson et al. |
| 6,824,866 B1 | 11/2004 | Glazer et al. |
| 6,830,890 B2 | 12/2004 | Lockhart et al. |
| 6,833,246 B2 | 12/2004 | Balasubramanian |
| 6,833,450 B1 | 12/2004 | McGall et al. |
| 6,835,938 B2 | 12/2004 | Ghosh et al. |
| 6,838,888 B2 | 1/2005 | Peck |
| 6,841,131 B2 | 1/2005 | Zimmermann et al. |
| 6,845,968 B2 | 1/2005 | Killeen et al. |
| 6,846,454 B2 | 1/2005 | Peck |
| 6,846,922 B1 | 1/2005 | Manoharan et al. |
| 6,852,850 B2 | 2/2005 | Myerson et al. |
| 6,858,720 B2 | 2/2005 | Myerson et al. |
| 6,879,915 B2 | 4/2005 | Cattell |
| 6,880,576 B2 | 4/2005 | Karp et al. |
| 6,884,580 B2 | 4/2005 | Caren et al. |
| 6,887,715 B2 | 5/2005 | Schembri |
| 6,890,723 B2 | 5/2005 | Perbost et al. |
| 6,890,760 B1 | 5/2005 | Webb |
| 6,893,816 B1 | 5/2005 | Beattie |
| 6,897,023 B2 | 5/2005 | Fu et al. |
| 6,900,047 B2 | 5/2005 | Bass |
| 6,900,048 B2 | 5/2005 | Perbost |
| 6,911,611 B2 | 6/2005 | Wong et al. |
| 6,914,229 B2 | 7/2005 | Corson et al. |
| 6,916,113 B2 | 7/2005 | Van De Goor et al. |
| 6,916,633 B1 | 7/2005 | Shannon |
| 6,919,181 B2 | 7/2005 | Hargreaves |
| 6,927,029 B2 | 8/2005 | Lefkowitz et al. |
| 6,929,951 B2 | 8/2005 | Corson et al. |
| 6,936,472 B2 | 8/2005 | Earhart et al. |
| 6,938,476 B2 | 9/2005 | Chesk |
| 6,939,673 B2 | 9/2005 | Bass et al. |
| 6,943,036 B2 | 9/2005 | Bass |
| 6,946,285 B2 | 9/2005 | Bass |
| 6,950,756 B2 | 9/2005 | Kincaid |
| 6,951,719 B1 | 10/2005 | Dupret et al. |
| 6,958,119 B2 | 10/2005 | Yin et al. |
| 6,960,464 B2 | 11/2005 | Jessee et al. |
| 6,969,449 B2 | 11/2005 | Maher et al. |
| 6,969,488 B2 | 11/2005 | Bridgham et al. |
| 6,976,384 B2 | 12/2005 | Hobbs et al. |
| 6,977,223 B2 | 12/2005 | George et al. |
| 6,987,263 B2 | 1/2006 | Hobbs et al. |
| 6,989,267 B2 | 1/2006 | Kim et al. |
| 6,991,922 B2 | 1/2006 | Dupret et al. |
| 7,008,037 B2 | 3/2006 | Caren et al. |
| 7,025,324 B1 | 4/2006 | Slocum et al. |
| 7,026,124 B2 | 4/2006 | Barth et al. |
| 7,027,930 B2 | 4/2006 | Cattell |
| 7,028,536 B2 | 4/2006 | Karp et al. |
| 7,029,854 B2 | 4/2006 | Collins et al. |
| 7,034,290 B2 | 4/2006 | Lu et al. |
| 7,041,445 B2 | 5/2006 | Chenchik et al. |
| 7,045,289 B2 | 5/2006 | Allawi et al. |
| 7,051,574 B2 | 5/2006 | Peck |
| 7,052,841 B2 | 5/2006 | Delenstarr |
| 7,062,385 B2 | 6/2006 | White et al. |
| 7,064,197 B1 | 6/2006 | Rabbani et al. |
| 7,070,932 B2 | 7/2006 | Leproust et al. |
| 7,075,161 B2 | 7/2006 | Barth |
| 7,078,167 B2 | 7/2006 | Delenstarr et al. |
| 7,078,505 B2 | 7/2006 | Bass et al. |
| 7,094,537 B2 | 8/2006 | Leproust et al. |
| 7,097,974 B1 | 8/2006 | Stahler et al. |
| 7,101,508 B2 | 9/2006 | Thompson et al. |
| 7,101,986 B2 | 9/2006 | Dellinger et al. |
| 7,105,295 B2 | 9/2006 | Bass et al. |
| 7,115,423 B1 | 10/2006 | Mitchell |
| 7,122,303 B2 | 10/2006 | Delenstarr et al. |
| 7,122,364 B1 | 10/2006 | Lyamichev et al. |
| 7,125,488 B2 | 10/2006 | Li |
| 7,125,523 B2 | 10/2006 | Sillman |
| 7,128,876 B2 | 10/2006 | Yin et al. |
| 7,129,075 B2 | 10/2006 | Gerard et al. |
| 7,135,565 B2 | 11/2006 | Dellinger et al. |
| 7,138,062 B2 | 11/2006 | Yin et al. |
| 7,141,368 B2 | 11/2006 | Fisher et al. |
| 7,141,807 B2 | 11/2006 | Joyce et al. |
| 7,147,362 B2 | 12/2006 | Caren et al. |
| 7,150,982 B2 | 12/2006 | Allawi et al. |
| 7,153,689 B2 | 12/2006 | Tolosko et al. |
| 7,163,660 B2 | 1/2007 | Lehmann |
| 7,166,258 B2 | 1/2007 | Bass et al. |
| 7,179,659 B2 | 2/2007 | Stolowitz et al. |
| 7,183,406 B2 | 2/2007 | Belshaw et al. |
| 7,192,710 B2 | 3/2007 | Gellibolian et al. |
| 7,193,077 B2 | 3/2007 | Dellinger et al. |
| 7,195,872 B2 | 3/2007 | Agrawal et al. |
| 7,198,939 B2 | 4/2007 | Dorsel et al. |
| 7,202,264 B2 | 4/2007 | Ravikumar et al. |
| 7,202,358 B2 | 4/2007 | Hargreaves |
| 7,205,128 B2 | 4/2007 | Ilsley et al. |
| 7,205,400 B2 | 4/2007 | Webb |
| 7,206,439 B2 | 4/2007 | Zhou et al. |
| 7,208,322 B2 | 4/2007 | Stolowitz et al. |
| 7,217,522 B2 | 5/2007 | Brenner |
| 7,220,573 B2 | 5/2007 | Shea et al. |
| 7,221,785 B2 | 5/2007 | Curry et al. |
| 7,226,862 B2 | 6/2007 | Staehler et al. |
| 7,227,017 B2 | 6/2007 | Mellor et al. |
| 7,229,497 B2 | 6/2007 | Stott et al. |
| 7,247,337 B1 | 7/2007 | Leproust et al. |
| 7,247,497 B2 | 7/2007 | Dahm et al. |
| 7,252,938 B2 | 8/2007 | Leproust et al. |
| 7,269,518 B2 | 9/2007 | Corson |
| 7,271,258 B2 | 9/2007 | Dellinger et al. |
| 7,276,336 B1 | 10/2007 | Webb et al. |
| 7,276,378 B2 | 10/2007 | Myerson |
| 7,276,599 B2 | 10/2007 | Moore et al. |
| 7,282,183 B2 | 10/2007 | Peck |
| 7,282,332 B2 | 10/2007 | Caren et al. |
| 7,282,705 B2 | 10/2007 | Brennen |
| 7,291,471 B2 | 11/2007 | Sampson et al. |
| 7,302,348 B2 | 11/2007 | Ghosh et al. |
| 7,306,917 B2 | 12/2007 | Prudent et al. |
| 7,314,599 B2 | 1/2008 | Roitman et al. |
| 7,323,320 B2 | 1/2008 | Oleinikov |
| 7,344,831 B2 | 3/2008 | Wolber et al. |
| 7,348,144 B2 | 3/2008 | Minor |
| 7,351,379 B2 | 4/2008 | Schleifer |
| 7,353,116 B2 | 4/2008 | Webb et al. |
| 7,361,906 B2 | 4/2008 | Ghosh et al. |
| 7,364,896 B2 | 4/2008 | Schembri |
| 7,368,550 B2 | 5/2008 | Dellinger et al. |
| 7,371,348 B2 | 5/2008 | Schleifer et al. |

(56) References Cited

U.S. PATENT DOCUMENTS

| | | |
|---|---|---|
| 7,371,519 B2 | 5/2008 | Wolber et al. |
| 7,371,580 B2 | 5/2008 | Yakhini et al. |
| 7,372,982 B2 | 5/2008 | Le Cocq |
| 7,384,746 B2 | 6/2008 | Lyamichev et al. |
| 7,385,050 B2 | 6/2008 | Dellinger et al. |
| 7,390,457 B2 | 6/2008 | Schembri |
| 7,393,665 B2 | 7/2008 | Brenner |
| 7,396,676 B2 | 7/2008 | Robotti et al. |
| 7,399,844 B2 | 7/2008 | Sampson et al. |
| 7,402,279 B2 | 7/2008 | Schembri |
| 7,411,061 B2 | 8/2008 | Myerson et al. |
| 7,413,709 B2 | 8/2008 | Roitman et al. |
| 7,417,139 B2 | 8/2008 | Dellinger et al. |
| 7,422,911 B2 | 9/2008 | Schembri |
| 7,427,679 B2 | 9/2008 | Dellinger et al. |
| 7,432,048 B2 | 10/2008 | Neri et al. |
| 7,435,810 B2 | 10/2008 | Myerson et al. |
| 7,439,272 B2 | 10/2008 | Xu |
| 7,476,709 B2 | 1/2009 | Moody et al. |
| 7,482,118 B2 | 1/2009 | Allawi et al. |
| 7,488,607 B2 | 2/2009 | Tom-Moy et al. |
| 7,504,213 B2 | 3/2009 | Sana et al. |
| 7,514,369 B2 | 4/2009 | Li et al. |
| 7,517,979 B2 | 4/2009 | Wolber |
| 7,524,942 B2 | 4/2009 | Wang et al. |
| 7,524,950 B2 | 4/2009 | Dellinger et al. |
| 7,527,928 B2 | 5/2009 | Neri et al. |
| 7,531,303 B2 | 5/2009 | Dorsel et al. |
| 7,534,561 B2 | 5/2009 | Sana et al. |
| 7,534,563 B2 | 5/2009 | Hargreaves |
| 7,537,936 B2 | 5/2009 | Dahm et al. |
| 7,541,145 B2 | 6/2009 | Prudent et al. |
| 7,544,473 B2 | 6/2009 | Brenner |
| 7,556,919 B2 | 7/2009 | Chenchik et al. |
| 7,563,600 B2 | 7/2009 | Oleinikov |
| 7,572,585 B2 | 8/2009 | Wang |
| 7,572,907 B2 | 8/2009 | Dellinger et al. |
| 7,572,908 B2 | 8/2009 | Dellinger et al. |
| 7,585,970 B2 | 9/2009 | Dellinger et al. |
| 7,588,889 B2 | 9/2009 | Wolber et al. |
| 7,595,350 B2 | 9/2009 | Xu |
| 7,604,941 B2 | 10/2009 | Jacobson |
| 7,604,996 B1 | 10/2009 | Stuelpnagel et al. |
| 7,608,396 B2 | 10/2009 | Delenstarr |
| 7,618,777 B2 | 11/2009 | Myerson et al. |
| 7,629,120 B2 | 12/2009 | Bennett et al. |
| 7,635,772 B2 | 12/2009 | McCormac |
| 7,648,832 B2 | 1/2010 | Jessee et al. |
| 7,651,762 B2 | 1/2010 | Xu et al. |
| 7,659,069 B2 | 2/2010 | Belyaev et al. |
| 7,678,542 B2 | 3/2010 | Lyamichev et al. |
| 7,682,809 B2 | 3/2010 | Sampson |
| 7,709,197 B2 | 5/2010 | Drmanac |
| 7,718,365 B2 | 5/2010 | Wang |
| 7,718,786 B2 | 5/2010 | Dupret et al. |
| 7,723,077 B2 | 5/2010 | Young et al. |
| 7,737,088 B1 | 6/2010 | Stahler et al. |
| 7,737,089 B2 | 6/2010 | Guimil et al. |
| 7,741,463 B2 | 6/2010 | Gormley et al. |
| 7,749,701 B2 | 7/2010 | Leproust et al. |
| 7,759,471 B2 | 7/2010 | Dellinger et al. |
| 7,776,021 B2 | 8/2010 | Borenstein et al. |
| 7,776,532 B2 | 8/2010 | Gibson et al. |
| 7,790,369 B2 | 9/2010 | Stahler et al. |
| 7,790,387 B2 | 9/2010 | Dellinger et al. |
| 7,807,356 B2 | 10/2010 | Sampson et al. |
| 7,807,806 B2 | 10/2010 | Allawi et al. |
| 7,811,753 B2 | 10/2010 | Eshoo |
| 7,816,079 B2 | 10/2010 | Fischer |
| 7,820,387 B2 | 10/2010 | Neri et al. |
| 7,829,314 B2 | 11/2010 | Prudent et al. |
| 7,855,281 B2 | 12/2010 | Dellinger et al. |
| 7,862,999 B2 | 1/2011 | Zheng et al. |
| 7,867,782 B2 | 1/2011 | Barth |
| 7,875,463 B2 | 1/2011 | Adaskin et al. |
| 7,879,541 B2 | 2/2011 | Kincaid |
| 7,879,580 B2 | 2/2011 | Carr et al. |
| 7,894,998 B2 | 2/2011 | Kincaid |
| 7,919,239 B2 | 4/2011 | Wang |
| 7,919,308 B2 | 4/2011 | Schleifer |
| 7,927,797 B2 | 4/2011 | Nobile et al. |
| 7,927,838 B2 | 4/2011 | Shannon |
| 7,932,025 B2 | 4/2011 | Carr et al. |
| 7,932,070 B2 | 4/2011 | Hogrefe et al. |
| 7,935,800 B2 | 5/2011 | Allawi et al. |
| 7,939,645 B2 | 5/2011 | Borns |
| 7,943,046 B2 | 5/2011 | Martosella et al. |
| 7,943,358 B2 | 5/2011 | Hogrefe et al. |
| 7,960,157 B2 | 6/2011 | Borns |
| 7,977,119 B2 | 7/2011 | Kronick et al. |
| 7,979,215 B2 | 7/2011 | Sampas |
| 7,998,437 B2 | 8/2011 | Berndt et al. |
| 7,999,087 B2 | 8/2011 | Dellinger et al. |
| 8,021,842 B2 | 9/2011 | Brenner |
| 8,021,844 B2 | 9/2011 | Wang |
| 8,034,917 B2 | 10/2011 | Yamada |
| 8,036,835 B2 | 10/2011 | Sampas et al. |
| 8,048,664 B2 | 11/2011 | Guan et al. |
| 8,053,191 B2 | 11/2011 | Blake |
| 8,058,001 B2 | 11/2011 | Crameri et al. |
| 8,058,004 B2 | 11/2011 | Oleinikov |
| 8,058,055 B2 | 11/2011 | Barrett et al. |
| 8,063,184 B2 | 11/2011 | Allawi et al. |
| 8,067,556 B2 | 11/2011 | Hogrefe et al. |
| 8,073,626 B2 | 12/2011 | Troup et al. |
| 8,076,064 B2 | 12/2011 | Wang |
| 8,076,152 B2 | 12/2011 | Robotti |
| 8,097,711 B2 | 1/2012 | Timar et al. |
| 8,137,936 B2 | 3/2012 | Macevicz |
| 8,148,068 B2 | 4/2012 | Brenner |
| 8,154,729 B2 | 4/2012 | Baldo et al. |
| 8,168,385 B2 | 5/2012 | Brenner |
| 8,168,388 B2 | 5/2012 | Gormley et al. |
| 8,173,368 B2 | 5/2012 | Staehler et al. |
| 8,182,991 B1 | 5/2012 | Kaiser et al. |
| 8,194,244 B2 | 6/2012 | Wang et al. |
| 8,198,071 B2 | 6/2012 | Goshoo et al. |
| 8,202,983 B2 | 6/2012 | Dellinger et al. |
| 8,202,985 B2 | 6/2012 | Dellinger et al. |
| 8,206,952 B2 | 6/2012 | Carr et al. |
| 8,213,015 B2 | 7/2012 | Kraiczek et al. |
| 8,242,258 B2 | 8/2012 | Dellinger et al. |
| 8,247,221 B2 | 8/2012 | Fawcett et al. |
| 8,263,335 B2 | 9/2012 | Carr et al. |
| 8,268,605 B2 | 9/2012 | Sorge et al. |
| 8,283,148 B2 | 10/2012 | Sorge et al. |
| 8,288,093 B2 | 10/2012 | Hall et al. |
| 8,298,767 B2 | 10/2012 | Brenner et al. |
| 8,304,273 B2 | 11/2012 | Stellacci et al. |
| 8,309,307 B2 | 11/2012 | Barrett et al. |
| 8,309,706 B2 | 11/2012 | Dellinger et al. |
| 8,309,710 B2 | 11/2012 | Sierzchala et al. |
| 8,314,220 B2 | 11/2012 | Mullinax et al. |
| 8,318,433 B2 | 11/2012 | Brenner |
| 8,318,479 B2 | 11/2012 | Domansky et al. |
| 8,357,489 B2 | 1/2013 | Chua et al. |
| 8,357,490 B2 | 1/2013 | Froehlich et al. |
| 8,367,016 B2 | 2/2013 | Quan et al. |
| 8,367,335 B2 | 2/2013 | Staehler et al. |
| 8,380,441 B2 | 2/2013 | Webb et al. |
| 8,383,338 B2 | 2/2013 | Kitzman et al. |
| 8,415,138 B2 | 4/2013 | Leproust |
| 8,435,736 B2 | 5/2013 | Gibson et al. |
| 8,445,205 B2 | 5/2013 | Brenner |
| 8,445,206 B2 | 5/2013 | Bergmann et al. |
| 8,470,996 B2 | 6/2013 | Brenner |
| 8,476,018 B2 | 7/2013 | Brenner |
| 8,476,598 B1 | 7/2013 | Pralle et al. |
| 8,481,292 B2 | 7/2013 | Casbon et al. |
| 8,481,309 B2 | 7/2013 | Zhang et al. |
| 8,491,561 B2 | 7/2013 | Borenstein et al. |
| 8,497,069 B2 | 7/2013 | Hutchison et al. |
| 8,500,979 B2 | 8/2013 | Elibol et al. |
| 8,501,454 B2 | 8/2013 | Liu et al. |

(56) References Cited

U.S. PATENT DOCUMENTS

| | | |
|---|---|---|
| 8,507,226 B2 | 8/2013 | Carr et al. |
| 8,507,239 B2 | 8/2013 | Lubys et al. |
| 8,507,272 B2 | 8/2013 | Zhang et al. |
| 8,530,197 B2 | 9/2013 | Li et al. |
| 8,552,174 B2 | 10/2013 | Dellinger et al. |
| 8,563,478 B2 | 10/2013 | Gormley et al. |
| 8,569,046 B2 | 10/2013 | Love et al. |
| 8,577,621 B2 | 11/2013 | Troup et al. |
| 8,586,310 B2 | 11/2013 | Mitra et al. |
| 8,614,092 B2 | 12/2013 | Zhang et al. |
| 8,642,755 B2 | 2/2014 | Sierzchala et al. |
| 8,664,164 B2 | 3/2014 | Ericsson et al. |
| 8,669,053 B2 | 3/2014 | Stuelpnagel et al. |
| 8,679,756 B1 | 3/2014 | Brenner et al. |
| 8,685,642 B2 | 4/2014 | Sampas |
| 8,685,676 B2 | 4/2014 | Hogrefe et al. |
| 8,685,678 B2 | 4/2014 | Casbon et al. |
| 8,715,933 B2 | 5/2014 | Oliver |
| 8,715,967 B2 | 5/2014 | Casbon et al. |
| 8,716,467 B2 | 5/2014 | Jacobson |
| 8,722,368 B2 | 5/2014 | Casbon et al. |
| 8,722,585 B2 | 5/2014 | Wang |
| 8,728,766 B2 | 5/2014 | Casbon et al. |
| 8,741,606 B2 | 6/2014 | Casbon et al. |
| 8,808,896 B2 | 8/2014 | Choo et al. |
| 8,808,986 B2 | 8/2014 | Jacobson et al. |
| 8,815,600 B2 | 8/2014 | Liu et al. |
| 8,889,851 B2 | 11/2014 | Leproust et al. |
| 8,932,994 B2 | 1/2015 | Gormley et al. |
| 8,962,532 B2 | 2/2015 | Shapiro et al. |
| 8,968,999 B2 | 3/2015 | Gibson et al. |
| 8,980,563 B2 | 3/2015 | Zheng et al. |
| 9,018,365 B2 | 4/2015 | Brenner |
| 9,023,601 B2 | 5/2015 | Oleinikov |
| 9,051,666 B2 | 6/2015 | Oleinikov |
| 9,073,962 B2 | 7/2015 | Fracchia et al. |
| 9,074,204 B2 | 7/2015 | Anderson et al. |
| 9,085,797 B2 | 7/2015 | Gebeyehu et al. |
| 9,133,510 B2 | 9/2015 | Andersen et al. |
| 9,139,874 B2 | 9/2015 | Myers et al. |
| 9,150,853 B2 | 10/2015 | Hudson et al. |
| 9,187,777 B2 | 11/2015 | Jacobson et al. |
| 9,194,001 B2 | 11/2015 | Brenner |
| 9,216,414 B2 | 12/2015 | Chu |
| 9,217,144 B2 | 12/2015 | Jacobson et al. |
| 9,279,149 B2 | 3/2016 | Efcavitch et al. |
| 9,286,439 B2 | 3/2016 | Shapiro et al. |
| 9,295,965 B2 | 3/2016 | Jacobson et al. |
| 9,315,861 B2 | 4/2016 | Hendricks et al. |
| 9,328,378 B2 | 5/2016 | Earnshaw et al. |
| 9,347,091 B2 | 5/2016 | Bergmann et al. |
| 9,375,748 B2 | 6/2016 | Harumoto et al. |
| 9,376,677 B2 | 6/2016 | Mir |
| 9,376,678 B2 | 6/2016 | Gormley et al. |
| 9,384,320 B2 | 7/2016 | Church |
| 9,384,920 B1 | 7/2016 | Bakulich |
| 9,388,407 B2 | 7/2016 | Jacobson |
| 9,394,333 B2 | 7/2016 | Wada et al. |
| 9,403,141 B2 | 8/2016 | Banyai et al. |
| 9,409,139 B2 | 8/2016 | Banyai et al. |
| 9,410,149 B2 | 8/2016 | Brenner et al. |
| 9,410,173 B2 | 8/2016 | Betts et al. |
| 9,416,411 B2 | 8/2016 | Stuelpnagel et al. |
| 9,422,600 B2 | 8/2016 | Ramu et al. |
| 9,487,824 B2 | 11/2016 | Kutyavin |
| 9,499,848 B2 | 11/2016 | Carr et al. |
| 9,523,122 B2 | 12/2016 | Zheng et al. |
| 9,528,148 B2 | 12/2016 | Zheng et al. |
| 9,534,251 B2 | 1/2017 | Young et al. |
| 9,555,388 B2 | 1/2017 | Banyai et al. |
| 9,568,839 B2 | 2/2017 | Stahler et al. |
| 9,580,746 B2 | 2/2017 | Leproust et al. |
| 9,670,529 B2 | 6/2017 | Osborne et al. |
| 9,670,536 B2 | 6/2017 | Casbon et al. |
| 9,677,067 B2 | 6/2017 | Toro et al. |
| 9,695,211 B2 | 7/2017 | Wada et al. |
| 9,718,060 B2 | 8/2017 | Venter et al. |
| 9,745,573 B2 | 8/2017 | Stuelpnagel et al. |
| 9,745,619 B2 | 8/2017 | Rabbani et al. |
| 9,765,387 B2 | 9/2017 | Rabbani et al. |
| 9,771,576 B2 | 9/2017 | Gibson et al. |
| 9,833,761 B2 | 12/2017 | Banyai et al. |
| 9,834,774 B2 | 12/2017 | Carstens |
| 9,839,894 B2 | 12/2017 | Banyai et al. |
| 9,879,283 B2 | 1/2018 | Ravinder et al. |
| 9,889,423 B2 | 2/2018 | Banyai et al. |
| 9,895,673 B2 | 2/2018 | Peck et al. |
| 9,925,510 B2 | 3/2018 | Jacobson et al. |
| 9,932,576 B2 | 4/2018 | Raymond et al. |
| 9,981,239 B2 | 5/2018 | Banyai et al. |
| 10,053,688 B2 | 8/2018 | Cox |
| 10,251,611 B2 | 4/2019 | Marsh et al. |
| 10,272,410 B2 | 4/2019 | Banyai et al. |
| 10,384,188 B2 | 8/2019 | Banyai et al. |
| 10,384,189 B2 | 8/2019 | Peck |
| 10,417,457 B2 | 9/2019 | Peck |
| 10,583,415 B2 | 3/2020 | Banyai et al. |
| 10,632,445 B2 | 4/2020 | Banyai et al. |
| 10,639,609 B2 | 5/2020 | Banyai et al. |
| 10,669,304 B2 | 6/2020 | Indermuhle et al. |
| 10,969,965 B2 | 4/2021 | Malina et al. |
| 2001/0018512 A1 | 8/2001 | Blanchard |
| 2001/0039014 A1 | 11/2001 | Bass et al. |
| 2001/0055761 A1 | 12/2001 | Kanemoto et al. |
| 2002/0012930 A1 | 1/2002 | Rothberg et al. |
| 2002/0025561 A1 | 2/2002 | Hodgson |
| 2002/0076716 A1 | 6/2002 | Sabanayagam et al. |
| 2002/0081582 A1 | 6/2002 | Gao et al. |
| 2002/0094533 A1 | 7/2002 | Hess et al. |
| 2002/0095073 A1 | 7/2002 | Jacobs et al. |
| 2002/0119459 A1 | 8/2002 | Griffiths |
| 2002/0132308 A1 | 9/2002 | Liu et al. |
| 2002/0155439 A1 | 10/2002 | Rodriguez et al. |
| 2002/0160536 A1 | 10/2002 | Regnier et al. |
| 2002/0164824 A1 | 11/2002 | Xiao et al. |
| 2003/0008411 A1 | 1/2003 | Van Dam et al. |
| 2003/0022207 A1 | 1/2003 | Balasubramanian et al. |
| 2003/0022240 A1 | 1/2003 | Luo et al. |
| 2003/0022317 A1 | 1/2003 | Jack et al. |
| 2003/0044781 A1 | 3/2003 | Korlach et al. |
| 2003/0058629 A1 | 3/2003 | Hirai et al. |
| 2003/0064398 A1 | 4/2003 | Barnes |
| 2003/0068633 A1 | 4/2003 | Belshaw et al. |
| 2003/0082719 A1 | 5/2003 | Schumacher et al. |
| 2003/0100102 A1 | 5/2003 | Rothberg et al. |
| 2003/0108903 A1 | 6/2003 | Wang et al. |
| 2003/0120035 A1 | 6/2003 | Gao et al. |
| 2003/0130827 A1 | 7/2003 | Bentzien et al. |
| 2003/0138782 A1 | 7/2003 | Evans |
| 2003/0143605 A1 | 7/2003 | Lok et al. |
| 2003/0148291 A1 | 8/2003 | Robotti |
| 2003/0148344 A1 | 8/2003 | Rothberg et al. |
| 2003/0171325 A1 | 9/2003 | Gascoyne et al. |
| 2003/0186226 A1 | 10/2003 | Brennan et al. |
| 2003/0228602 A1 | 12/2003 | Parker et al. |
| 2003/0228620 A1 | 12/2003 | Du Breuil Lastrucci |
| 2004/0009498 A1 | 1/2004 | Short |
| 2004/0043509 A1 | 3/2004 | Stahler et al. |
| 2004/0053362 A1 | 3/2004 | De Luca et al. |
| 2004/0086892 A1 | 5/2004 | Crothers et al. |
| 2004/0087008 A1 | 5/2004 | Schembri |
| 2004/0106130 A1 | 6/2004 | Besemer et al. |
| 2004/0106728 A1 | 6/2004 | McGall et al. |
| 2004/0110133 A1 | 6/2004 | Xu et al. |
| 2004/0175710 A1 | 9/2004 | Haushalter |
| 2004/0175734 A1 | 9/2004 | Stahler et al. |
| 2004/0191810 A1 | 9/2004 | Yamamoto |
| 2004/0213795 A1 | 10/2004 | Collins et al. |
| 2004/0219663 A1 | 11/2004 | Page et al. |
| 2004/0236027 A1 | 11/2004 | Maeji et al. |
| 2004/0248161 A1 | 12/2004 | Rothberg et al. |
| 2004/0253242 A1 | 12/2004 | Bowdish et al. |
| 2004/0259146 A1 | 12/2004 | Friend et al. |
| 2005/0022895 A1 | 2/2005 | Barth et al. |

(56) References Cited

U.S. PATENT DOCUMENTS

| | | |
|---|---|---|
| 2005/0049402 A1 | 3/2005 | Babcook et al. |
| 2005/0049796 A1 | 3/2005 | Webb et al. |
| 2005/0053968 A1 | 3/2005 | Bharadwaj et al. |
| 2005/0079510 A1 | 4/2005 | Berka et al. |
| 2005/0100932 A1 | 5/2005 | Lapidus et al. |
| 2005/0112608 A1 | 5/2005 | Grossman et al. |
| 2005/0112636 A1 | 5/2005 | Hurt et al. |
| 2005/0112679 A1 | 5/2005 | Myerson et al. |
| 2005/0124022 A1 | 6/2005 | Srinivasan et al. |
| 2005/0137805 A1 | 6/2005 | Lewin et al. |
| 2005/0208513 A1 | 9/2005 | Agbo et al. |
| 2005/0214778 A1 | 9/2005 | Peck et al. |
| 2005/0214779 A1 | 9/2005 | Peck et al. |
| 2005/0227235 A1 | 10/2005 | Carr et al. |
| 2005/0255477 A1 | 11/2005 | Carr et al. |
| 2005/0266045 A1 | 12/2005 | Canham et al. |
| 2005/0277125 A1 | 12/2005 | Benn et al. |
| 2005/0282158 A1 | 12/2005 | Landegren |
| 2005/0287585 A1 | 12/2005 | Oleinikov |
| 2006/0003381 A1 | 1/2006 | Gilmore et al. |
| 2006/0003958 A1 | 1/2006 | Melville et al. |
| 2006/0012784 A1 | 1/2006 | Ulmer |
| 2006/0012793 A1 | 1/2006 | Harris |
| 2006/0019084 A1 | 1/2006 | Pearson |
| 2006/0024678 A1 | 2/2006 | Buzby |
| 2006/0024711 A1 | 2/2006 | Lapidus et al. |
| 2006/0024721 A1 | 2/2006 | Pedersen |
| 2006/0076482 A1 | 4/2006 | Hobbs et al. |
| 2006/0078909 A1 | 4/2006 | Srinivasan et al. |
| 2006/0078927 A1 | 4/2006 | Peck et al. |
| 2006/0078937 A1 | 4/2006 | Korlach et al. |
| 2006/0127920 A1 | 6/2006 | Church et al. |
| 2006/0134638 A1 | 6/2006 | Mulligan et al. |
| 2006/0160138 A1 | 7/2006 | Church |
| 2006/0171855 A1 | 8/2006 | Yin et al. |
| 2006/0202330 A1 | 9/2006 | Reinhardt et al. |
| 2006/0203236 A1 | 9/2006 | Ji et al. |
| 2006/0203237 A1 | 9/2006 | Ji et al. |
| 2006/0207923 A1 | 9/2006 | Li |
| 2006/0219637 A1 | 10/2006 | Killeen et al. |
| 2007/0031857 A1 | 2/2007 | Makarov et al. |
| 2007/0031877 A1 | 2/2007 | Stahler et al. |
| 2007/0043516 A1 | 2/2007 | Gustafsson et al. |
| 2007/0054127 A1 | 3/2007 | Hergenrother et al. |
| 2007/0059692 A1 | 3/2007 | Gao et al. |
| 2007/0087349 A1 | 4/2007 | Staehler et al. |
| 2007/0099196 A1 | 5/2007 | Kauppinen et al. |
| 2007/0099208 A1 | 5/2007 | Drmanac et al. |
| 2007/0122817 A1 | 5/2007 | Church et al. |
| 2007/0128635 A1 | 6/2007 | Macevicz |
| 2007/0141557 A1 | 6/2007 | Raab et al. |
| 2007/0196834 A1 | 8/2007 | Cerrina et al. |
| 2007/0196854 A1 | 8/2007 | Stahler et al. |
| 2007/0207482 A1 | 9/2007 | Church et al. |
| 2007/0207487 A1 | 9/2007 | Emig et al. |
| 2007/0231800 A1 | 10/2007 | Roberts et al. |
| 2007/0233403 A1 | 10/2007 | Alwan et al. |
| 2007/0238104 A1 | 10/2007 | Barrett et al. |
| 2007/0238106 A1 | 10/2007 | Barrett et al. |
| 2007/0238108 A1 | 10/2007 | Barrett et al. |
| 2007/0259344 A1 | 11/2007 | Leproust et al. |
| 2007/0259345 A1 | 11/2007 | Sampas |
| 2007/0259346 A1 | 11/2007 | Gordon et al. |
| 2007/0259347 A1 | 11/2007 | Gordon et al. |
| 2007/0269870 A1 | 11/2007 | Church et al. |
| 2008/0085511 A1 | 4/2008 | Peck et al. |
| 2008/0085514 A1 | 4/2008 | Peck et al. |
| 2008/0087545 A1 | 4/2008 | Jensen et al. |
| 2008/0161200 A1 | 7/2008 | Yu et al. |
| 2008/0182296 A1 | 7/2008 | Chanda et al. |
| 2008/0214412 A1 | 9/2008 | Stahler et al. |
| 2008/0227160 A1 | 9/2008 | Kool |
| 2008/0233616 A1 | 9/2008 | Liss |
| 2008/0287320 A1 | 11/2008 | Baynes et al. |
| 2008/0300842 A1 | 12/2008 | Govindarajan et al. |
| 2008/0308884 A1 | 12/2008 | Kalvesten |
| 2008/0311628 A1 | 12/2008 | Shoemaker |
| 2009/0036664 A1 | 2/2009 | Peter |
| 2009/0053704 A1 | 2/2009 | Novoradovskaya et al. |
| 2009/0062129 A1 | 3/2009 | McKernan et al. |
| 2009/0074771 A1 | 3/2009 | Koenig et al. |
| 2009/0087840 A1 | 4/2009 | Baynes et al. |
| 2009/0088679 A1 | 4/2009 | Wood et al. |
| 2009/0105094 A1 | 4/2009 | Heiner et al. |
| 2009/0170802 A1 | 7/2009 | Stahler et al. |
| 2009/0176280 A1 | 7/2009 | Hutchison, III et al. |
| 2009/0181861 A1 | 7/2009 | Li et al. |
| 2009/0194483 A1 | 8/2009 | Robotti et al. |
| 2009/0230044 A1 | 9/2009 | Bek |
| 2009/0238722 A1 | 9/2009 | Mora-Fillat et al. |
| 2009/0239759 A1 | 9/2009 | Balch |
| 2009/0246788 A1 | 10/2009 | Albert et al. |
| 2009/0263802 A1 | 10/2009 | Drmanac |
| 2009/0285825 A1 | 11/2009 | Kini et al. |
| 2009/0324546 A1 | 12/2009 | Notka et al. |
| 2010/0004143 A1 | 1/2010 | Shibahara |
| 2010/0008851 A1 | 1/2010 | Nicolaides et al. |
| 2010/0009872 A1 | 1/2010 | Eid et al. |
| 2010/0047805 A1 | 2/2010 | Wang |
| 2010/0051967 A1 | 3/2010 | Bradley et al. |
| 2010/0069250 A1 | 3/2010 | White, III et al. |
| 2010/0090341 A1 | 4/2010 | Wan et al. |
| 2010/0099103 A1 | 4/2010 | Hsieh et al. |
| 2010/0111768 A1 | 5/2010 | Banerjee et al. |
| 2010/0160463 A1 | 6/2010 | Wang et al. |
| 2010/0167950 A1 | 7/2010 | Juang et al. |
| 2010/0173364 A1 | 7/2010 | Evans et al. |
| 2010/0216648 A1 | 8/2010 | Staehler et al. |
| 2010/0256017 A1 | 10/2010 | Larman et al. |
| 2010/0258487 A1 | 10/2010 | Zelechonok et al. |
| 2010/0272711 A1 | 10/2010 | Feldman et al. |
| 2010/0286290 A1 | 11/2010 | Lohmann et al. |
| 2010/0292102 A1 | 11/2010 | Nouri |
| 2010/0300882 A1 | 12/2010 | Zhang et al. |
| 2010/0323404 A1 | 12/2010 | Lathrop |
| 2011/0009607 A1 | 1/2011 | Komiyama et al. |
| 2011/0082055 A1 | 4/2011 | Fox et al. |
| 2011/0114244 A1 | 5/2011 | Yoo et al. |
| 2011/0114549 A1 | 5/2011 | Yin et al. |
| 2011/0124049 A1 | 5/2011 | Li et al. |
| 2011/0124055 A1 | 5/2011 | Carr et al. |
| 2011/0126929 A1 | 6/2011 | Velasquez-Garcia et al. |
| 2011/0171651 A1 | 7/2011 | Richmond |
| 2011/0172127 A1 | 7/2011 | Jacobson et al. |
| 2011/0201057 A1 | 8/2011 | Carr et al. |
| 2011/0217738 A1 | 9/2011 | Jacobson |
| 2011/0230653 A1 | 9/2011 | Novoradovskaya et al. |
| 2011/0254107 A1 | 10/2011 | Bulovic et al. |
| 2011/0287435 A1 | 11/2011 | Grunenwald et al. |
| 2012/0003713 A1 | 1/2012 | Hansen et al. |
| 2012/0021932 A1 | 1/2012 | Mershin et al. |
| 2012/0027786 A1 | 2/2012 | Gupta et al. |
| 2012/0028843 A1 | 2/2012 | Ramu et al. |
| 2012/0032366 A1 | 2/2012 | Ivniski et al. |
| 2012/0046175 A1 | 2/2012 | Rodesch et al. |
| 2012/0050411 A1 | 3/2012 | Mabritto et al. |
| 2012/0094847 A1 | 4/2012 | Warthmann et al. |
| 2012/0128548 A1 | 5/2012 | West et al. |
| 2012/0129704 A1 | 5/2012 | Gunderson et al. |
| 2012/0149602 A1 | 6/2012 | Friend et al. |
| 2012/0164127 A1 | 6/2012 | Short et al. |
| 2012/0164633 A1 | 6/2012 | Laffler |
| 2012/0164691 A1 | 6/2012 | Eshoo et al. |
| 2012/0184724 A1 | 7/2012 | Sierzchala et al. |
| 2012/0220497 A1 | 8/2012 | Jacobson et al. |
| 2012/0231968 A1 | 9/2012 | Bruhn et al. |
| 2012/0238737 A1 | 9/2012 | Dellinger et al. |
| 2012/0258487 A1 | 10/2012 | Chang et al. |
| 2012/0264653 A1 | 10/2012 | Carr et al. |
| 2012/0270750 A1 | 10/2012 | Oleinikov |
| 2012/0270754 A1 | 10/2012 | Blake |
| 2012/0283140 A1 | 11/2012 | Chu |
| 2012/0288476 A1 | 11/2012 | Hartmann et al. |
| 2012/0289691 A1 | 11/2012 | Dellinger et al. |

(56) References Cited

U.S. PATENT DOCUMENTS

| | | |
|---|---|---|
| 2012/0315670 A1 | 12/2012 | Jacobson et al. |
| 2012/0322681 A1 | 12/2012 | Kung et al. |
| 2013/0005585 A1 | 1/2013 | Anderson et al. |
| 2013/0005612 A1 | 1/2013 | Carr et al. |
| 2013/0014790 A1 | 1/2013 | Van Gerpen |
| 2013/0017642 A1 | 1/2013 | Milgrew et al. |
| 2013/0017977 A1 | 1/2013 | Oleinikov |
| 2013/0017978 A1 | 1/2013 | Kavanagh et al. |
| 2013/0035261 A1 | 2/2013 | Sierzchala et al. |
| 2013/0040836 A1 | 2/2013 | Himmler et al. |
| 2013/0045483 A1 | 2/2013 | Treusch et al. |
| 2013/0053252 A1 | 2/2013 | Xie et al. |
| 2013/0059296 A1 | 3/2013 | Jacobson et al. |
| 2013/0059761 A1 | 3/2013 | Jacobson et al. |
| 2013/0065017 A1 | 3/2013 | Sieber |
| 2013/0109595 A1 | 5/2013 | Routenberg |
| 2013/0109596 A1 | 5/2013 | Peterson et al. |
| 2013/0123129 A1 | 5/2013 | Zeiner et al. |
| 2013/0130321 A1 | 5/2013 | Staehler et al. |
| 2013/0137161 A1 | 5/2013 | Zhang et al. |
| 2013/0137173 A1 | 5/2013 | Zhang et al. |
| 2013/0137174 A1 | 5/2013 | Zhang et al. |
| 2013/0137861 A1 | 5/2013 | Leproust et al. |
| 2013/0164308 A1 | 6/2013 | Foletti et al. |
| 2013/0165328 A1 | 6/2013 | Previte et al. |
| 2013/0196864 A1 | 8/2013 | Govindarajan et al. |
| 2013/0225421 A1 | 8/2013 | Li et al. |
| 2013/0244884 A1 | 9/2013 | Jacobson et al. |
| 2013/0252849 A1 | 9/2013 | Hudson et al. |
| 2013/0261027 A1 | 10/2013 | Li et al. |
| 2013/0281308 A1 | 10/2013 | Kung et al. |
| 2013/0289246 A1 | 10/2013 | Crowe et al. |
| 2013/0296192 A1 | 11/2013 | Jacobson et al. |
| 2013/0296194 A1 | 11/2013 | Jacobson et al. |
| 2013/0298265 A1 | 11/2013 | Cunnac et al. |
| 2013/0309725 A1 | 11/2013 | Jacobson et al. |
| 2013/0323725 A1 | 12/2013 | Peter et al. |
| 2013/0330778 A1 | 12/2013 | Zeiner et al. |
| 2014/0011226 A1 | 1/2014 | Bernick et al. |
| 2014/0018441 A1 | 1/2014 | Fracchia et al. |
| 2014/0031240 A1 | 1/2014 | Behlke et al. |
| 2014/0038240 A1 | 2/2014 | Temme et al. |
| 2014/0106394 A1 | 4/2014 | Ko et al. |
| 2014/0141982 A1 | 5/2014 | Jacobson et al. |
| 2014/0170665 A1 | 6/2014 | Hiddessen et al. |
| 2014/0178992 A1 | 6/2014 | Nakashima et al. |
| 2014/0221250 A1 | 8/2014 | Vasquez et al. |
| 2014/0274729 A1 | 9/2014 | Kurn et al. |
| 2014/0274741 A1 | 9/2014 | Hunter et al. |
| 2014/0303000 A1 | 10/2014 | Armour et al. |
| 2014/0309119 A1 | 10/2014 | Jacobson et al. |
| 2014/0309142 A1 | 10/2014 | Tian |
| 2015/0010953 A1 | 1/2015 | Lindstrom et al. |
| 2015/0012723 A1 | 1/2015 | Park et al. |
| 2015/0031089 A1 | 1/2015 | Lindstrom |
| 2015/0038373 A1 | 2/2015 | Banyai et al. |
| 2015/0056609 A1 | 2/2015 | Daum et al. |
| 2015/0057625 A1 | 2/2015 | Coulthard |
| 2015/0065357 A1 | 3/2015 | Fox |
| 2015/0065393 A1 | 3/2015 | Jacobson |
| 2015/0099870 A1 | 4/2015 | Bennett et al. |
| 2015/0119293 A1 | 4/2015 | Short |
| 2015/0120265 A1 | 4/2015 | Amirav-Drory et al. |
| 2015/0159152 A1 | 6/2015 | Allen et al. |
| 2015/0183853 A1 | 7/2015 | Sharma et al. |
| 2015/0191524 A1 | 7/2015 | Smith et al. |
| 2015/0191719 A1 | 7/2015 | Hudson et al. |
| 2015/0196917 A1 | 7/2015 | Kay et al. |
| 2015/0203839 A1 | 7/2015 | Jacobson et al. |
| 2015/0211047 A1 | 7/2015 | Borns |
| 2015/0225782 A1 | 8/2015 | Walder et al. |
| 2015/0240232 A1 | 8/2015 | Zamore et al. |
| 2015/0240280 A1 | 8/2015 | Gibson et al. |
| 2015/0261664 A1 | 9/2015 | Goldman et al. |
| 2015/0269313 A1 | 9/2015 | Church |
| 2015/0293102 A1 | 10/2015 | Shim |
| 2015/0307875 A1 | 10/2015 | Happe et al. |
| 2015/0321191 A1 | 11/2015 | Kendall et al. |
| 2015/0322504 A1 | 11/2015 | Lao et al. |
| 2015/0344927 A1 | 12/2015 | Sampson et al. |
| 2015/0353921 A9 | 12/2015 | Tian |
| 2015/0353994 A1 | 12/2015 | Myers et al. |
| 2015/0361420 A1 | 12/2015 | Hudson et al. |
| 2015/0361422 A1 | 12/2015 | Sampson et al. |
| 2015/0361423 A1 | 12/2015 | Sampson et al. |
| 2015/0368687 A1 | 12/2015 | Saaem et al. |
| 2015/0376602 A1 | 12/2015 | Jacobson et al. |
| 2016/0001247 A1 | 1/2016 | Oleinikov |
| 2016/0002621 A1 | 1/2016 | Nelson et al. |
| 2016/0002622 A1 | 1/2016 | Nelson et al. |
| 2016/0010045 A1 | 1/2016 | Cohen et al. |
| 2016/0017394 A1 | 1/2016 | Liang et al. |
| 2016/0017425 A1 | 1/2016 | Ruvolo et al. |
| 2016/0019341 A1 | 1/2016 | Harris et al. |
| 2016/0024138 A1 | 1/2016 | Gebeyehu et al. |
| 2016/0024576 A1 | 1/2016 | Chee |
| 2016/0026753 A1 | 1/2016 | Krishnaswami et al. |
| 2016/0026758 A1 | 1/2016 | Jabara et al. |
| 2016/0032396 A1 | 2/2016 | Diehn et al. |
| 2016/0046973 A1 | 2/2016 | Efcavitch et al. |
| 2016/0046974 A1 | 2/2016 | Efcavitch et al. |
| 2016/0082472 A1 | 3/2016 | Perego et al. |
| 2016/0089651 A1 | 3/2016 | Banyai |
| 2016/0090422 A1 | 3/2016 | Reif et al. |
| 2016/0090592 A1 | 3/2016 | Banyai et al. |
| 2016/0096160 A1 | 4/2016 | Banyai et al. |
| 2016/0097051 A1 | 4/2016 | Jacobson et al. |
| 2016/0102322 A1 | 4/2016 | Ravinder et al. |
| 2016/0108466 A1 | 4/2016 | Nazarenko et al. |
| 2016/0122755 A1 | 5/2016 | Hall et al. |
| 2016/0122800 A1 | 5/2016 | Bernick et al. |
| 2016/0152972 A1 | 6/2016 | Stapleton et al. |
| 2016/0168611 A1 | 6/2016 | Efcavitch et al. |
| 2016/0184788 A1 | 6/2016 | Hall et al. |
| 2016/0200759 A1 | 7/2016 | Srivastava et al. |
| 2016/0215283 A1 | 7/2016 | Braman et al. |
| 2016/0229884 A1 | 8/2016 | Indermuhle et al. |
| 2016/0230175 A1 | 8/2016 | Carstens |
| 2016/0230221 A1 | 8/2016 | Bergmann et al. |
| 2016/0251651 A1 | 9/2016 | Banyai et al. |
| 2016/0253890 A1 | 9/2016 | Rabinowitz et al. |
| 2016/0256846 A1 | 9/2016 | Smith et al. |
| 2016/0264958 A1 | 9/2016 | Toro et al. |
| 2016/0289758 A1 | 10/2016 | Akeson et al. |
| 2016/0289839 A1 | 10/2016 | Harumoto et al. |
| 2016/0303535 A1 | 10/2016 | Banyai et al. |
| 2016/0304862 A1 | 10/2016 | Igawa et al. |
| 2016/0304946 A1 | 10/2016 | Betts et al. |
| 2016/0310426 A1 | 10/2016 | Wu |
| 2016/0310927 A1 | 10/2016 | Banyai et al. |
| 2016/0318016 A1 | 11/2016 | Hou et al. |
| 2016/0333340 A1 | 11/2016 | Wu |
| 2016/0339409 A1 | 11/2016 | Banyai et al. |
| 2016/0340672 A1 | 11/2016 | Banyai et al. |
| 2016/0348098 A1 | 12/2016 | Stuelpnagel et al. |
| 2016/0354752 A1 | 12/2016 | Banyai et al. |
| 2016/0355880 A1 | 12/2016 | Gormley et al. |
| 2017/0017436 A1 | 1/2017 | Church |
| 2017/0066844 A1 | 3/2017 | Glanville |
| 2017/0067099 A1 | 3/2017 | Zheng et al. |
| 2017/0073664 A1 | 3/2017 | McCafferty et al. |
| 2017/0073731 A1 | 3/2017 | Zheng et al. |
| 2017/0081660 A1 | 3/2017 | Cox et al. |
| 2017/0081716 A1 | 3/2017 | Peck |
| 2017/0088887 A1 | 3/2017 | Makarov et al. |
| 2017/0095785 A1 | 4/2017 | Banyai et al. |
| 2017/0096706 A1 | 4/2017 | Behlke et al. |
| 2017/0114404 A1 | 4/2017 | Behlke et al. |
| 2017/0141793 A1 | 5/2017 | Strauss et al. |
| 2017/0147748 A1 | 5/2017 | Staehler et al. |
| 2017/0151546 A1 | 6/2017 | Peck et al. |
| 2017/0159044 A1 | 6/2017 | Toro et al. |
| 2017/0175110 A1 | 6/2017 | Jacobson et al. |
| 2017/0218537 A1 | 8/2017 | Olivares |

(56) References Cited

U.S. PATENT DOCUMENTS

| | | |
|---|---|---|
| 2017/0233764 A1 | 8/2017 | Young et al. |
| 2017/0247473 A1 | 8/2017 | Short |
| 2017/0249345 A1 | 8/2017 | Malik et al. |
| 2017/0253644 A1 | 9/2017 | Steyaert et al. |
| 2017/0298432 A1 | 10/2017 | Holt |
| 2017/0320061 A1 | 11/2017 | Venter et al. |
| 2017/0327819 A1 | 11/2017 | Banyai et al. |
| 2017/0355984 A1 | 12/2017 | Evans et al. |
| 2017/0357752 A1 | 12/2017 | Diggans |
| 2017/0362589 A1 | 12/2017 | Banyai et al. |
| 2018/0029001 A1 | 2/2018 | Banyai et al. |
| 2018/0051278 A1 | 2/2018 | Cox et al. |
| 2018/0051280 A1 | 2/2018 | Gibson et al. |
| 2018/0068060 A1 | 3/2018 | Ceze et al. |
| 2018/0104664 A1 | 4/2018 | Fernandez |
| 2018/0126355 A1 | 5/2018 | Peck et al. |
| 2018/0142289 A1 | 5/2018 | Zeitoun et al. |
| 2018/0171509 A1 | 6/2018 | Cox |
| 2018/0236425 A1 | 8/2018 | Banyai et al. |
| 2018/0253563 A1 | 9/2018 | Peck et al. |
| 2018/0264428 A1 | 9/2018 | Banyai et al. |
| 2018/0273936 A1 | 9/2018 | Cox et al. |
| 2018/0282721 A1 | 10/2018 | Cox et al. |
| 2018/0291445 A1 | 10/2018 | Betts et al. |
| 2018/0312834 A1 | 11/2018 | Cox et al. |
| 2018/0326388 A1 | 11/2018 | Banyai et al. |
| 2018/0334712 A1 | 11/2018 | Singer et al. |
| 2018/0346585 A1 | 12/2018 | Zhang et al. |
| 2018/0355351 A1 | 12/2018 | Nugent et al. |
| 2019/0060345 A1 | 2/2019 | Harrison et al. |
| 2019/0083596 A1 | 3/2019 | Orentas et al. |
| 2019/0118154 A1 | 4/2019 | Marsh et al. |
| 2019/0135926 A1 | 5/2019 | Glanville |
| 2019/0224711 A1 | 7/2019 | Demeris, Jr. |
| 2019/0240636 A1 | 8/2019 | Peck et al. |
| 2019/0244109 A1 | 8/2019 | Bramlett et al. |
| 2019/0314783 A1 | 10/2019 | Banyai et al. |
| 2019/0318132 A1 | 10/2019 | Peck |
| 2019/0352635 A1 | 11/2019 | Toro et al. |
| 2019/0366293 A1 | 12/2019 | Banyai et al. |
| 2019/0366294 A1 | 12/2019 | Banyai et al. |
| 2020/0017907 A1 | 1/2020 | Zeitoun et al. |
| 2020/0102611 A1 | 4/2020 | Zeitoun et al. |
| 2020/0156037 A1 | 5/2020 | Banyai et al. |
| 2020/0181667 A1 | 6/2020 | Wu et al. |
| 2020/0222875 A1 | 7/2020 | Peck et al. |
| 2020/0299322 A1 | 9/2020 | Indermuhle et al. |
| 2020/0299684 A1 | 9/2020 | Toro et al. |
| 2020/0308575 A1 | 10/2020 | Sato |
| 2020/0325235 A1 | 10/2020 | Tabibiazar et al. |
| 2020/0342143 A1 | 10/2020 | Peck |
| 2021/0002710 A1 | 1/2021 | Gantt et al. |
| 2021/0040476 A1 | 2/2021 | Cox et al. |
| 2021/0071168 A1 | 3/2021 | Nugent et al. |
| 2021/0102192 A1 | 4/2021 | Tabibiazar et al. |
| 2021/0102195 A1 | 4/2021 | Sato et al. |
| 2021/0102198 A1 | 4/2021 | Cox et al. |
| 2021/0115594 A1 | 4/2021 | Cox et al. |
| 2021/0129108 A1 | 5/2021 | Marsh et al. |
| 2021/0142182 A1 | 5/2021 | Bramlett et al. |
| 2021/0147830 A1 | 5/2021 | Liss |
| 2021/0170356 A1 | 6/2021 | Peck et al. |
| 2021/0179724 A1 | 6/2021 | Sato et al. |
| 2021/0207197 A1 | 7/2021 | Gantt et al. |
| 2021/0332078 A1 | 10/2021 | Wu |
| 2021/0348220 A1 | 11/2021 | Zeitoun et al. |
| 2021/0355194 A1 | 11/2021 | Sato et al. |

FOREIGN PATENT DOCUMENTS

| | | |
|---|---|---|
| CN | 1771336 A | 5/2006 |
| CN | 101277758 A | 10/2008 |
| CN | 102159726 A | 8/2011 |
| CN | 103907117 A | 7/2014 |
| CN | 104520864 A | 4/2015 |
| CN | 104562213 A | 4/2015 |
| CN | 104734848 A | 6/2015 |
| CN | 105637097 A | 6/2016 |
| DE | 10260805 A1 | 7/2004 |
| EP | 0090789 A1 | 10/1983 |
| EP | 0126621 B1 | 8/1990 |
| EP | 0753057 A1 | 1/1997 |
| EP | 1314783 A1 | 5/2003 |
| EP | 1363125 A2 | 11/2003 |
| EP | 1546387 A2 | 6/2005 |
| EP | 1153127 B1 | 7/2006 |
| EP | 1728860 A1 | 12/2006 |
| EP | 1072010 B1 | 4/2010 |
| EP | 2175021 A2 | 4/2010 |
| EP | 2330216 A1 | 6/2011 |
| EP | 1343802 B1 | 5/2012 |
| EP | 2504449 A1 | 10/2012 |
| EP | 2751729 A1 | 7/2014 |
| EP | 2872629 A1 | 5/2015 |
| EP | 2928500 A1 | 10/2015 |
| EP | 2971034 A1 | 1/2016 |
| EP | 3030682 A2 | 6/2016 |
| EP | 3044228 A4 | 4/2017 |
| EP | 2994509 B1 | 6/2017 |
| EP | 3204518 A1 | 8/2017 |
| JP | H07505530 A | 6/1995 |
| JP | 2001518086 A | 10/2001 |
| JP | 2002511276 A | 4/2002 |
| JP | 2002536977 A | 11/2002 |
| JP | 2002538790 A | 11/2002 |
| JP | 2006503586 A | 2/2006 |
| JP | 2006238724 A | 9/2006 |
| JP | 2008505642 A | 2/2008 |
| JP | 2008097189 A | 4/2008 |
| JP | 2008523786 A | 7/2008 |
| JP | 2008214343 A | 9/2008 |
| JP | 2009294195 A | 12/2009 |
| JP | 2016527313 A | 9/2016 |
| WO | WO-9015070 A1 | 12/1990 |
| WO | WO-9210092 A1 | 6/1992 |
| WO | WO-9210588 A1 | 6/1992 |
| WO | WO-9309668 A1 | 5/1993 |
| WO | WO-9320242 A1 | 10/1993 |
| WO | WO-9525116 A1 | 9/1995 |
| WO | WO-9526397 A1 | 10/1995 |
| WO | WO-9615861 A1 | 5/1996 |
| WO | WO-9710365 A1 | 3/1997 |
| WO | WO-9822541 A2 | 5/1998 |
| WO | WO-9841531 A2 | 9/1998 |
| WO | WO-9942813 A1 | 8/1999 |
| WO | WO-9953101 A1 | 10/1999 |
| WO | WO-0013017 A2 | 3/2000 |
| WO | WO-0018957 A1 | 4/2000 |
| WO | WO-0042559 A1 | 7/2000 |
| WO | WO-0042560 A2 | 7/2000 |
| WO | WO-0042561 A2 | 7/2000 |
| WO | WO-0049142 A1 | 8/2000 |
| WO | WO-0053617 A1 | 9/2000 |
| WO | WO-0156216 A2 | 8/2001 |
| WO | WO-0210443 A1 | 2/2002 |
| WO | WO-0156216 A3 | 3/2002 |
| WO | WO-0220537 A2 | 3/2002 |
| WO | WO-0224597 A2 | 3/2002 |
| WO | WO-0227638 A1 | 4/2002 |
| WO | WO-0233669 A1 | 4/2002 |
| WO | WO-02072791 A2 | 9/2002 |
| WO | WO-03040410 A1 | 5/2003 |
| WO | WO-03046223 A1 | 6/2003 |
| WO | WO-03054232 A2 | 7/2003 |
| WO | WO-03060084 A2 | 7/2003 |
| WO | WO-03064026 A1 | 8/2003 |
| WO | WO-03064027 A2 | 8/2003 |
| WO | WO-03064699 A2 | 8/2003 |
| WO | WO-03065038 A2 | 8/2003 |
| WO | WO-03066212 A2 | 8/2003 |
| WO | WO-03089605 A2 | 10/2003 |
| WO | WO-03093504 A1 | 11/2003 |
| WO | WO-03100012 A2 | 12/2003 |
| WO | WO-2004024886 A2 | 3/2004 |

(56) References Cited

FOREIGN PATENT DOCUMENTS

| | | |
|---|---|---|
| WO | WO-2004029220 A2 | 4/2004 |
| WO | WO-2004029586 A1 | 4/2004 |
| WO | WO-2004031351 A2 | 4/2004 |
| WO | WO-2004031399 A2 | 4/2004 |
| WO | WO-2004059556 A2 | 7/2004 |
| WO | WO-03060084 A3 | 8/2004 |
| WO | WO-2005014850 A2 | 2/2005 |
| WO | WO-2005051970 A2 | 6/2005 |
| WO | WO-2005059096 A2 | 6/2005 |
| WO | WO-2005059097 A2 | 6/2005 |
| WO | WO-2005093092 A2 | 10/2005 |
| WO | WO-2006023144 | 3/2006 |
| WO | WO-2006044956 A1 | 4/2006 |
| WO | WO-2006076679 A1 | 7/2006 |
| WO | WO-2006116476 A1 | 11/2006 |
| WO | WO-2007073171 A2 | 6/2007 |
| WO | WO-2007109221 A2 | 9/2007 |
| WO | WO-2007118214 A2 | 10/2007 |
| WO | WO-2007120627 A2 | 10/2007 |
| WO | WO-2007137242 A2 | 11/2007 |
| WO | WO-2008003116 A2 | 1/2008 |
| WO | WO-2008006078 A2 | 1/2008 |
| WO | WO-2008027558 A2 | 3/2008 |
| WO | WO-2008045380 | 4/2008 |
| WO | WO-2008054543 A2 | 5/2008 |
| WO | WO-2008063134 A1 | 5/2008 |
| WO | WO-2008063135 A1 | 5/2008 |
| WO | WO-2008068280 A1 | 6/2008 |
| WO | WO-2008103474 A1 | 8/2008 |
| WO | WO-2008109176 A2 | 9/2008 |
| WO | WO-2009132876 A1 | 11/2009 |
| WO | WO-2010001251 A2 | 1/2010 |
| WO | WO-2010025310 A2 | 3/2010 |
| WO | WO-2010025566 A1 | 3/2010 |
| WO | WO-2010027512 A2 | 3/2010 |
| WO | WO-2010089412 A1 | 8/2010 |
| WO | WO-2010141249 A2 | 12/2010 |
| WO | WO-2010141433 A2 | 12/2010 |
| WO | WO-2011020529 A2 | 2/2011 |
| WO | WO-2010141433 A3 | 4/2011 |
| WO | WO-2011053957 A2 | 5/2011 |
| WO | WO-2011056644 A2 | 5/2011 |
| WO | WO-2011056872 A2 | 5/2011 |
| WO | WO-2011066185 A1 | 6/2011 |
| WO | WO-2011066186 A1 | 6/2011 |
| WO | WO-2011085075 A2 | 7/2011 |
| WO | WO-2011103468 A2 | 8/2011 |
| WO | WO-2011109031 A1 | 9/2011 |
| WO | WO-2011143556 A1 | 11/2011 |
| WO | WO-2011150168 A1 | 12/2011 |
| WO | WO-2011161413 A2 | 12/2011 |
| WO | WO-2012013913 A1 | 2/2012 |
| WO | WO-2012061832 A1 | 5/2012 |
| WO | WO-2012078312 A2 | 6/2012 |
| WO | WO-2012154201 A1 | 11/2012 |
| WO | WO-2012149171 A1 | 11/2012 |
| WO | WO-2013010062 A2 | 1/2013 |
| WO | WO-2013030827 A1 | 3/2013 |
| WO | WO-2013032850 A2 | 3/2013 |
| WO | WO-2013036668 A1 | 3/2013 |
| WO | WO-2013049227 A2 | 4/2013 |
| WO | WO-2013101896 A1 | 7/2013 |
| WO | WO-2013134881 A1 | 9/2013 |
| WO | WO-2013154770 A1 | 10/2013 |
| WO | WO-2013177220 A1 | 11/2013 |
| WO | WO-2013170168 A1 | 11/2013 |
| WO | WO-2014004393 A1 | 1/2014 |
| WO | WO-2014008447 A1 | 1/2014 |
| WO | WO-2014021938 A1 | 2/2014 |
| WO | WO-2014035693 A2 | 3/2014 |
| WO | WO-2014088693 A1 | 6/2014 |
| WO | WO-2014089160 A1 | 6/2014 |
| WO | WO-2014093330 A1 | 6/2014 |
| WO | WO-2014093694 A1 | 6/2014 |
| WO | WO-2014151117 A1 | 9/2014 |
| WO | WO-2014151696 A1 | 9/2014 |
| WO | WO-2014160004 A1 | 10/2014 |
| WO | WO-2014160059 A1 | 10/2014 |
| WO | WO-2014206304 A1 | 12/2014 |
| WO | WO-2015017527 A2 | 2/2015 |
| WO | WO-2015021080 A2 | 2/2015 |
| WO | WO-2015021280 A1 | 2/2015 |
| WO | WO-2015031689 A1 | 3/2015 |
| WO | WO-2015040075 A1 | 3/2015 |
| WO | WO-2015054292 A1 | 4/2015 |
| WO | WO-2015066174 A1 | 5/2015 |
| WO | WO-2015081114 A2 | 6/2015 |
| WO | WO-2015081142 A1 | 6/2015 |
| WO | WO-2015081440 A1 | 6/2015 |
| WO | WO-2015090879 A1 | 6/2015 |
| WO | WO-2015095404 A2 | 6/2015 |
| WO | WO-2015120403 A1 | 8/2015 |
| WO | WO-2015136072 A1 | 9/2015 |
| WO | WO-2015160004 A1 | 10/2015 |
| WO | WO-2015175832 A1 | 11/2015 |
| WO | WO-2016007604 A1 | 1/2016 |
| WO | WO-2016011080 A2 | 1/2016 |
| WO | WO-2016022557 A1 | 2/2016 |
| WO | WO-2016053883 A1 | 4/2016 |
| WO | WO-2016055956 A1 | 4/2016 |
| WO | WO-2016065056 A1 | 4/2016 |
| WO | WO-2016126882 A1 | 8/2016 |
| WO | WO-2016126987 A1 | 8/2016 |
| WO | WO-2016130868 A2 | 8/2016 |
| WO | WO-2016161244 A2 | 10/2016 |
| WO | WO-2016162127 A1 | 10/2016 |
| WO | WO-2016164779 A1 | 10/2016 |
| WO | WO-2016172377 A1 | 10/2016 |
| WO | WO-2016173719 A1 | 11/2016 |
| WO | WO-2016183100 A1 | 11/2016 |
| WO | WO-2017049231 A1 | 3/2017 |
| WO | WO-2017053450 A1 | 3/2017 |
| WO | WO-2017059399 A1 | 4/2017 |
| WO | WO-2017095958 A1 | 6/2017 |
| WO | WO-2017100441 A1 | 6/2017 |
| WO | WO-2017118761 A1 | 7/2017 |
| WO | WO-2017158103 A1 | 9/2017 |
| WO | WO-2017214574 A1 | 12/2017 |
| WO | WO-2018026920 A1 | 2/2018 |
| WO | WO-2018038772 A1 | 3/2018 |
| WO | WO-2018057526 A2 | 3/2018 |
| WO | WO-2018094263 A1 | 5/2018 |
| WO | WO-2018112426 A1 | 6/2018 |
| WO | WO-2018119246 A1 | 6/2018 |
| WO | WO-2018156792 A1 | 8/2018 |
| WO | WO-2018170164 A1 | 9/2018 |
| WO | WO-2018170169 A1 | 9/2018 |
| WO | WO-2018170559 A1 | 9/2018 |
| WO | WO-2018200380 A1 | 11/2018 |
| WO | WO-2018231872 A1 | 12/2018 |
| WO | WO-2019014781 A1 | 1/2019 |
| WO | WO-2019051501 A1 | 3/2019 |
| WO | WO-2019079769 A1 | 4/2019 |
| WO | WO-2019084500 A1 | 5/2019 |
| WO | WO-2019136175 A1 | 7/2019 |
| WO | WO-2019222706 A1 | 11/2019 |
| WO | WO-2020139871 A1 | 7/2020 |
| WO | WO-2020176362 A1 | 9/2020 |
| WO | WO-2020176678 A1 | 9/2020 |
| WO | WO-2020176680 A1 | 9/2020 |
| WO | WO-2020257612 A1 | 12/2020 |
| WO | WO-2021119193 A2 | 6/2021 |

OTHER PUBLICATIONS

Alberts et al.: Molecular Biology of the Cell. 4th edition. New York: Garland Science; 2002. The Generation of Antibody Diversity. https://www.ncbi.nlm.nih.gov/books/NBK26860/.

Alexeyev et al.: Gene synthesis, bacterial expression and purification of the Rickettsia prowazekii ATP/ADP translocase, Biochimica et Biophysics Acta, 1419:299-306, 1999.

Al-Housseiny et al.: Control of interfacial instabilities using flow geometry Nature Physics, 8:747-750, 2012.

(56) References Cited

OTHER PUBLICATIONS

Almagro et al.: Progress and Challenges in the Design and Clinical Development of Antibodies for Cancer Therapy. Frontiers in immunology; 8, 1751 (2018) doi:10.3389/fimmu.2017.01751 https://www.frontiersin.org/articles/10.3389/fimmu.2017.01751/full.

Amblard et al.: A magnetic manipulator for studying local rheology and micromechanical properties of biological systems, Rev. Sci. Instrum., 67(3):18-827, 1996.

Andoni and Indyk. Near-Optimal Hashing Algorithms for Approximate Nearest Neighbor in High Dimensions, Communications of the ACM, 51(1):117-122, 2008.

Arand et al.: Structure of Rhodococcus erythropolis limonene-1,2-epoxide hydrolase reveals a novel active site. EMBO J. 22:2583-2592 (2003).

Arkles et al.: The Role of Polarity in the Structure of Silanes Employed in Surface Modification. Silanes and Other Coupling Agents. 5:51-64, 2009.

Arkles. Hydrophobicity, Hydrophilicity Reprinted with permission from the Oct. 2006 issue of Paint & Coatings Industry magazine, Retrieved on Mar. 19, 2016, 10 pages.

Assembly manual for the POSaM: The ISB Piezoelelctric Oligonucleotide Synthesizer and Microarrayer, The Institute for Systems Biology, May 28, 2004 (50 pages).

Assi et al.: Massive-parallel adhesion and reactivity—measurements using simple and inexpensive magnetic tweezers. J. Appl. Phys. 92(9):5584-5586 (2002).

ATDBio. Nucleic Acid Structure, Nucleic Acids Book, 9 pages, published on Jan. 22, 2005. from: http://www.atdbio.com/content/5/Nucleic-acid-structure.

ATDBio. Solid-Phase Oligonucleotide Synthesis, Nucleic Acids Book, 20 pages, Published on Jul. 31, 2011. from: http://www.atdbio.com/content/17/Solid-phase-oligonucleotide-synthesis.

Au et al.: Gene synthesis by a LCR-based approach: high level production of Leptin-L54 using synthetic gene in *Escherichia coli*. Biochemical and Biophysical Research Communications 248:200-203 (1998).

Baedeker et al.: Overexpression of a designed 2.2kb gene of eukaryotic phenylalanine ammonialyase in *Escherichia coli*. FEBS Letters, 457:57-60, 1999.

Barbee et al.: Magnetic Assembly of High-Density DNA Arrays for Genomic Analyses. Anal Chem. 80(6):2149-2154, 2008.

Barton et al.: A desk electrohydrodynamic jet printing system. Mechatronics, 20:611-616, 2010.

Beaucage et al.: Advances in the synthesis of oligonucleotides by the phosphoramidite approach. Tetrahedron. 48:2223-2311, 1992.

Beaucage et al.: Deoxynucleoside phosphoramidites—A new class of key intermediates for deoxypolynucleotide synthesis. Tetrahedron Lett. 22(20):1859-1862, 1981.

Beaucage et al.: The Chemical synthesis of DNA/RNA Chapter 2 in: Encyclopedia of Cell Biology, 1:36-53, 2016.

Beaulieu et al.: PCR candidate region mismatch scanning adaptation to quantitative, high-throughput genotyping, Nucleic Acids Research, 29(5): 1114-1124, 2001.

Beigelman et al.: Base-modified phosphoramidite analogs of pyrimidine ribonucleosides for RNA structure-activity studies. Methods Enzymol. 317:39-65, 2000.

Bethge et al.: Reverse synthesis and 3'-modification of RNA. Jan. 1, 2011, pp. 64-64, XP055353420. Retrieved from the Internet: URL:http://www.is3na.org/assets/events/Category%202-Medicinal %20Chemistry%20of%20Oligonucleotides%20%2864-108%29.pdf.

Binkowski et al.: Correcting errors in synthetic DNA through consensus shuffling. Nucleic Acids Research, 33(6):e55, 8 pages, 2005.

Biswas et al.: Identification and characterization of a thermostable MutS homolog from Thennus aquaticus, The Journal of Biological Chemistry, 271(9):5040-5048, 1996.

Biswas et al.: Interaction of MutS protein with the major and minor grooves of a heteroduplex DNA, The Journal of Biological Chemistry, 272(20):1 3355-13364, 1997.

Bjornson et al.: Differential and simultaneous adenosine Di- and Triphosphate binding by MutS, The Journal of Biological Chemistry, 278(20):18557-18562, 2003.

Blanchard et al.: High-Density Oligonucleotide Arrays, Biosensors & Bioelectronics, 11(6/7):687-690, 1996.

Blanchard: Genetic Engineering, Principles and Methods, vol. 20, Ed. J. Sedlow, New York: Plenum Press, p. 111-124, 1979.

Blawat et al.: Forward error correction for DNA data storage. Procedia Computer Science, 80:1011-1022, 2016.

Bonini and Mondino, Adoptive T-cell therapy for cancer: The era of engineered T cells. European Journal of Immunology, 45:2457-2469, 2015.

Bornholt et al.: A DNA-Based Archival Storage System, in International Conference on Architectural Support for Programming Languages and Operating Systems (ASPLOS), Apr. 2-6, 2016, Atlanta, GA, 2016, 637-649.

Borovkov et al.: High-quality gene assembly directly from unpurified mixtures of microassay-synthesized oligonucleotides. Nucleic Acid Research, 38(19):e180, 10 pages, 2010.

Brunet: Aims and methods of biosteganography. Journal of Biotechnology, 226:56-64, 2016.

Buermans et al.: Next Generation sequencing technology: Advances and applications, Biochimica et Biophysica Acta (BBA)—Molecular Basis of Disease, 1842:1931-1941, 2014.

Butler et al.: In situ synthesis of oligonucleotide arrays by using surface tension. J Am Chem Soc. 123(37):8887-94, 2001.

Calvert. Lithographically patterned self-assembled films. In: Organic Thin Films and Surfaces: Directions for The Nineties, vol. 20, p. 109, ed. By Abraham Ulman, San Diego: Academic Press, 1995.

Cardelli. Two-Domain DNA Strand Displacement, Electron. Proc. Theor. Comput. Sci., 26:47-61, 2010.

Carlson. Time for New DNA Synthesis and Sequencing Cost Curves, 2014. [Online], Available: http://www.synthesis.cc/synthesis/2014/02/time_for_new_cost_curves_2014. 10 pages.

Carr et al.: Protein-mediated error correction for de novo DNA synthesis. Nucleic Acids Res. 32(20):e162, 9 pages, 2004.

Carter and Friedman. DNA synthesis and Biosecurity: Lessons learned and options for the future. J. Craig Venter Institute, La Jolla, CA, 28 pages, Oct. 2015.

Caruthers. Chemical synthesis of deoxyoligonucleotides by the phosphoramidite method. In Methods in Enzymology, Chapter 15, 154:287-313, 1987.

Caruthers, The Chemical Synthesis of DNA/RNA: Our Gift to Science. J. Biol. Chem., 288(2):1420-1427, 2013.

Caruthers. Gene synthesis machines: DNA chemistry and its uses. Science 230(4723):281-285 (1985).

Casmiro et al.: PCR-based gene synthesis and protein NMR spectroscopy, Structure, 5(11):1407-1412, 1997.

CeGaT. Tech Note available at https://www.cegat.de/web/wp-content/uploads/2018/06/Twist-Exome-Tech-Note.pdf (4 pgs.) (2018).

Cello et al.: Chemical synthesis of poliovirus cDNA: generation of infectious virus in the absence of natural template. Science. 297(5583):1016-8, 2000.

Chalmers et al.: Scaling up the ligase chain reaction-based approach to gene synthesis. Biotechniques. 30(2):249-52, 2001.

Chan et al.: Natural and engineered nicking endonucleases—from cleavage mechanism to engineering of strand-specificity. Nucleic Acids Res. 39(1):1-18, 2011.

Chen et al.: Programmable chemical controllers made from DNA, Nat. Nanotechnol., 8(10):755-762, 2013.

Chen et al.: Chemical modification of gene silencing oligonucleotides for drug discovery and development. Drug Discov Today. 10(8):587-93 2005.

Cheng et al.: High throughput parallel synthesis of oligonucleotides with 1536 channel synthesizer. Nucleic Acids Res. 30(18):e93, 2002.

Chilamakuri et al.: Performance comparison of four exome capture systems for deep sequencing. BMC Genomics 15(1):449 (2014).

Cho et al.: Capillary passive valve in microfluidic systems. NSTI-Nanotech. 2004; 1:263-266.

Chrisey et al.: Fabrication of patterned DNA surfaces Nucleic Acids Research, 24(15):3040-3047 (1996).

(56) References Cited

OTHER PUBLICATIONS

Chung et al.: One-step preparation of competent Escherichia coli: Transformation and storage of bacterial cells in the same solution. Proc Natl Acad Sci USA. Apr. 1989;86(7):2172-2175.
Church et al.: Next-generation digital information storage in DNA. Science, 337:6102, 1628-1629, 2012.
Cleary et al.: Production of complex nucleic acid libraries using highly parallel in situ oligonucleotide synthesis. Nature Methods, 1(13):241-248, 2004.
Cohen et al.: Human population: The next half century. Science, 302:1172-1175, 2003.
CRICK. On protein synthesis. Symp Soc Exp Biol12:138-163,1958.
Cruse et al.: Atlas of Immunology, Third Edition. Boca Raton:CRC Press (pp. 282-283) (2010).
Cutler et al.: High-throughput variation detection and genotyping using microarrays, Genome Research, vol. 11, 1913-19 (2001).
Dahl et al.: Circle-to-circle amplification for precise and sensitive DNA analysis. Proc Natl Acad Sci U S A. Mar. 30, 2004;101(13):4548-53. Epub Mar. 15, 2004.
De Mesmaeker et al.: Backbone modifications in oligonucleotides and peptide nucleic acid systems. Curr Opin Struct Biol. Jun. 1995;5(3):343-55.
De Silva et al.: New Trends of Digital Data Storage in DNA. BioMed Res Int. 2016:8072463 (2016).
Deamer et al.: Characterization of nucleic acids by nanopore analysis, Ace. Cham. Res., vol. 35, No. 10, 817-825 (2002).
Deaven. The Human Genome Project: Recombinant clones for mapping and sequencing DNA. Los Alamos Science, 20:218-249, 1992.
Deng et al.: Targeted bisulfite sequencing reveals changes in DNA methylation associated with nuclear reprogramming Nature Biotechnology, 27:352-360 (2009).
Dietrich et al.: Gene assembly based on blunt-ended double-stranded DNA-modules, Biotechnology Techniques, vol. 12, No. 1, 49-54 (Jan. 1998).
Dillon et al.: Exome sequencing has higher diagnostic yield compared to simulated disease-specific panels in children with suspected monogenic disorders. Eur J Hum Genet 26(5):644-651 (2018).
Dormitzer et al.: Synthetic generation of influenza vaccine viruses for rapid response to pandemics. Sci Translational Medicine, 5(185):185ra68, 14 pages, 2013.
Doudna et al.: Genome editing. The new frontier of genome engineering with CRISPR-Cas9. Science 346(6213):1258096-1-1258096-9, 2014.
Douthwaite et al.: Affinity maturation of a novel antagonistic human monoclonal antibody with a long VH CDR3 targeting the Class A GPCR formyl-peptide receptor 1; mAbs, vol. 7, Iss. 1, pp. 152-166 (Jan. 1, 2015).
Dower et al.: High efficiency transformation of E.coli by high voltage electroporation. Nucleic Acids Res. 16(13):6127-45 (1988).
Dressman et al.: Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Drmanac et al.: Human genome sequencing using unchained base reads on self-assembling DNA nanoarrays. Science. Jan. 1, 2010;327(5961):78-81. doi: 10.1126/science.1181498. Epub Nov. 5, 2009.
Droege and Hill. The Genome Sequencer FLXTM System-Longer reads, more applications, straight forward bioinformatics and more complete data sets Journal of Biotechnology, 136:3-10, 2008.
Duffy et al.: Rapid Prototyping of Microfluidic Systems in Poly(dimethylsiloxane). Anal Chem. Dec. 1, 1998;70(23):4974-84. doi: 10.1021/ac980656z.
Duggan et al.: Expression profiling using cDNA microarrays. Nat Genet. Jan. 1999;21(1 Suppl):10-4.
Dvorsky. Living Bacteria Can Now Store Data. GIZMODO internet publication. Retrieved from https://gizmodo.com/living-bacteria-can-now-store-data-1781773517 (4 pgs) (Jun. 10, 2016).

Eadie et al.: Guanine modification during chemical DNA synthesis. Nucleic Acids Res. Oct. 26, 1987;15(20):8333-49.
Eisen: A phylogenomic study of the MutS family of proteins, Nucleic Acids Research, vol. 26, No. 18, 4291-4300 (1998).
Ellis et al.: DNA assembly for synthetic biology: from parts to pathways and beyond. Integr Biol (Camb). Feb. 2011;3(2):109-18. doi: 10.1039/c0ib00070a. Epub Jan. 19, 2011.
El-Sagheer et al.: Biocompatible artificial DNA linker that is read through by DNA polymerases and is functional in *Escherichia coli*. Proc Natl Acad Sci USA. Jul. 12, 2011;108(28):11338-43. doi: 10.1073/pnas.1101519108. Epub Jun. 27, 2011.
Elsik et al.: The Genome sequence of taurine cattle: A window of ruminant biology and evolution. Science, 324:522-528, 2009.
Elsner et al.: 172 nm excimer VUV-triggered photodegradation and micropatterning of aminosilane films, Thin Solid Films, 517:6772-6776 (2009).
Engler et al.: A one pot, one step, precision cloning method with high throughput capability. PLoS One. 2008;3(11):e3647. doi: 10.1371/journal.pone.0003647. Epub Nov. 5, 2008.
Engler et al.: Golden gate shuffling: a one-pot DNA shuffling method based on type IIs restriction enzymes. PLoS One. 2009;4(5):e5553. doi: 10.1371/journal.pone.0005553. Epub May 14, 2009.
Erlich and Zielinski. DNA fountain enables a robust and efficient storage architecture. Science, 355(6328):950-054, 2017.
Eroshenko et al.: Gene Assembly from Chip-Synthesized Oligonucleotides; Current Protocols in Chemical biology 4: 1-17 (2012).
European Patent Application No. 12827479.2 Extended European Search Report dated May 18, 2015.
European Patent Application No. 12827479.2 Partial European Search Report dated Jan. 29, 2015.
European Patent Application No. 14834665.3 Communication dated Jan. 16, 2018.
European Patent Application No. 14834665.3 extended European Search Report dated Apr. 28, 2017.
European Patent Application No. 14834665.3 Further Examination Report dated Nov. 28, 2018.
European Patent Application No. 14834665.3 Office Action dated May 2, 2018.
European Patent Application No. 16847497.1 Extended European Search Report dated Jan. 9, 2019.
European Patent Application No. 16871446.7 European Search Report dated Apr. 10, 2019.
European Patent Application No. 16871446.7 First Official Action dated Nov. 13, 2019.
European Patent Application No. 17844060.8 Extended Search Report dated Apr. 20, 2020.
Evans et al.: DNA Repair Enzymes. Current Protocols in Molecular Biology 84:III:3.9:3.9.1-3.9.12 http://www.ncbi.nlm.nih.gov/pubmed/18972391 (Published online Oct. 1, 2008 Abstract only provided).
Fahy et al.: Self-sustained sequence replication (3SR): an isothermal transcription-based amplification system alternative to PCR. PCR Methods Appl. Aug. 1991;1(1):25-33.
Fedoryak et al.: Brominated hydroxyquinoline as a photolabile protecting group with sensitivity to multiphoton excitation, Org. Lett., vol. 4, No. 2, 3419-3422 (2002).
Ferretti et al.: Total synthesis of a gene for bovine rhodopsin. PNAS, 83:599-603 (1986).
Finger et al.: The wonders of Flap Endonucleases: Structure, function, mechanism and regulation. Subcell Biochem., 62:301-326, 2012.
Fodor et al.: Light-directed, spatially addressable parallel chemical synthesis. Science. 251(4995):767-773 (1991).
Fogg et al.: Structural basis for uracil recognition by archaeal family B DNA polymerases. Nature Structural Biology, 9(12):922-927, 2002.
Foldesi et al.: The synthesis of deuterionucleosides. Nucleosides Nucleotides Nucleic Acids. Oct.-Dec. 2000;19(10-12):1615-56.
Frandsen et al.: Efficient four fragment cloning for the construction of vectors for targeted gene replacement in filamentous fungi. BMC Molecular Biology 2008, 9:70.
Frandsen. Experimental setup. Dec. 7, 2010, 3 pages. http://www.rasmusfrandsen.dk/experimental_setup.htm.

(56) References Cited

OTHER PUBLICATIONS

Frandsen. The USER Friendly technology. USER cloning. Oct. 7, 2010, 2 pages. http://www.rasmusfrandsen.dk/user_cloning.htm.
Fullwood et al.: Next-generation DNA sequencing of paired-end tags [PET] for transcriptome and genome analysis Genome Research, 19:521-532, 2009.
Galka et al.: QuickLib, a method for building fully synthetic plasmid libraries by seamless cloning of degenerate oligonucleotides. Plos One, 12, e0175146:1-9 (2017).
Galka et al.: QuickLib, a method for building fully synthetic plasmid libraries by seamless cloning of degenerate oligonucleotides. Plos One, 12, e0175146:S1 figure (2017).
Galka et al.: QuickLib, a method for building fully synthetic plasmid libraries by seamless cloning of degenerate oligonucleotides. Plos One, 12, e0175146:S1 Table (2017).
Galka et al.: QuickLib, a method for building fully synthetic plasmid libraries by seamless cloning of degenerate oligonucleotides. Plos One, 12, e0175146:S2 figure (2017).
Galneder et al.: Microelectrophoresis of a bilayer-coated silica bead in an optical trap: application to enzymology. Biophysical Journal, vol. 80, No. 5, 2298-2309 (May 2001).
Gao et al.: A method for the generation of combinatorial antibody libraries using pIX phage display. PNAS 99(20):12612-12616 (2002).
Gao et al.: A flexible light-directed DNA chip synthesis gated by deprotection using solution photogenerated acids. Nucleic Acids Res. Nov. 15, 2001;29(22):4744-50.
Gao et al.: Thermodynamically balanced inside-out (TBIO) PCR-based gene synthesis: a novel method of primer design for high-fidelity assembly of longer gene sequences. Nucleic Acids Res. Nov. 15, 2003;31(22):e143.
Garaj et al.: Graphene as a subnanometre trans-electrode membrane. Nature. Sep. 9, 2010;467(7312):190-3. doi: 10.1038/nature09379.
Garbow et al.: Optical tweezing electrophoresisof isolated, highly charged colloidal spheres, Colloids and Surfaces A: Physiochem. Eng. Aspects, vol. 195, 227-241 (2001).
GeneArt Seamless Cloning and Assembly Kits. Life Technologies Synthetic Biology. 8 pages, available online Jun. 15, 2012.
Genomics 101. An Introduction to the Genomic Workflow. 2016 edition, 64 pages. Available at: http://www.frontlinegenomics.com/magazine/6757/genomics-101/.
Geu-Flores et al.: USER fusion: a rapid and efficient method for simultaneous fusion and cloning of multiple PCR products. Nucleic Acids Res. 2007;35(7):e55. Epub Mar. 27, 2007.
Gibson Assembly. Product Listing. Application Overview. 2 pages, available online Dec. 16, 2014.
Gibson et al.: Creation of a Bacterial Cell Controlled by A Chemically Synthesized Genome. Science 329(5989):52-56 (2010).
Gibson et al.: Complete chemical synthesis, assembly, and cloning of a Mycoplasma genitalium genome. Science. Feb. 29, 2008;319(5867):1215-20. doi: 10.1126/science.1151721. Epub Jan. 24, 2008.
Goldfeder et al.: Medical implications of technical accuracy in genome sequencing. Genome Med 8(1):24 (2016).
Goldman et al.: Towards practical, high-capacity, low-maintenance information storage in synthesized DNA, Nature, 494(7435):77-80, 2013.
Gosse et al.: Magnetic tweezers: micromanipulation and force measurement at the molecular level, Biophysical Journal, vol. 8, 3314-3329 (Jun. 2002).
Grass et al.: Robust chemical preservation of digital information on DNA in silica with error-correcting codes, Angew. Chemie—Int. Ed., 54(8):2552-2555, 2015.
Greagg et al.: A read-ahead function in archaeal DNA polymerases detects promutagenic template-strand uracil. Proc. Nat. Acad. Sci. USA, 96:9045-9050, 1999.
Grovenor. Microelectronic materials. Graduate Student Series in Materials Science and Engineering. Bristol, England: Adam Hilger, 1989; p. 113-123.
Gu et al.: Depletion of abundant sequences by hybridization (DASH): using Cas9 to remove unwanted high-abundance species in sequencing libraries and molecular counting applications. Genome Biology, 17:41, 13 pages, 2016.
Haber et al.: Magnetic tweezers for DNA micromanipulation, Rev. Sci. Instrum., vol. 71, No. 12, 4561-4570 (Dec. 2000).
Han et al.: Linking T-cell receptor sequence to functional phenotype at the single-cell level. Nat Biotechnol 32(7):684-692 (2014).
Hanahan and Cold Spring Harbor Laboratory. Studies on transformation of Escherichia coli with plasmids J. Mol. Biol. 166:557-580 (1983).
Hanahan et al.: Plasmid transformation of Escherichia coli and other bacteria. Methods Enzymol, vol. 204, p. 63-113 (1991).
Harada et al.: Unexpected substrate specificity of T4 DNA ligase revealed by in vitro selection. Nucleic Acids Res. May 25, 1993; 21(10):2287-91.
Hauser et al.: Trends in GPCR drug discovery: new agents, targets and indications. Nature Reviews Drug Discovery, 16, 829-842 (2017). doi:10.1038/nrd.2017.178 https://www.nature.com/articles/nrd.2017.178.
Heckers et al.: Error analysis of chemically synthesized polynucleotides, BioTechniques, vol. 24, No. 2, 256-260 (1998).
Herzer et al.: Fabrication of patterned silane based self-assembled monolayers by photolithography and surface reactions on silicon-oxide substrates Chem. Commun., 46:5634-5652 (2010).
Hoover et al.: DNAWorks: an automated method for designing oligonucleotides for PCR-based gene synthesis, Nucleic Acids Research, vol. 30, No. 10, e43, 7 pages (2002).
Hosu et al.: Magnetic tweezers for intracellular applications•, Rev. Sci. Instrum., vol. 74, No. 9, 4158-4163 (Sep. 2003).
Hötzel et al.: A strategy for risk mitigation of antibodies with fast clearance. mAbs, 4(6), 753-760 (2012). doi:10.4161/mabs.22189 https://www.ncbi.nlm.nih.gov/pubmed/23778268.
Huang et al.: Three-dimensional cellular deformation analysis with a two-photon magnetic manipulator workstation, Biophysical Journal, vol. 8 2, No. 4, 2211-2223 (Apr. 2002).
Hughes et al.: Expression profiling using microarrays fabricated by an ink-jet oligonucleotide synthesizer Nat Biotech 4:342-347 (2001).
Hughes et al.: Principles of early drug discovery. Br J Pharmacol 162(2):1239-1249, 2011.
Hutchison et al.: Cell-free cloning using phi29 DNA polymerase. Proc Natl Acad Sci U S A. Nov. 29, 2005;102(48):17332-6. Epub Nov. 14, 2005.
Imgur: The magic of the internet. Uploaded May 10, 2012, 2 pages, retrieved from: https://imgur.com/mEWuW.
In-Fusion Cloning: Accuracy, Not Background. Cloning & Competent Cells, ClonTech Laboratories, 3 pages, available online Jul. 6, 2014.
International Application No. PCT/US2017/026232 International Preliminary Report on Patentability dated Feb. 26, 2019.
International Application No. PCT/US2017/045105 International Preliminary Report on Patentability dated Feb. 5, 2019.
International Application No. PCT/US2017/052305 International Preliminary Report on Patentability dated Apr. 30, 2019.
International Application No. PCT/US2017/062391 International Preliminary Report on Patentability dated May 21, 2019.
International Application No. PCT/US2018/019268 International Preliminary Report on Patentability dated Sep. 6, 2019.
International Application No. PCT/US2018/050511 International Search Report and Written Opinion dated Jan. 11, 2019.
International Application No. PCT/US2018/057857 International Search Report and Written Opinion dated Mar. 18, 2019.
International Application No. PCT/US2019/012218 International Search Report and Written Opinion dated Mar. 21, 2019.
International Application No. PCT/US2019/032992 International Search Report and Written Opinion dated Oct. 28, 2019.
International Application No. PCT/US2019/032992 Invitation to Pay Additional Fees dated Sep. 6, 2019.
Jackson et al.: Recognition of DNA base mismatches by a rhodium intercalator, J. Am. Chem. Soc., vol. 19, 12986-12987 (1997).
Jacobs et al.: DNAglycosylases: In DNA repairand beyond. Chromosoma 121:1-20 (2012)—http://www.ncbi.nlm.nih.gov/pmc/articles/PMC3260424/.

(56) References Cited

OTHER PUBLICATIONS

⁎ Acobus et al.: Optimal cloning of PCR fragments by homologous recombination in *Escherichia soli*. PLoS One 10(3):e0119221 (2015).
Jager et al.: Simultaneous Humoral and Cellular: Immune Response against Cancer—Testis Antigen NY-ES0-1: Definition of Human Histocompatibility Leukocyte Antigen (HLA)-A2-binding Peptide Epitopes. J. Exp. Med. 187(2):265-270 (1998).
Jinek et al.: A Programmable dual-RNA-guided DNA endonuclease in adaptive bacterial immunity. Science, 337:816-821, 2012.
Jo et al.: Engineering therapeutic antibodies targeting G-protein-coupled receptors; Experimental & Molecular Medicine; 48; 9 pages (2016).
Karagiannis and El-Osta. RNA interference and potential therapeutic applications of short interfering RNAs Cancer Gene Therapy, 12:787-795, 2005.
Ke et al.: Influence of neighboring base pairs on the stability of single base bulges and base pairs in a DNA fragment, Biochemistry, Vo. 34, 4593-4600 (1995).
Kelley et al.: Single-base mismatch detection based on charge transduction through DNA, Nucleic Acids Research, vol. 27, No. 24, 4830-4837 (1999).
Kim et al.: High-resolution patterns of quantum dots formed by electrohydrodynamic jet printing for light-emitting diodes. Nano Letters, 15:969-973, 2015.
Kim et al.: Site specific cleavage of DNA-RNA hybrids by zinc finger/Fok I cleavage domain fusions Gene, vol. 203, 43-49 (1997).
Kim et al.: Chimeric restriction endonuclease, Proc. Natl. Acad. Sci. USA, vol. 91, 883-887 (Feb. 1994).
Kim, The interaction between Z-ONA and the Zab domain of double-stranded RNA adenosine deaminase characterized using fusion nucleases, The Journal of Biological Chemistry, vol. 274, No. 27, 19081-19086 (1999).
Kinde et al.: Detection and quantification of rare mutations with massively parallel sequencing. Proc Natl Acad Sci U S A. Jun. 7, 2011;108(23):9530-5. Epub May 17, 2011.
Kodumal et al.: Total synthesis of long DNA sequences: synthesis of a contiguous 32-kb polyketide synthase gene cluster. Proc Natl Acad Sci U S A. Nov. 2, 2004;101(44):15573-8. Epub Oct. 20, 2004.
Koike-Yusa et al.: Genome-wide recessive genetic screening in mammalian cells with a lentiviral CRISPR-guide RNA library. Nature Biotechnology, 32:267-273, 2014 (with three pages of supplemental Online Methods).
Kong et al.: Parallel gene synthesis in a microfluidic device. Nucleic Acids Res., 35(8):e61 (2007).
Kong. Microfluidic Gene Synthesis. MIT Thesis. Submitted to the program in Media Arts and Sciences, School of Architecture and Planning, in partial fulfillment of the requirements for the degree of Doctor of Philosophy in Media Arts and Sciences at the Massachusetts Institute of Technology. 143 pages Jun. 2008.
Kopp et al.: Chemical amplification: continuous-flow PCR on a chip, Science, vol. 280, 1046-1048 (May 15, 1998).
Kosuri and Church. Large-scale de novo DNA synthesis: technologies and applications, Nature Methods, 11:499-507, 2014. Available at: http://www.nature.com/nmeth/journal/v11/n5/full/nmeth.2918.html.
Kosuri et al.: A scalable gene synthesis platform using high-fidelity DNA microchips Nat.Biotechnol., 28(12):1295-1299, 2010.
Krayden, Inc.: A Guide to Silane Solutions. Silane coupling agents. 7 pages. Published on May 31, 2005 at: http://krayden.com/pdf/xia_silane_chemistry.pdf.
Lagally et al.: Single-Molecule DNA Amplification and Analysis in an Integrated Microfluidic Device. Analytical Chemistry. 2001;73(3): 565-570.
Lahue et al., DNA mismatch correction in a defined system, Science, vol. 425; No. 4914, 160-164 (Jul. 14, 1989).
Lambrinakos, A. et al.: Reactivity of potassium permanganate and tetraethylammonium chloride with mismatched bases and a simple mutation detection protocol,Nucleic Acids Research, vol. 27, No. 8, 1866-1874 (1999).

Landegren et al.: A ligase-mediated gene detection technique. Science. Aug. 26, 1988;241(4869):1077-80.
Lang, Matthew J. et al.: An automated two-dimensional optical force clamp for single molecule studies, Biophysical Journal, vol. 83, 491-501 (Jul. 2002).
Lashkari et al.: An automated multiplex oligonucleotide synthesizer: development of high-throughput, low-cost DNA synthesis. Proc Natl Acad Sci U S A. Aug. 15, 1995;92(17):7912-5.
Lausted et al.: POSaM: a fast, flexible, open-source, inkjet oligonucleotide synthesizer and microarrayer, Genome Biology, 5:R58, 17 pages, 2004. available at https://www.ncbi.nlm.nih.gov/pmc/articles/PMC507883/.
Leamon et al.: A massively parallel PicoTiterPlate based platform for discrete picoliter-scale polymerase chain reactions. Electrophoresis. Nov. 2003;24(21):3769-77.
Lee et al.: Microelectromagnets for the control of magnetic nanoparticles, Appl. Phys. Lett., vol. 79, No. 20, 3308-3310 (Nov. 12, 2001).
Lee et al.: A microfluidic oligonucleotide synthesizer. Nucleic Acids Research 2010 vol. 38(8):2514-2521. DOI: 10.1093/nar/gkq092.
Lee: Covalent End-Immobilization of Oligonucleotides onto Solid Surfaces; Thesis, Massachusetts Institute of Technology, Aug. 2001 (315 pages).
Leproust et al.: Synthesis of high-quality libraries of long (150mer) oligonucleotides by a novel depurination controlled process, Nucleic Acids Research, 35(8):2522-2540, 2010.
Leproust et al.: Agilent's Microarray Platform: How High-Fidelity DNA Synthesis Maximizes the Dynamic Range of Gene Expression Measurements. 2008; 1-12. http://www.miltenyibiotec.eom/~/media/Files/Navigation/Genomic%20Services/Agilent_DNA_Microarray_Platform.ashx.
Lesnikowski et al.: Nucleic acids and nucleosides containing carboranes. J. Organometallic Chem. 1999; 581:156-169.
Leumann. DNA analogues: from supramolecular principles to biological properties. Bioorg Med Chem. Apr. 2002;10(4):841-54.
Levene et al.: Zero-mode waveguides for single-molecule analysis at high concentrations. Science. Jan. 31, 2003;299(5607):682-6.
Lewontin and Harti, Population genetics in forensic DNA typing. Science, 254:1745-1750, 1991.
Li et al.: Beating Bias in the Directed Evolution of Proteins: Combining High-Fidelity on-Chip Solid-Phase Gene Synthesis with Efficient Gene Assembly for Combinatorial Library Construction. ChemBioChem 19:221-228 (2018).
Li et al.: Beating bias in the directed evolution of proteins: Combining high-fidelity on-chip solid-phase gene synthesis with efficient gene assembly for combinatorial library construction. First published Nov. 24, 2017, 2 pages, retrieved from: https://doi.org/10.1002/cbic.201700540.
Light source unit for printable patterning VUV-Aligner/ USHIO Inc., Link here: https://www.ushio.co.jp/en/products/1005.html, published Apr. 25, 2016, printed from the internet on Aug. 2, 2016, 3 pages.
Limbachiya et al.: Natural data storage: A review on sending information from now to then via Nature. ACM Journal on Emerging Technologies in Computing Systems, V(N):Article A, May 19, 2015, 17 pages.
Link Technologies. Product Guide 2010. Nov. 27, 2009, 136 pages. XP055353191. Retrieved from the Internet: URL:http://www.linktech.co.uk/documents/517/517.pdf.
Lipshutz, Robert J. et al.: High density synthetic oligonucleotide arrays, Nature Genetics Supplement, vol. 21, 20-24 (Jan. 1999).
Lishanski, Alia et al.: Mutation detection by mismatch binding protein, MutS, in amplified DNA: application to the cystic fibrosis gene, Proc. Natl. Acad. Sci. USA, vol. 91, 2674-2678 (Mar. 1994).
Liu et al.: Comparison of Next-Generation Sequencing Systems. J Biomed Biotechnol 2012: 251364 (2012).
Liu et al.: Rational design of CXCR4 specific antibodies with elongated CDRs. JACS, 136:10557-10560, 2014.
Liu et al.: Enhanced Signals and Fast Nucleic Acid Hybridization By Microfluidic Chaotic Mixing. Angew. Chem. Int. Ed. 2006; 45:3618-3623.
Lizardi et al.: Mutation detection and single-molecule counting using isothermal rolling-circle amplification. Nat Genet. Jul. 1998;19(3):225-32.

(56) References Cited

OTHER PUBLICATIONS

Li et al.: Functional domains in Fok I restriction endonuclease, Proc. Natl. Acad. Sci. USA, 89:4275-4279, 1992.

Lu et al.: Methyl-directed repair of DNA base-pair mismatches in vitro, Proc. Natl. Acad. Sci. USA, 80:4639-4643, 1983.

Lund et al.: A validated system for ligation-free uracilexcision based assembly of expression vectors for mammalian cell engineering. DTU Systems of Biology. 2011. 1 page. http://www.lepublicsystemepco.com/files/modules/gestion_rubriques/REF-B036-Lund_Anne%20Mathilde.pdf.

Ma et al.: Versatile surface functionalization of cyclic olefin copolymer (COC) with sputtered SiO2 thin film for potential BioMEMS applications. Journal of Materials Chemistry, 11 pages, 2009.

Ma et al.: DNA synthesis, assembly and application in synthetic biology. Current Opinion in Chemical Biology. 16:260-267, 2012.

Mahato et al.: Modulation of gene expression by antisense and antigene oligodeoxynucleotides and small interfering RNA Expert Opin. Drug Delivery, 2(1):3-28, 2005.

Margulies et al.: Genome sequencing in open microfabricated high-density picolitre reactors. Nature. 437(7057):376-80, 2005.

Martinez-Torrecuadrada et al.: Targeting the Extracellular Domain of Fibroblast Growth Factor Receptor 3 with Human Single-Chain Fv Antibodies Inhibits Bladder Carcinoma Cell Line Proliferation; Clinical Cancer Research; vol. 11; pp. 6282-6290 (2005).

Matteucci et al.: Synthesis of deoxyoligonucleotides on a polymer support. J. Am. Chem. Soc. 103(11):3185-3191, 1981.

Matzas et al.: Next generation gene synthesis by targeted retrieval of bead-immobilized, sequence verified DNA clones from a high throughput pyrosequencing device. Nat. Biotechnol., 28(12):1291-1294, 2010.

Mazor et al.: Isolation of Full-Length IgG Antibodies from Combinatorial Libraries Expressed in *Escherichia coli*; Antony S. Dimitrov (ed.), Therapeutic Antibodies: Methods and Protocols, vol. 525, Chapter 11, pp. 217-239 (2009).

McBride & Caruthers. An investigation of several deoxynucleoside phosphoramidites useful for synthesizing deoxyoligonucleotides. Tetrahedron Lett. 24: 245-248, 1983.

McGall et al.: Light-directed synthesis of high-density oligonucleotide arrays using semiconductor photoresists. Proc Natl Acad Sci U S A. 93(24):13555-60, 1996.

McGall et al.: The Efficiency of Light-Directed Synthesis of DNA Arrays on Glass Substrates. J. Am. Chem. Soc. 119(22):5081-5090, 1997.

Mei et al.: Cell-free protein synthesis in microfluidic array devices Biotechnol. Prog., 23(6):1305-1311,2007.

Mendel-Hartvig. Padlock probes and rolling circle amplification. New possibilities for sensitive gene detection. Comprehensive Summaries of Uppsala Dissertations from the Faculty of Medicine 1175. Uppsala University. 2002, 39 pages, http://www.diva-portal.org/smash/get/diva2:161926/FULLTEXT01. pdf.

Meyers and Friedland, Knowledge-based simulation of genetic regulation in bacteriophage lambda. Nucl. Acids Research, 12(1):1-16, 1984.

Meynert et al.: Quantifying single nucleotide variant detection sensitivity in exome sequencing. BMC Bioinformatics 14:195 (2013).

Meynert et al.: Variant detection sensitivity and biases in whole genome and exome sequencing. BMC Bioinformatics 15:247 (2014).

Milo and Phillips. Numbers here reflect the No. of protein coding genes and excludes tRNA and non-coding RNA. Cell Biology by the Numbers, p. 286, 2015.

Mitra et al.: In situ localized amplification and contact replication of many individual DNA molecules. Nucleic Acids Res. 27(24):e34, 1999.

Morin et al.: Profiling the HeLa S3 transcriptome using randomly primed cDNA and massively parallel short-read sequencing. Biotechniques, 45:81-94, 2008.

Morris and Stauss. Optimizing T-cell receptor gene therapy for hematologic malignancies. Blood, 127(26):3305-3311, 2016.

Muller et al.: Protection and labelling of thymidine by a fluorescent photolabile group, Helvetica Chimica Acta, vol. 84, 3735-3741 (2001).

Mulligan. Commercial Gene Synthesis Technology PowerPoint presentation. BlueHeron® Biotechnology. Apr. 5, 2006 (48 pgs).

Nakatani et al.: Recognition of a single guanine bulge by 2-Acylamino-1,8-naphthyridine, J. Am. Chem. Soc., vol. 122, 2172-2177 (2000).

Neiman M.S.: Negentropy principle in information processing systems. Radiotekhnika, 1966, No. 11, p. 2-9.

Neiman M.S.: On the bases of the theory of information retrieval. Radiotekhnika, 1967, No. 5, p. 2-10.

Neiman M.S.: On the molecular memory systems and the directed mutations. Radiotekhnika, 1965, No. 6, pp. 1-8.

Neiman M.S.: On the relationships between the reliability, performance and degree of microminiaturization at the molecular-atomic level. Radiotekhnika, 1965, No. 1, pp. 1-9.

Neiman M.S.: Some fundamental issues of microminiaturization. Radiotekhnika, 1964, No. 1, pp. 3-12.

Nishikura. A short primer on RNAi: RNA-directed RNA polymerase acts as a key catalyst Cell, 107:415-418, 2001.

Nour-Eldin et al.: USER Cloning and USER Fusion: The Ideal Cloning Techniques for Small and Big Laboratories. Plant Secondary Metabolism Engineering. Methods in Molecular Biology vol. 643, 2010, pp. 185-200.

Ochman et al.: Genetic applications of an inverse polymerase chain reaction. Genetics. Nov. 1988;120(3):621-3.

Organick et al.: Random access in large-scale DNA data storage. Nature Biotechnology, Advance Online Publication, 8 pages, 2018.

Organick et al.: Scaling up DNA data storage and random access retrieval, bioRxiv, preprint first posted online Mar. 7, 2017, 14 pages.

Pan et al.: An approach for global scanning of single nucleotide variations. Proc Natl Acad Sci USA. Jul. 9, 2002;99(14):9346-51.

Pankiewicz. Fluorinated nucleosides. Carbohydr Res. Jul. 10, 2000;327(1-2):87-105.

Paul et al.: Acid binding and detritylation during oligonucleotide synthesis. Nucleic Acids Research. 15. pp. 3048-3052 (1996).

PCT/IL2012/000326 International Preliminary Report on Patentability dated Dec. 5, 2013.

PCT/IL2012/000326 International Search Report dated Jan. 29, 2013.

PCT/US2014/049834 International Preliminary Report on Patentability dated Feb. 18, 2016.

PCT/US2014/049834 International Search Report and Written Opinion dated Mar. 19, 2015.

PCT/US2014/049834, Invitation to Pay Additional Fees and, where applicable, protest fee, mailed Jan. 5, 2015.

PCT/US2015/043605 International Preliminary Report on Patentability dated Feb. 16, 2017.

PCT/US2015/043605 International Search Report and Written Opinion dated Jan. 6, 2016.

PCT/US2015/043605 Invitation To Pay Additional Fees dated Oct. 28, 2015.

PCT/US2016/016459 International Preliminary Report on Patentability dated Aug. 17, 2017.

PCT/US2016/016459 International Search Report and Written Opinion dated Apr. 13, 2016.

PCT/US2016/016636 International Preliminary Report on Patentability dated Aug. 17, 2017.

PCT/US2016/016636 International Search Report and Written Opinion dated May 2, 2016.

PCT/US2016/028699 International Preliminary Report on Patentability dated Nov. 2, 2017.

PCT/US2016/028699 International Search Report and Written Opinion dated Jul. 29, 2016.

PCT/US2016/031674 International Preliminary Report on Patentability dated Nov. 23, 2017.

PCT/US2016/031674 International Search Report and Written Opinion dated Aug. 11, 2016.

PCT/US2016/052336 International Preliminary Report on Patentability dated Mar. 29, 2018.

PCT/US2016/052336 International Search Report and Written Opinion dated Dec. 7, 2016.

(56) References Cited

OTHER PUBLICATIONS

PCT/US2016/052916 International Preliminary Report on Patentability dated Apr. 5, 2018.
PCT/US2016/052916 International Search Report and Written Opinion dated Dec. 30, 2016.
PCT/US2016/064270 International Preliminary Report on Patentability dated Jun. 14, 2018.
PCT/US2016/064270 International Search Report and Written Opinion dated Apr. 28, 2017.
PCT/US2017/026232 International Search Report and Written Opinion dated Aug. 28, 2017.
PCT/US2017/036868 International Search Report and Written Opinion dated Aug. 11, 2017.
PCT/US2017/045105 International Search Report and Written Opinion dated Oct. 20, 2017.
PCT/US2017/052305 International Search Report and Written Opinion dated Feb. 2, 2018.
PCT/US2017/062391 International Search Report and Written Opinion dated Mar. 28, 2018.
PCT/US2017/066847 International Search Report and Written Opinion dated May 4, 2018.
PCT/US2018/022487 International Search Report and Written Opinion dated Aug. 1, 2018.
PCT/US2018/022493 International Search Report and Written Opinion dated Aug. 1, 2018.
PCT/US2018/037152 International Preliminary Report on Patentability dated Dec. 26, 2019.
PCT/US2018/037152 International Search Report and Written Opinion dated Aug. 28, 2018.
PCT/US2018/037161 International Preliminary Report on Patentability dated Dec. 17, 2019.
PCT/US2018/037161 International Search Report and Written Opinion dated Oct. 22, 2018.
PCT/US2018/037161 Invitation to Pay Additional Fees dated Aug. 27, 2018.
PCT/US2018/050511 International Preliminary Report on Patentability dated Mar. 26, 2020.
PCT/US2018/056783 International Preliminary Report on Patentability dated Apr. 30, 2020.
PCT/US2018/056783 International Search Report and Written Opinion of the International Searching Authority dated Dec. 20, 2018.
PCT/US2018/057857 International Preliminary Report on Patentability dated Apr. 28, 2020.
PCT/US2018/19268 International Search Report and Written Opinion dated Jun. 26, 2018.
PCT/US2018/19268 Invitation to Pay Additional Fees and, where applicable, protest fee dated May 2, 2018.
PCT/US2018/22487 Invitation to Pay Additional Fees and, where applicable, protest fee dated May 31, 2018.
PCT/US2018/22493 Invitation to Pay Additional Fees and, where applicable, protest fee dated May 31, 2018.
PCT/US2019/068435 International Search Report and Written Opinion dated Apr. 23, 2020.
PCT/US2020/019986 Invitation to Pay Additional Fees dated Jun. 5, 2020.
PCT/US2020/019988 Invitation to Pay Additional Fees dated Jun. 8, 2020.
Pease et al.: Light-generated oligonucleotide arrays for rapid DNA sequence analysis. Proc Natl Acad Sci U S A. May 24, 1994;91(11):5022-6.
Peisajovich et al.: BBF RFC 28: A method for combinatorial multi-part assembly based on the type-IIs restriction enzyme aarI. Sep. 16, 2009, 7 pages.
Pellois et al.: Individually addressable parallel peptide synthesis on microchips, Nature Biotechnology, vol. 20 , 922-926 (Sep. 2002).
Petersen et al.: LNA: a versatile tool for therapeutics and genomics. Trends Biotechnol. Feb. 2003;21(2):74-81.
Pierce and Wangh. Linear-after-the-exponential polymerase chain reaction and allied technologies Real-time detection strategies for rapid, reliable diagnosis from single cells Methods Mol. Med. 132:65-85 (2007) (Abstract only).
Pierce et al.: Linear-after-the-exponential polymerase chain reaction and allied technologies. Real-time detection strategies for rapid, reliable diagnosis from single cells. Methods Mol Med. 2007;132:65-85.
Pirrung. How to make a DNA chip. Angew. Chem. Int. Ed., 41:1276-1289, 2002.
Plesa et al.: Multiplexed gene synthesis in emulsions for exploring protein functional landscapes. Science, 10.1126/science.aao5167, 10 pages, 2018.
Pon. Solid-phase supports for oligonucleotide synthesis. Methods Mol Biol. 1993;20:465-96.
Poster. Reimagine Genome Scale Research. 2016, 1 page. Available at http://www2.twistbioscience.com/Oligo_Pools_CRISPR_poster.
Powers et al.: Optimal strategies for the chemical and enzymatic synthesis of bihelical deoxyribonucleic acids. J Am Chem Soc., 97(4):875-884, 1975.
Pray. Discovery of DNA Structure and Function: Watson and Crick, Nature Education, 2008, 6 pages, available at: http://www.nature.com/scitable/topicpage/discovery-of-dna-structure-and-function-watson-397.
Prodromou et al.: Recursive PCR: a novel technique for total gene synthesis. Protein Eng. Dec. 1992;5(8):827-9.
PubChem Data Sheet Acetonitrile. Printed from website https://pubchem.ncbi.nlm.nig.gov/ pp. 1-124 (2020).
PubChem Data Sheet Methylene Chloride. Printed from website https://pubchem.ncbi.nlm.nih.gov/ pp. 1-140 (2020).
Puigbo. Optimizer: a web server for optimizing the codon usage of DNA sequences. Nucleic Acid Research, 35(14):126-131, 2007.
Qian and Winfree. Scaling up digital circuit computation with DNA strand displacement cascades. Science, 332(6034):196-1201, 2011.
Qian, et al.: Neural network computation with DNA strand displacement cascades, Nature, 475(7356):368-372, 2011.
Quan et al.: Parallel on-chip gene synthesis and application to optimization of protein expression, Nature Biotechnology, 29(5):449-452, 2011.
Rafalski and Morgante. Corn and humans: recombination and linkage disequilibrium in two genomes of similar size. Trends in Genetics, 20(2):103-111, 2004.
Raje and Murma, A Review of electrohydrodynamic-inkjet printing technology. International Journal of Emerging Technology and Advanced Engineering, 4(5):174-183, 2014.
Rajpal et al.: A general method for greatly improving the affinity of antibodies by using combinatorial libraries. Proc. Natl. Acad. Sci. 102(24):8466-8471 (2005).
Rastegari et al.: XNOR-Net: ImageNet Classification Using Binary Convolutional Neural Networks, in ECCV 2016, Part IV, LNCS 9908, p. 525-542, 2016.
Reimagine SequenceSpace, Reimagine Research, Twist Bioscience, Product Brochure, Published Apr. 6, 2016 online at: www2.twistbioscience.com/TB_Product_Brochure_04.2016, 8 pages.
RF Electric discharge type excimer lamp. Products Catalog. Excimer lamp light source flat excimer, 16 pages dated Jan. 2016. From: http://www.hamamatsu.com/jp/en/product/category/1001/3026/index.html.
Richmond et al.: Amplification and assembly of chip-eluted DNA (AACED): a method for high-throughput gene synthesis. Nucleic Acids Res. Sep. 24, 2004;32(17):5011-8. Print 2004.
Roche. Restriction Enzymes from Roche Applied Science—A Tradition of Premium Quality and Scientific Support. FAQS and Ordering Guide. Roche Applied Science. Accessed Jan. 12, 2015, 37 pages.
Rogozin et al.: Origin and evolution of spliceosomal introns. Biology Direct, 7:11, 2012.
Ruminy et al.: Long-range identification of hepatocyte nuclear factor-3 (FoxA) high and low-affinity binding Sites with a chimeric nuclease, J. Mol. Bioi., vol. 310, 523-535 (2001).
Saaem et al.: In situ synthesis of DNA microarray on functionalized cyclic olefin copolymer substrate ACS Applied Materials & Interfaces, 2(2):491-497, 2010.

(56) References Cited

OTHER PUBLICATIONS

Saboulard et al.: High-throughput site-directed mutagenesis using oligonucleotides synthesized on DNA chips. Biotechniques. Sep. 2005;39(3):363-8.
Sacconi et al.: Three-dimensional magneto-optic trap for microobject manipulation, Optics Letters, vol. 26, No. 17, 1359-1361 (Sep. 1, 2001).
Saiki et al.: Analysis of enzymatically amplified beta-globin and HLA-DQ alpha DNA with allele-specific oligonucleotide probes. Nature 324:163-166 (1986).
Sandhu et al.: Dual asymmetric PCR: one-step construction of synthetic genes. Biotechniques. Jan. 1992;12(1):14-6.
Sargolzaei et al.: Extent of linkage disequilibrium in Holstein cattle in North America. J.Dairy Science, 91:2106-2117, 2007.
Schaller et al.: Studies on Polynucleotides. XXV.1 The Stepwise Synthesis of Specific Deoxyribopolynucleotides (5). Further Studies on the Synthesis of Internucleotide Bond by the Carbodiimide Method. The Synthesis of Suitably Protected Dinucleotides as Intermediates in the Synthesis of Higher Oligonucleotides. J. Am. Chem. Soc. 1963; 85(23):3828-3835.
Schmalzing et al.: Microchip electrophoresis: a method for highspeed SNP detection. Nucleic Acids Res 28(9):E43 (2000).
Schmitt et al.: New strategies in engineering T-cell receptor genemodified T cells to more effectively target malignancies. Clinical Cancer Research, 21(23):5191-5197, 2015.
Seelig et al.: Enzyme-Free Nucleic Acid Logic Circuits, Science 314(5805):1585-1588, 2006.
Sharan et al.: Recombineering: a homologous recombination-based method of genetic engineering. Nat Profile 4(2):1-37 (originally pp. 206-223) (2009).
Sharpe and Mount. Genetically modified T cells in cancer therapy: opportunities and challenges. Disease Models and Mechanisms, 8:337-350, 2015.
Sierzchala, Agnieszka B et al.: Solid-phase oligodeoxynucleotide synthesis : a two-step cycle using peroxy anion deprotection, J. Am. Chem. Soc., vol. 125, No. 44, 13427-13441 (2003).
Simonyan and Zisserman. Very Deep Convolutional Networks for Large-Scale Image Recognition, Published as a conference paper at Int. Conf. Learn. Represent., pp. 1-14, 2015.
Singh-Gasson. Sangeet et al.: Maskless fabrication of light-directed oligonucleotide microarrays using a digital micromirror array, Nature Biotechnology, vol. 17, 974-978 (Oct. 1999).
Skerra. Phosphorothioate primers improve the amplification of DNA sequences by DNA polymerases with proofreading activity. Nucleic Acids Res. Jul. 25, 1992; 20(14):3551-4.
Smith et al.: Removal of Polymerase-Produced mutant sequences from PCR products, Proc. Natl. Acad. Sci. USA, vol. 94, 6847-6850 (Jun. 1997).
Smith et al.: Generating a synthetic genome by whole genome assembly: phiX174 bacteriophage from synthetic oligonucleotides. Proc Natl Acad Sci U S A. Dec. 23, 2003;100(26):15440-5. Epub Dec. 2, 2003.
Smith et al.: Generation of cohesive ends on PCR products by UDG-mediated excision of dU, and application for cloning into restriction digest-linearized vectors. PCR Methods Appl. May 1993;2(4):328-32.
Smith et al.: Mutation detection with MutH, MutL, and MutS mismatch repair proteins, Proc. Natl. Acad. Sci. USA, vol. 93, 4374-4379 (Apr. 1996).
Smith et al.: Direct mechanical measurements of the elasticity of single DNA molecules using magnetic beads, Science, vol. 258, 1122-1126 (Nov. 13, 1992).
Solomon et al.: Genomics at Agilent: Driving Value in DNA Sequencing.https://www.agilent.com/labs/features/2010_genomics. html, 8 pages (Aug. 5, 2010).
Soni et al.: Progress toward ultrafast DNA sequencing using solidstate nanopores. Clin Chem. Nov. 2007;53(11):1996-2001. Epub Sep. 21, 2007.

Southern et al.: Analyzing and comparing nucleic acid sequences by hybridization to arrays of oligonucleotides: evaluation using experimental models. Genomics. Aug. 1992;13(4):1008-17.
Sproat et al.: An efficient method for the isolation and purification of oligoribonucleotides. Nucleosides & Nucleotides. 1995; 14(1 &2):255-273.
Srivannavit et al.: Design and fabrication of microwell array chips for a solution-based, photogenerated acid-catalyzed parallel oligonuclotide DNA synthesis. Sensors and Actuators A, 116:150-160, 2004.
Srivastava et al.: RNA synthesis: phosphoramidites for RNA synthesis in the reverse direction. Highly efficient synthesis and application to convenient introduction of ligands, chromophores and modifications of synthetic RNA at the 3'-end, Nucleic Acids Symposium Series, 52(1):103-104, 2008.
Steel. The Flow-Thru Chip A Three-dimensional biochip platform. In: Schena, Microarray Biochip Technology, Chapter 5, Natick, MA: Eaton Publishing, 2000, 33 pages.
Stemmer et al.: Single-step assembly of a gene and entire plasmid from large numbers of oligodeoxyribonucleotides. Gene. Oct. 16, 1995;164(1):49-53.
Stryer. DNA Probes and genes can be synthesized by automated solid-phase methods. Biochemistry, 3rd edition, New York: W.H. Freeman and Company, 1988; 123-125.
Stutz et al.: Novel fluoride-labile nucleobase-protecting groups for the synthesis of 3'(2')-O-amino-acylated RNA sequences. Helv. Chim. Acta. 2000; 83(9):2477-2503.
Sullivan et al.: Library construction and evaluation for site saturation mutagenesis. Enzyme Microb. Technol. 53:70-77 (2013).
Sun et al.: Structure-Guided Triple-Code Saturation Mutagenesis: Efficient Tuning of the Stereoselectivity of an Epoxide Hydrolase. ACS Catal. 6:1590-1597 (2016).
Takahashi. Cell-free cloning using multiply-primed rolling circle amplification with modified RNA primers. Biotechniques. Jul. 2009;47(1):609-15. doi: 10.2144/000113155.
Tanase et al.: Magnetic trapping of multicomponent nanowires, The Johns Hopkins University, Baltimore, Maryland, p. 1-3 (Jun. 25, 2001).
Taylor et al.: Impact of surface chemistry and blocking strategies on DNA microarrays. Nucleic Acids Research, 31(16):e87, 19 pages, 2003.
The Hood Laboratory, Beta Group. Assembly Manual for the POSaM: The ISB Piezoelelctric Oligonucleotide Synthesizer and Microarrayer, Inkjet Microarrayer Manual Version 1.2, 50 pages, May 28, 2004.
The SLIC. Gibson, OPEC and SLiCE assembly methods (and GeneArt Seamless, In-Fusion Cloning). 5 pages, available online Sep. 2, 2010.
Tian et al.: Accurate multiplex gene synthesis from programmable DNA microchips. Nature. Dec. 23, 2004;432(7020):1050-4.
Tsai et al.: Dimeric CRISPR RNA-guided FokI nucleases for highly specific genome editing Nat. Biotechnol., 32(6):569-576, 2014.
Twist Bioscience | White Paper. DNA-Based Digital Storage. Retrieved from the internet, Twistbioscience.com, Mar. 27, 2018, 5 pages.
U.S. Appl. No. 14/241,874 Final Office Action dated Jan. 28, 2019.
U.S. Appl. No. 14/241,874 Office Action dated Feb. 27, 2017.
U.S. Appl. No. 14/241,874 Office Action dated Jul. 14, 2016.
U.S. Appl. No. 14/241,874 Office Action dated May 4, 2018.
U.S. Appl. No. 14/452,429 Notice of Allowance dated Jun. 7, 2016.
U.S. Appl. No. 14/452,429 Office Action dated Oct. 21, 2015.
U.S. Appl. No. 14/452,429 Restriction Requirement dated Dec. 12, 2014.
U.S. Appl. No. 14/885,962 Notice of Allowance dated Nov. 8, 2017 and Sep. 29, 2017.
U.S. Appl. No. 14/885,962 Office Action dated Dec. 16, 2016.
U.S. Appl. No. 14/885,962 Office Action dated Sep. 8, 2016.
U.S. Appl. No. 14/885,962 Restriction Requirement dated Mar. 1, 2016.
U.S. Appl. No. 14/885,963 Notice of Allowance dated May 24, 2016.
U.S. Appl. No. 14/885,963 Office Action dated Feb. 5, 2016.
U.S. Appl. No. 14/885,965 Office Action dated Aug. 28, 2018.
U.S. Appl. No. 14/885,965 Office Action dated Aug. 30, 2017.

(56) References Cited

OTHER PUBLICATIONS

U.S. Appl. No. 14/885,965 Office Action dated Feb. 10, 2017.
U.S. Appl. No. 14/885,965 Office Action dated Feb. 18, 2016.
U.S. Appl. No. 14/885,965 Office Action dated Jan. 4, 2018.
U.S. Appl. No. 14/885,965 Office Action dated Jul. 7, 2016.
U.S. Appl. No. 15/015,059 Final Office Action dated Jul. 17, 2019.
U.S. Appl. No. 15/015,059 Office Action dated Aug. 19, 2019.
U.S. Appl. No. 15/015,059 Office Action dated Feb. 7, 2019.
U.S. Appl. No. 15/135,434 Notice of Allowance dated Feb. 9, 2018.
U.S. Appl. No. 15/135,434 Office Action dated Nov. 30, 2017.
U.S. Appl. No. 15/135,434 Restriction Requirement dated Jul. 12, 2017.
U.S. Appl. No. 15/151,316 Office Action dated Jun. 7, 2018.
U.S. Appl. No. 15/151,316 Office Action dated Oct. 4, 2019.
U.S. Appl. No. 15/151,316 Final Office Action dated Feb. 21, 2019.
U.S. Appl. No. 15/154,879 Notice of Allowance dated Feb. 1, 2017.
U.S. Appl. No. 15/156,134 Final Office Action dated Jan. 3, 2020.
U.S. Appl. No. 15/156,134 Office Action dated Apr. 4, 2019.
U.S. Appl. No. 15/187,714 Final Office Action dated Sep. 17, 2019.
U.S. Appl. No. 15/187,714 Office Action dated Apr. 4, 2019.
U.S. Appl. No. 15/187,714 Restriction Requirement dated Sep. 17, 2018.
U.S. Appl. No. 15/187,721 Notice of Allowance dated Dec. 7, 2016.
U.S. Appl. No. 15/187,721 Office Action dated Oct. 14, 2016.
U.S. Appl. No. 15/233,835 Notice of Allowance dated Oct. 4, 2017.
U.S. Appl. No. 15/233,835 Office Action dated Feb. 8, 2017.
U.S. Appl. No. 15/233,835 Office Action dated Jul. 26, 2017.
U.S. Appl. No. 15/233,835 Restriction Requirement dated Nov. 4, 2016.
U.S. Appl. No. 15/245,054 Office Action dated Mar. 21, 2017.
U.S. Appl. No. 15/245,054 Office Action dated Oct. 19, 2016.
U.S. Appl. No. 15/268,422 Final Office Action dated Oct. 3, 2019.
U.S. Appl. No. 15/268,422 Office Action dated Mar. 1, 2019.
U.S. Appl. No. 15/268,422 Restriction Requirement dated Oct. 4, 2018.
U.S. Appl. No. 15/272,004 Office Action dated Jun. 12, 2020.
U.S. Appl. No. 15/377,547 Final Office Action dated Feb. 8, 2019.
U.S. Appl. No. 15/377,547 Office Action dated Jul. 27, 2018.
U.S. Appl. No. 15/377,547 Office Action dated Mar. 24, 2017.
U.S. Appl. No. 15/377,547 Office Action dated Nov. 30, 2017.
U.S. Appl. No. 15/433,909 Non-Final Office Action dated Feb. 8, 2019.
U.S. Appl. No. 15/433,909 Restriction Requirement dated Sep. 17, 2018.
U.S. Appl. No. 15/602,991 Final Office Action dated Dec. 13, 2018.
U.S. Appl. No. 15/602,991 Notice of Allowance dated Oct. 25, 2017.
U.S. Appl. No. 15/602,991 Office Action dated May 31, 2018.
U.S. Appl. No. 15/602,991 Office Action dated May 31, 2019.
U.S. Appl. No. 15/602,991 Office Action dated Sep. 21, 2017.
U.S. Appl. No. 15/603,013 Final Office Action dated Nov. 6, 2019.
U.S. Appl. No. 15/603,013 Office Action dated Jan. 30, 2018.
U.S. Appl. No. 15/603,013 Office Action dated Jul. 10, 2018.
U.S. Appl. No. 15/603,013 Office Action dated Oct. 20, 2017.
U.S. Appl. No. 15/619,322 Final Office Action dated Mar. 30, 2020.
U.S. Appl. No. 15/619,322 Office Action dated Aug. 14, 2019.
U.S. Appl. No. 15/682,100 Office Action dated Jan. 2, 2018.
U.S. Appl. No. 15/682,100 Restriction Requirement dated Nov. 8, 2017.
U.S. Appl. No. 15/709,274 Notice of Allowance dated Apr. 3, 2019.
U.S. Appl. No. 15/729,564 Final Office Action dated Dec. 13, 2018.
U.S. Appl. No. 15/729,564 Office Action dated Jan. 8, 2018.
U.S. Appl. No. 15/729,564 Office Action dated Jun. 6, 2018.
U.S. Appl. No. 15/729,564 Office Action dated May 30, 2019.
U.S. Appl. No. 15/816,995 Office Action dated May 19, 2020.
U.S. Appl. No. 15/816,995 Office Action dated Sep. 20, 2019.
U.S. Appl. No. 15/816,995 Restriction Requirement dated Apr. 4, 2019.
U.S. Appl. No. 15/835,342 Office Action dated Dec. 2, 2019.
U.S. Appl. No. 15/835,342 Restriction Requirement dated Sep. 10, 2019.
U.S. Appl. No. 15/844,395 Office Action dated Jan. 24, 2020.
U.S. Appl. No. 15/844,395 Restriction Requirement dated May 17, 2019.
U.S. Appl. No. 15/860,445 Final Office Action dated Dec. 13, 2018.
U.S. Appl. No. 15/860,445 Office Action dated May 30, 2018.
U.S. Appl. No. 15/921,479 Final Office Action dated Jun. 15, 2020.
U.S. Appl. No. 15/921,479 Office Action dated Nov. 12, 2019.
U.S. Appl. No. 15/921,479 Restriction Requirement dated May 24, 2019.
U.S. Appl. No. 15/921,537 Office Action dated Apr. 1, 2020.
U.S. Appl. No. 15/960,319 Office Action dated Aug. 16, 2019.
U.S. Appl. No. 15/991,992 Office Action dated May 21, 2020.
U.S. Appl. No. 15/991,992 Restriction Requirement dated Mar. 10, 2020.
U.S. Appl. No. 16/006,581 Office Action dated Sep. 25, 2019.
U.S. Appl. No. 16/031,784 Office Action dated May 12, 2020.
U.S. Appl. No. 16/039,256 Restriction Requirement dated May 18, 2020.
U.S. Appl. No. 16/128,372 Restriction Requirement dated May 18, 2020.
U.S. Appl. No. 16/165,952 Office Action dated Mar. 12, 2020.
U.S. Appl. No. 16/239,453 Office Action dated May 11, 2020.
U.S. Appl. No. 16/239,453 Office Action dated Nov. 7, 2019.
U.S. Appl. No. 16/384,678 Office Action dated Jan. 21, 2020.
U.S. Appl. No. 16/409,608 Office Action dated Sep. 9, 2019.
U.S. Appl. No. 16/530,717 Final Office Action dated Apr. 15, 2020.
U.S. Appl. No. 16/530,717 Office Action dated Sep. 6, 2019.
U.S. Appl. No. 16/535,777 Office Action dated Jan. 23, 2020.
U.S. Appl. No. 16/535,779 First Action Interview dated Feb. 10, 2020.
U.S. Appl. No. 14/452,429 Office Action dated Apr. 9, 2015.
U.S. Appl. No. 15/603,013 Office Action dated Jun. 26, 2019.
Unger et al.: Monolithic microfabricated valves and pumps by multilayer soft lithography. Science. Apr. 7, 2000;288(5463):113-6.
Vaijayanthi et al.: Recent advances in oligonucleotide synthesis and their applications. Indian J Biochem Biophys. Dec. 2003;40(6):377-91.
Van Den Brulle et al.: A novel solid phase technology for high-throughput gene synthesis. Biotechniques. 2008; 45(3):340-343.
Van Der Werf et al.: Limonene-1,2-epoxide hydrolase from Rhodococcus erythropolis DCL14 belongs to a novel class of epoxide hydrolases. J. Bacteriol. 180:5052-5057 (1998).
Van Tassell et al.: SNP discovery and allele frequency estimation by deep sequencing of reduced representation libraries. Nature Methods, 5:247-252, 2008.
Vargeese et al.: Efficient activation of nucleoside phosphoramidites with 4,5-dicyanoimidazole during oligonucleotide synthesis. Nucleic Acids Res. Feb. 15, 1998;26(4):1046-50.
Verma et al.: Modified oligonucleotides: synthesis and strategy for users. Annu Rev Biochem 67:99-134 (1998).
Vincent et al.: Helicase-dependent isothermal DNA amplification. EMBO Rep. Aug. 2004;5(8):795-800.
Visscher et al.: Construction of multiple-beam optical traps with nanometer-resolution position sensing, IEEE Journal of Selected Topics in Quantum Electronics, vol. 2, No. 4, 1066-1076 (Dec. 1996).
Voldmans et al.: Holding forces of single-particle dielectrophoretic traps. Biophysical Journal, vol. 80, No. 1, 531-541 (Jan. 2001).
Vos et al.: AFLP: A new technique for DNA fingerprinting. Nucleic Acids Res. Nov. 11, 1995;23(21):4407-14.
Wagner et al.: Nucleotides, Part LXV, Synthesis of 2'-Deoxyribonucleoside 5'-Phosphoramidites: New Building Blocks for the Inverse (5'-3')-Oligonucleotide Approach. Helvetica Chimica Acta, 83(8):2023-2035, 2000.
Wah et al.: Structure of Fok I has implications for DNA cleavage, Proc. Natl. Acad. Sci. USA, vol. 95, 10564-10569 (Sep. 1998).
Wah et al.: Structure of the multimodular endonuclease Fok I bound to DNA, Nature, vol. 388, 97-100 (Jul. 1997).
Walker et al.: Strand displacement amplification—an isothermal, in vitro DNA amplification technique. Nucleic Acids Res. Apr. 11, 1992;20(7):1691-6.

(56) References Cited

OTHER PUBLICATIONS

Wan et al.: Deep Learning for Content-Based Image Retrieval: A comprehensive study, in Proceedings of the 22nd ACM International Conference on Multimedia—Nov. 3-7, 2014, Orlando, FL, p. 157-166, 2014.
Warr et al.: Exome Sequencing: current and future perspectives. G3: (Bethesda) 5(8):1543-1550 (2015).
Weber et al.: A modular cloning system for standardized assembly of multigene constructs. PLoS One. Feb. 1, 20118;6(2):e16765. doi: 10.1371/journal.pone.0016765.
Welz et al.: 5-(Benzylmercapto)-1H-tetrazole as activator for 2'-O-TBDMS phosphoramidite building blocks in RNA synthesis. Tetrahedron Lett. 2002; 43(5):795-797.
Westin et al.: Anchored multiplex amplification on a microelectronic chip array Nature Biotechnology, 18:199-202 (2000) (abstract only).
Whitehouse et al.: Analysis of the mismatch and insertion/deletion binding properties of Thermus thermophilus, HB8, MutS, Biochemical and Biophysical Research Communications, vol. 233, 834-837 (1997).
Wiedenheft et al.: RNA-guided genetic silencing systems in bacteria and archaea. Nature 482:331-338 (2012).
Wijshoff. Structure and fluid-dynamics in Piezo inkjet printheads. Thesis. Venio, The Netherlands, published 2008, p. 1-185.
Wirtz. Direct measurement of the transport properties of a single DNA molecule, Physical Review Letters, vol. 75, No. 12, 2436-2439 (Sep. 18, 1995).
Withers-Martinez et al.: PCR-based gene synthesis as an efficient approach for expression of the A+ T-rich malaria genome, Protein Engineering, vol. 12, No. 12, 1113-1120 (1999).
Wood et al.: Human DNA repair genes, Science, vol. 291, 1284-1289 (Feb. 16, 2001).
Wosnick et al.: Rapid construction of large synthetic genes: total chemical synthesis of two different versions of the bovine prochymosin gene. Gene. 1987;60(1):115-27.
Wright and Church. An open-source oligomicroarray standard for human and mouse. Nature Biotechnology, 20:1082-1083, 2002.
Wu et al.: RNA-mediated gene assembly from DNA arrays. Angew Chem Int Ed Engl. May 7, 2012;51(19):4628-32. doi: 10.1002/anie.201109058.
Wu et al.: Sequence-Specific Capture of Protein-DNA Complexes for Mass Spectrometric Protein Identification PLoS ONE. Oct. 20, 2011, vol. 6, No. 10.
Wu et al.: Specificity of the nick-closing activity of bacteriophage T4 DNA ligase. Gene. 1989;76(2):245-54.
Wu et al.: An improvement of the on-line electrophoretic concentration method for capillary electrophoresis of proteins an experimental factors affecting he concentration effect, Analytical Sciences, vol. 16, 329-331 (Mar. 2000).
Xiong et al.: Chemical gene synthesis: Strategies, softwares, error corrections, and applications. FEMS Microbiol. Rev., 32:522-540, 2008.
Xiong et al.: A simple, rapid, high-fidelity and cost-effective PCR-based two-step DNA synthesis method for long gene sequences. Nucleic Acids Res. 2004, 32(12):e98.
Xiong et al.: Non-polymerase-cycling-assembly-based chemical gene synthesis: Strategies, methods, and progress. Biotechnology Advances. 26(2):121-134, 2008.
Xu et al.: Design of 240,000 orthogonal 25mer DNA barcode probes. PNAS, 106(7):2289-2294, 2009.
Yang et al.: Purification, cloning, and characterization of the CEL I nuclease, Biochemistry, 39(13):3533-35, 2000.
Yazdi et al.: A Rewritable, Random-Access DNA-Based Storage System, Scientific Reports, 5, Article No. 14138, 27 pages, 2015.
Yehezkel et al.: De novo DNA synthesis using single molecule PCR Nucleic Acids Research, 36(17):e107, 2008.
Yes HMDS vapor prime process application note Prepared by UC Berkeley and University of Texas at Dallas and re-printed by Yield Engineering Systems, Inc., 6 pages (http://www.yieldengineering.com/Portals/0/HMDS%20Application%20Note.pdf (Published online Aug. 23, 2013).
Youil et al.: Detection of 81 of 81 known mouse Beta-Globin promoter mutations with T4 Endonuclease VII—The EMC Method. Genomics, 32:431-435, 1996.
Young et al.: Two-step total gene synthesis method. Nucleic Acids Res. 32(7):e59, 2004.
Zhang and Seelig. Dynamic DNA nanotechnology using strand-displacement reactions, Nat. Chem., 3(2):103-113, 2011.
Zheleznaya et al.: Nicking endonucleases. Biochemistry (Mose). 74(13):1457-66, 2009.
Zheng et al.: Manipulating the Stereoselectivity of Limonene Epoxide Hydrolase by Directed Evolution Based on Iterative Saturation Mutagenesis. J. Am. Chem. Soc. 132:15744-15751 (2010).
Zhirnov et al.: Nucleic acid memory. Nature Materials, 15:366, 2016.
Zhou et al.: Microfluidic PicoArray synthesis of oligodeoxynucleotides and simultaneous assembling of multiple DNA sequences Nucleic Acids Research, 32(18):5409-5417, 2004.
Zhou et al.: Establishment and application of a loop-mediated isothermal amplification (LAMP) system for detection of cry1Ac transgenic sugarcane Scientific Reports May 9, 2014, vol. 4, No. 4912.
Chervin et al.: Design of T-cell receptor libraries with diverse binding properties to examine adoptive T-cell responses. Gene Therapy. 20(6):634-644 (2012).
European Patent Application No. 17881617.9 European Search Report and Written Opinion dated Jul. 2, 2020.
Malecek et al.: Engineering improved T cell receptors using an alanine-scan guided T cell display selection system. Journal of Immunological Methods. Elsevier Science Publishers. 392(1):1-11 (2013).
PCT/US2019/012218 International Preliminary Report on Patentability dated Jul. 16, 2020.
U.S. Appl. No. 15/151,316 Final Office Action dated Jul. 9, 2020.
Bai. A Novel Human scFv Library with Non-Combinatorial Synthetic CDR Diversity. PLoS One. 10(10):1-18 (2015).
Berg: Biochemistry. 5th ED. New York (2002) 148-149.
Borda et al.: Secret writing by DNA hybridization. Acta Technica Napocensis Electronics and Telecommunications. 50(2):21-24 (2008).
Cui et al.: Information Security Technology Based on DNA Computing. International Workshop on Anti-Counterfeiting, Security and Identification (ASID); IEEE Xplore 4 pages (2007).
Fernández-Quintero et al.: Characterizing the Diversity of the CDR-H3 Loop Conformational Ensembles in Relationship to Antibody Binding Properties. Front. Immunol. 9:1-11 (2019).
GE Healthcare. AKTA oligopilot plus. Data File 18-114-66 AD©. 8 pages (2006).
GE Healthcare. Robust and cost-efficient oligonucleotide synthesis. Application Note 28-4058-08 AA. 4 pages (2005).
Geetha et al.: Survey on Security Mechanisms for Public Cloud Data. 2016 International Conference on Emerging Trends in Engineering, Technology and Science (ICETETS). 8 pages (2016).
Goodwin et al.: immunoglobulin heavy chain variable region, partial [*Homo sapiens*], Genbank entry (online). National Institute of Biotechnology Information. (2018) https://www.ncbi.nim.nih.gov/protein/AXA12486.1.
Hopcroft et al.: What is the Young's Modulus of Silicon?. Journal of Microelectromechanical Systems. 19(2):229-238 (2010).
Hudson: Matrix Assisted Synthetic Transformations: A Mosaic of Diverse Contributions. Journal of Combinatorial Chemistry. 1(6):403-457 (1999).
Jaiswal et al.: An architecture for creating collaborative semantically capable scientific data sharing infrastructures. Proceeding WIDM '06 Proceedings of the 8th annual ACM international workshop on Web information and data management. ACM Digital Library pp. 75-82 (2006).
Jang et al.: Characterization of T cell repertoire of blood, tumor, and ascites in ovarian cancer patients using next generation sequencing. Oncoimmunology, 4(11):e1030561:1-10 (2015).
Kalva et al.: Gibson Deletion: a novel application of isothermal in vitro recombination. Biological Procedures Online. 20(1):1-10 (2018).

(56) References Cited

OTHER PUBLICATIONS

Kosuri, et al. A scalable gene synthesis by selective amplification of DNA pools from high-fidelity microchips. Nature Biotechnology. 2010; 28:1295-1299.
Lebl et al.: Economical Parallel Oligonucleotide and Peptide Synthesizer—Pet Oligator. Int. J. Peptide Res. Ther. 13(1-2):367-376 (2007).
MLAB 2321 Molecular Diagnostics for Clinical Laboratory Science. Mar. 6, 2015.
Momentiv. Technical Data Sheet. Silquest A-1100. Momentiv. 1-6 (2020).
(Novartis Institutes for Biomedical Research) Immunoglobulin Heavy Chain [Homo sapiens]. National Center for Biotechnology Information. Genbank Entry, pp. 1-2 (2018) https://www.ncbi.nlm.nih.gov/nuccore/MH975524.1ttps://https://www.ncbi.nlm.nih.gov/nuccore/MH975524.1.
(Novartis Institutes for Biomedical Research) Immunoglobulin Lambda Chain [Homo sapiens]. National Center for Biotechnology Information. Genbank Entry, pp. 1-2 (2018) https://www.ncbi.nlm.nih.gov/nuccore/MH975524.1.
Nucleic acid thermodynamics. Wikipedia. Feb. 4, 2021.
O'Driscoll et al.: Synthetic DNA: The next generation of big data storage. Bioengineered. 4(3):123-125 (2013).
Opposition to European Patent No. 3030682 filed Mar. 3, 2021.
PCT/US2019/032992 International Preliminary Report on Patentability dated Nov. 24, 2020.
PCT/US2019/068435 International Preliminary Report on Patentability dated Jul. 8, 2021.
PCT/US2020/019371 International Search Report and Written Opinion dated Jun. 25, 2020.
PCT/US2020/019986 International Search Report and Written Opinion dated Jul. 29, 2020.
PCT/US2020/019988 International Search Report and Written Opinion dated Jul. 29, 2020.
PCT/US2020/038679 International Search Report and Written Opinion dated Oct. 28, 2020.
PCT/US2020/052291 International Search Report and Written Opinion dated Mar. 10, 2021.
PCT/US2020/052291 Invitation to Pay Additional Fees dated Dec. 31, 2020.
PCT/US2020/052306 International Search Report and Written Opinion dated Mar. 2, 2021.
PCT/US2020/052306 Invitation to Pay Additional Fees dated Dec. 18, 2020.
PCT/US2020/064106 International Search Report and Written Opinion dated Jun. 3, 2021.
PCT/US2020/064106 Invitation to Pay Additional Fees dated Apr. 9, 2021.
Pigott et al.: The Use of a Novel Discovery Platform to Identify Peptide-Grafted Antibodies that Activate GLP-1 Receptor Signaling. Innovative Targeting Solutions Inc. (2013) XP055327428 retrieved from the internet: http://www.innovativetargeting.com/wo-content/uploads/2013/12/Pigott-et-al-Antibody-Engineering-2013.pdf.
Ponsel. High Affinity, Developability and Functional Size: The Holy Grail of Combinatorial Antibody Library Generation. Molecules. 16:3675-3700 (2011).
PubChem Data Sheet Dichloromethane. Printed from website https://pubchem.ncbi.nlm.nih.gov/compound/Dichloromethane (2020).
Regep et al.: The H3 loop of antibodies shows unique structural characteristics. Proteins. 85(7):1311-1318 (2017).
Shipman et al.: Molecular recordings by directed CRISPR spacer acquisition. Science. 353(6298):1-16 (2016).
U.S. Appl. No. 15/156,134 Final Office Action dated Aug. 18, 2021.
U.S. Appl. No. 15/156,134 Office Action dated Nov. 25, 2020.
U.S. Appl. No. 15/245,054 Notice of Allowance dated Dec. 14, 2017.
U.S. Appl. No. 15/272,004 Final Office Action dated Mar. 18, 2021.
U.S. Appl. No. 15/619,322 Final Office Action dated Jul. 9, 2021.
U.S. Appl. No. 15/619,322 Office Action dated Nov. 4, 2020.
U.S. Appl. No. 15/835,342 Final Office Action dated Sep. 8, 2020.
U.S. Appl. No. 15/835,342 Office Action dated Apr. 16, 2021.
U.S. Appl. No. 15/902,855 Restriction Requirement dated Apr. 6, 2021.
U.S. Appl. No. 15/921,479 Office Action dated Apr. 27, 2021.
U.S. Appl. No. 16/039,256 Final Office Action dated Mar. 30, 2021.
U.S. Appl. No. 16/039,256 Office Action dated Aug. 20, 2020.
U.S. Appl. No. 16/128,372 Final Office Action dated Mar. 18, 2021.
U.S. Appl. No. 16/128,372 Office Action dated Oct. 8, 2020.
U.S. Appl. No. 16/384,678 Final Office Action dated Oct. 15, 2020.
U.S. Appl. No. 16/535,777 Final Office Action dated Oct. 20, 2020.
U.S. Appl. No. 16/535,777 Office Action dated Feb. 8, 2021.
U.S. Appl. No. 16/712,678 Restriction Requirement dated Aug. 25, 2021.
U.S. Appl. No. 16/798,275 Office Action dated Feb. 10, 2021.
U.S. Appl. No. 16/854,719 Restriction Requirement dated Jul. 28, 2021.
U.S. Appl. No. 16/906,555 Office Action dated Aug. 17, 2021.
U.S. Appl. No. 17/154,906 Restriction Requirement dated Jul. 26, 2021.
Van der Velde: Thesis. Finding the Strength of Glass. Delft University of Technology. 1-16 (2015).
Xu et al.: Coordination between the Polymerase and 5'-Nuclease Components of DNA Polymerase I of *Escherichia coli*. The Journal of Biological Chemistry. 275(27):20949-20955 (2000).
Yazdi et al.: DNA-Based Storage: Trends and Methods. IEEE Transactions on Molecular, Biological and Multi-Scale Communications. IEEE. 1(3):230-248 (2016).
De Graff et al.: Glucagon-Like Peptide-1 and its Class B G Protein-Coupled Receptors: A Long March to Therapeutic Successes. Pharmacol Rev. 68(4):954-1013 (2016).
PCT/US2020/019371 International Preliminary Report on Patentability dated Sep. 2, 2021.
PCT/US2020/019986 International Preliminary Report on Patentability dated Sep. 10, 2021.
PCT/US2020/019988 International Preliminary Report on Patentability dated Sep. 10, 2021.
U.S. Appl. No. 17/154,906 Office Action dated Nov. 10, 2021.
U.S. Appl. No. 16/712,678 Office Action dated Nov. 26, 2021.
U.S. Appl. No. 16/737,401 Restriction Requirement dated Nov. 15, 2021.
U.S. Appl. No. 16/802,439 Restriction Requirement dated Oct. 1, 2021.
U.S. Appl. No. 16/854,719 Office Action dated Nov. 24, 2021.
U.S. Appl. No. 16/798,275 Final Office Action dated Aug. 30, 2021.

METHODS FOR SEAMLESS NUCLEIC ACID ASSEMBLY

CROSS-REFERENCE

This is a continuation application of U.S. patent application Ser. No. 16/006,581, filed Jun. 12, 2018, which claims the benefit of U.S. Provisional Patent Application No. 62/663,089 filed Apr. 26, 2018; and U.S. Provisional Patent Application No. 62/518,496 filed on Jun. 12, 2017, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 6, 2018, is named 44854-746_301_SL.txt and is 1,585 bytes in size.

BACKGROUND

De novo nucleic acid synthesis is a powerful tool for basic biological research and biotechnology applications. While various methods are known for the synthesis of relatively short fragments of nucleic acids on a small scale, these techniques suffer from scalability, automation, speed, accuracy, and cost. Thus, a need remains for efficient methods of seamless nucleic acid assembly.

BRIEF SUMMARY

Provided herein are methods for nucleic acid synthesis and assembly, comprising: (a) providing a plurality of polynucleotides; and (b) mixing the plurality of polynucleotides with an exonuclease, a flap endonuclease, a polymerase, and a ligase, wherein the plurality of polynucleotides are annealed in a processive predetermined order based on a complementary sequence between adjacent polynucleotides. Further provided herein are methods for nucleic acid synthesis and assembly, wherein the exonuclease is exonuclease III. Further provided herein are methods for nucleic acid synthesis and assembly, wherein the flap endonuclease is flap endonuclease 1, exonuclease 1, XPG, Dna2, or GEN1. Further provided herein are methods for nucleic acid synthesis and assembly, wherein the polymerase comprises 5' to 3' polymerase activity. Further provided herein are methods for nucleic acid synthesis and assembly, wherein the polymerase is a DNA polymerase. Further provided herein are methods for nucleic acid synthesis and assembly, wherein the ligase catalyzes joining of at least two nucleic acids. Further provided herein are methods for nucleic acid synthesis and assembly, wherein a concentration of the flap endonuclease 1 is in a range of about 0.32 U to about 4.8 U. Further provided herein are methods for nucleic acid synthesis and assembly, wherein a concentration of the exonuclease III is in a range of about 0.1 U to about 10 U. Further provided herein are methods for nucleic acid synthesis and assembly, wherein a concentration of the exonuclease III is in a range of about 0.5 U to about 1.0 U. Further provided herein are methods for nucleic acid synthesis and assembly, wherein a concentration of the exonuclease III is in a range of about 1.0 U to about 2.0 U. Further provided herein are methods for nucleic acid synthesis and assembly, wherein a concentration of the polymerase is in a range of about 0.1 U to about 2 U. Further provided herein are methods for nucleic acid synthesis and assembly, wherein a concentration of the polymerase is about 0.1 U. Further provided herein are methods for nucleic acid synthesis and assembly, wherein a concentration of the polymerase is about 0.2 U. Further provided herein are methods for nucleic acid synthesis and assembly, wherein a concentration of the ligase is up to about 2.0 U. Further provided herein are methods for nucleic acid synthesis and assembly, wherein a concentration of the ligase is in a range of about 4.0 U to about 8.0 U.

Provided herein are methods for nucleic acid synthesis and assembly, comprising: (a) providing a first double stranded nucleic acid; (b) providing a second double stranded nucleic acid; (c) providing a third double stranded nucleic acid comprising in 5' to 3' order: a 5' flanking adapter sequence, a first homology sequence to the first double stranded nucleic acid, a second homology sequence to the second double stranded nucleic acid, and a 3' flanking adapter sequence; and (d) mixing the first double stranded nucleic acid, the second double stranded nucleic acid, and the third double stranded nucleic acid with a reaction mixture comprising an exonuclease, a flap endonuclease, a polymerase, and a ligase. Further provided herein are methods for nucleic acid synthesis and assembly, wherein the exonuclease is exonuclease III. Further provided herein are methods for nucleic acid synthesis and assembly, wherein the flap endonuclease is flap endonuclease 1, exonuclease 1, XPG, Dna2, or GEN1. Further provided herein are methods for nucleic acid synthesis and assembly, wherein an amount of the flap endonuclease 1 provided is about 0.32 U to about 4.8 U. Further provided herein are methods for nucleic acid synthesis and assembly, wherein an amount of the flap endonuclease 1 provided is less than about 5.0 U. Further provided herein are methods for nucleic acid synthesis and assembly, wherein the polymerase comprises 5' to 3' polymerase activity. Further provided herein are methods for nucleic acid synthesis and assembly, wherein the polymerase is a DNA polymerase. Further provided herein are methods for nucleic acid synthesis and assembly, wherein the ligase catalyzes joining of at least two nucleic acids. Further provided herein are methods for nucleic acid synthesis and assembly, wherein the first homology sequence or the second homology sequence is about 10 to about 100 base pairs. Further provided herein are methods for nucleic acid synthesis and assembly, wherein the first homology sequence and the second homology sequence are each independently about 10 to about 100 base pairs. Further provided herein are methods for nucleic acid synthesis and assembly, wherein the first homology sequence or the second homology sequence is about 20 to about 80 base pairs. Further provided herein are methods for nucleic acid synthesis and assembly, wherein the first homology sequence and the second homology sequence are each independently about 20 to about 80 base pairs. Further provided herein are methods for nucleic acid synthesis and assembly, wherein the first homology sequence or the second homology sequence is about 40 base pairs. Further provided herein are methods for nucleic acid synthesis and assembly, wherein the first homology sequence and the second homology sequence are each independently about 40 base pairs. Further provided herein are methods for nucleic acid synthesis and assembly, wherein a concentration of the exonuclease III is in a range of about 0.1 U to about 10 U. Further provided herein are methods for nucleic acid synthesis and assembly, wherein a concentration of the exonuclease III is in a range of about 0.5 U to about 1.0 U. Further provided herein are methods for nucleic acid synthesis and assembly, wherein a concentration of the exonuclease III is in a range of about 1.0 U to about 2.0 U. Further provided herein are methods for nucleic acid synthesis and assembly, wherein a concentration of the polymerase is present in an amount of about 0.1 U to about 2 U. Further provided herein are methods for nucleic acid synthesis and assembly, wherein a concentration of the polymerase is about 0.1 U to about 0.2 U. Further provided herein are methods for nucleic acid synthesis and assembly, wherein a concentration of the ligase is up to about 2.0 U. Further provided herein are methods for nucleic acid synthesis and assembly, wherein a concentration of the ligase is in a range of about 4.0 U to about 8.0 U. Further provided herein are methods for nucleic acid synthesis and assembly, wherein a concentration of the ligase is in a range of about 0.5 U to about 1.0 U. Further provided herein are methods for nucleic acid synthesis and assembly, wherein the first double stranded nucleic acid, the second double stranded nucleic acid, or the third double stranded nucleic acid or any combination thereof is a linear fragment. Further provided herein are methods for nucleic acid synthesis and assembly, wherein a product following step (d) is a linear fragment. Further provided herein are methods for nucleic acid synthesis and assembly, wherein a product following step (d) is a circular fragment.

Provided herein are methods for nucleic acid assembly, comprising: (a) providing a first double stranded nucleic acid comprising in 5' to 3' order: a 5' flanking adapter sequence, a homology sequence, an insert sequence, and a 3' flanking adapter sequence; (b) providing a second double stranded nucleic acid comprising in 5' to 3' order: a 5' flanking adapter sequence, a homology sequence, an insert sequence, and a 3' flanking adapter sequence; and (c) mixing the first double stranded nucleic acid and the second double stranded nucleic acid with a reaction mixture comprising an exonuclease, a flap endonuclease, a polymerase, and a ligase. Further provided herein are methods for nucleic acid assembly, wherein the exonuclease is exonuclease III. Further provided herein are methods for nucleic acid assembly, wherein the flap endonuclease is flap endonuclease 1, exonuclease 1, XPG, Dna2, or GEN1. Further provided herein are methods for nucleic acid assembly, wherein an amount of the flap endonuclease 1 provided is about 0.32 U to about 4.8 U. Further provided herein are methods for nucleic acid assembly, wherein an amount of the flap endonuclease 1 provided is less than about 5.0 U. Further provided herein are methods for nucleic acid assembly, wherein the polymerase comprises 5' to 3' polymerase activity. Further provided herein are methods for nucleic acid assembly, wherein the polymerase is a DNA polymerase. Further provided herein are methods for nucleic acid assembly, wherein the ligase catalyzes joining of at least two nucleic acids. Further provided herein are methods for nucleic acid assembly, wherein the homology sequence of the first double stranded nucleic acid or the homology sequence of the second double stranded nucleic acid is about 10 to about 100 base pairs. Further provided herein are methods for nucleic acid assembly, wherein the homology sequence of the first double stranded nucleic acid and the homology sequence of the second double stranded nucleic acid are each independently about 10 to about 100 base pairs. Further provided herein are methods for nucleic acid assembly, wherein the homology sequence of the first double stranded nucleic acid or the homology sequence of the second double stranded nucleic acid is about 20 to about 80 base pairs. Further provided herein are methods for nucleic acid assembly, wherein the homology sequence of the first double stranded nucleic acid and the homology sequence of the second double stranded nucleic acid are each independently about 20 to about 80 base pairs. Further provided herein are methods for nucleic acid assembly, wherein the homology sequence of the first double stranded nucleic acid or the homology sequence of the second double stranded nucleic acid is about 40 base pairs. Further provided herein are methods for nucleic acid assembly, wherein the homology sequence of the first double stranded nucleic acid and the homology sequence of the second double stranded nucleic acid are each independently about 40 base pairs. Further provided herein are methods for nucleic acid assembly, wherein a concentration of the exonuclease III is in a range of about 0.1 U to about 10 U. Further provided herein are methods for nucleic acid assembly, wherein a concentration of the exonuclease III is in a range of about 0.5 U to about 1.0 U. Further provided herein are methods for nucleic acid assembly, wherein a concentration of the exonuclease III is in a range of about 1.0 U to about 2.0 U. Further provided herein are methods for nucleic acid assembly, wherein a concentration of the polymerase is present in an amount of about 0.1 U to about 2 U. Further provided herein are methods for nucleic acid assembly, wherein a concentration of the polymerase is about 0.1 U to about 0.2 U. Further provided herein are methods for nucleic acid assembly, wherein a concentration of the ligase is up to about 2.0 U. Further provided herein are methods for nucleic acid assembly, wherein a concentration of the ligase is in a range of about 4.0 U to about 8.0 U. Further provided herein are methods for nucleic acid assembly, wherein a concentration of the ligase is in a range of about 0.5 U to about 1.0 U. Further provided herein are methods for nucleic acid assembly, wherein the first double stranded nucleic acid or the second double stranded nucleic acid is a linear fragment. Further provided herein are methods for nucleic acid assembly, wherein a product following step (c) is a linear fragment. Further provided herein are methods for nucleic acid assembly, wherein a product following step (c) is a circular fragment.

Provided herein are methods for nucleic acid assembly, comprising: (a) providing a first double stranded nucleic acid comprising in 5' to 3' order: a 5' flanking adapter sequence, a homology sequence, an insert sequence, and a 3' flanking adapter sequence; (b) providing a second double stranded nucleic acid comprising in 5' to 3' order: a 5' flanking adapter sequence, a homology sequence, an insert sequence, and a 3' flanking adapter sequence; and (c) mixing the first double stranded nucleic acid and the second double stranded nucleic acid with a reaction mixture comprising an exonuclease, a flap endonuclease, a polymerase, and a ligase at a temperature of about 30° C. to about 60° C. Further provided herein are methods for nucleic acid assembly, wherein the exonuclease is exonuclease III. Further provided herein are methods for nucleic acid assembly, wherein the flap endonuclease is flap endonuclease 1, exonuclease 1, XPG, Dna2, or GEN1. Further provided herein are methods for nucleic acid assembly, wherein a concentration of the flap endonuclease 1 is in a range of about 0.32 U to about 4.8 U. Further provided herein are methods for nucleic acid assembly, wherein the polymerase comprises 5' to 3' polymerase activity. Further provided herein are methods for nucleic acid assembly, wherein the polymerase is a DNA polymerase. Further provided herein are methods for nucleic acid assembly, wherein the ligase catalyzes joining of at least two nucleic acids. Further provided herein are methods for nucleic acid assembly, wherein the homology sequence of the first double stranded nucleic acid or the homology sequence of the second double stranded nucleic acid is about 10 to about 100 base pairs. Further provided herein are methods for nucleic acid assembly, wherein the homology sequence of the first double stranded nucleic acid and the homology sequence of the second double stranded nucleic acid are each independently about 10 to about 100 base pairs. Further provided herein are methods for nucleic acid assembly, wherein the homology sequence of the first double stranded nucleic acid or the homology sequence of the second double stranded nucleic acid is about 20 to about 80 base pairs. Further provided herein are methods for nucleic acid assembly, wherein the homology sequence of the first double stranded nucleic acid and the homology sequence of the second double stranded nucleic acid are each independently about 20 to about 80 base pairs. Further provided herein are methods for nucleic acid assembly, wherein the homology sequence of the first double stranded nucleic acid or the homology sequence of the second double stranded nucleic acid is about 40 base pairs. Further provided herein are methods for nucleic acid assembly, wherein the homology sequence of the first double stranded nucleic acid and the homology sequence of the second double stranded nucleic acid are each independently about 40 base pairs. Further provided herein are methods for nucleic acid assembly, wherein a concentration of the exonuclease III is in a range of about 0.1 U to about 10 U. Further provided herein are methods for nucleic acid assembly, wherein a concentration of the exonuclease III is in a range of about 0.5 U to about 1.0 U. Further provided herein are methods for nucleic acid assembly, wherein a concentration of the exonuclease III is in a range of about 1.0 U to about 2.0 U. Further provided herein are methods for nucleic acid assembly, wherein a concentration of the polymerase is in a range of about 0.1 U to about 2 U. Further provided herein are methods for nucleic acid assembly, wherein a concentration of the polymerase is about 0.1 U. Further provided herein are methods for nucleic acid assembly, wherein a concentration of the polymerase is about 0.2 U. Further provided herein are methods for nucleic acid assembly, wherein a concentration of the ligase is up to about 2.0 U. Further provided herein are methods for nucleic acid assembly, wherein a concentration of the ligase is in a range of about 4.0 U to about 8.0 U. Further provided herein are methods for nucleic acid assembly, wherein a concentration of the ligase is in a range of 0.5 U to about 1.0 U. Further provided herein are methods for nucleic acid assembly, wherein the first double stranded nucleic acid or the second double stranded nucleic acid is a linear fragment. Further provided herein are methods for nucleic acid assembly, wherein a product following step (c) is a linear fragment. Further provided herein are methods for nucleic acid assembly, wherein a product following step (c) is a circular fragment.

Provided herein are methods for nucleic acid assembly, comprising: (a) providing a first double stranded nucleic acid comprising in 5' to 3' order: a 5' flanking adapter, a homology sequence, an insert sequence, and a 3' flanking adapter sequence; (b) providing a second double stranded nucleic acid comprising in 5' to 3' order: a 5' flanking adapter, a homology sequence, an insert sequence, and a 3' flanking adapter sequence; and (c) mixing the first double stranded nucleic acid and the second double stranded nucleic acid with a reaction mixture comprising, a flap endonuclease, wherein the flap endonuclease results in a 5' overhang; a polymerase; and a ligase.

Provided herein are methods for nucleic acid assembly, comprising: (a) providing a first double stranded nucleic acid comprising in 5' to 3' order: a 5' flanking adapter sequence, a homology sequence, an insert sequence, and a 3' flanking adapter sequence; (b) providing a second double stranded nucleic acid comprising in 5' to 3' order: a 5' flanking adapter sequence, a homology sequence, an insert sequence, and a 3' flanking adapter sequence; and (c) mixing the first double stranded nucleic acid and the second double stranded nucleic acid with a reaction mixture comprising about 0.5 U to about 1.0 U of an exonuclease, about 0.32 U to about 4.8 U of a flap endonuclease, about 0.1 U to about 2 U of a polymerase, and up to about 2.0 U of a ligase.

Provided herein are methods for nucleic acid assembly, comprising: (a) providing a first double stranded nucleic acid comprising in 5' to 3' order: a 5' flanking adapter sequence, a homology sequence, an insert sequence, and a 3' flanking adapter sequence; (b) providing a second double stranded nucleic acid comprising in 5' to 3' order: a 5' flanking adapter sequence, a homology sequence, an insert sequence, and a 3' flanking adapter sequence; and (c) mixing the first double stranded nucleic acid and the second double stranded nucleic acid with a reaction mixture comprising about 0.32 U to about 4.8 U of a flap endonuclease, about 0.1 U to about 2 U of a polymerase, and up to about 2.0 U of a ligase.

Provided herein are methods for nucleic acid assembly, comprising: (a) providing a plurality of polynucleotides, wherein each of the polynucleotides do not comprise a terminal region of sequence homology to another polynucleotide of the plurality of polynucleotides; and (b) mixing the plurality of polynucleotides with an exonuclease, an endonuclease, a polymerase, and a ligase, wherein the plurality of polynucleotides are annealed in a processive predetermined order based on a complementary sequence between adjacent polynucleotides. Further provided herein are methods for nucleic acid assembly, wherein the exonuclease is exonuclease III. Further provided herein are methods for nucleic acid assembly, wherein the endonuclease is a flap endonuclease. Further provided herein are methods for nucleic acid assembly, wherein the flap endonuclease is flap endonuclease 1, exonuclease 1, XPG, Dna2, or GEN1. Further provided herein are methods for nucleic acid assembly, wherein a concentration of the flap endonuclease 1 is in a range of about 0.32 U to about 4.8 U. Further provided herein are methods for nucleic acid assembly, wherein the polymerase comprises 5' to 3' polymerase activity. Further provided herein are methods for nucleic acid assembly, wherein the polymerase is a DNA polymerase. Further provided herein are methods for nucleic acid assembly, wherein the ligase catalyzes joining of at least two nucleic acids. Further provided herein are methods for nucleic acid assembly, wherein a concentration of the exonuclease III is in a range of about 0.1 U to about 10 U. Further provided herein are methods for nucleic acid assembly, wherein a concentration of the polymerase is in a range of about 0.01 U to about 2 U. Further provided herein are methods for nucleic acid assembly, wherein a concentration of the polymerase is about 0.1 U. Further provided herein are methods for nucleic acid assembly, wherein a concentration of the polymerase is about 0.01 U. Further provided herein are methods for nucleic acid assembly, wherein a concentration of the ligase is up to about 2.0 U.

Provided herein are methods for nucleic acid assembly, comprising: (a) providing a first double stranded nucleic acid; (b) providing a second double stranded nucleic acid; (c) providing a third double stranded nucleic acid comprising in 5' to 3' order: a 5' flanking adapter sequence, a first homology sequence to the first double stranded nucleic acid, a second homology sequence to the second double stranded nucleic acid, and a 3' flanking adapter sequence, wherein the first double stranded nucleic acid, the second double stranded nucleic acid, and the third double stranded nucleic acid comprise non-homologous sequences at terminal regions; and (d) mixing the first double stranded nucleic acid, the second double stranded nucleic acid, and the third double stranded nucleic acid with a reaction mixture comprising an exonuclease, an endonuclease, a polymerase, and a ligase. Further provided herein are methods for nucleic acid assembly, wherein the exonuclease is exonuclease III. Further provided herein are methods for nucleic acid assembly, wherein the endonuclease is a flap endonuclease. Further provided herein are methods for nucleic acid assembly, wherein the flap endonuclease is flap endonuclease 1, exonuclease 1, XPG, Dna2, or GEN1. Further provided herein are methods for nucleic acid assembly, wherein a concentration of the flap endonuclease 1 provided is about 0.32 U to about 4.8 U. Further provided herein are methods for nucleic acid assembly, wherein the endonuclease is flap endonuclease 1 provided in a concentration less than about 5.0 U. Further provided herein are methods for nucleic acid assembly, wherein the polymerase comprises 5' to 3' polymerase activity. Further provided herein are methods for nucleic acid assembly, wherein the polymerase is a DNA polymerase. Further provided herein are methods for nucleic acid assembly, wherein the ligase catalyzes joining of at least two nucleic acids. Further provided herein are methods for nucleic acid assembly, wherein the homology sequence of the first double stranded nucleic acid or the homology sequence of the second double stranded nucleic acid is about 10 to about 100 base pairs. Further provided herein are methods for nucleic acid assembly, wherein the homology sequence of the first double stranded nucleic acid and the homology sequence of the second double stranded nucleic acid are each independently about 10 to about 100 base pairs. Further provided herein are methods for nucleic acid assembly, wherein the homology sequence of the first double stranded nucleic acid or the homology sequence of the second double stranded nucleic acid is about 20 to about 80 base pairs. Further provided herein are methods for nucleic acid assembly, wherein the homology sequence of the first double stranded nucleic acid and the homology sequence of the second double stranded nucleic acid are each independently about 20 to about 80 base pairs. Further provided herein are methods for nucleic acid assembly, wherein the homology sequence of the first double stranded nucleic acid or the homology sequence of the second double stranded nucleic acid is about 40 base pairs. Further provided herein are methods for nucleic acid assembly, wherein the homology sequence of the first double stranded nucleic acid and the homology sequence of the second double stranded nucleic acid are each independently about 40 base pairs. Further provided herein are methods for nucleic acid assembly, wherein a concentration of the exonuclease III is in a range of about 0.1 U to about 10 U. Further provided herein are methods for nucleic acid assembly, wherein a concentration of the polymerase is in a range of about 0.01 U to about 2 U. Further provided herein are methods for nucleic acid assembly, wherein a concentration of the ligase is up to about 2.0 U. Further provided herein are methods for nucleic acid assembly, wherein the first double stranded nucleic acid, the second double stranded nucleic acid, or the third double stranded nucleic acid, or any combination thereof is a linear fragment. Further provided herein are methods for nucleic acid assembly, wherein a product following step (d) is a linear fragment. Further provided herein are methods for nucleic acid assembly, wherein a product following step (d) is a circular fragment.

Provided herein are methods for nucleic acid assembly, comprising: (a) providing a first double stranded nucleic acid comprising in 5' to 3' order: a 5' flanking adapter sequence, a homology sequence, an insert sequence, and a 3' flanking adapter sequence; (b) providing a second double stranded nucleic acid comprising in 5' to 3' order: a 5' flanking adapter sequence, a homology sequence, an insert sequence, and a 3' flanking adapter sequence; and (c) mixing the first double stranded nucleic acid and the second double stranded nucleic acid with a reaction mixture comprising an exonuclease, an endonuclease, a polymerase, and a ligase. Further provided herein are methods for nucleic acid assembly, wherein the exonuclease is exonuclease III. Further provided herein are methods for nucleic acid assembly, wherein the endonuclease is a flap endonuclease. Further provided herein are methods for nucleic acid assembly, wherein the flap endonuclease is flap endonuclease 1, exonuclease 1, XPG, Dna2, or GEN1. Further provided herein are methods for nucleic acid assembly, wherein a concentration of the flap endonuclease 1 provided is about 0.32 U to about 4.8 U. Further provided herein are methods for nucleic acid assembly, wherein a concentration of the flap endonuclease 1 provided is less than about 5.0 U. Further provided herein are methods for nucleic acid assembly, wherein the polymerase comprises 5' to 3' polymerase activity. Further provided herein are methods for nucleic acid assembly, wherein the polymerase is a DNA polymerase. Further provided herein are methods for nucleic acid assembly, wherein the ligase catalyzes joining of at least two nucleic acids. Further provided herein are methods for nucleic acid assembly, wherein the homology sequence of the first double stranded nucleic acid or the homology sequence of the second double stranded nucleic acid is about 10 to about 100 base pairs. Further provided herein are methods for nucleic acid assembly, wherein the homology sequence of the first double stranded nucleic acid and the homology sequence of the second double stranded nucleic acid are each independently about 10 to about 100 base pairs. Further provided herein are methods for nucleic acid assembly, wherein the homology sequence of the first double stranded nucleic acid or the homology sequence of the second double stranded nucleic acid is about 20 to about 80 base pairs. Further provided herein are methods for nucleic acid assembly, wherein the homology sequence of the first double stranded nucleic acid and the homology sequence of the second double stranded nucleic acid are each independently about 20 to about 80 base pairs. Further provided herein are methods for nucleic acid assembly, wherein the homology sequence of the first double stranded nucleic acid or the homology sequence of the second double stranded nucleic acid is about 40 base pairs. Further provided herein are methods for nucleic acid assembly, wherein the homology sequence of the first double stranded nucleic acid and the homology sequence of the second double stranded nucleic acid are each independently about 40 base pairs. Further provided herein are methods for nucleic acid assembly, wherein a concentration of the exonuclease III is in a range of about 0.1 U to about 10 U. Further provided herein are methods for nucleic acid assembly, wherein a concentration of the polymerase is in a range of about 0.1 U to about 2 U. Further provided herein are methods for nucleic acid assembly, wherein a concentration of the polymerase is about 0.01 U to about 0.2 U. Further provided herein are methods for nucleic acid assembly, wherein a concentration of the ligase is up to about 2.0 U. Further provided herein are methods for nucleic acid assembly, wherein the first double stranded nucleic acid or the second double stranded nucleic acid or any combination thereof is a linear fragment. Further provided herein are methods for nucleic acid assembly, wherein a product following step (c) is a linear fragment.

Further provided herein are methods for nucleic acid assembly, wherein a product following step (c) is a circular fragment.

Provided herein are methods for nucleic acid assembly, comprising: (a) providing a first double stranded nucleic acid comprising in 5' to 3' order: a 5' flanking adapter sequence, a homology sequence, an insert sequence, and a 3' flanking adapter sequence; (b) providing a second double stranded nucleic acid comprising in 5' to 3' order: a 5' flanking adapter sequence, a homology sequence, an insert sequence, and a 3' flanking adapter sequence; and (c) mixing the first double stranded nucleic acid and the second double stranded nucleic acid with a reaction mixture comprising an exonuclease, an endonuclease, a polymerase, and a ligase at a temperature of about 30° C. to about 60° C. Further provided herein are methods for nucleic acid assembly, wherein the exonuclease is exonuclease III. Further provided herein are methods for nucleic acid assembly, wherein the endonuclease is a flap endonuclease. Further provided herein are methods for nucleic acid assembly, wherein the flap endonuclease is flap endonuclease 1, exonuclease 1, XPG, Dna2, or GEN1. Further provided herein are methods for nucleic acid assembly, wherein a concentration of the flap endonuclease 1 is in a range of about 0.32 U to about 4.8 U. Further provided herein are methods for nucleic acid assembly, wherein the polymerase comprises 5' to 3' polymerase activity. Further provided herein are methods for nucleic acid assembly, wherein the polymerase is a DNA polymerase. Further provided herein are methods for nucleic acid assembly, wherein the ligase catalyzes joining of at least two nucleic acids. Further provided herein are methods for nucleic acid assembly, wherein the homology sequence of the first double stranded nucleic acid or the homology sequence of the second double stranded nucleic acid is about 10 to about 100 base pairs. Further provided herein are methods for nucleic acid assembly, wherein the homology sequence of the first double stranded nucleic acid and the homology sequence of the second double stranded nucleic acid are each independently about 10 to about 100 base pairs. Further provided herein are methods for nucleic acid assembly, wherein the homology sequence of the first double stranded nucleic acid or the homology sequence of the second double stranded nucleic acid is about 20 to about 80 base pairs. Further provided herein are methods for nucleic acid assembly, wherein the homology sequence of the first double stranded nucleic acid and the homology sequence of the second double stranded nucleic acid are each independently about 20 to about 80 base pairs. Further provided herein are methods for nucleic acid assembly, wherein the homology sequence of the first double stranded nucleic acid or the homology sequence of the second double stranded nucleic acid is about 40 base pairs. Further provided herein are methods for nucleic acid assembly, wherein the homology sequence of the first double stranded nucleic acid and the homology sequence of the second double stranded nucleic acid are each independently about 40 base pairs. Further provided herein are methods for nucleic acid assembly, wherein a concentration of the exonuclease III is in a range of about 0.1 U to about 10 U. Further provided herein are methods for nucleic acid assembly, wherein a concentration of the polymerase is in a range of about 0.01 U to about 2 U. Further provided herein are methods for nucleic acid assembly, wherein a concentration of the polymerase is about 0.1 U. Further provided herein are methods for nucleic acid assembly, wherein a concentration of the polymerase is about 0.01 U. Further provided herein are methods for nucleic acid assembly, wherein a concentration of the ligase is up to about 2.0 U. Further provided herein are methods for nucleic acid assembly, wherein the first double stranded nucleic acid or the second double stranded nucleic acid or any combination thereof is a linear fragment. Further provided herein are methods for nucleic acid assembly, wherein a product following step (c) is a linear fragment. Further provided herein are methods for nucleic acid assembly, wherein a product following step (c) is a circular fragment.

Provided herein are methods for nucleic acid assembly, comprising: (a) providing a first double stranded nucleic acid comprising in 5' to 3' order: a 5' flanking adapter, a homology sequence, an insert sequence, and a 3' flanking adapter sequence; (b) providing a second double stranded nucleic acid comprising in 5' to 3' order: a 5' flanking adapter, a homology sequence, an insert sequence, and a 3' flanking adapter sequence; and (c) mixing the first double stranded nucleic acid and the second double stranded nucleic acid with a reaction mixture comprising, an endonuclease, wherein the endonuclease results in a 5' overhang; a polymerase; and a ligase.

Provided herein are methods for nucleic acid assembly, comprising: (a) providing a first double stranded nucleic acid comprising in 5' to 3' order: a 5' flanking adapter sequence, a homology sequence, an insert sequence, and a 3' flanking adapter sequence; (b) providing a second double stranded nucleic acid comprising in 5' to 3' order: a 5' flanking adapter sequence, a homology sequence, an insert sequence, and a 3' flanking adapter sequence; and (c) mixing the first double stranded nucleic acid and the second double stranded nucleic acid with a reaction mixture comprising about 0.5 U to about 1.0 U of an exonuclease, about 0.32 U to about 4.8 U of an endonuclease, about 0.01 U to about 2 U of a polymerase, and up to about 2.0 U of a ligase.

Provided herein are methods for nucleic acid assembly, comprising: (a) providing a first double stranded nucleic acid comprising in 5' to 3' order: a 5' flanking adapter sequence, a homology sequence, an insert sequence, and a 3' flanking adapter sequence; (b) providing a second double stranded nucleic acid comprising in 5' to 3' order: a 5' flanking adapter sequence, a homology sequence, an insert sequence, and a 3' flanking adapter sequence; and (c) mixing the first double stranded nucleic acid and the second double stranded nucleic acid with a reaction mixture comprising about 0.32 U to about 4.8 U of an endonuclease, about 0.01 U to about 2 U of a polymerase, and up to about 2.0 U of a ligase.

Provided herein are methods for nucleic acid assembly, comprising: (a) providing a first double stranded nucleic acid comprising in 5' to 3' order: a 5' flanking adapter sequence, a homology sequence, an insert sequence, and a 3' flanking adapter sequence; (b) providing a second double stranded nucleic acid comprising in 5' to 3' order: a 5' flanking adapter sequence, a homology sequence, an insert sequence, and a 3' flanking adapter sequence; and (c) mixing the first double stranded nucleic acid and the second double stranded nucleic acid with a reaction mixture comprising at least one enzyme comprising 3' or 5' exonuclease activity, a polymerase, and a ligase, wherein the at least one enzyme comprising 3' or 5' exonuclease activity removes a 5' flanking adapter sequence or 3' flanking adapter sequence. Further provided herein are methods for nucleic acid assembly, wherein the at least one enzyme comprising 3' or 5' exonuclease activity is exonuclease III. Further provided herein are methods for nucleic acid assembly, wherein the polymerase comprises 5' to 3' polymerase activity. Further provided herein are methods for nucleic acid assembly, wherein the polymerase is a DNA polymerase. Further provided herein are methods for nucleic acid assembly, wherein the ligase catalyzes joining of at least two nucleic acids. Further provided herein are methods for nucleic acid assembly, wherein the homology sequence of the first double stranded nucleic acid or the homology sequence of the second double stranded nucleic acid is about 40 base pairs. Further provided herein are methods for nucleic acid assembly, wherein the homology sequence of the first double stranded nucleic acid and the homology sequence of the second double stranded nucleic acid are each independently about 40 base pairs. Further provided herein are methods for nucleic acid assembly, wherein the homology sequence of the first double stranded nucleic acid or the homology sequence of the second double stranded nucleic acid is about 10 to about 100 base pairs. Further provided herein are methods for nucleic acid assembly, wherein the homology sequence of the first double stranded nucleic acid and the homology sequence of the second double stranded nucleic acid are each independently about 10 to about 100 base pairs. Further provided herein are methods for nucleic acid assembly, wherein the homology sequence of the first double stranded nucleic acid or the homology sequence of the second double stranded nucleic acid is about 20 to about 80 base pairs. Further provided herein are methods for nucleic acid assembly, wherein the homology sequence of the first double stranded nucleic acid and the homology sequence of the second double stranded nucleic acid are each independently about 20 to about 80 base pairs. Further provided herein are methods for nucleic acid assembly, wherein a concentration of the exonuclease III is in a range of about 0.1 U to about 10 U.

Provided herein are methods for nucleic acid assembly, comprising: (a) providing at least 10 different fragments, wherein each of the at least 10 different fragments do not comprise a terminal region of sequence homology to another fragment of the at least 10 different fragments; and (b) mixing the at least 10 different fragments with a plurality of enzymes, wherein the plurality of enzymes is selected from an endonuclease, an exonuclease, a polymerase, and a ligase to form a nucleic acid. Further provided herein are methods for nucleic acid assembly, wherein the nucleic acid is attached to a vector sequence. Further provided herein are methods for nucleic acid assembly, wherein the nucleic acid is 50 bases to 200 bases in length. Further provided herein are methods for nucleic acid assembly, wherein the nucleic acid is 100 bases to 2000 bases in length. Further provided herein are methods for nucleic acid assembly, wherein the exonuclease is exonuclease III. Further provided herein are methods for nucleic acid assembly, wherein the endonuclease is a flap endonuclease. Further provided herein are methods for nucleic acid assembly, wherein the flap endonuclease is flap endonuclease 1, exonuclease 1, XPG, Dna2, or GEN1. Further provided herein are methods for nucleic acid assembly, wherein the polymerase comprises 5' to 3' polymerase activity. Further provided herein are methods for nucleic acid assembly, wherein the polymerase is a DNA polymerase. Further provided herein are methods for nucleic acid assembly, wherein the ligase catalyzes joining of at least two nucleic acids.

Provided herein are methods for nucleic acid assembly, comprising: (a) providing a plurality of polynucleotides, wherein each of the polynucleotides do not comprise a terminal region of sequence homology to another polynucleotide of the plurality of polynucleotides; and (b) mixing the plurality of polynucleotides with a 3' to 5' exonuclease, a thermostable endonuclease, a high fidelity polymerase, and a thermostable ligase, wherein the plurality of polynucleotides are annealed in a processive predetermined order based on a complementary sequence between adjacent polynucleotides. Further provided herein are methods for nucleic acid assembly, wherein the exonuclease is exonuclease III. Further provided herein are methods for nucleic acid assembly, wherein the endonuclease is a flap endonuclease. Further provided herein are methods for nucleic acid assembly, wherein the flap endonuclease is flap endonuclease 1, exonuclease 1, XPG, Dna2, or GEN1. Further provided herein are methods for nucleic acid assembly, wherein the endonuclease is flap endonuclease 1 provided in a concentration of ranging from about 0.32 U to about 4.8 U. Further provided herein are methods for nucleic acid assembly, wherein the polymerase comprises 5' to 3' polymerase activity. Further provided herein are methods for nucleic acid assembly, wherein the polymerase is a DNA polymerase. Further provided herein are methods for nucleic acid assembly, wherein the ligase catalyzes joining of at least two nucleic acids. Further provided herein are methods for nucleic acid assembly, wherein a concentration of the exonuclease III is in a range of about 0.1 U to about 10 U. Further provided herein are methods for nucleic acid assembly, wherein a concentration of the polymerase is in a range of about 0.01 U to about 2 U. Further provided herein are methods for nucleic acid assembly, wherein a concentration of the ligase is up to about 2.0 U.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Definitions

Figure 1A:
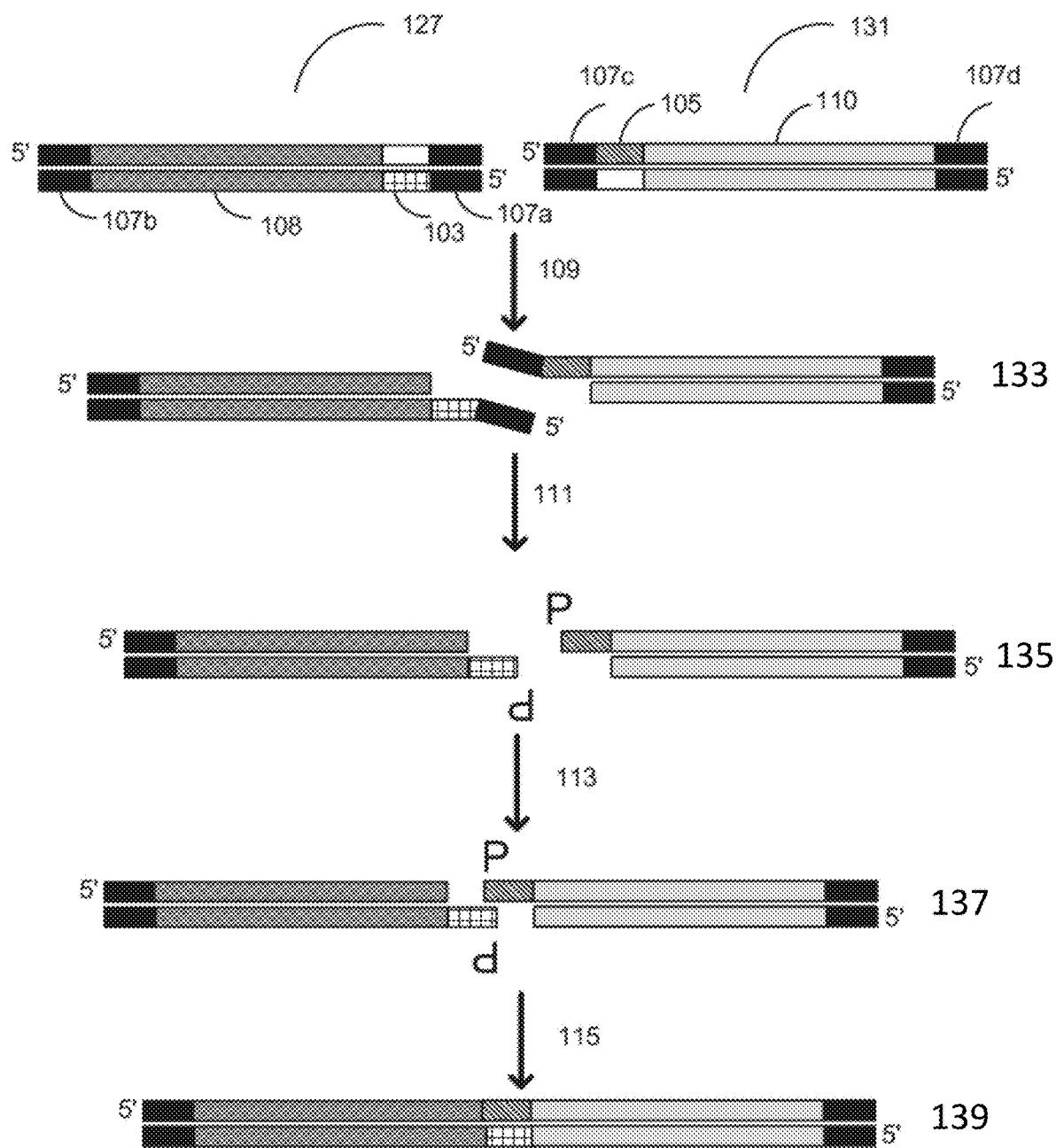
FIG. 1A depicts a schematic for flap endonuclease mediated nucleic acid assembly.

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "nucleic acid" encompasses double- or triple-stranded nucleic acids, as well as single-stranded molecules. In double- or triple-stranded nucleic acids, the nucleic acid strands need not be coextensive (i.e., a double-stranded nucleic acid need not be double-stranded along the entire length of both strands). Nucleic acid sequences, when provided, are listed in the 5' to 3' direction, unless stated otherwise. Methods described herein provide for the generation of isolated nucleic acids. Methods described herein additionally provide for the generation of isolated and purified nucleic acids. A "nucleic acid" as referred to herein can comprise at least 5, 10, 20, 30, 40, 50, 60, 70, 80, 90, 100, 125, 150, 175, 200, 225, 250, 275, 300, 325, 350, 375, 400, 425, 450, 475, 500, 600, 700, 800, 900, 1000, 1100, 1200, 1300, 1400, 1500, 1600, 1700, 1800, 1900, 2000, or more bases in length. Moreover, provided herein are methods for the synthesis of any number of polypeptide-segments encoding nucleotide sequences, including sequences encoding non-ribosomal peptides (NRPs), sequences encoding non-ribosomal peptide-synthetase (NRPS) modules and synthetic variants, polypeptide segments of other modular proteins, such as antibodies, polypeptide segments from other protein families, including non-coding DNA or RNA, such as regulatory sequences e.g. promoters, transcription factors, enhancers, siRNA, shRNA, RNAi, miRNA, small nucleolar RNA derived from microRNA, or any functional or structural DNA or RNA unit of interest. The following are non-limiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, complementary DNA (cDNA), which is a DNA representation of mRNA, usually obtained by reverse transcription of messenger RNA (mRNA) or by amplification; DNA molecules produced synthetically or by amplification, genomic DNA, recombinant polynucleotides, branched polynucleotides, plasmids, vectors, isolated DNA of any sequence, isolated RNA of any sequence, nucleic acid probes, and primers. cDNA encoding for a gene or gene fragment referred to herein may comprise at least one region encoding for exon sequences without an intervening intron sequence in the genomic equivalent sequence.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

Primers referred to in the exemplary workflows mentioned herein as "universal primers," are short polynucleotides that recognize a primer binding site common to multiple DNA fragments. However, these workflows are not limited to only use of universal primers, and fragment-specific primers may be incorporated in addition or alternatively. In addition, while exemplary workflows described herein refer to assembly of gene fragments, they are not limited as such and are applicable to the assembly of longer nucleic acids in general.

Seamless Nucleic Acid Assembly

Provided herein are methods for assembly of nucleic acids with increased efficiency and accuracy. Further provided herein are methods of assembly of nucleic acids into long genes. Polynucleotides described herein are assembled into longer nucleic acids by assembly methods comprising an endonuclease or an exonuclease, optionally in conjunction with additional enzymes.

An exemplary process for assembly of nucleic acids using a flap endonuclease is depicted in FIG. 1A. Flap endonuclease mediated nucleic acid assembly is performed with first gene fragment 127 and second gene fragment 131. A bottom strand of the first gene fragment 127 is designed to comprise from 5' to 3' a first universal primer binding sequence 107a, a homology sequence 103, an insert sequence 108, and a second universal primer binding sequence 107b. A top strand of second gene fragment 131 is designed to comprise from 5' to 3' a first universal primer binding sequence 107c, a homology sequence 105, an insert sequence 110, and a second universal primer binding sequence 107d. The first gene fragment 127 and the second gene fragment 131 are contacted with a reaction mixture comprising an exonuclease, a flap endonuclease, a polymerase, and a ligase. The exonuclease digests 109 a 3' end to expose homology sites resulting in fragments 133. In some instances, the exonuclease is exonuclease III. A flap endonuclease cleaves 111 a 5' flap resulting in fragments 135. In some instances, the flap endonuclease is flap endonuclease 1 (FEN-1). A polymerase fills in gaps 113 and leaves a nick resulting in fragments 137. A ligase then seals 115 the nick resulting in fragments 139.

Figure 1B:
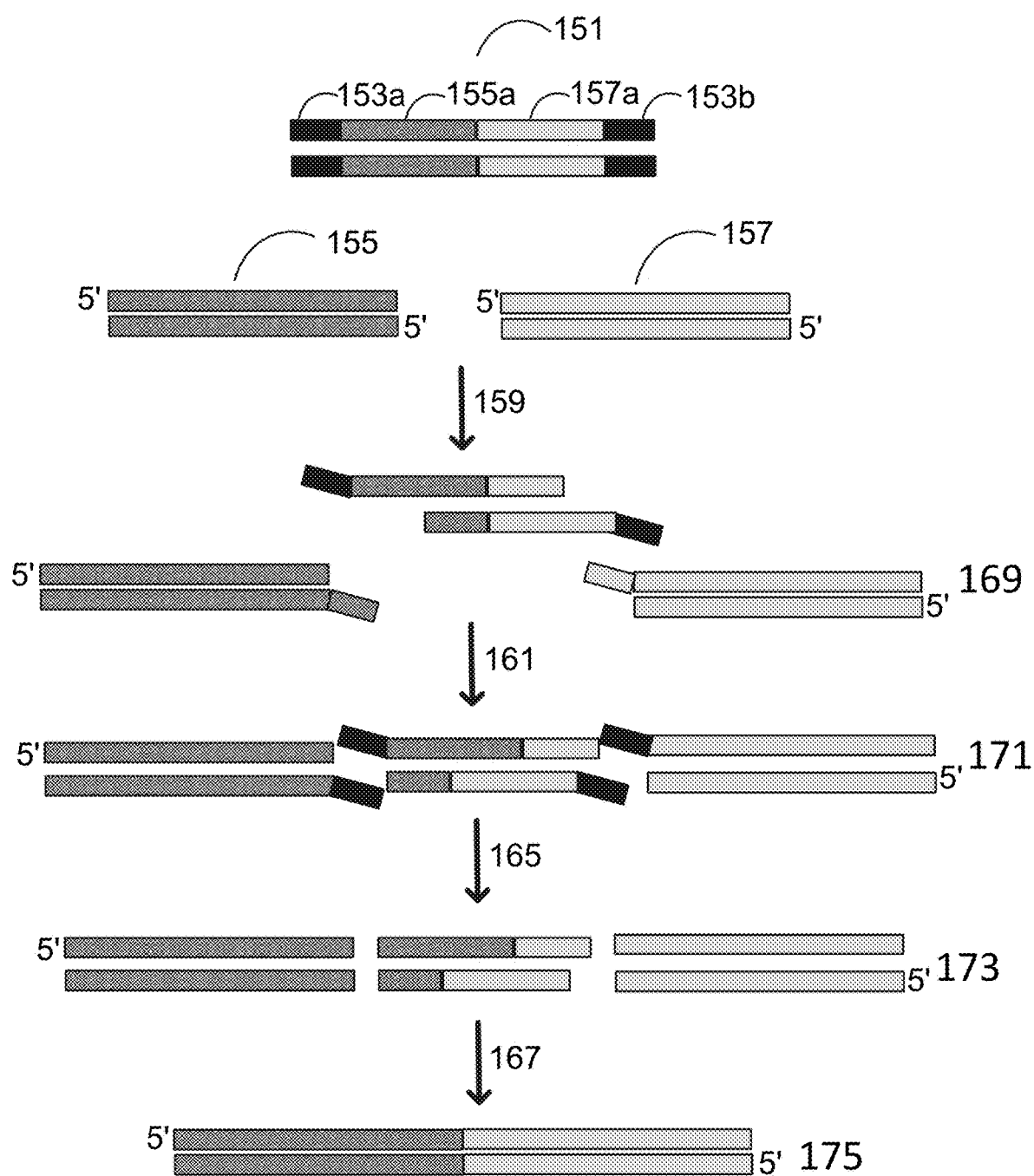
FIG. 1B depicts a schematic for flap endonuclease mediated nucleic acid assembly using a bridge assembly.

An exemplary process for assembly of nucleic acids using a flap endonuclease and a bridge assembly method is depicted in FIG. 1B. Flap endonuclease mediated nucleic acid assembly is performed with a double stranded nucleic acid bridge 151, first gene fragment 155, and second gene fragment 157. The double stranded nucleic acid bridge 151 comprises a first universal primer binding sequence 153a, a first homology sequence 155a homologous to the first gene fragment 155, a second homology sequence 157a homologous to the second gene fragment 157, and a second universal primer binding sequence 153b. The double stranded nucleic acid bridge 151, first gene fragment 155, and second gene fragment 157 are contacted with a reaction mixture comprising an exonuclease, a flap endonuclease, a polymerase, and a ligase. The exonuclease digests 159 a 3' end to expose homology sites resulting in fragments 169. In some instances, the exonuclease is exonuclease III. A polymerase fills in gaps 161 and leaves a nick resulting in fragments 171. A flap endonuclease cleaves 165 a 5' flap resulting in fragments 173. In some instances, the flap endonuclease is flap endonuclease 1 (FEN-1). A ligase then seals 167 the nick resulting in fragments 175. In some instances, the ligase is ampligase.

Provided herein are methods for enzymatic mediated nucleic acid assembly. In some instances, the enzymatic mediated nucleic acid assembly comprises addition of homologous sequences to gene fragments. In some instances, de novo synthesized gene fragments already comprise homology sequences. In some instances, the enzymatic mediated nucleic acid assembly comprises use of an enzymatic mixture. In some instances, the enzymatic mixture comprises an endonuclease. In some instances, the enzymatic mixture optionally comprises an exonuclease, a polymerase, or a ligase. In some instances, the enzymatic mixture comprises an exonuclease, an endonuclease, a polymerase, and a ligase. In some instances, the enzymatic mixture comprises an endonuclease, a polymerase, and a ligase. In some instances, the endonuclease is a flap endonuclease. In some instances, enzymatic mediated nucleic acid assembly results in improved efficiency. In some instances, the enzymatic mixture comprises enzymes that are not restriction enzymes. In some instances, the enzymatic mixture comprises enzymes that are structure specific enzymes. In some instances, the enzymatic mixture comprises enzymes that are structure specific enzymes and not sequence specific enzymes.

Provided herein are methods where site-specific base excision reagents comprising one or more enzymes are used as cleavage agents that cleave only a single-strand of double-stranded DNA at a cleavage site. A number of repair enzymes are suitable alone or in combination with other agents to generate such nicks. An exemplary list of repair enzymes is provided in Table 1. Homologs or non-natural variants of the repair enzymes, including those in Table 1, are also be used according to various embodiments. Any of the repair enzymes for use according to the methods and compositions described herein may be naturally occurring, recombinant or synthetic. In some instances, a DNA repair enzyme is a native or an in vitro-created chimeric protein with one or more activities. Cleavage agents, in various embodiments, comprise enzymatic activities, including enzyme mixtures, which include one or more of nicking endonucleases, AP endonucleases, glycosylases and lyases involved in base excision repair.

Repair enzymes are found in prokaryotic and eukaryotic cells. Some enzymes having applicability herein have glycosylase and AP endonuclease activity in one molecule. AP endonucleases are classified according to their sites of incision. Class I AP endonucleases and class II AP endonucleases incise DNA at the phosphate groups 3' and 5' to the baseless site leaving 3'-OH and 5'-phosphate termini. Class III and class IV AP endonucleases also cleave DNA at the phosphate groups 3' and 5 'to the baseless site, but they generate a 3'-phosphate and a 5'-OH. Examples of polynucleotide cleavage enzymes used include DNA repair enzymes are listed in Table 1.

TABLE 1

DNA Repair Enzymes.

| Gene Name | Activity | Accession Number |
| --- | --- | --- |
| UNG | Uracil-DNA glycosylase | NM_080911 |
| SMUG1 | Uracil-DNA glycosylase | NM_014311 |
| MBD4 | Removes U or T opposite G at CpG sequences | NM_003925 |
| TDG | Removes U, T or ethenoC opposite G | NM_003211 |
| OGG1 | Removes 8-oxoG opposite C | NM_016821 |
| MUTYH (MYH) | Removes A opposite 8-oxoG | NM_012222 |
| NTHL1 (NTH1) | Removes Ring-saturated or fragmented pyrimidines | NM_002528 |
| MPG | Removes 3-meA, ethenoA, hypoxanthine | NM_002434 |
| NEIL1 | Removes thymine glycol | NM_024608 |
| NEIL2 | Removes oxidative products of pyrimidines | NM_145043 |
| XPC | Binds damaged DNA as complex with RAD23B, CETN2 | NM_004628 |
| RAD23B (HR23B) | Binds damaged DNA as complex with XPC, CETN2 | NM_002874 |
| CETN2 | Binds damaged DNA as complex with XPC, RAD23B | NM_004344 |
| RAD23A (HR23A) | Substitutes for HR23B | NM_005053 |
| XPA | Binds damaged DNA in preincision complex | NM_000380 |
| RPA1 | Binds DNA in preincision complex | NM_002945 |
| RPA2 | Binds DNA in preincision complex | NM_002946 |
| RPA3 | Binds DNA in preincision complex | NM_002947 |
| ERCC5 (XPG) | 3' incision | NM_000123 |
| ERCC1 | 5' incision subunit | NM_001983 |
| ERCC4 (XPF) | 5' incision subunit | NM_005236 |
| LIG1 | DNA joining | NM_000234 |
| CKN1(CSA) | Cockayne syndrome; Needed for transcription-coupled NER | NM_000082 |
| ERCC6 (CSB) | Cockayne syndrome; Needed for transcription-coupled NER | NM_000124 |
| XAB2 (HCNP) | Cockayne syndrome; Needed for transcription-coupled NER | NM_020196 |
| DDB1 | Complex defective in XP group E | NM_001923 |
| DDB2 | DDB1, DDB2 | NM_000107 |
| MMS19L (MMS 19) | Transcription and NER | NM_022362 |
| FEN1 (DNase IV) | Flap endonuclease | NM_004111 |
| SPO11 | endonuclease | NM_012444 |
| FLJ35220 (ENDOV) | incision 3' of hypoxanthine and uracil | NM_173627 |
| FANCA | Involved in tolerance or repair of DNA crosslinks | NM_000135 |
| FANCB | Involved in tolerance or repair of DNA crosslinks | NM_152633 |
| FANCC | Involved in tolerance or repair of DNA crosslinks | NM_000136 |
| FANCD2 | Involved in tolerance or repair of DNA crosslinks | NM_033084 |
| FANCE | Involved in tolerance or repair of DNA crosslinks | NM_021922 |
| FANCF | Involved in tolerance or repair of DNA crosslinks | NM_022725 |

TABLE 1-continued

DNA Repair Enzymes.

| Gene Name | Activity | Accession Number |
| --- | --- | --- |
| FANCG (XRCC9) | Involved in tolerance or repair of DNA crosslinks | NM_004629 |
| FANCL | Involved in tolerance or repair of DNA crosslinks | NMO18062 |
| DCLRE1A (SNM1) | DNA crosslink repair | NM_014881 |
| DCLRE1B (SNM1B) | Related to SNM1 | NM_022836 |
| NEIL3 | Resembles NEIL1 and NEIL2 | NM_18248 |
| ATRIP (TREX1) | ATR-interacting protein 5' alternative ORF of the TREX1/ATRIP gene | NM_130384 |
| NTH | Removes damaged pyrimidines | NP_416150.1 |
| NEI | Removes damaged pyrimidines | NP_415242.1 |
| NFI | Deoxyinosine 3' endonuclease | NP_418426.1 |
| MUTM | Formamidopyrimidine DNA glycosylase | NP_418092.1 |
| UNG | Uracil-DNA glycosylase | NP_417075.1 |
| UVRA | DNA excision repair enzyme complex | NP_418482.1 |
| UVRB | DNA excision repair enzyme complex | NP_415300.1 |
| UVRC | DNA excision repair enzyme complex | NP_416423.3 |
| DENV | Pyrimidine dimer glycosylase | NP_049733.1 |

Provided herein are methods for enzymatic mediated nucleic acid assembly, wherein gene fragments or genes for assembly comprise a homology sequence. In some instances, the homology sequence comprises at least or about 5, 10, 20, 30, 40, 50, 60, 70, 80, 90, 100, or more than 100 base pairs. In some instance, the number of base pairs is 40 base pairs. In some instances, the number of base pairs has a range of about 5 to 100, 10 to 90, 20 to 80, 30 to 70, or 40 to 60 base pairs.

Provided herein are methods for enzymatic mediated nucleic acid assembly, wherein gene fragments or genes for assembly do not comprise a homology sequence. In some instances, methods for enzymatic mediated nucleic acid assembly of de novo synthesized gene fragments without a homology sequence comprise assembly using a nucleic acid bridge. In some instances, the nucleic acid bridge comprises DNA or RNA. In some instances, the nucleic acid bridge comprises DNA. In some instances, the nucleic acid bridge is double stranded. In some instances, the nucleic acid bridge is single stranded.

Provided herein are methods for enzymatic mediated nucleic acid assembly using a nucleic acid bridge, wherein the nucleic acid bridge comprises one or more universal primer binding sequences. In some instances, the nucleic acid bridge comprises at least or about 1, 2, 3, 4, 5, 6, 7, 8, or more than 8 universal primer binding sequences. In some instances, the nucleic acid bridge further comprises a homology sequence. In some instances, the homology sequence is homologous to a de novo synthesized gene fragment. In some instances, the nucleic acid bridge further comprises one or more homology sequences. For example, the nucleic acid bridge comprises one or more homology sequences that are homologous to different de novo synthesized gene fragments. In some instances, the nucleic acid bridge comprises 1, 2, 3, 4, 5, 6, 7, 8, 9, 10, or more than 10 homology sequences. In some instances, the homology sequence comprises at least or about 5, 10, 20, 30, 40, 50, 60, 70, 80, 90, 100, or more than 100 base pairs. In some instances, the number of base pairs is 40 base pairs. In some instance, the number of base pairs is 50 base pairs. In some instances, the number of base pairs has a range of about 5 to 100, 10 to 90, 20 to 80, 30 to 70, or 40 to 60 base pairs.

Provided herein are methods for enzymatic mediated nucleic acid assembly, wherein a double stranded nucleic acid is contacted with an enzyme comprising exonuclease activity. In some instances, the exonuclease comprises 3' exonuclease activity. Exemplary exonucleases comprising 3'exonuclease activity include, but are not limited to, exonuclease I, exonuclease III, exonuclease V, exonuclease VII, and exonuclease T. In some instances, the exonuclease comprises 5' exonuclease activity. Exemplary exonucleases comprising 5' exonuclease activity include, but are not limited to, exonuclease II, exonuclease IV, exonuclease V, exonuclease VI, exonuclease VII, exonuclease VIII, T5 exonuclease, and T7 exonuclease. In some instances, the exonuclease is exonuclease III (ExoIII). Exonucleases include wild-type exonucleases and derivatives, chimeras, and/or mutants thereof. Mutant exonucleases include enzymes comprising one or more mutations, insertions, deletions or any combination thereof within the amino acid or nucleic acid sequence of an exonuclease.

In some instances, the exonuclease is used at a temperature optimal for enzymatic activity, for example, a temperature in a range of about 25-80° C., 25-70° C., 25-60° C., 25-50° C., or 25-40° C. In some instances, the temperature is about 37° C. In some instances, the temperature is about 50° C. In some instances, the temperature is about 55° C. In some instances, the temperature is about 65° C. In some instances, the temperature is at least or about 15° C., 20° C., 25° C., 30° C., 35° C., 40° C., 45° C., 50° C., 55° C., 60° C., 65° C., 70° C., 75° C., 80° C., or more than 80° C.

In some instances, methods for enzymatic mediated nucleic acid assembly do not comprise using an exonuclease. In some instances, methods for enzymatic mediated nucleic acid assembly comprise using an exonuclease. In some instances, one or more exonucleases are used. For example, at least or about 1, 2, 3, 4, 5, 6, or more than 6 exonucleases are used. In some instances, the exonuclease comprises 5' to 3' exonuclease activity. In some instances, the exonuclease comprises 3' to 5' exonuclease activity. In some instances, methods comprise contacting double stranded DNA with an endonuclease. In some instances, the endonuclease is a flap endonuclease. In some instances, methods comprise contacting double stranded DNA with a flap endonuclease, a ligase, or a polymerase. In some instances, the flap endonuclease is flap endonuclease 1.

Provided herein are methods wherein a double stranded nucleic acid is treated with an enzyme comprising endonuclease activity. In some instances, the endonuclease comprises 5' nuclease activity. In some instances, the endonuclease comprises 3' nuclease activity. In some instances, the endonuclease is a flap endonuclease. In some instances, the flap endonuclease comprises 5' nuclease activity. In some instances, the flap endonuclease is a member of a 5'-nuclease family of enzymes. Exemplary 5'-nuclease enzymes include, but are not limited to, flap endonuclease 1, exonuclease 1, xeroderma pigmentosum complementation group G (XPG), Dna2, and gap endonuclease 1 (GEN1). In some instances, the flap endonuclease is flap endonuclease 1. In some instances, the flap endonuclease comprises 3' nuclease activity. Exemplary flap endonucleases with 3' nuclease activity include, but are not limited to, RAG1, RAG2, and MUS81. In some instances, the flap endonuclease is an archaeal, bacteria, yeast, plant, or mammalian flap endonuclease. Exemplary 5'-nuclease and 3' nuclease enzymes are seen in Table 2.

TABLE 2

Exemplary Nuclease Enzymes

| Name | Species | Protein Accession Number |
|---|---|---|
| flap endonuclease 1 | Homo sapiens | NP_004102.1 |
| flap endonuclease 1 | Mus musculus | NP_001258544.1 |
| flap endonuclease 1 | Pyrococcus furiosis | O93634 |
| exonuclease 1 | Homo sapiens | AAH07491.1 |
| XPG | Homo sapiens | EAX09071.1 |
| Dna2 | Homo sapiens | NP_001073918.2 |
| GEN1 | Homo sapiens | NP_001123481.2 |
| RAG1 | Homo sapiens | AAH37344.1 GI |
| RAG2 | Homo sapiens | NP_001230715. |
| MUS81 | Homo sapiens | Q96NY9.3 |

In some instances, the endonuclease is used at a temperature optimal for enzymatic activity, for example, a temperature of 25-80° C., 25-70° C., 25-60° C., 25-50° C., or 25-40° C. In some instances, the temperature is about 50° C. In some instances, the temperature is about 55° C. In some instances, the temperature is about 65° C. In some instances, the temperature is at least or about 15° C., 20° C., 25° C., 30° C., 35° C., 40° C., 45° C., 50° C., 55° C., 60° C., 65° C., 70° C., 75° C., 80° C., or more than 80° C. In some instances, the endonuclease is a thermostable endonuclease. A thermostable endonuclease may include endonucleases that are functional at temperatures at least or about 60° C., 65° C., 70° C., 75° C., 80° C., or more than 80° C. In some instances, the endonuclease is a flap endonuclease. In some instances, the flap endonuclease is a thermostable flap endonuclease.

Provided herein are methods for nucleic acid assembly, wherein the ratio of the endonuclease to the exonuclease is from about 0.1:1 to about 1:5. In some instances, the endonuclease is a flap endonuclease. In some instances, the ratio of the endonuclease to the exonuclease is at least or about 0.2:1, 0.25:1, 0.5:1, 0.75:1, 1:1, 1:1.5, 1:2, 1:3, 1:4, 1:5, or more than 1:5. In some instances, the ratio of the endonuclease to the exonuclease is at least or about 1:1, 1:0.9, 1:0.85, 1:0.8, 1:0.75, 1:0.7, 1:0.65, 1:0.6, 1:0.55, 1:0.5, 1:0.45, 1:0.4, 1:0.35, 1:0.3, 1:0.25, 1:0.2, 1:0.15, 1:0.1, or less than 1:0.1.

Provided herein are methods for nucleic acid assembly comprising an exonuclease, wherein the concentration of the exonuclease is from about 0.1 U to about 20 U or more. For example, the concentration of the exonuclease is at least or about 0.1 U, 0.25 U, 0.5 U, 0.75 U, 1 U, 1.6 U, 2 U, 3 U, 4 U, 5 U, 6 U, 7 U, 8 U, 9 U, 10 U, 12 U, 14 U, 16 U, 18 U, 20 U, or more than 20 U. In some instances, the concentration of the exonuclease is in a range of about 0.5 U to about 1.0 U. In some instances, the concentration of the exonuclease is from about 1.0 U to about 2.0 U. In some instances, the concentration of the exonuclease is about 1.6 U. In some instances, the concentration of the exonuclease is about 5.0 U. In some instances, the concentration of the exonuclease ranges from about 0.1 U to 20 U, 0.25 U to 18 U, 0.5 U to 16 U, 0.75 U to 14 U, 1 U to 12 U, 2 U to 10 U, 3 U to 9 U, or 4 U to 8 U.

Methods described herein for enzymatic mediated nucleic acid assembly may comprise an endonuclease, wherein the concentration of the endonuclease is from about 0.25 U to about 12 U or more. In some instances, the endonuclease is a flap endonuclease. Exemplary concentrations of the endonuclease, include, but are not limited to, at least or about 0.25 U, 0.5 U, 0.75 U, 1 U, 2 U, 3 U, 4 U, 5 U, 6 U, 7 U, 8 U, 9 U, 10 U, 11 U, 12 U, or more than 12 U. In some instances, the concentration of the endonuclease is 0.32 U.

In some instances, the concentration of the endonuclease is 1.6 U. In some instances, the concentration of the endonuclease is in a range of about 0.32 U to about 4.8 U. In some instances, the concentration of the endonuclease is in a range of about 0.25 U to 12 U, 0.5 U to 11 U, 0.75 U to 10 U, 1 U to 9 U, 2 U to 8 U, 3 U to 7 U, or 4 U to 6 U.

Provided herein are methods for enzymatic mediated nucleic acid assembly, wherein a double stranded nucleic acid is mixed with a polymerase. In some instances, the polymerase is a DNA polymerase. In some instances, the polymerase is a high fidelity polymerase. A high fidelity polymerase may include polymerases that result in accurate replication or amplification of a template nucleic acid. In some instances, the DNA polymerase is a thermostable DNA polymerase. The DNA polymerase may be from any family of DNA polymerases including, but not limited to, Family A polymerase, Family B polymerase, Family C polymerase, Family D polymerase, Family X polymerase, and Family Y polymerase. In some instances, the DNA polymerase is from a genus including, but not limited to, *Thermus, Bacillus, Thermococcus, Pyrococcus, Aeropyrum, Aquifex, Sulfolobus, Pyrolobus,* or *Methanopyrus*.

Polymerases described herein for use in an amplification reaction may comprise various enzymatic activities. Polymerases are used in the methods of the invention, for example, to extend primers to produce extension products. In some instances, the DNA polymerase comprises 5' to 3' polymerase activity. In some instances, the DNA polymerase comprises 3' to 5' exonuclease activity. In some instances, the DNA polymerase comprises proofreading activity. Exemplary polymerases include, but are not limited to, DNA polymerase (I, II, or III), T4 DNA polymerase, T7 DNA polymerase, Bst DNA polymerase, Bca polymerase, Vent DNA polymerase, Pfu DNA polymerase, and Taq DNA polymerase. Non-limiting examples of thermostable DNA polymerases include, but are not limited to, Taq, Phusion® DNA polymerase, Q5® High Fidelity DNA Polymerase, LongAmp® DNA polymerase, Expand High Fidelity polymerase, HotTub polymerase, Pwo polymerase, Tfl polymerase, Tli polymerase, UlTma polymerase, Pfu polymerase, KOD DNA polymerase, JDF-3 DNA polymerase, PGB-D DNA polymerase, Tgo DNA polymerase, *Pyrolobus furmarius* DNA polymerase, Vent polymerase, and Deep Vent polymerase.

Described herein are methods comprising a DNA polymerase, wherein a concentration of the DNA polymerase is from about 0.1 U to about 2 U, or more than 2 U. In some instances, the concentration of the DNA polymerase is about 0.1 U. In some instances, the concentration of the DNA polymerase is about 0.2 U. In some instances, the concentration of the DNA polymerase is about 0.01 U. In some instances, the concentration of the DNA polymerase is in a range of at least or about 0.005 U to 2 U, 0.005 U to 1 U, 0.005 U to 0.5 U, 0.01 U to 1 U, 0.1 U to 0.5 U, 0.1 U to 0.5 U, 0.1 U to 1 U, 0.1 U to 1.5 U, 0.1 U to 2 U, 0.5 U to 1.0 U, 0.5 U to 1.5 U, 0.5 U to 2 U, 1 U to 1.5 U, 1.0 U to 2.0 U, or 1.5 U to 2 U.

The DNA polymerase for use in methods described herein are used at a temperature optimal for enzymatic activity, for example, a temperature of 25-80° C., 25-70° C., 25-60° C., 25-50° C., or 25-40° C. In some instances, the temperature is about 50° C. In some instances, the temperature is about 55° C. In some instances, the temperature is about 65° C. In some instances, the temperature is at least or about 15° C., 20° C., 25° C., 30° C., 35° C., 40° C., 45° C., 50° C., 55° C., 60° C., 65° C., 70° C., 75° C., 80° C., or more than 80° C.

Methods described herein for enzymatic mediated nucleic acid assembly may comprise an amplification reaction, wherein the amplification reaction comprises a universal primer binding sequence. In some instances, the universal primer binding sequence is capable of binding the same 5' or 3' primer. In some instances, the universal primer binding sequence is shared among a plurality of target nucleic acids in the amplification reaction.

Provided herein are methods for enzymatic mediated nucleic acid assembly, wherein a double stranded nucleic acid is treated with a ligase. Ligases as described herein may function to join nucleic acid fragments. For example, the ligase functions to join adjacent 3'-hydroxylated and 5'-phosphorylated termini of DNA. Ligases include, but are not limited to, *E. coli* ligase, T4 ligase, mammalian ligases (e.g., DNA ligase I, DNA ligase II, DNA ligase III, DNA ligase IV), thermostable ligases, and fast ligases. In some instances, the ligase is a thermostable ligase. In some instances, the ligase is Ampligase.

The concentration of the ligase may vary. In some instances, the concentration of the ligase is in a range of about 0 U to about 2 U. An exemplary concentration of the ligase is about 0.5 U. In some instances, the concentration of the ligase is about 1.0 U. In some instances, the concentration of the ligase is about 5.0 U. In some instances, the concentration of the ligase is in a range of at least or about 0 U to 0.25 U, 0 U to 0.5 U, 0 U to 1 U, 0 U to 1.5 U, 0 U to 2 U, 0.25 U to 0.5 U, 0.25 U to 1.0 U, 0.25 U to 1.5 U, 0.25 U to 2.0 U, 0.5 U to 1.0 U, 0.5 U to 1.5 U, 0.5 U to 2.0 U, 1.0 U to 1.5 U, 1.0 U to 2.0 U, 1.5 U to 2.0 U, 2.0 U to 4.0 U, 4.0 U to 6.0 U, 4.0 U to 8.0 U, 6.0 U to 10.0 U.

In some instances, the ligase is used at a temperature optimal for enzymatic activity, for example, a temperature of 25-80° C., 25-70° C., 25-60° C., 25-50° C., or 25-40° C. In some instances, the temperature is about 50° C. In some instances, the temperature is about 55° C. In some instances, the temperature is about 65° C. In some instances, the temperature is at least or about 15° C., 20° C., 25° C., 30° C., 35° C., 40° C., 45° C., 50° C., 55° C., 60° C., 65° C., 70° C., 75° C., 80° C., or more than 80° C.

Provided herein are methods for enzymatic mediated nucleic acid assembly, wherein a number of gene fragments are assembled. In some instances, the gene fragments are assembled processively or sequentially. In some instances, the gene fragments are assembled into a vector. In some instances, the gene fragments are assembled for long linear gene assembly. In some instances, the number of gene fragments is at least or about 2, 3, 4, 5, 6, 7, 8, 9, 10, or more than 10 gene fragments. In some instances, the number of gene fragments is at least or about 10, 11, 12, 13, 14, 15, 16, 17, 18, 19, 20, or more than 20 gene fragments. In some instances, the number of gene fragments is in a range of about 1 to 2, 1 to 3, 1 to 4, 1 to 5, 1 to 6, 1 to 7, 1 to 8, 1 to 9, 1 to 10, 2 to 3, 2 to 4, 2 to 5, 2 to 6, 2 to 7, 2 to 8, 2 to 9, 2 to 10, 3 to 4, 3 to 5, 3 to 6, 3 to 7, 3 to 8, 3 to 9, 3 to 10, 4 to 5, 4 to 6, 4 to 7, 4 to 8, 4 to 9, 4 to 10, 5 to 6, 5 to 7, 5 to 8, 5 to 9, 5 to 10, 6 to 7, 6 to 8, 6 to 9, 6 to 10, 7 to 8, 7 to 9, 7 to 10, 8 to 9, 8 to 10, or 9 to 10. In some instances, the number of gene fragments is about 1 to about 20, about 2 to about 18, about 3 to about 17, about 4 to about 16, about 6 to about 14, or about 8 to about 12.

Provided herein are methods for enzymatic mediated nucleic acid assembly, wherein a ratio of gene fragments assembled is about 0.2:1, 0.25:1, 0.5:1, 0.75:1, 1:1, 1:1.5, 1:2, 1:3, 1:4, 1:5, or more than 1:5. For example, if two gene fragments are assembled, a ratio of the first gene fragment to the second gene fragment is 1:1. In some instances, a ratio of the first gene fragment to the second gene fragment is at least or about 1:1, 1:0.9, 1:0.85, 1:0.8, 1:0.75, 1:0.7, 1:0.65, 1:0.6, 1:0.55, 1:0.5, 1:0.45, 1:0.4, 1:0.35, 1:0.3, 1:0.25, 1:0.2, 1:0.15, 1:0.1, or less than 1:0.1.

Methods as described herein for enzymatic mediated nucleic acid assembly may comprise assembly of one or more gene fragments into a vector, wherein a ratio of the one or more gene fragments to the vector varies. In some instances, a ratio of the one or more gene fragments to the vector is at least or about 0.2:1, 0.25:1, 0.5:1, 0.75:1, 1:1, 1:1.5, 1:2, 1:3, 1:4, 1:5, or more than 1:5. In some instances, a ratio of the one or more gene fragments to the vector is at least or about 1:1, 1:0.9, 1:0.85, 1:0.8, 1:0.75, 1:0.7, 1:0.65, 1:0.6, 1:0.55, 1:0.5, 1:0.45, 1:0.4, 1:0.35, 1:0.3, 1:0.25, 1:0.2, 1:0.15, 1:0.1, or less than 1:0.1.

Methods as described herein for enzymatic mediated nucleic acid assembly may comprise assembly of oligonucleotide populations for assembly into a vector. In some instances, overlap extension PCR is performed for assembly of oligonucleotide populations. In some instances, the oligonucleotide population comprises at least or about 2, 3, 4, 5, 6, 7, 8, 9, 10, 15, 20, 25, 30, 35, 40, 45, 50, 60, 70, 80, 90, 100, 200, or more than 200 oligonucleotides. In some instances, the oligonucleotide population are assembled to generate a long nucleic acid comprising at least or about 50, 100, 200, 250 300, 400, 500, 600, 700, 800, 900, 1000, 1100, 1300, 1400, 1500, 1600, 1700, 1800, 2000, 2400, 2600, 2800, 3000, 3200, 3400, 3600, 3800, 4000, 4200, 4400, 4600, 4800, 5000, 6000, 7000, 8000, 9000, 10000, or more than 10000 bases.

Methods as described herein for enzymatic mediated nucleic acid assembly may comprise multiplexed gene assembly. In some instances, multiple sequences are assembled in a single reaction. In some instances, at least or about 2, 3, 4, 5, 6, 7, 8, 9, 10, 15, 20, 25, 30, 35, 40, 45, 50, 60, 70, 80, 90, 100, 200, or more than 200 sequences are assembled in a single reaction. Sequences assembled by multiplex gene assembly, in some instances, are inserted into a vector.

Methods for enzymatic mediated nucleic acid assembly may comprise assembly of one or more gene fragments using a nucleic acid bridge, wherein a ratio of the one or more gene fragments to the nucleic acid bridge varies. In some instances, a ratio of the one or more gene fragments to the nucleic acid bridge is at least or about 0.2:1, 0.25:1, 0.5:1, 0.75:1, 1:1, 1:1.5, 1:2, 1:3, 1:4, 1:5, or more than 1:5. In some instances, a ratio of the one or more gene fragments to the nucleic acid bridge is at least or about 1:1, 1:0.9, 1:0.85, 1:0.8, 1:0.75, 1:0.7, 1:0.65, 1:0.6, 1:0.55, 1:0.5, 1:0.45, 1:0.4, 1:0.35, 1:0.3, 1:0.25, 1:0.2, 1:0.15, 1:0.1, or less than 1:0.1.

Provided herein are methods for enzymatic mediated nucleic acid assembly of gene fragments, wherein a total size of the number of gene fragments that are assembled is at least or about 50, 100, 200, 250 300, 400, 500, 600, 700, 800, 900, 1000, 1100, 1300, 1400, 1500, 1600, 1700, 1800, 2000, 2400, 2600, 2800, 3000, 3200, 3400, 3600, 3800, 4000, 4200, 4400, 4600, 4800, 5000, 6000, 7000, 8000, 9000, 10000, or more than 10000 bases. In some instances, a total size of the number of gene fragments that are assembled is in a range of about 300 to 1,000, 300 to 2,000, 300 to 3,000, 300 to 4,000, 300 to 5,000, 300 to 6,000, 300 to 7,000, 300 to 8,000, 300 to 9,000, 300 to 10,000, 1,000 to 2,000, 1,000 to 3,000, 1,000 to 4,000, 1,000 to 5,000, 1,000 to 6,000, 1,000 to 7,000, 1,000 to 8,000, 1,000 to 9,000, 1,000 to 10,000, 2,000 to 3,000, 2,000 to 4,000, 2,000 to 5,000, 2,000 to 6,000, 2,000 to 7,000, 2,000 to 8,000, 2,000 to 9,000, 2,000 to 10,000, 3,000 to 4,000, 3,000 to 5,000, 3,000 to 6,000, 3,000 to 7,000, 3,000 to 8,000, 3,000 to 9,000, 3,000 to 10,000, 4,000 to 5,000, 4,000 to 6,000, 4,000 to 7,000, 4,000 to 8,000, 4,000 to 9,000, 4,000 to 10,000, 5,000 to 6,000, 5,000 to 7,000, 5,000 to 8,000, 5,000 to 9,000, 5,000 to 10,000, 6,000 to 7,000, 6,000 to 8,000, 6,000 to 9,000, 6,000 to 10,000, 7,000 to 8,000, 7,000 to 9,000, 7,000 to 10,000, 8,000 to 9,000, 8,000 to 10,000, or 9,000 to 10,000 bases.

Methods described herein comprising enzymatic mediated nucleic acid assembly result in a high percentage of correct assembly. In some instances, the percentage of correct assembly is at least or about 60%, 65%, 70%, 75%, 80%, 85%, 90%, 95%, 97%, 99%, or more than 99%. In some instances, the percentage of average correct assembly is at least or about 60%, 65%, 70%, 75%, 80%, 85%, 90%, 95%, 97%, 99%, or more than 99%. In some instances, the percentage of correct assembly is 100%.

Methods as described herein comprising enzymatic mediated nucleic acid assembly result in a low percentage of misassembly. In some instances, the percentage misassembly rate is at most 5%, 10%, 15%, 20%, 25%, 30%, 35%, 40%, 45%, 50%, 55%, or 60%. In some instances, the percentage misassembly rate is about 1% to about 25%, about 5% to about 20%, or about 10% to about 15%. In some instances, the average misassembly rate is at most 5%, 10%, 15%, 20%, 25%, 30%, 35%, 40%, 45%, 50%, 55%, or 60%. In some instances, the average misassembly rate is about 1% to about 25%, about 5% to about 20%, or about 10% to about 15%.

Methods described herein comprising enzymatic mediated nucleic acid assembly result in increased efficiency. In some instances, efficiency is measured by number of colony forming units. In some instances, methods described herein result in at least or about 100, 200, 300, 400, 500, 600, 700, 800, 900, 1000, 2000, 3000, 4000, 5000, 6000, 7000, 8000, 9000, 10000, 12000, 14000, 16000, 18000, 20000, 25000, 30000, 35000, 40000, 50000, 60000, 70000, 80000, 90000, 100000, or more than 100000 colony forming units.

Systems for Synthesis of Nucleic Acids and Seamless Assembly

Polynucleotide Synthesis

Figure 2:
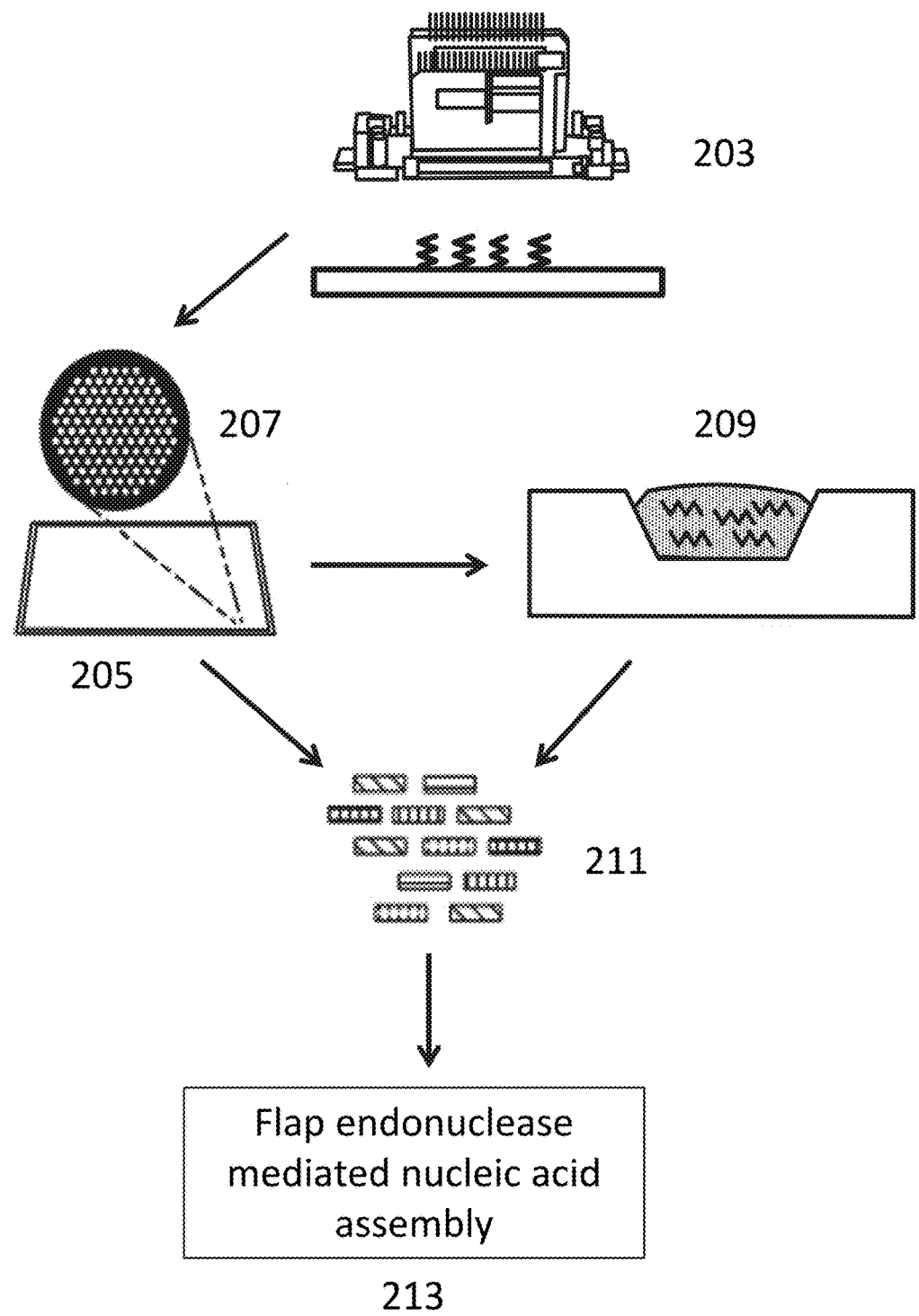
FIG. 2 depicts systems for polynucleotide synthesis and flap endonuclease mediated nucleic acid assembly.

Provided herein are methods for seamless assembly of nucleic acids following generation of polynucleotides by de novo synthesis by methods described herein. An exemplary workflow is seen in FIG. 2. A computer readable input file comprising a nucleic acid sequence is received. A computer processes the nucleic acid sequence to generate instructions for synthesis of the polynucleotide sequence or a plurality of polynucleotide sequences collectively encoding the nucleic acid sequence. Instructions are transmitted to a material deposition device 203 for synthesis of the plurality of polynucleotides based on the plurality of nucleic acid sequences. The material deposition device 203, such as a polynucleotide acid synthesizer, is designed to release reagents in a step wise fashion such that multiple polynucleotides extend, in parallel, one residue at a time to generate oligomers with a predetermined nucleic acid sequence. The material deposition device 203 generates oligomers on an array 205 that includes multiple clusters 207 of loci for polynucleotide acid synthesis and extension. However, the array need not have loci organized in clusters. For example, the loci can be uniformly spread across the array. De novo polynucleotides are synthesized and removed from the plate and an assembly reaction commenced in a collection chamber 209 followed by formation population of longer polynucleotides 211. The collection chamber may comprise a sandwich of multiple surfaces (e.g., a top and bottom surface) or well or channel in containing transferred material from the synthesis surface. De novo polynucleotides can also be synthesized and removed from the plate to form a population of longer polynucleotides 211. The population of longer polynucleotides 211 can then be partitioned into droplets or subject to PCR. The population of longer polynucleotides 211 is then subject to nucleic acid assembly by flap endonuclease mediated nucleic acid assembly 213.

Provided herein are systems for seamless assembly of nucleic acids following generation of polynucleotides by de novo synthesis by methods described herein. In some instances, the system comprises a computer, a material deposition device, a surface, and a nucleic acid assembly surface. In some instances, the computer comprises a readable input file with a nucleic acid sequence. In some instances, the computer processes the nucleic acid sequence to generate instructions for synthesis of the polynucleotide sequence or a plurality of polynucleotide sequences collectively encoding for the nucleic acid sequence. In some instances, the computer provides instructions to the material deposition device for the synthesis of the plurality of polynucleotide acid sequences. In some instances, the material deposition device deposits nucleosides on the surface for an extension reaction. In some instances, the surface comprises a locus for the extension reaction. In some instances, the locus is a spot, well, microwell, channel, or post. In some instances, the plurality of polynucleotide acid sequences is synthesized following the extension reaction. In some instances, the plurality of polynucleotide acid sequences is removed from the surface and prepared for nucleic acid assembly. In some instances, the nucleic acid assembly comprises flap endonuclease mediated nucleic acid assembly.

Provided herein are methods for polynucleotide synthesis involving phosphoramidite chemistry. In some instances, polynucleotide synthesis comprises coupling a base with phosphoramidite. In some instances, polynucleotide synthesis comprises coupling a base by deposition of phosphoramidite under coupling conditions, wherein the same base is optionally deposited with phosphoramidite more than once, i.e., double coupling. In some instances, polynucleotide synthesis comprises capping of unreacted sites. In some cases, capping is optional. In some instances, polynucleotide synthesis comprises oxidation. In some instances, polynucleotide synthesis comprises deblocking or detritylation. In some instances, polynucleotide synthesis comprises sulfurization. In some cases, polynucleotide synthesis comprises either oxidation or sulfurization. In some instances, between one or each step during a polynucleotide synthesis reaction, the substrate is washed, for example, using tetrazole or acetonitrile. Time frames for any one step in a phosphoramidite synthesis method include less than about 2 min, 1 min, 50 sec, 40 sec, 30 sec, 20 sec, or 10 sec.

Polynucleotide synthesis using a phosphoramidite method comprises the subsequent addition of a phosphoramidite building block (e.g., nucleoside phosphoramidite) to a growing polynucleotide chain for the formation of a phosphite triester linkage. Phosphoramidite polynucleotide synthesis proceeds in the 3' to 5' direction. Phosphoramidite polynucleotide synthesis allows for the controlled addition of one nucleotide to a growing nucleic acid chain per synthesis cycle. In some instances, each synthesis cycle comprises a coupling step. Phosphoramidite coupling involves the formation of a phosphite triester linkage between an activated nucleoside phosphoramidite and a nucleoside bound to the substrate, for example, via a linker. In some instances, the nucleoside phosphoramidite is provided to the substrate activated. In some instances, the nucleoside phosphoramidite is provided to the substrate with an activator. In some instances, nucleoside phosphoramidites are provided to the substrate in a 1.5, 2, 3, 4, 5, 6, 7, 8, 9, 10, 11, 12, 13, 14, 15, 16, 17, 18, 19, 20, 25, 30, 35, 40, 50, 60, 70, 80, 90, 100-fold excess or more over the substrate-bound nucleosides. In some instances, the addition of nucleoside phosphoramidite is performed in an anhydrous environment, for example, in anhydrous acetonitrile. Following addition of a nucleoside phosphoramidite, the substrate is optionally washed. In some instances, the coupling step is repeated one or more additional times, optionally with a wash step between nucleoside phosphoramidite additions to the substrate. In some instances, a polynucleotide synthesis method used herein comprises 1, 2, 3 or more sequential coupling steps. Prior to coupling, in many cases, the nucleoside bound to the substrate is de-protected by removal of a protecting group, where the protecting group functions to prevent polymerization. A common protecting group is 4,4'-dimethoxytrityl (DMT).

Following coupling, phosphoramidite polynucleotide synthesis methods optionally comprise a capping step. In a capping step, the growing polynucleotide is treated with a capping agent. A capping step is useful to block unreacted substrate-bound 5'-OH groups after coupling from further chain elongation, preventing the formation of polynucleotides with internal base deletions. Further, phosphoramidites activated with 1H-tetrazole may react, to a small extent, with the O6 position of guanosine. Without being bound by theory, upon oxidation with $I_2$/water, this side product, possibly via O6-N7 migration, may undergo depurination. The apurinic sites may end up being cleaved in the course of the final deprotection of the polynucleotide thus reducing the yield of the full-length product. The O6 modifications may be removed by treatment with the capping reagent prior to oxidation with $I_2$/water. In some instances, inclusion of a capping step during polynucleotide synthesis decreases the error rate as compared to synthesis without capping. As an example, the capping step comprises treating the substrate-bound polynucleotide with a mixture of acetic anhydride and 1-methylimidazole. Following a capping step, the substrate is optionally washed.

In some instances, following addition of a nucleoside phosphoramidite, and optionally after capping and one or more wash steps, the substrate bound growing nucleic acid is oxidized. The oxidation step comprises oxidation of the phosphite triester into a tetracoordinated phosphate triester, a protected precursor of the naturally occurring phosphate diester internucleoside linkage. In some cases, oxidation of the growing polynucleotide is achieved by treatment with iodine and water, optionally in the presence of a weak base (e.g., pyridine, lutidine, collidine). Oxidation may be carried out under anhydrous conditions using, e.g. tert-Butyl hydroperoxide or (1S)-(+)-(10-camphorsulfonyl)-oxaziridine (CSO). In some methods, a capping step is performed following oxidation. A second capping step allows for substrate drying, as residual water from oxidation that may persist can inhibit subsequent coupling. Following oxidation, the substrate and growing polynucleotide is optionally washed. In some instances, the step of oxidation is substituted with a sulfurization step to obtain polynucleotide phosphorothioates, wherein any capping steps can be performed after the sulfurization. Many reagents are capable of the efficient sulfur transfer, including but not limited to 3-(Dimethylaminomethylidene)amino)-3H-1,2,4-dithiazole-3-thione, DDTT, 3H-1,2-benzodithiol-3-one 1,1-dioxide, also known as Beaucage reagent, and N,N,N'N'-Tetraethylthiuram disulfide (TETD).

In order for a subsequent cycle of nucleoside incorporation to occur through coupling, the protected 5' end of the substrate bound growing polynucleotide is removed so that the primary hydroxyl group is reactive with a next nucleoside phosphoramidite. In some instances, the protecting group is DMT and deblocking occurs with trichloroacetic acid in dichloromethane. Conducting detritylation for an extended time or with stronger than recommended solutions of acids may lead to increased depurination of solid support-bound polynucleotide and thus reduces the yield of the desired full-length product. Methods and compositions of the invention described herein provide for controlled deblocking conditions limiting undesired depurination reactions. In some cases, the substrate bound polynucleotide is washed after deblocking. In some cases, efficient washing after deblocking contributes to synthesized polynucleotides having a low error rate.

Methods for the synthesis of polynucleotides typically involve an iterating sequence of the following steps: application of a protected monomer to an actively functionalized surface (e.g., locus) to link with either the activated surface, a linker or with a previously deprotected monomer; deprotection of the applied monomer so that it is reactive with a subsequently applied protected monomer; and application of another protected monomer for linking. One or more intermediate steps include oxidation or sulfurization. In some cases, one or more wash steps precede or follow one or all of the steps.

Methods for phosphoramidite based polynucleotide synthesis comprise a series of chemical steps. In some instances, one or more steps of a synthesis method involve reagent cycling, where one or more steps of the method comprise application to the substrate of a reagent useful for the step. For example, reagents are cycled by a series of liquid deposition and vacuum drying steps. For substrates comprising three-dimensional features such as wells, microwells, channels and the like, reagents are optionally passed through one or more regions of the substrate via the wells and/or channels.

Polynucleotides synthesized using the methods and/or substrates described herein comprise at least about 20, 30, 40, 50, 60, 70, 75, 80, 90, 100, 120, 150, 200, 500 or more bases in length. In some instances, at least about 1 pmol, 10 pmol, 20 pmol, 30 pmol, 40 pmol, 50 pmol, 60 pmol, 70 pmol, 80 pmol, 90 pmol, 100 pmol, 150 pmol, 200 pmol, 300 pmol, 400 pmol, 500 pmol, 600 pmol, 700 pmol, 800 pmol, 900 pmol, 1 nmol, 5 nmol, 10 nmol, 100 nmol or more of an polynucleotide is synthesized within a locus. Methods for polynucleotide synthesis on a surface provided herein allow for synthesis at a fast rate. As an example, at least 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 100, 125, 150, 175, 200 nucleotides per hour, or more are synthesized. Nucleotides include adenine, guanine, thymine, cytosine, uridine building blocks, or analogs/modified versions thereof. In some instances, libraries of polynucleotides are synthesized in parallel on a substrate. For example, a substrate comprising about or at least about 100; 1,000; 10,000; 100,000; 1,000,000; 2,000,000; 3,000,000; 4,000,000; or 5,000,000 resolved loci is able to support the synthesis of at least the same number of distinct polynucleotides, wherein a polynucleotide encoding a distinct sequence is synthesized on a resolved locus.

Various suitable methods are known for generating high density polynucleotide arrays. In an exemplary workflow, a substrate surface layer is provided. In the example, chemistry of the surface is altered in order to improve the polynucleotide synthesis process. Areas of low surface energy are generated to repel liquid while areas of high surface energy are generated to attract liquids. The surface itself may be in the form of a planar surface or contain variations in shape, such as protrusions or microwells which increase surface area. In the workflow example, high surface energy molecules selected serve a dual function of supporting DNA chemistry, as disclosed in International Patent Application Publication WO/2015/021080, which is herein incorporated by reference in its entirety.

In situ preparation of polynucleotide arrays is generated on a solid support and utilizes a single nucleotide extension process to extend multiple oligomers in parallel. A deposition device, such as a polynucleotide synthesizer, is designed to release reagents in a step wise fashion such that multiple polynucleotides extend, in parallel, one residue at a time to generate oligomers with a predetermined nucleic acid sequence. In some cases, polynucleotides are cleaved from the surface at this stage. Cleavage includes gas cleavage, e.g., with ammonia or methylamine.

Substrates

Devices used as a surface for polynucleotide synthesis may be in the form of substrates which include, without limitation, homogenous array surfaces, patterned array surfaces, channels, beads, gels, and the like. Provided herein are substrates comprising a plurality of clusters, wherein each cluster comprises a plurality of loci that support the attachment and synthesis of polynucleotides. The term "locus" as used herein refers to a discrete region on a structure which provides support for polynucleotides encoding for a single predetermined sequence to extend from the surface. In some instances, a locus is on a two dimensional surface, e.g., a substantially planar surface. In some instances, a locus is on a three-dimensional surface, e.g., a well, microwell, channel, or post. In some instances, a surface of a locus comprises a material that is actively functionalized to attach to at least one nucleotide for polynucleotide synthesis, or preferably, a population of identical nucleotides for synthesis of a population of polynucleotides. In some instances, polynucleotide refers to a population of polynucleotides encoding for the same nucleic acid sequence. In some cases, a surface of a substrate is inclusive of one or a plurality of surfaces of a substrate. The average error rates for polynucleotides synthesized within a library described here using the systems and methods provided are often less than 1 in 1000, less than about 1 in 2000, less than about 1 in 3000 or less often without error correction.

Provided herein are surfaces that support the parallel synthesis of a plurality of polynucleotides having different predetermined sequences at addressable locations on a common support. In some instances, a substrate provides support for the synthesis of more than 50, 100, 200, 400, 600, 800, 1000, 1200, 1400, 1600, 1800, 2,000; 5,000; 10,000; 20,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more non-identical polynucleotides. In some cases, the surfaces provide support for the synthesis of more than 50, 100, 200, 400, 600, 800, 1000, 1200, 1400, 1600, 1800, 2,000; 5,000; 10,000; 20,000; 50,000; 100,000; 200, 000; 300,000; 400,000; 500,000; 600,000; 700,000; 800, 000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more polynucleotides encoding for distinct sequences. In some instances, at least a portion of the polynucleotides have an identical sequence or are configured to be synthesized with an identical sequence. In some instances, the substrate provides a surface environment for the growth of polynucleotides having at least 80, 90, 100, 120, 150, 175, 200, 225, 250, 275, 300, 325, 350, 375, 400, 425, 450, 475, 500 bases or more.

Provided herein are methods for polynucleotide synthesis on distinct loci of a substrate, wherein each locus supports the synthesis of a population of polynucleotides. In some cases, each locus supports the synthesis of a population of polynucleotides having a different sequence than a population of polynucleotides grown on another locus. In some instances, each polynucleotide sequence is synthesized with 1, 2, 3, 4, 5, 6, 7, 8, 9 or more redundancy across different loci within the same cluster of loci on a surface for polynucleotide synthesis. In some instances, the loci of a substrate are located within a plurality of clusters. In some instances, a substrate comprises at least 10, 500, 1000, 2000, 3000, 4000, 5000, 6000, 7000, 8000, 9000, 10000, 11000, 12000, 13000, 14000, 15000, 20000, 30000, 40000, 50000 or more clusters. In some instances, a substrate comprises more than 2,000; 5,000; 10,000; 100,000; 200,000; 300,000; 400,000; 500,000; 600,000; 700,000; 800,000; 900,000; 1,000,000; 1,100,000; 1,200,000; 1,300,000; 1,400,000; 1,500,000; 1,600,000; 1,700,000; 1,800,000; 1,900,000; 2,000,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; or 10,000,000 or more distinct loci. In some instances, a substrate comprises about 10,000 distinct loci. The amount of loci within a single cluster is varied in different instances. In some cases, each cluster includes 1, 2, 3, 4, 5, 6, 7, 8, 9, 10, 20, 30, 40, 50, 60, 70, 80, 90, 100, 120, 130, 150, 200, 300, 400, 500 or more loci. In some instances, each cluster includes about 50-500 loci. In some instances, each cluster includes about 100-200 loci. In some instances, each cluster includes about 100-150 loci. In some instances, each cluster includes about 109, 121, 130 or 137 loci. In some instances, each cluster includes about 19, 20, 61, 64 or more loci.

In some instances, the number of distinct polynucleotides synthesized on a substrate is dependent on the number of distinct loci available on the substrate. In some instances, the density of loci within a cluster of a substrate is at least or about 1, 10, 25, 50, 65, 75, 100, 130, 150, 175, 200, 300, 400, 500, 1,000 or more loci per $mm^2$. In some cases, a substrate comprises 10-500, 25-400, 50-500, 100-500, 150-500, 10-250, 50-250, 10-200, or 50-200 $mm^2$. In some instances, the distance between the centers of two adjacent loci within a cluster is from about 10-500, from about 10-200, or from about 10-100 um. In some instances, the distance between two centers of adjacent loci is greater than about 10, 20, 30, 40, 50, 60, 70, 80, 90 or 100 um. In some instances, the distance between the centers of two adjacent loci is less than about 200, 150, 100, 80, 70, 60, 50, 40, 30, 20 or 10 um. In some instances, each locus independently has a width of about 0.5, 1, 2, 3, 4, 5, 6, 7, 8, 9, 10, 20, 30, 40, 50, 60, 70, 80, 90 or 100 um. In some cases, each locus independently has a width of about 0.5-100, 0.5-50, 10-75, or 0.5-50 um.

In some instances, the density of clusters within a substrate is at least or about 1 cluster per 100 $mm^2$, 1 cluster per 10 $mm^2$, 1 cluster per 5 $mm^2$, 1 cluster per 4 $mm^2$, 1 cluster per 3 $mm^2$, 1 cluster per 2 $mm^2$, 1 cluster per 1 $mm^2$, 2 clusters per 1 $mm^2$, 3 clusters per 1 $mm^2$, 4 clusters per 1 $mm^2$, 5 clusters per 1 $mm^2$, 10 clusters per 1 $mm^2$, 50 clusters per 1 $mm^2$ or more. In some instances, a substrate comprises from about 1 cluster per 10 $mm^2$ to about 10 clusters per 1 $mm^2$. In some instances, the distance between the centers of two adjacent clusters is at least or about 50, 100, 200, 500, 1000, 2000, or 5000 um. In some cases, the distance between the centers of two adjacent clusters is between about 50-100, 50-200, 50-300, 50-500, or 100-2000 um. In some cases, the distance between the centers of two adjacent clusters is between about 0.05-50, 0.05-10, 0.05-5, 0.05-4, 0.05-3, 0.05-2, 0.1-10, 0.2-10, 0.3-10, 0.4-10, 0.5-10, 0.5-5, or 0.5-2 mm. In some cases, each cluster independently has a cross section of about 0.5 to 2, about 0.5 to 1, or about 1 to 2 mm. In some cases, each cluster independently has a cross section of about 0.5, 0.6, 0.7, 0.8, 0.9, 1, 1.1, 1.2, 1.3, 1.4, 1.5, 1.6, 1.7, 1.8, 1.9 or 2 mm. In some cases, each cluster independently has an interior cross section of about 0.5, 0.6, 0.7, 0.8, 0.9, 1, 1.1, 1.15, 1.2, 1.3, 1.4, 1.5, 1.6, 1.7, 1.8, 1.9 or 2 mm.

In some instances, a substrate is about the size of a standard 96 well plate, for example between about 100 to about 200 mm by between about 50 to about 150 mm. In some instances, a substrate has a diameter less than or equal to about 1000, 500, 450, 400, 300, 250, 200, 150, 100 or 50 mm. In some instances, the diameter of a substrate is between about 25-1000, 25-800, 25-600, 25-500, 25-400, 25-300, or 25-200 mm. In some instances, a substrate has a planar surface area of at least about 100; 200; 500; 1,000; 2,000; 5,000; 10,000; 12,000; 15,000; 20,000; 30,000; 40,000; 50,000 $mm^2$ or more. In some instances, the thickness of a substrate is between about 50-2000, 50-1000, 100-1000, 200-1000, or 250-1000 mm.

Surface Materials

Substrates, devices, and reactors provided herein are fabricated from any variety of materials suitable for the methods, compositions, and systems described herein. In certain instances, substrate materials are fabricated to exhibit a low level of nucleotide binding. In some instances, substrate materials are modified to generate distinct surfaces that exhibit a high level of nucleotide binding. In some instances, substrate materials are transparent to visible and/or UV light. In some instances, substrate materials are sufficiently conductive, e.g., are able to form uniform electric fields across all or a portion of a substrate. In some instances, conductive materials are connected to an electric ground. In some instances, the substrate is heat conductive or insulated. In some instances, the materials are chemical resistant and heat resistant to support chemical or biochemical reactions, for example polynucleotide synthesis reaction processes. In some instances, a substrate comprises flexible materials. For flexible materials, materials can include, without limitation: nylon, both modified and unmodified, nitrocellulose, polypropylene, and the like. In some instances, a substrate comprises rigid materials. For rigid materials, materials can include, without limitation: glass; fuse silica; silicon, plastics (for example polytetraflouroethylene, polypropylene, polystyrene, polycarbonate, and blends thereof, and the like); metals (for example, gold, platinum, and the like). The substrate, solid support or reactors can be fabricated from a material selected from the group consisting of silicon, polystyrene, agarose, dextran, cellulosic polymers, polyacrylamides, polydimethylsiloxane (PDMS), and glass. The substrates/solid supports or the microstructures, reactors therein may be manufactured with a combination of materials listed herein or any other suitable material known in the art.

Surface Architecture

Provided herein are substrates for the methods, compositions, and systems described herein, wherein the substrates have a surface architecture suitable for the methods, compositions, and systems described herein. In some instances, a substrate comprises raised and/or lowered features. One benefit of having such features is an increase in surface area to support polynucleotide synthesis. In some instances, a substrate having raised and/or lowered features is referred to as a three-dimensional substrate. In some cases, a three-dimensional substrate comprises one or more channels. In some cases, one or more loci comprise a channel. In some cases, the channels are accessible to reagent deposition via a deposition device such as a polynucleotide synthesizer. In some cases, reagents and/or fluids collect in a larger well in fluid communication with one or more channels. For example, a substrate comprises a plurality of channels corresponding to a plurality of loci within a cluster, and the plurality of channels are in fluid communication with one well of the cluster. In some methods, a library of polynucleotides is synthesized in a plurality of loci of a cluster.

Provided herein are substrates for the methods, compositions, and systems described herein, wherein the substrates are configured for polynucleotide synthesis. In some instances, the structure is configured to allow for controlled flow and mass transfer paths for polynucleotide synthesis on a surface. In some instances, the configuration of a substrate allows for the controlled and even distribution of mass transfer paths, chemical exposure times, and/or wash efficacy during polynucleotide synthesis. In some instances, the configuration of a substrate allows for increased sweep efficiency, for example by providing sufficient volume for growing a polynucleotide such that the excluded volume by the growing polynucleotide does not take up more than 50, 45, 40, 35, 30, 25, 20, 15, 14, 13, 12, 11, 10, 9, 8, 7, 6, 5, 4, 3, 2, 1%, or less of the initially available volume that is available or suitable for growing the polynucleotide. In some instances, a three-dimensional structure allows for managed flow of fluid to allow for the rapid exchange of chemical exposure.

Provided herein are substrates for the methods, compositions, and systems relating to enzymatic mediated nucleic acid assembly and polynucleotide synthesis described herein, wherein the substrates comprise structures configured for housing enzymatic reactions described herein. In some instances, segregation is achieved by physical structure. In some instances, segregation is achieved by differential functionalization of the surface generating active and passive regions for polynucleotide synthesis. In some instances, differential functionalization is achieved by alternating the hydrophobicity across the substrate surface, thereby creating water contact angle effects that cause beading or wetting of the deposited reagents. Employing larger structures can decrease splashing and cross-contamination of distinct polynucleotide synthesis locations with reagents of the neighboring spots. In some cases, a device, such as a polynucleotide synthesizer, is used to deposit reagents to distinct polynucleotide synthesis locations. Substrates having three-dimensional features are configured in a manner that allows for the synthesis of a large number of polynucleotides (e.g., more than about 10,000) with a low error rate (e.g., less than about 1:500, 1:1000, 1:1500, 1:2,000; 1:3,000; 1:5,000; or 1:10,000). In some cases, a substrate comprises features with a density of about or greater than about 1, 5, 10, 20, 30, 40, 50, 60, 70, 80, 100, 110, 120, 130, 140, 150, 160, 170, 180, 190, 200, 300, 400 or 500 features per $mm^2$.

A well of a substrate may have the same or different width, height, and/or volume as another well of the substrate. A channel of a substrate may have the same or different width, height, and/or volume as another channel of the substrate. In some instances, the diameter of a cluster or the diameter of a well comprising a cluster, or both, is between about 0.05-50, 0.05-10, 0.05-5, 0.05-4, 0.05-3, 0.05-2, 0.05-1, 0.05-0.5, 0.05-0.1, 0.1-10, 0.2-10, 0.3-10, 0.4-10, 0.5-10, 0.5-5, or 0.5-2 mm. In some instances, the diameter of a cluster or well or both is less than or about 5, 4, 3, 2, 1, 0.5, 0.1, 0.09, 0.08, 0.07, 0.06, or 0.05 mm. In some instances, the diameter of a cluster or well or both is between about 1.0 and about 1.3 mm. In some instances, the diameter of a cluster or well, or both is about 1.150 mm. In some instances, the diameter of a cluster or well, or both is about 0.08 mm. The diameter of a cluster refers to clusters within a two-dimensional or three-dimensional substrate.

In some instances, the height of a well is from about 20-1000, 50-1000, 100-1000, 200-1000, 300-1000, 400-1000, or 500-1000 um. In some cases, the height of a well is less than about 1000, 900, 800, 700, or 600 um.

In some instances, a substrate comprises a plurality of channels corresponding to a plurality of loci within a cluster, wherein the height or depth of a channel is 5-500, 5-400, 5-300, 5-200, 5-100, 5-50, or 10-50 um. In some cases, the height of a channel is less than 100, 80, 60, 40, or 20 um.

In some instances, the diameter of a channel, locus (e.g., in a substantially planar substrate) or both channel and locus (e.g., in a three-dimensional substrate wherein a locus corresponds to a channel) is from about 1-1000, 1-500, 1-200, 1-100, 5-100, or 10-100 um, for example, about 90, 80, 70, 60, 50, 40, 30, 20 or 10 um. In some instances, the diameter of a channel, locus, or both channel and locus is less than about 100, 90, 80, 70, 60, 50, 40, 30, 20 or 10 um. In some instances, the distance between the center of two adjacent channels, loci, or channels and loci is from about 1-500, 1-200, 1-100, 5-200, 5-100, 5-50, or 5-30, for example, about 20 um.

Surface Modifications

Provided herein are methods for polynucleotide synthesis on a surface, wherein the surface comprises various surface modifications. In some instances, the surface modifications are employed for the chemical and/or physical alteration of a surface by an additive or subtractive process to change one or more chemical and/or physical properties of a substrate surface or a selected site or region of a substrate surface. For example, surface modifications include, without limitation, (1) changing the wetting properties of a surface, (2) functionalizing a surface, i.e., providing, modifying or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface.

In some cases, the addition of a chemical layer on top of a surface (referred to as adhesion promoter) facilitates structured patterning of loci on a surface of a substrate. Exemplary surfaces for application of adhesion promotion include, without limitation, glass, silicon, silicon dioxide and silicon nitride. In some cases, the adhesion promoter is a chemical with a high surface energy. In some instances, a second chemical layer is deposited on a surface of a substrate. In some cases, the second chemical layer has a low surface energy. In some cases, surface energy of a chemical layer coated on a surface supports localization of droplets on the surface. Depending on the patterning arrangement selected, the proximity of loci and/or area of fluid contact at the loci are alterable.

In some instances, a substrate surface, or resolved loci, onto which nucleic acids or other moieties are deposited, e.g., for polynucleotide synthesis, are smooth or substantially planar (e.g., two-dimensional) or have irregularities, such as raised or lowered features (e.g., three-dimensional features). In some instances, a substrate surface is modified with one or more different layers of compounds. Such modification layers of interest include, without limitation, inorganic and organic layers such as metals, metal oxides, polymers, small organic molecules and the like.

In some instances, resolved loci of a substrate are functionalized with one or more moieties that increase and/or decrease surface energy. In some cases, a moiety is chemically inert. In some cases, a moiety is configured to support a desired chemical reaction, for example, one or more processes in a polynucleotide acid synthesis reaction. The surface energy, or hydrophobicity, of a surface is a factor for determining the affinity of a nucleotide to attach onto the surface. In some instances, a method for substrate functionalization comprises: (a) providing a substrate having a surface that comprises silicon dioxide; and (b) silanizing the surface using, a suitable silanizing agent described herein or otherwise known in the art, for example, an organofunctional alkoxysilane molecule. Methods and functionalizing agents are described in U.S. Pat. No. 5,474,796, which is herein incorporated by reference in its entirety.

In some instances, a substrate surface is functionalized by contact with a derivatizing composition that contains a mixture of silanes, under reaction conditions effective to couple the silanes to the substrate surface, typically via reactive hydrophilic moieties present on the substrate surface. Silanization generally covers a surface through self-assembly with organofunctional alkoxysilane molecules. A variety of siloxane functionalizing reagents can further be used as currently known in the art, e.g., for lowering or increasing surface energy. The organofunctional alkoxysilanes are classified according to their organic functions.

Computer Systems

Any of the systems described herein, may be operably linked to a computer and may be automated through a computer either locally or remotely. In some instances, the methods and systems of the invention further comprise software programs on computer systems and use thereof. Accordingly, computerized control for the synchronization of the dispense/vacuum/refill functions such as orchestrating and synchronizing the material deposition device movement, dispense action and vacuum actuation are within the bounds of the invention. The computer systems may be programmed to interface between the user specified base sequence and the position of a material deposition device to deliver the correct reagents to specified regions of the substrate.

Figure 3:
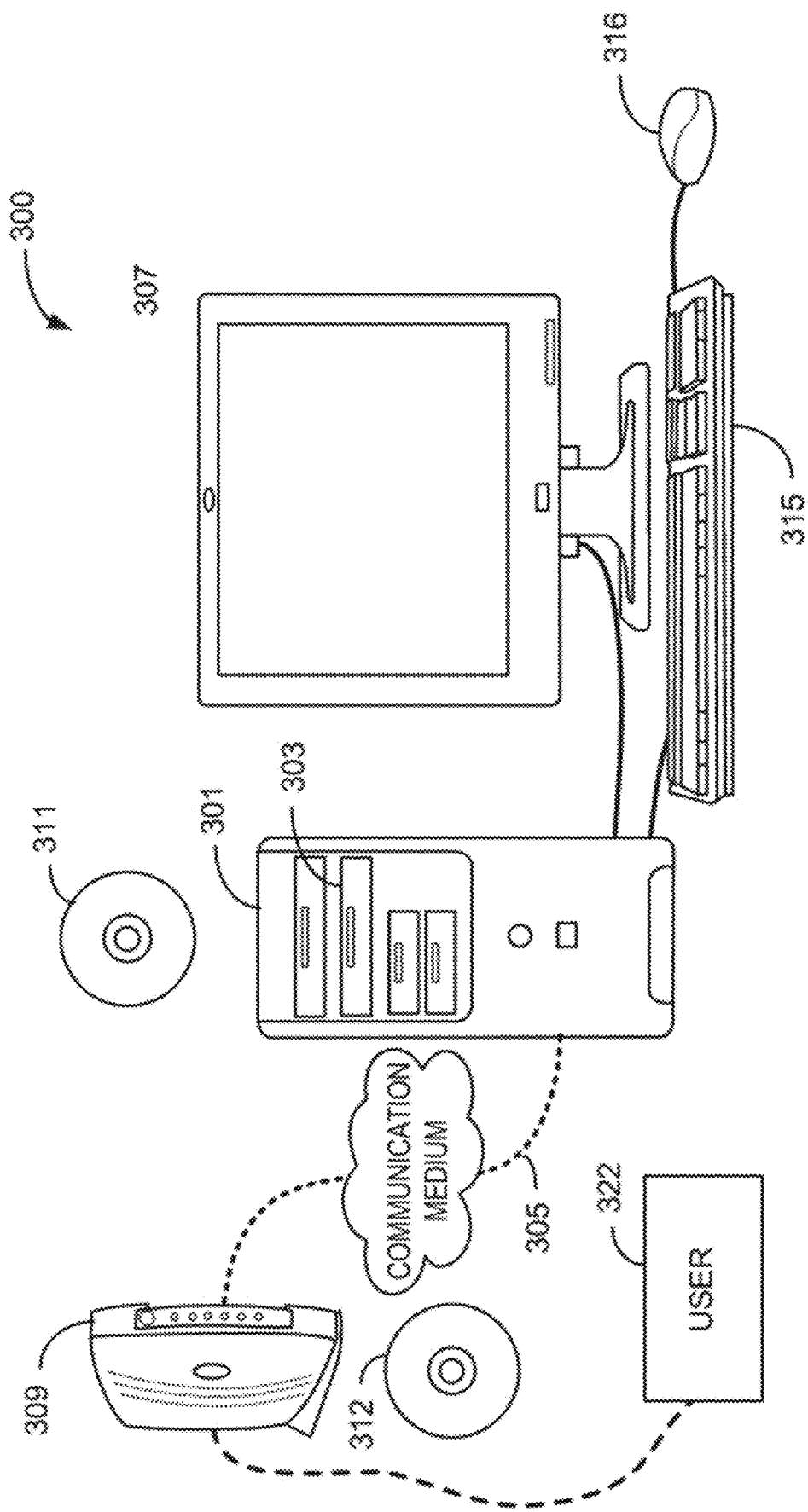
FIG. 3 illustrates a computer system.

The computer system 300 illustrated in FIG. 3 may be understood as a logical apparatus that can read instructions from media 311 and/or a network port 305, which can optionally be connected to server 309 having fixed media 312. The system, such as shown in FIG. 3, can include a CPU 301, disk drives 303, optional input devices such as a keyboard 315 and/or mouse 316 and optional monitor 307. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 322 as illustrated in FIG. 3.

Figure 4:
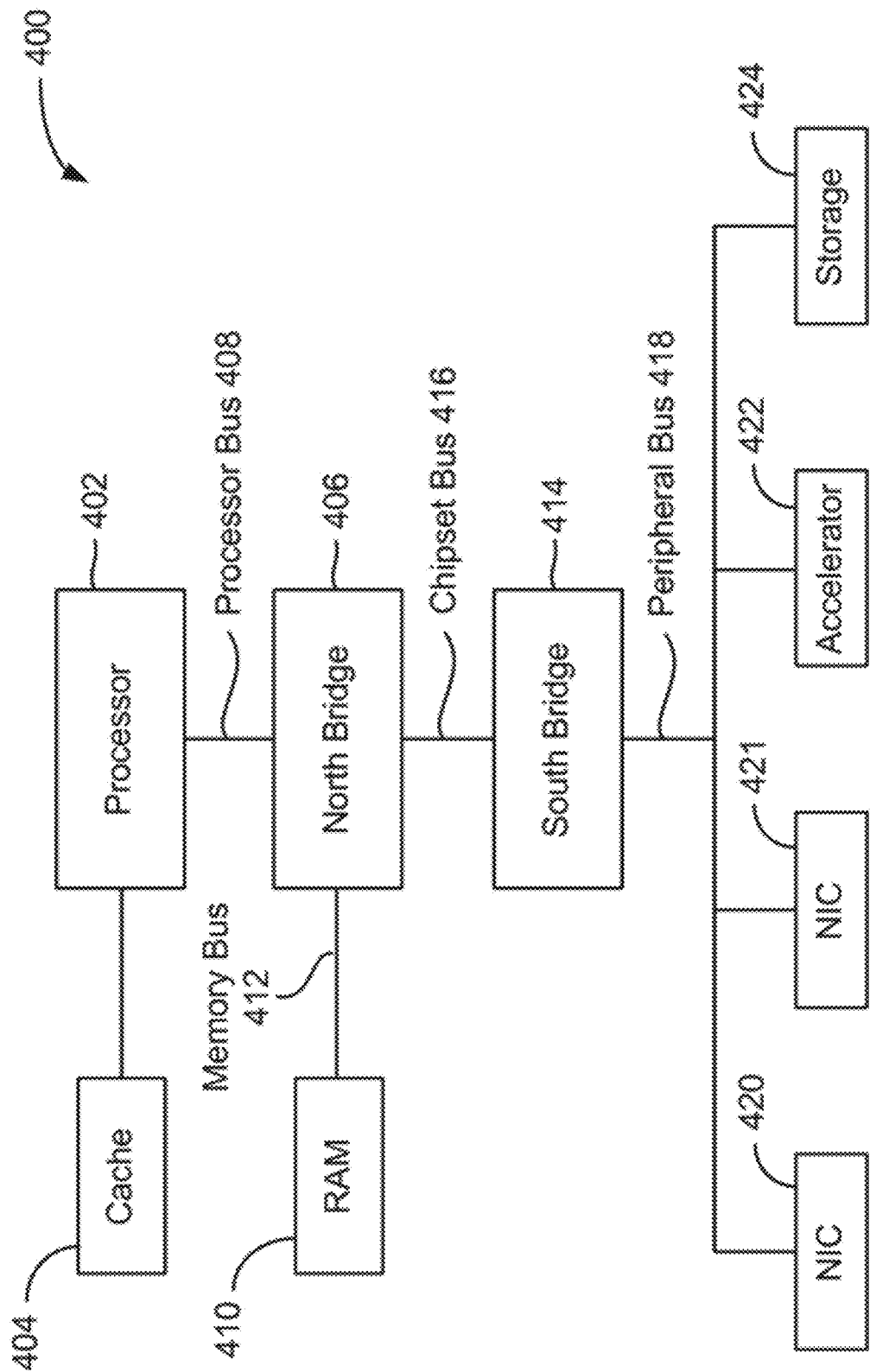
FIG. 4 is a block diagram illustrating architecture of a computer system.

FIG. 4 is a block diagram illustrating architecture of a computer system 400 that can be used in connection with example embodiments of the present invention. As depicted in FIG. 4, the example computer system can include a processor 402 for processing instructions. Non-limiting examples of processors include: Intel® Xeon® processor, AMD Opteron™ processor, Samsung 32-bit RISC ARM 1176JZ(F)-S v1.0 processor, ARM Cortex-A8 Samsung S5PC100 processor, ARM Cortex-A8 Apple A4 processor, Marvell PXA 930 processor, or a functionally-equivalent processor. Multiple threads of execution can be used for parallel processing. In some instances, multiple processors or processors with multiple cores can also be used, whether in a single computer system, in a cluster, or distributed across systems over a network comprising a plurality of computers, cell phones, and/or personal data assistant devices.

As illustrated in FIG. 4, a high speed cache 404 can be connected to, or incorporated in, the processor 402 to provide a high speed memory for instructions or data that have been recently, or are frequently, used by processor 402. The processor 402 is connected to a north bridge 406 by a processor bus 408. The north bridge 406 is connected to random access memory (RAM) 410 by a memory bus 412 and manages access to the RAM 410 by the processor 402. The north bridge 406 is also connected to a south bridge 414 by a chipset bus 416. The south bridge 414 is, in turn, connected to a peripheral bus 418. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 418. In some alternative architectures, the functionality of the north bridge can be incorporated into the processor instead of using a separate north bridge chip. In some instances, system 400 can include an accelerator card 422 attached to the peripheral bus 418. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 424 and can be loaded into RAM 410 and/or cache 404 for use by the processor. The system 400 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present invention. In this example, system 400 also includes network interface cards (NICs) 420 and 421 connected to the peripheral bus for providing network interfaces to external storage, such as Network Attached Storage (NAS) and other computer systems that can be used for distributed parallel processing.

Figure 5:
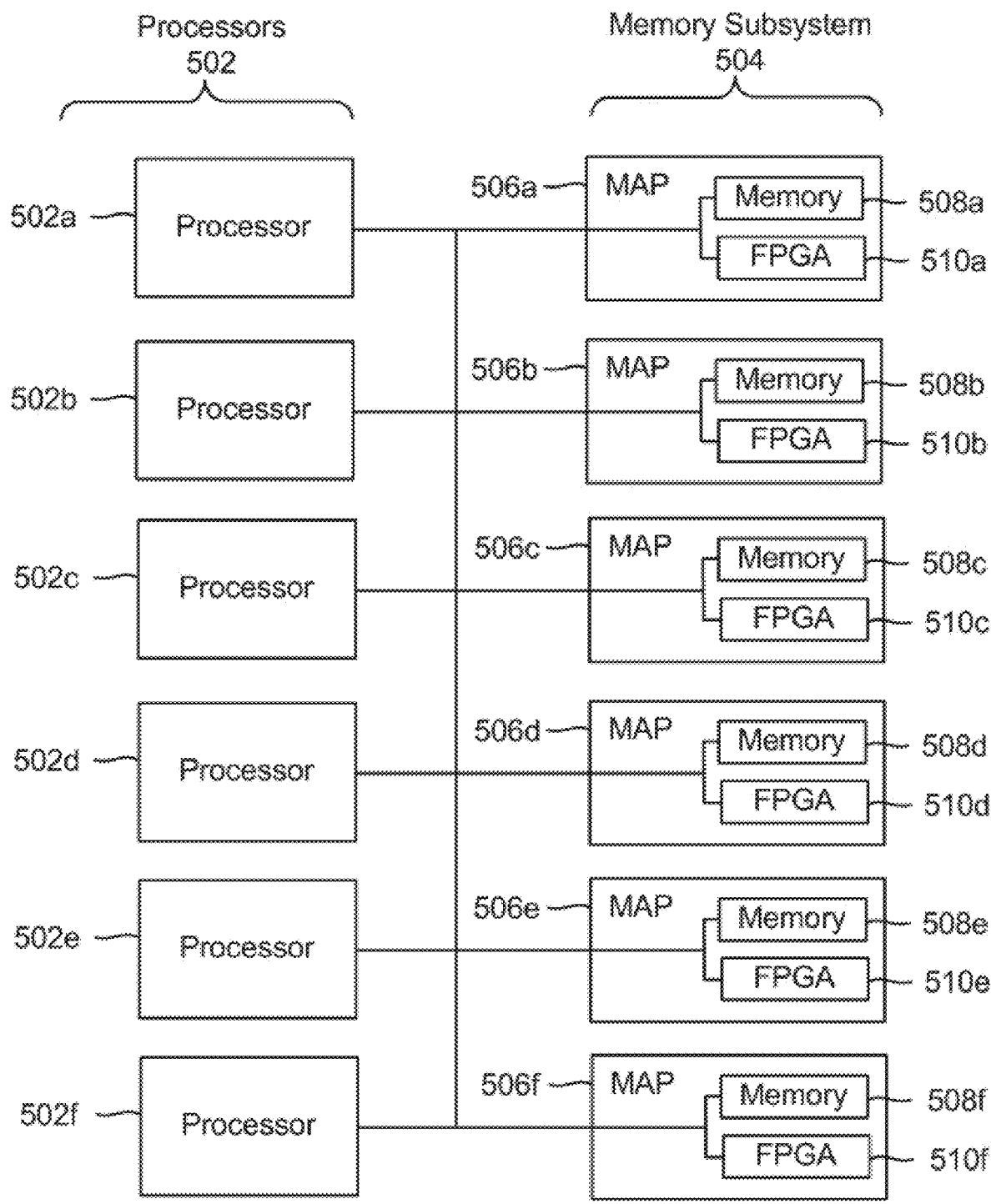
FIG. 5 is a block diagram of a multiprocessor computer system using a shared virtual address memory space.

FIG. 5 is a block diagram of a multiprocessor computer system using a shared virtual address memory space in accordance with an example embodiment. The system includes a plurality of processors 502a-f that can access a shared memory subsystem 504. The system incorporates a plurality of programmable hardware memory algorithm processors (MAPs) 506a-f in the memory subsystem 504. Each MAP 506a-f can comprise a memory 508a-f and one or more field programmable gate arrays (FPGAs) 510a-f The MAP provides a configurable functional unit and particular algorithms or portions of algorithms can be provided to the FPGAs 510a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 508a-f, allowing it to execute tasks independently of, and asynchronously from, the respective microprocessor 502a-f In this configuration, a MAP can feed results directly to another MAP for pipelining and parallel execution of algorithms.

Figure 6:
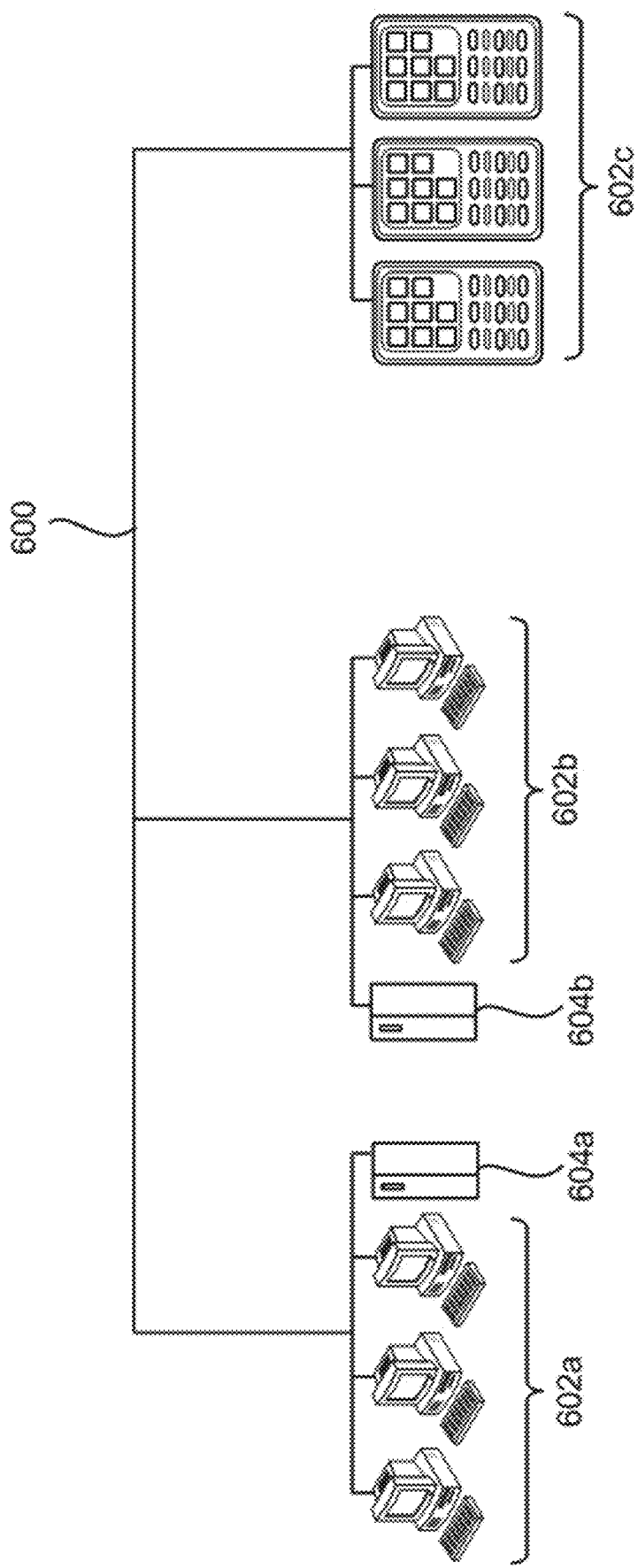
FIG. 6 is a diagram demonstrating a network configured to incorporate a plurality of computer systems, a plurality of cell phones and personal data assistants, and Network Attached Storage (NAS).

FIG. 6 is a diagram showing a network with a plurality of computer systems 602a and 602b, a plurality of cell phones and personal data assistants 602c, and Network Attached Storage (NAS) 604a and 604b. In example embodiments, systems 602a, 602b, and 602c can manage data storage and optimize data access for data stored in Network Attached Storage (NAS) 604a and 604b. A mathematical model can be used for the data and be evaluated using distributed parallel processing across computer systems 602a and 602b, and cell phone and personal data assistant systems 602c. Computer systems 602a and 602b, and cell phone and personal data assistant systems 602c can also provide parallel processing for adaptive data restructuring of the data stored in Network Attached Storage (NAS) 604a and 604b. FIG. 6 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface. In some instances, processors can maintain separate memory spaces and transmit data through network interfaces, back plane or other connectors for parallel processing by other processors. In some instances, some or all of the processors can use a shared virtual address memory space.

Any of the systems described herein may comprise sequence information stored on non-transitory computer readable storage media. In some instances, any of the systems described herein comprise a computer input file. In some instances, the computer input file comprises sequence information. In some instances, the computer input file comprises instructions for synthesis of a plurality of polynucleotide sequences. In some instances, the instructions are received by a computer. In some instances, the instructions are processed by the computer. In some instances, the instructions are transmitted to a material deposition device. In some instances, the non-transitory computer readable storage media is encoded with a program including instructions executable by the operating system of an optionally networked digital processing device. In some instances, a computer readable storage medium is a tangible component of a digital processing device. In some instances, a computer readable storage medium is optionally removable from a digital processing device. In some instances, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some instances, the program and instructions are permanently, substantially permanently, semi-permanently, or non-transitorily encoded on the media.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Functionalization of a Substrate Surface

A substrate was functionalized to support the attachment and synthesis of a library of polynucleotides. The substrate surface was first wet cleaned using a piranha solution comprising 90% $H_2SO_4$ and 10% $H_2O_2$ for 20 minutes. The substrate was rinsed in several beakers with deionized water, held under a deionized water gooseneck faucet for 5 min, and dried with $N_2$. The substrate was subsequently soaked in $NH_4OH$ (1:100; 3 mL:300 mL) for 5 min, rinsed with DI water using a handgun, soaked in three successive beakers with deionized water for 1 min each, and then rinsed again with deionized water using the handgun. The substrate was then plasma cleaned by exposing the substrate surface to $O_2$. A SAMCO PC-300 instrument was used to plasma etch $O_2$ at 250 watts for 1 min in downstream mode.

The cleaned substrate surface was actively functionalized with a solution comprising N-(3-triethoxysilylpropyl)-4-hydroxybutyramide using a YES-1224P vapor deposition oven system with the following parameters: 0.5 to 1 torr, 60 min, 70° C., 135° C. vaporizer. The substrate surface was resist coated using a Brewer Science 200X spin coater. SPR™ 3612 photoresist was spin coated on the substrate at 2500 rpm for 40 sec. The substrate was pre-baked for 30 min at 90° C. on a Brewer hot plate. The substrate was subjected to photolithography using a Karl Suss MA6 mask aligner instrument. The substrate was exposed for 2.2 sec and developed for 1 min in MSF 26A. Remaining developer was rinsed with the handgun and the substrate soaked in water for 5 min. The substrate was baked for 30 min at 100° C. in the oven, followed by visual inspection for lithography defects using a Nikon L200. A cleaning process was used to remove residual resist using the SAMCO PC-300 instrument to $O_2$ plasma etch at 250 watts for 1 min.

The substrate surface was passively functionalized with a 100 μL solution of perfluorooctyltrichlorosilane mixed with 10 μL light mineral oil. The substrate was placed in a chamber, pumped for 10 min, and then the valve was closed to the pump and left to stand for 10 min. The chamber was vented to air. The substrate was resist stripped by performing two soaks for 5 min in 500 mL NMP at 70° C. with ultrasonication at maximum power (9 on Crest system). The substrate was then soaked for 5 min in 500 mL isopropanol at room temperature with ultrasonication at maximum power. The substrate was dipped in 300 mL of 200 proof ethanol and blown dry with $N_2$. The functionalized surface was activated to serve as a support for polynucleotide synthesis.

Example 2: Synthesis of a 50-Mer Sequence on an Oligonucleotide Synthesis Device A two dimensional oligonucleotide synthesis device was assembled into a flowcell, which was connected to a flowcell (Applied Biosystems ("ABI394 DNA Synthesizer")). The two-dimensional oligonucleotide synthesis device was uniformly functionalized with N-(3-TRIETHOXYSILYLPROPYL)-4-HYDROXYBUTYRAMIDE (Gelest) was used to synthesize an exemplary polynucleotide of 50 bp ("50-mer polynucleotide") using polynucleotide synthesis methods described herein.

The sequence of the 50-mer was as described in SEQ ID NO.: 1. 5'AGACAATCAACCAT-TTGGGGTGGACAGCCTTGACCTCTAGACTTCGG-CAT##TTTTTTTTTT3' (SEQ ID NO.: 1), where # denotes Thymidine-succinyl hexamide CED phosphoramidite (CLP-2244 from ChemGenes), which is a cleavable linker enabling the release of polynucleotides from the surface during deprotection.

The synthesis was done using standard DNA synthesis chemistry (coupling, capping, oxidation, and deblocking) according to the protocol in Table 3 and ABI394 DNA Synthesizer.

TABLE 3

Synthesis Protocol

| General DNA Synthesis | Table 3 | |
|---|---|---|
| Process Name | Process Step | Time (sec) |
| WASH (Acetonitrile Wash Flow) | Acetonitrile System Flush | 4 |
| | Acetonitrile to Flowcell | 23 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 6 |
| | Activator + Phosphoramidite to Flowcell | 6 |
| | Activator to Flowcell | 0.5 |
| | Activator + Phosphoramidite to Flowcell | 5 |
| | Activator to Flowcell | 0.5 |
| | Activator + Phosphoramidite to Flowcell | 5 |
| | Activator to Flowcell | 0.5 |
| | Activator + Phosphoramidite to Flowcell | 5 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 5 |
| | Activator + Phosphoramidite to Flowcell | 18 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| CAPPING (CapA + B, 1:1, Flow) | CapA + B to Flowcell | 15 |

TABLE 3-continued

Synthesis Protocol

| General DNA Synthesis | Table 3 | |
|---|---|---|
| Process Name | Process Step | Time (sec) |
| WASH (Acetonitrile Wash Flow) | Acetonitrile System Flush | 4 |
| | Acetonitrile to Flowcell | 15 |
| | Acetonitrile System Flush | 4 |
| OXIDATION (Oxidizer Flow) | Oxidizer to Flowcell | 18 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 15 |
| | Acetonitrile System Flush | 4 |
| | Acetonitrile to Flowcell | 15 |
| | N2 System Flush | 4 |
| | Acetonitrile System Flush | 4 |
| | Acetonitrile to Flowcell | 23 |
| | N2 System Flush | 4 |
| | Acetonitrile System Flush | 4 |
| DEBLOCKING (Deblock Flow) | Deblock to Flowcell | 36 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 18 |
| | N2 System Flush | 4.13 |
| | Acetonitrile System Flush | 4.13 |
| | Acetonitrile to Flowcell | 15 |

The phosphoramidite/activator combination was delivered similar to the delivery of bulk reagents through the flowcell. No drying steps were performed as the environment stays "wet" with reagent the entire time.

The flow restrictor was removed from the ABI394 DNA Synthesizer to enable faster flow. Without flow restrictor, flow rates for amidites (0.1M in ACN), Activator, (0.25M Benzoylthiotetrazole ("BTT"; 30-3070-xx from GlenResearch) in ACN), and Ox (0.02M 12 in 20% pyridine, 10% water, and 70% THF) were roughly ~100 uL/sec, for acetonitrile ("ACN") and capping reagents (1:1 mix of CapA and CapB, wherein CapA is acetic anhydride in THF/Pyridine and CapB is 16% 1-methylimidizole in THF), roughly ~200 uL/sec, and for Deblock (3% dichloroacetic acid in toluene), roughly ~300 uL/sec (compared to ~50 uL/sec for all reagents with flow restrictor). The time to completely push out Oxidizer was observed, the timing for chemical flow times was adjusted accordingly and an extra ACN wash was introduced between different chemicals. After polynucleotide synthesis, the chip was deprotected in gaseous ammonia overnight at 75 psi. Five drops of water were applied to the surface to recover polynucleotides. The recovered polynucleotides were then analyzed on a BioAnalyzer small RNA chip (data not shown).

Example 3: Synthesis of a 100-Mer Sequence on an Oligonucleotide Synthesis Device The same process as described in Example 2 for the synthesis of the 50-mer sequence was used for the synthesis of a 100-mer polynucleotide ("100-mer polynucleotide"; 5' CGGGATCCTTATCGTCATCGTCGTACA-GATCCCGACCCATTTGCTGTCCACCAGTCAT GCTAGCCATACCATGATGATGATGATGAT-GAGAACCCCGCAT##TTTTTTTTTT3', where # denotes Thymidine-succinyl hexamide CED phosphoramidite (CLP-2244 from ChemGenes); SEQ ID NO.: 2) on two different silicon chips, the first one uniformly functionalized with N-(3-TRIETHOXYSILYLPROPYL)-4-HYDROXYBU- TYRAMIDE and the second one functionalized with 5/95 mix of 11-acetoxyundecyltriethoxysilane and n-decyltriethoxysilane, and the polynucleotides extracted from the surface were analyzed on a BioAnalyzer instrument (data not shown).

All ten samples from the two chips were further PCR amplified using a forward (5'ATGCGGGGTTCTCATCATC3'; SEQ ID NO.: 3) and a reverse (5'CGGGATCCTTATCGTCATCG3'; SEQ ID NO.: 4) primer in a 50 uL PCR mix (25 uL NEB Q5 mastermix, 2.5 uL 10 uM Forward primer, 2.5 uL 10 uM Reverse primer, 1 uL polynucleotide extracted from the surface, and water up to 50 uL) using the following thermalcycling program:

98° C., 30 sec
98° C., 10 sec; 63° C., 10 sec; 72° C., 10 sec; repeat 12 cycles
72° C., 2 min The PCR products were also run on a BioAnalyzer (data not shown), demonstrating sharp peaks at the 100-mer position. Next, the PCR amplified samples were cloned, and Sanger sequenced. Table 4 summarizes the results from the Sanger sequencing for samples taken from spots 1-5 from chip 1 and for samples taken from spots 6-10 from chip 2.

TABLE 4

Sequencing Results

| Spot | Error rate | Cycle efficiency |
|---|---|---|
| 1 | 1/763 bp | 99.87% |
| 2 | 1/824 bp | 99.88% |
| 3 | 1/780 bp | 99.87% |
| 4 | 1/429 bp | 99.77% |
| 5 | 1/1525 bp | 99.93% |
| 6 | 1/1615 bp | 99.94% |
| 7 | 1/531 bp | 99.81% |
| 8 | 1/1769 bp | 99.94% |
| 9 | 1/854 bp | 99.88% |
| 10 | 1/1451 bp | 99.93% |

Thus, the high quality and uniformity of the synthesized polynucleotides were repeated on two chips with different surface chemistries. Overall, 89%, corresponding to 233 out of 262 of the 100-mers that were sequenced were perfect sequences with no errors. Table 5 summarizes error characteristics for the sequences obtained from the polynucleotides samples from spots 1-10.

TABLE 5

Error Characteristics

| | Sample ID/Spot no. | | | | |
|---|---|---|---|---|---|
| | OSA_0046/1 | OSA_0047/2 | OSA_0048/3 | OSA_0049/4 | OSA_0050/5 |
| Total Sequences | 32 | 32 | 32 | 32 | 32 |
| Sequencing Quality | 25 of 28 | 27 of 27 | 26 of 30 | 21 of 23 | 25 of 26 |
| Oligo Quality | 23 of 25 | 25 of 27 | 22 of 26 | 18 of 21 | 24 of 25 |
| ROI Match Count | 2500 | 2698 | 2561 | 2122 | 2499 |
| ROI Mutation | 2 | 2 | 1 | 3 | 1 |
| ROI Multi Base Deletion | 0 | 0 | 0 | 0 | 0 |
| ROI Small Insertion | 1 | 0 | 0 | 0 | 0 |
| ROI Single Base Deletion | 0 | 0 | 0 | 0 | 0 |
| Large Deletion Count | 0 | 0 | 1 | 0 | 0 |
| Mutation: G > A | 2 | 2 | 1 | 2 | 1 |
| Mutation: T > C | 0 | 0 | 0 | 1 | 0 |
| ROI Error Count | 3 | 2 | 2 | 3 | 1 |
| ROI Error Rate | Err: ~1 in 834 | Err: ~1 in 1350 | Err: ~1 in 1282 | Err: ~1 in 708 | Err: ~1 in 2500 |
| ROI Minus Primer Error Rate | MP Err: ~1 in 763 | MP Err: ~1 in824 | MP Err: ~1 in 780 | MP Err: ~1 in 429 | MP Err: ~1 in 1525 |

| | Sample ID/Spot no. | | | | |
|---|---|---|---|---|---|
| | OSA_0051/6 | OSA_0052/7 | OSA_0053/8 | OSA_0054/9 | OSA_0055/10 |
| Total Sequences | 32 | 32 | 32 | 32 | 32 |
| Sequencing Quality | 29 of 30 | 27 of 31 | 29 of 31 | 28 of 29 | 25 of 28 |
| Oligo Quality | 25 of 29 | 22 of 27 | 28 of 29 | 26 of 28 | 20 of 25 |
| ROI Match Count | 2666 | 2625 | 2899 | 2798 | 2348 |
| ROI Mutation | 0 | 2 | 1 | 2 | 1 |
| ROI Multi Base Deletion | 0 | 0 | 0 | 0 | 0 |
| ROI Small Insertion | 0 | 0 | 0 | 0 | 0 |
| ROI Single Base Deletion | 0 | 0 | 0 | 0 | 0 |

TABLE 5-continued

| Error Characteristics | | | | | |
|---|---|---|---|---|---|
| Large Deletion Count | 1 | 1 | 0 | 0 | 0 |
| Mutation: G > A | 0 | 2 | 1 | 2 | 1 |
| Mutation: T > C | 0 | 0 | 0 | 0 | 0 |
| ROI Error Count | 1 | 3 | 1 | 2 | 1 |
| ROI Error Rate | Err: ~1 in 2667 | Err: ~1 in 876 | Err: ~1 in 2900 | Err: ~1 in 1400 | Err: ~1 in 2349 |
| ROI Minus Primer Error Rate | MP Err: ~1 in 1615 | MP Err: ~1 in 531 | MP Err: ~1 in 1769 | MP Err: ~1 in 854 | MP Err: ~1 in 1451 |

Example 4. Flap Endonuclease Mediated Nucleic Acid Assembly

Flap Endonuclease Mediated Nucleic Acid Assembly Reaction

A flap endonuclease mediated nucleic acid assembly reaction was prepared. Water, dNTP's (New England Biolabs), Ampligase buffer (Epicentre), ExoIII (New England Biolabs), Phusion (New England Biolabs), Ampligase (Epicentre), and Fen' (New England Biolabs) according to the concentrations in Table 6 below were combined and aliquoted into 96 well plates. DNA and vector were added in the concentrations as indicated in Table 6. Plates were sealed, mixed for 30 seconds at 1000 rpm, and briefly centrifuged. Plates were incubated at 50° C. with 105° C. heated lid for 30 minutes and then cooled to 4° C. Reactions were diluted 1:5 in 40 uL of cold buffer.

TABLE 6

| Reaction Concentrations | |
|---|---|
| Reagent | Final Concentration |
| Vector | 4 nM |
| Gene Fragment 1 | 4 nM |
| dNTP | .2 mM |
| 10X Ampligase buffer | 1X |
| ExoIII | 10 U |
| Phusion | 0.2 U |
| Ampligase | 1 U |
| Fen1 | 3.2 U |
| Water | Remaining water up to 10 uL |

In Vitro PCR Assay

Figure 7:
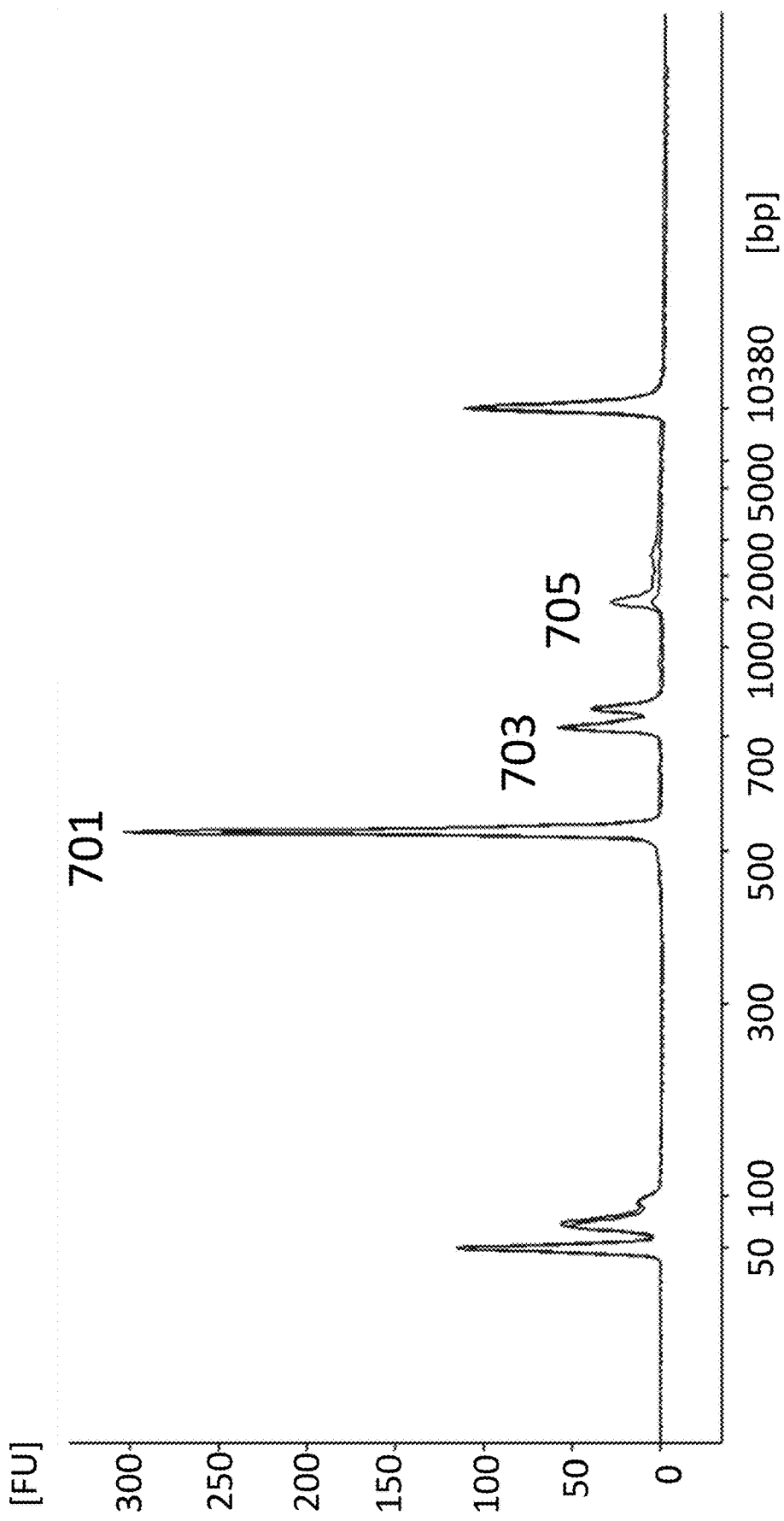
FIG. 7 is a plot from a BioAnalyzer reading with nucleotide bases on the x-axis and fluorescent units on the y-axis.

Following preparation of the flap endonuclease mediated nucleic acid assembly reaction, PCR amplification was performed. A 25 uL PCR reaction was performed according to reaction conditions in Table 7 below and amplified using thermocycler conditions according to Table 8. PCR products were analyzed on a BioAnalyzer (Agilent) (FIG. 7). Unspecified background band 701, circular vector 703, and assembled DNA inserted into the vector 705 were detected.

TABLE 7

| PCR Reaction Conditions | |
|---|---|
| Reagent | Reaction Volume (uL) |
| Water | 16.5 |
| 10X Thermopol Buffer | 2.5 |
| 10 mM dNTP | 0.5 |
| PCR Primer 1 100 uM | 0.125 |
| PCR Primer 2 100 uM | 0.125 |

TABLE 7-continued

| PCR Reaction Conditions | |
|---|---|
| Reagent | Reaction Volume (uL) |
| Diluted Reaction Product | 5 |
| Taq polymerase | 0.25 |
| Total Volume | 25 |

TABLE 8

| Thermocycler Conditions | | |
|---|---|---|
| Temperature | Time | Number of Cycles |
| 95° C. | 30 seconds | 1 |
| 95° C. | 20 seconds | 25 |
| 55° C. | 20 seconds | |
| 68° C. | 3 minutes | |
| 68° C. | 5 minutes | 1 |
| 4° C. | Indefinite | |

Transformation

Following the PCR reaction, 2 uL of the diluted reactions were electroporated into 20 uL of electrocompetent cells 10G (Lucigen). Cells were recovered with 600 uL prewarmed Lucigen recovery media. Samples were serially diluted 1:2 into Lucigen recovery media and 7 uL was spotted onto a Lennox+Carb plate. Plates were grown overnight (about 16 hours) at 37° C. overnight. The reaction efficiency was determined by counting colonies to determine Colony Forming Units (CFU) using the CFU formula: (# of colonies*total reaction volume)/(plating volume*dilution factor).

The colony counts of E. coli transformants is seen in Table 9. The fold change was determined by the number of colonies with insert (1× dilution) compared to the number of colonies with no insert.

TABLE 9

| Colony Counts | | | | |
|---|---|---|---|---|
| Reaction | Number of Colonies with No Insert | Number of Colonies with Insert (1X Dilution) | Number of Colonies with Insert (10X Dilution) | Fold Change |
| 50 C.-Exo | 19 | 23 | | 1.2 |
| 50° C. 10 U ExoIII | 58 | 929 | 100 | 16 |
| 65° C. 10 U ExoIII | 25 | 33 | | 1.3 |

A correlation of the in vitro PCR assay (FIG. 7) to the number of E. coli transformants as a read out of assembled constructs (Table 10) was observed. Specifically a linearized vector was assembled with 1 DNA insert containing 40 base pair of homology to each other. Colony formulation in E coil correlates to the re-circularization of the vector after being assembled with the insert. The peak size from the in vitro PCR assay correlated to the number of E. coli colony counts after transformation. The negative control reactions lacked DNA insert and showed low levels of background colonies.

Figure 8:
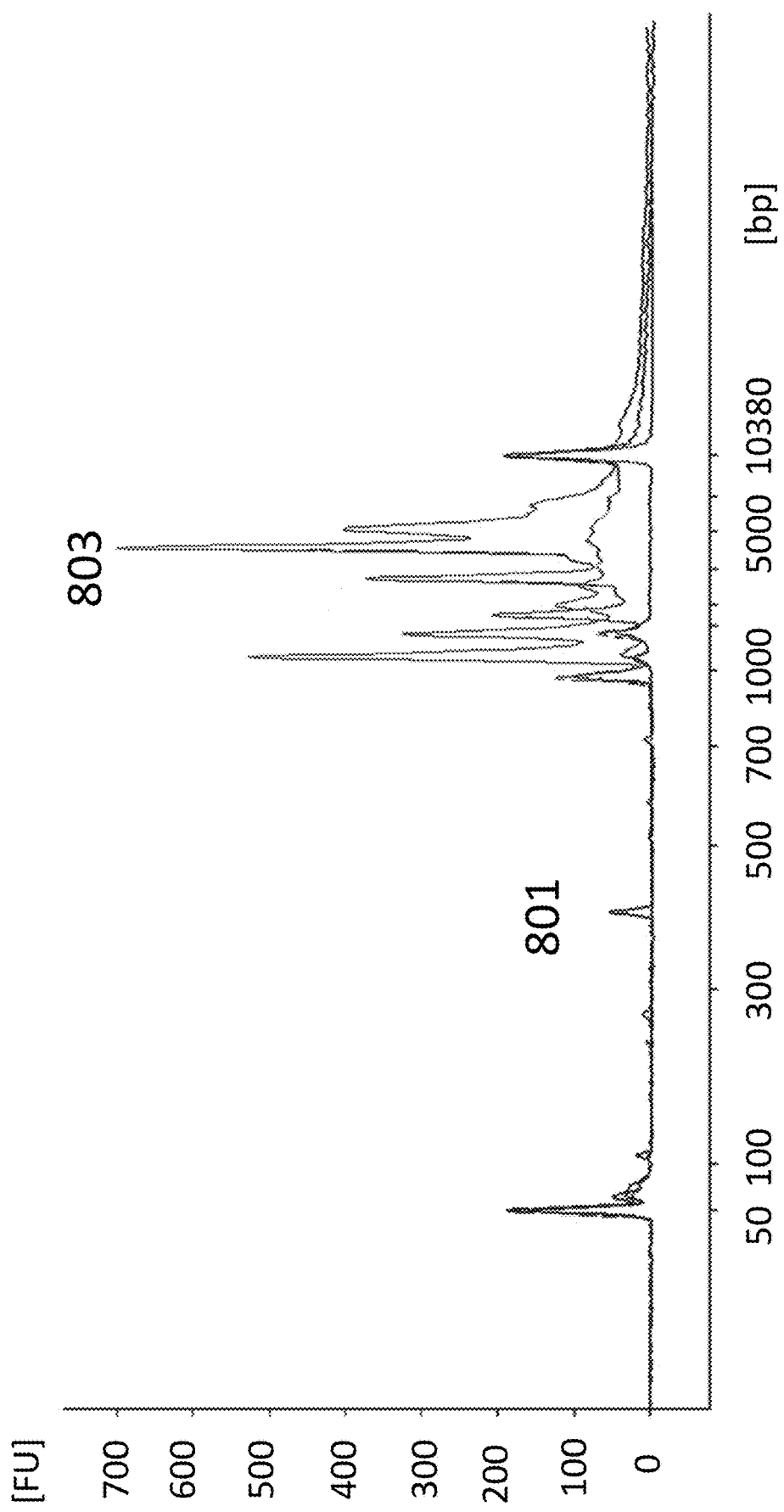
FIG. 8 is a plot from a BioAnalyzer reading with nucleotide bases on the x-axis and fluorescent units on the y-axis.

Example 5. Flap Endonuclease Mediated Nucleic Acid Assembly with Three Gene Fragments A flap endonuclease mediated nucleic acid assembly reaction was performed similar to Example 4. Three DNA fragments were inserted into a vector. Following preparation of the flap endonuclease mediated nucleic acid assembly reaction, PCR amplification was performed similar to Example 4. PCR products were analyzed on a BioAnalyzer (Agilent) (FIG. 8). Re-circularized digested vector 801 and assembled DNA inserted in the vector 803 were detected.

Example 6. Flap Endonuclease Mediated Nucleic Acid Assembly with Varying Concentrations of Fen1 and ExoIII A flap endonuclease mediated nucleic acid assembly reaction was prepared similarly to Example 4. Varying conditions were tested as seen in Table 10.

TABLE 10

Reaction Conditions

| Sample | Reaction Condition |
|---|---|
| 1 | Baseline |
| 2 | No Ampligase |
| 3 | No Phusion |
| 4 | No Fen1 |
| 5 | 2X Fen1 (6.4 U Fen1) |
| 6 | 0.5X Fen1(1.7 U Fen1) |
| 7 | 2X Fen1 (6.4 U Fen1) 2X ExoIII (20 U ExoIII) |
| 8 | 0.5X Fen1(1.7 U Fen1) 0.5X ExoIII (5 U ExoIII) |
| 9 | 0.25X Fen1 (0.8 U Fen1) 0.25X ExoIII (2.5 U ExoIII) |
| 10 | Reaction conditions from in vitro recombination cloning |

Figure 9:
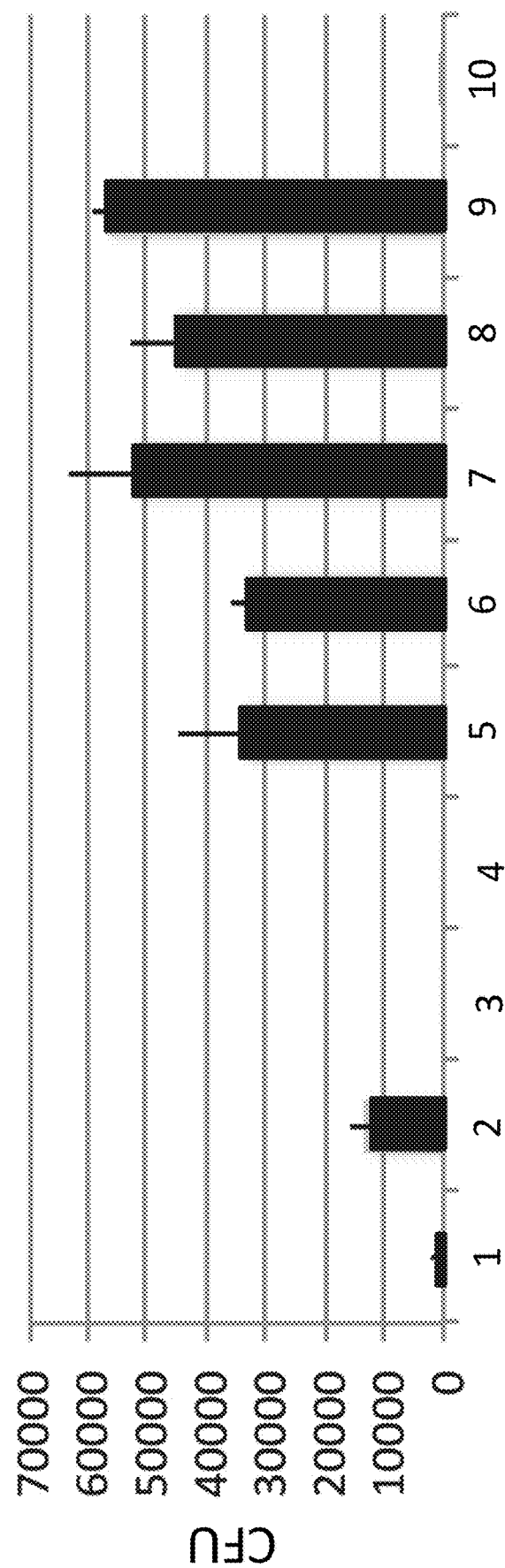
FIG. 9 is a plot of colony forming units (CFU) with varying concentrations of ExoIII and Fen1.

The number of colonies was counted for each sample as seen in FIG. 9. Data showed that colony counts with titrated Fen1 and ExoIII were significantly higher than baseline and correlated to higher amplification products in the in vitro PCR assay.

Colonies were isolated, and assemblies were assayed by colony PCR. Reactions were run on a Fragment Analyzer (capillary gel electrophoresis). Proper assemblies were determined by size of PCR product (data not shown).

Isolated colonies were grown overnight and miniprepped to isolate the assembled vector DNA. Samples were analyzed by next-generation sequencing. The varying Fen' and ExoIII concentrations resulted in varying amount of correctly assembled constructs as seen in Table 11. All of the universal primer flanking sequences were removed in the passed samples. In the 7/10 samples that had the proper size in the colony PCR, all 7 passed NGS at the homology sites.

TABLE 11

Colony Data

| Reaction | Colonies Picked | % Correct Size by Colony PCR | % Passed NGS Analysis |
|---|---|---|---|
| Baseline − insert | 1 | 0 | 0 |
| Baseline + insert | 7 | 0 | 0 |
| 2X Fen1 (6.4 U Fen1) | 10 | 70 | 70 |
| 2X Fen1 (6.4 U Fen1) 2X ExoIII (20 U ExoIII) | 10 | 0 | 0 |
| 0.5X Fen1(1.7 U Fen1) 0.5X ExoIII (5 U ExoIII) | 10 | 50 | 30-50 |
| 0.25X Fen1 (0.8 U Fen1) 0.25X ExoIII (2.5 U ExoIII) | 10 | 20 | 20 |

Example 7. Flap Endonuclease Mediated Nucleic Acid Assembly with Varying Concentrations of Enzymes A flap endonuclease mediated nucleic acid assembly reaction was prepared similarly to Example 4. Three gene fragments were inserted into a vector. Experiments were performed using reaction conditions according to Table 12 below as a baseline and variations on Phusion, Ampligase, ExoIII, and Fen1 concentrations. The concentrations of Phusion, Ampligase, ExoIII, and Fen1 used are shown in Table 13.

TABLE 12

Reaction Conditions

| Reagent | Final Concentration |
|---|---|
| Vector | 4 nM |
| Gene Fragment | 4 nM |
| dNTP | 0.2 mM |
| 10X Ampligase buffer | 1X |
| ExoIII | 1 U |

TABLE 13

Enzyme Concentrations

| | |
|---|---|
| 1 | 0.32 U Fen1 |
| | 1 U ExoIII |
| | 0.2 U Phusion |
| | 1 U Ampligase |
| 2 | 0.32 U Fen1 |
| | 1 U ExoIII |
| | 0.1 U Phusion |
| | 0.5 U Ampligase |
| 3 | 0.32 U Fen1 |
| | 1 U ExoIII |
| | 0.1 U Phusion |
| | 1.0 U Ampligase |
| 4 | 0.32 U Fen1 |
| | 1 U ExoIII |
| | 0.05 U Phusion |
| | 1.0 U Ampligase |
| 5 | 0.32 U Fen1 |
| | 1.5 U ExoIII |
| | 0.2 U Phusion |
| | 1.0 U Ampligase |
| 6 | 4.8 U Fen1 |
| | 1.0 U ExoIII |
| | 0.2 U Phusion |
| | 1.0 U Ampligase |
| 7 | 0.32 U Fen1 |
| | 0.5 U ExoIII |

TABLE 13-continued

| | Enzyme Concentrations |
|---|---|
| 8 | 0.05 U Phusion<br>1.0 U Ampligase<br>0.32 U Fen1<br>1.0 U ExoIII<br>0.1 U Phusion<br>0.1 U Ampligase |
| 9 | 0.32 U Fen1<br>1.0 U ExoIII<br>0.1 U Phusion<br>0.25 U Ampligase |
| 10 | 0.32 U Fen1<br>1.0 U ExoIII<br>0.2 U Phusion<br>0.5 U Ampligase |
| 11 | 0.32 U Fen1<br>1.0 U ExoIII<br>0.2 U Phusion<br>0.25 U Ampligase |
| 12 | 0.32 U Fen1<br>0.5 U ExoIII<br>0.1 U Phusion<br>1.0 U Ampligase |
| 13 | 3.2 U Fen1<br>1.0 U ExoIII<br>0.2 U Phusion<br>1.0 U Ampligase |
| 14 | 0.32 U Fen1<br>0.5 U ExoIII<br>0.2 U Phusion<br>1.0 U Ampligase |
| 15 | 0.32 U Fen1<br>1.5 U ExoIII<br>0.1 U Phusion<br>1.0 U Ampligase |
| 16 | 0.32 U Fen1<br>1.5 U ExoIII<br>0.05 U Phusion<br>1.0 U Ampligase |
| 17 | 3.2 U Fen1<br>0.5 U ExoIII<br>0.2 U Phusion<br>0.5 U Ampligase |
| 18 | 3.2 U Fen1<br>1.0 U ExoIII<br>0.2 U Phusion<br>0.5 U Ampligase |
| 19 | 3.2 U Fen1<br>1.0 U ExoIII<br>0.2 U Phusion<br>0 U Ampligase |
| 20 | 4.8 U Fen1<br>0.5 U ExoIII<br>0.2 U Phusion<br>1.0 U Ampligase |
| 21 | 0.32 U Fen1<br>1.5 U ExoIII<br>0.5 U Phusion<br>1.0 U Ampligase |
| 22 | 3.2 U Fen1<br>0.5 U ExoIII<br>0.2 U Phusion<br>1.0 U Ampligase |
| 23 | 0.32 U Fen1<br>1.0 U ExoIII<br>0.2 U Phusion<br>0.1 U Ampligase |
| 24 | 0.32 U Fen1<br>0.5 U ExoIII<br>0.5 U Phusion<br>1.0 U Ampligase |
| 25 | 0.32 U Fen1<br>1.0 U ExoIII<br>0.5 U Phusion<br>1.0 U Ampligase |
| 26 | 3.2 U Fen1<br>10.0 U ExoIII<br>0.2 U Phusion<br>1.0 U Ampligase |
| 27 | 3.2 U Fen1<br>5.0 U ExoIII<br>0.2 U Phusion<br>1.0 U Ampligase |

Figure 10:
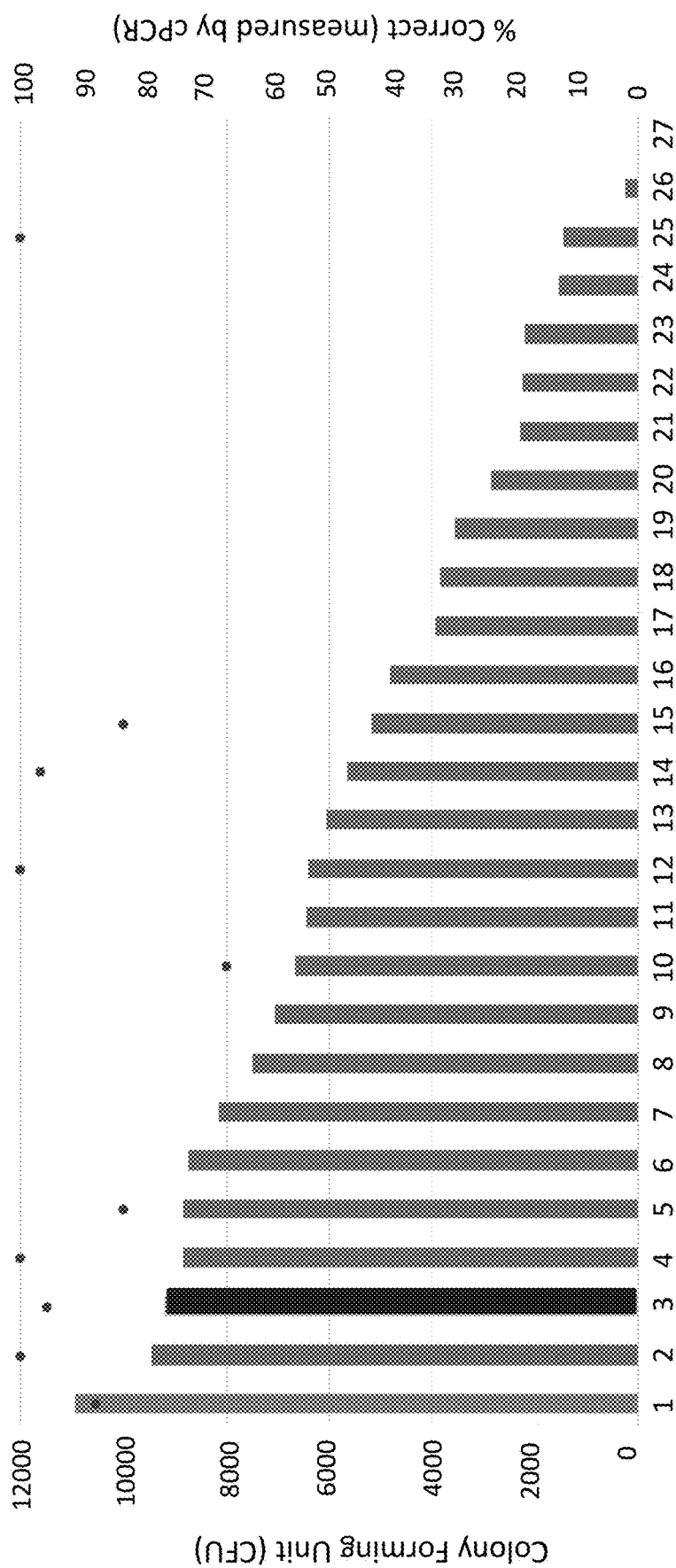
FIG. 10 is a plot of colony forming units (CFU) and percentage of correct assembly of flap endonuclease mediated nucleic acid assembly reactions with varying enzyme concentrations

Referring to FIG. 10, the average colony forming unit (CFU) (gray bars) were measured for each of the different enzyme ratios. The percentage of correct assembly was also measured (black circles) as determined by colony PCR (cPCR). The data presented is an average of the results.

Using the different enzyme ratios, there was increased number of CFUs and improved percentage of correct assembly (FIG. 10). Reaction condition comprising 0.32 U Fen1, 1 U ExoIII, 0.2 U Phusion, and 1 U Ampligase resulted in the highest increase in the number of CFUs as compared to other reaction conditions and a percentage of correct assembly of more than 85%.

Example 8. Flap Endonuclease Mediated Nucleic Acid Assembly of 1.8 kb Fragment

Figure 11:
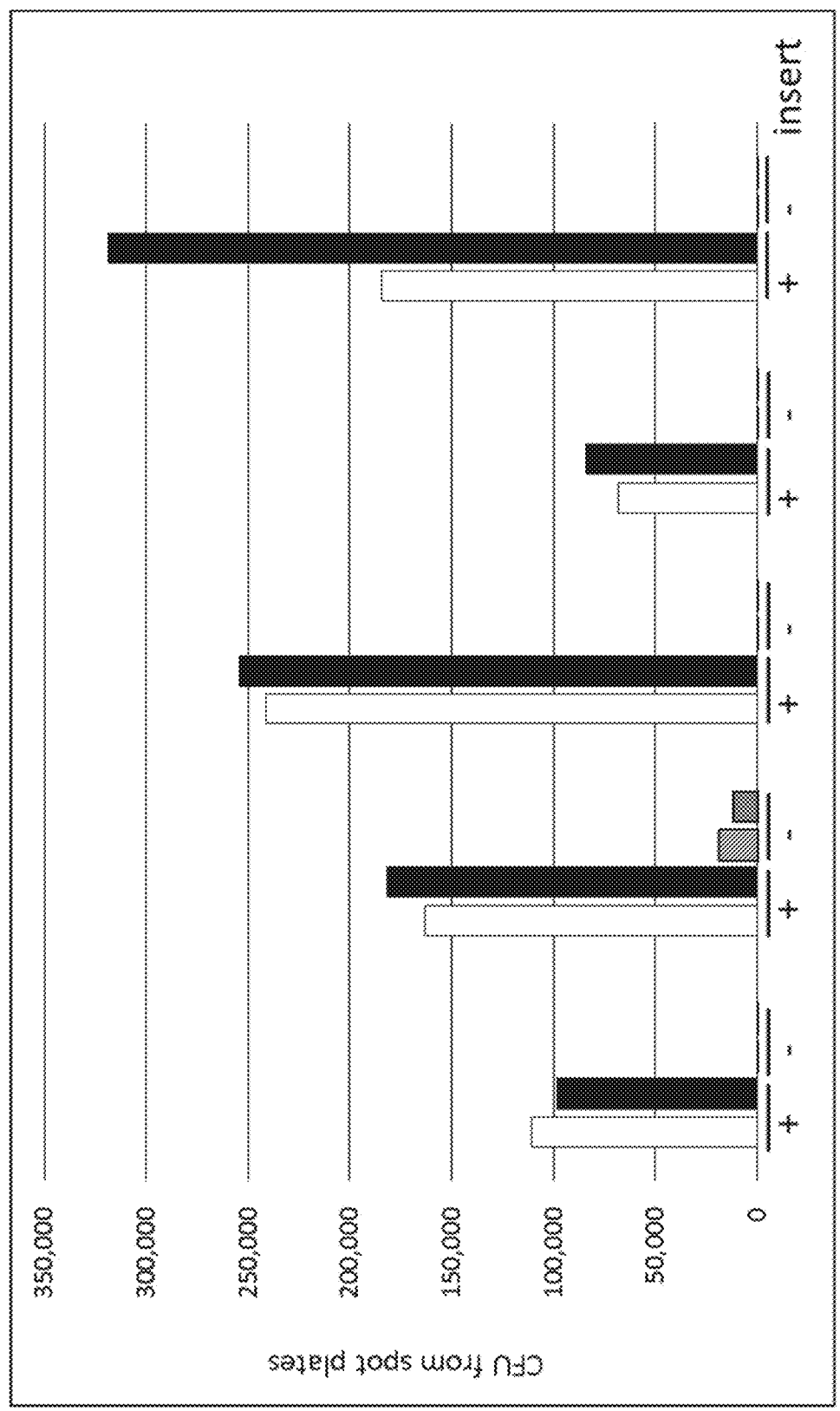
FIG. 11 is a plot of colony forming units (CFU) of a 1.8 kb assembly.

A flap endonuclease mediated nucleic acid assembly reaction was prepared similarly to Example 4. Flap endonuclease mediated nucleic acid assembly reactions were performed using enzyme concentrations of 1 U ExoIII, 0.2 U Phusion, 1 U Ampligase, and 0.32 U Fen1 with insert (white bars) and without insert (hashed bars, third bar from left). Flap endonuclease mediated nucleic acid assembly reactions were also tested using enzyme concentrations of 1 U ExoIII, 0.1 U Phusion, 1 U Ampligase, and 0.32 U Fen1 with insert (black bars) and without insert (hashed bars, fourth from left). Colony forming units from spot plates were then measured (Y-axis). Referring to FIG. 11, there was an increased number of CFUs in reactions comprising insert as compared to reactions without insert.

Figure 12:
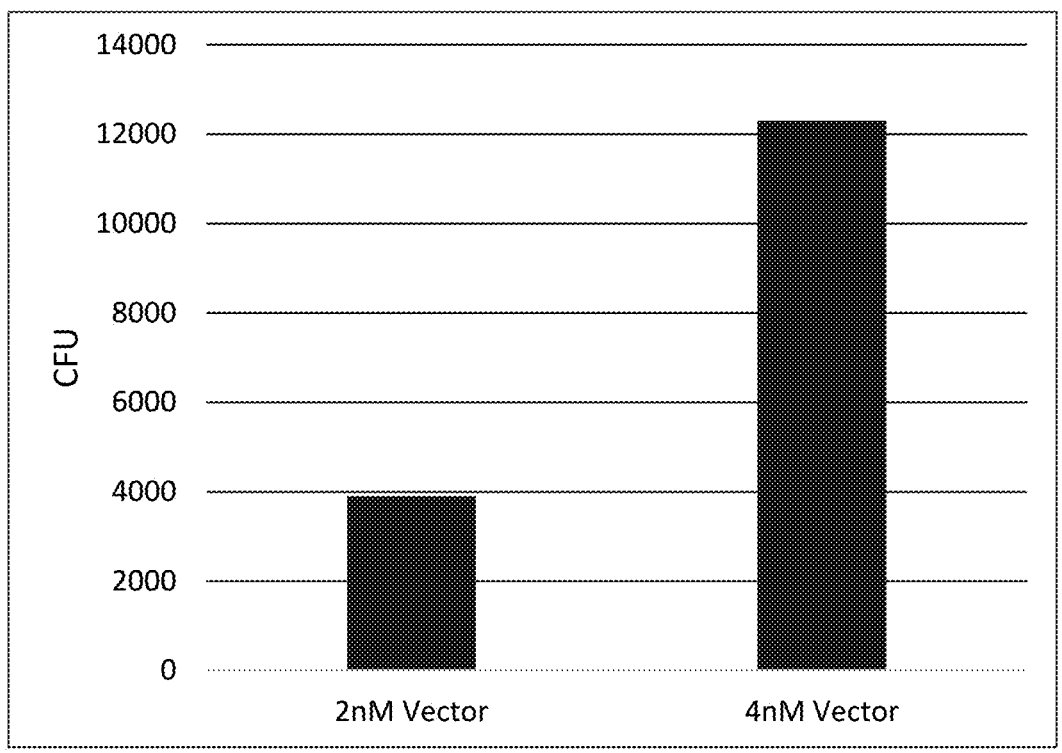
FIG. 12 is a plot of flap endonuclease mediated nucleic acid assembly with two fragments of DNA.

Example 9. Flap Endonuclease Mediated Nucleic Acid Assembly of Two DNA Fragments A flap endonuclease mediated nucleic acid assembly reaction was prepared similarly to Example 4. Different amounts of input DNA or linearized vector on colony forming units (CFU) were assayed. The amount of input DNA tested was 2 nM or 4 nM of linearized vector. Referring to FIG. 12, two fragments of DNA were assembled and there was a positive correlation with the amount of starting material to the amount of colony forming units.

Example 10. Multi-Piece DNA Assembly into a DNA Vector

A flap endonuclease mediated nucleic acid assembly reaction was prepared similarly to Example 4. Experiments were performed using reaction concentrations of the reagents as seen in Table 14. The reactions were prepared on ice, and following addition of the various reagents, the reactions were incubated at 50° C. for 30 minutes. The reactions were then diluted 1:5 and transformed into E. coli.

TABLE 14

Method 1 Reaction Concentrations

| Reagent | 5 uL reaction | Final Concentration |
| --- | --- | --- |
| dNTP (10 mM) | 0.1 | .2 mM |
| 10x Ampligase buffer | 0.5 | 1X |
| ExoIII (100 U/uL) | 0.005 | 0.1 U/uL |
| Phusion (2 U/uL) | 0.05 | 0.02 U/uL |
| Ampligase (5 U/uL) | 0.1 | 0.1 U/uL |
| Fen1 (32 U/uL) | 0.005 | 0.032 U/uL |
| Vector DNA | | 20 fmol |
| Insert DNA | | 40 fmol/Insert |
| Water* | To 5 uL | |

Figure 13:
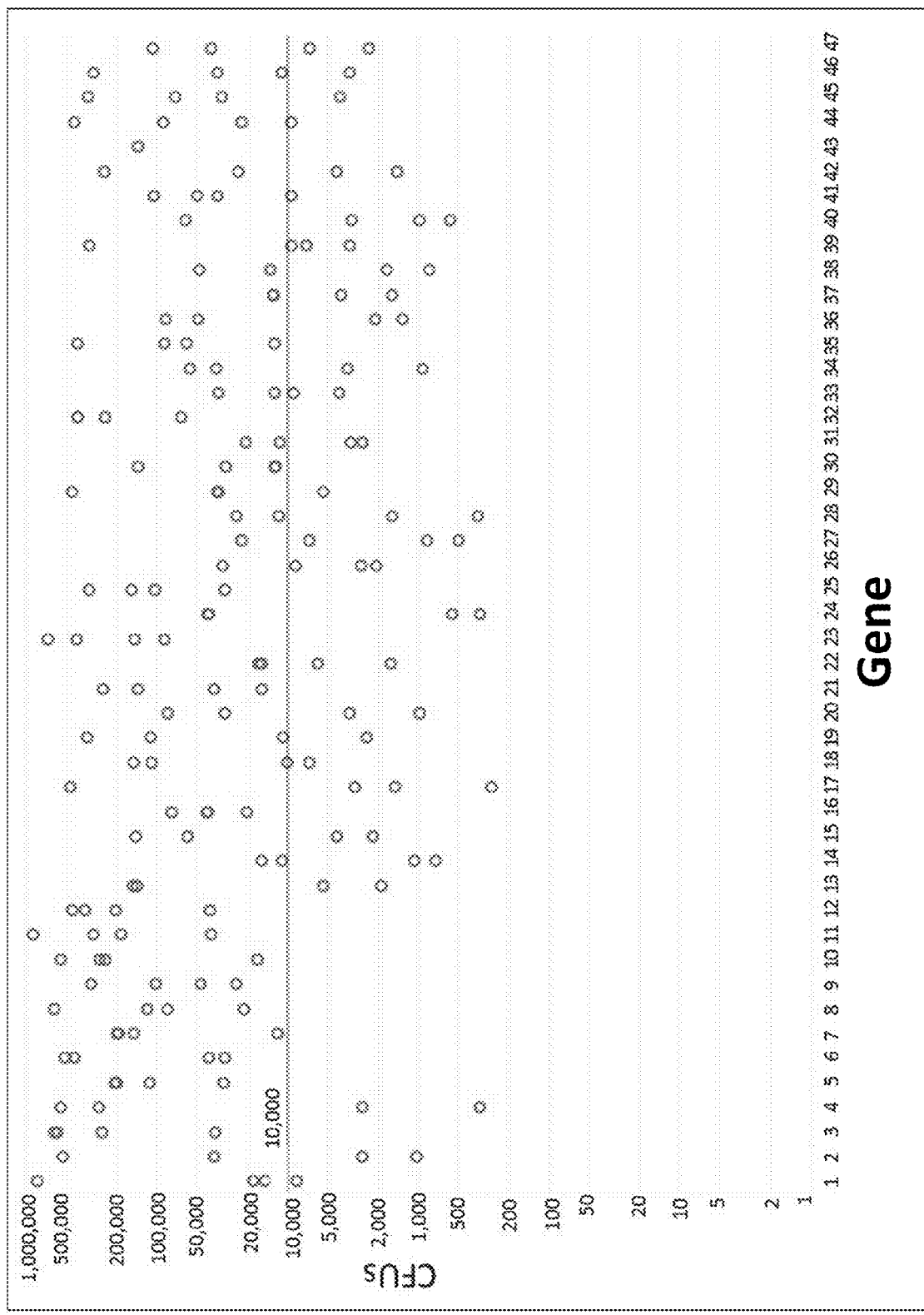
FIG. 13 is a plot of colony forming units (y-axis) for several genes (x-axis) of flap endonuclease mediated nucleic acid assembly with multiple fragments of DNA into a DNA vector.

Colony forming units (CFUs) were then measured. As seen in FIG. 13, colony forming units (y-axis) was measured for the different genes tested (x-axis). From the data, the flap endonuclease mediated nucleic acid assembly reaction according to the reaction conditions described resulted in high CFUs and assembly fidelity rates.

Example 11. Multi-Piece DNA Assembly into a DNA Vector Using High Amount of ExoIII A flap endonuclease mediated nucleic acid assembly reaction was prepared similarly to Example 4 and Example 10. The concentration of ExoIII was increased 16 fold as compared to Example 10. The reaction concentrations are seen in Table 15. The reactions were prepared on ice, and following addition of the various reagents, the reactions were incubated at 65° C. for 30 minutes. The reactions were then diluted 1:5 and transformed into E. coli.

TABLE 15

Method 2 Reaction Concentrations

| Reagent | 5 uL reaction | Final Concentration |
| --- | --- | --- |
| dNTP (10 mM) | 0.1 | .2 mM |
| 10x Ampligase buffer | 0.5 | 1x |
| ExoIII 100 U/uL | 0.08 | 1.6 U/uL |
| Phusion 2 U/uL | 0.05 | 0.02 U/uL |
| Ampligase 5 U/uL | 0.1 | 0.1 U/uL |
| Fen1 32 U/uL | 0.005 | 0.032 U/uL |
| Vector DNA | | 20 fmol |
| Insert DNA | | 40 fmol/Insert |
| Water* | To 5 uL | |

Figure 14A:
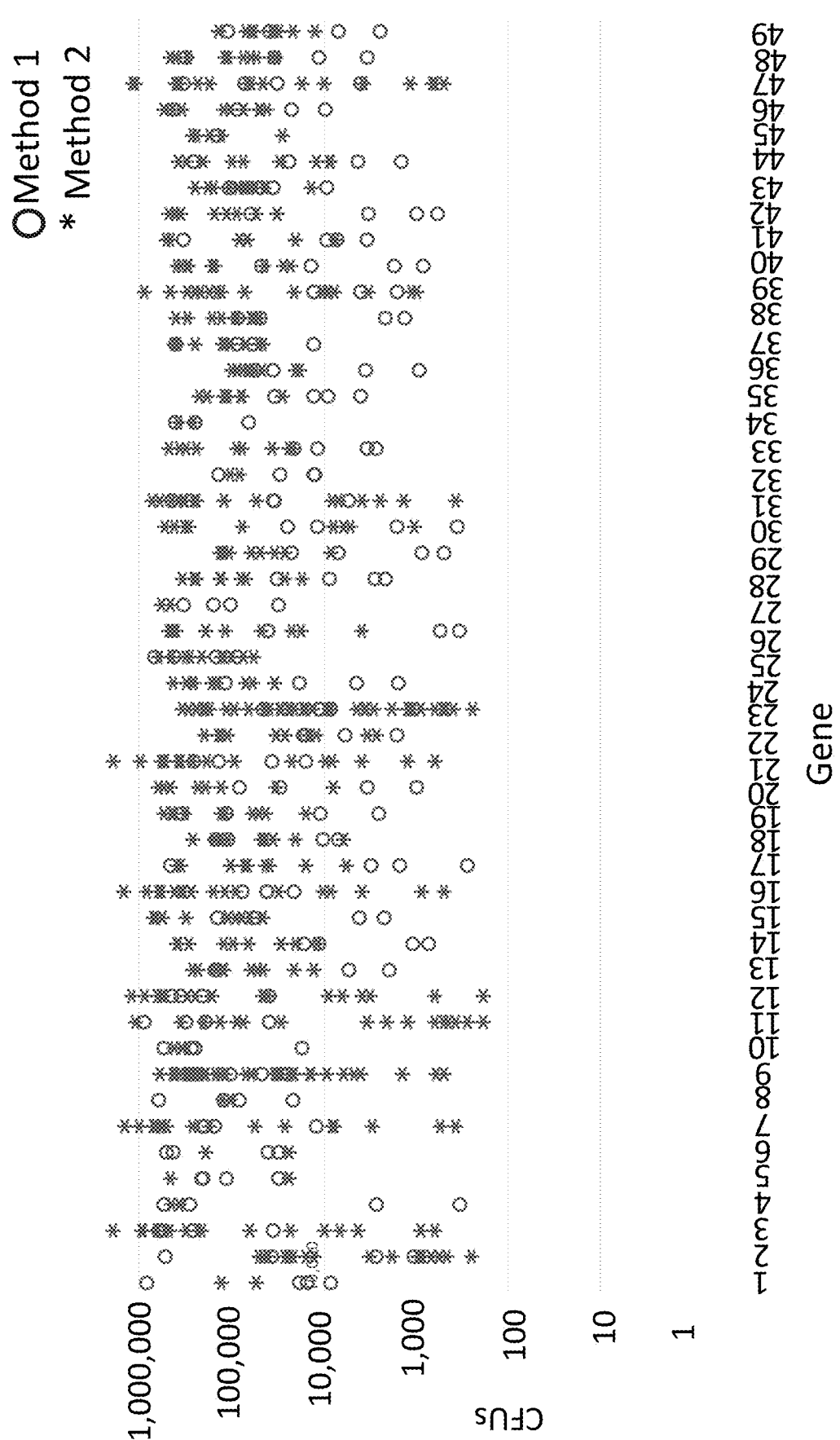
FIG. 14A is a plot of colony forming units (y-axis) for several genes (x-axis) of flap endonuclease mediated nucleic acid assembly with increased concentration of ExoIII with multiple fragments of DNA into a DNA vector.

Colony forming units were then measured. As seen in FIG. 14A, colony forming units (y-axis) was measured for the different genes tested (x-axis) using reaction concentration according to Method 1 (Table 14) and reaction concentrations according to Method 2 (Table 15). Results from FIG. 14A show higher CFU and greater assembly fidelity using Method 2.

Figure 14B:
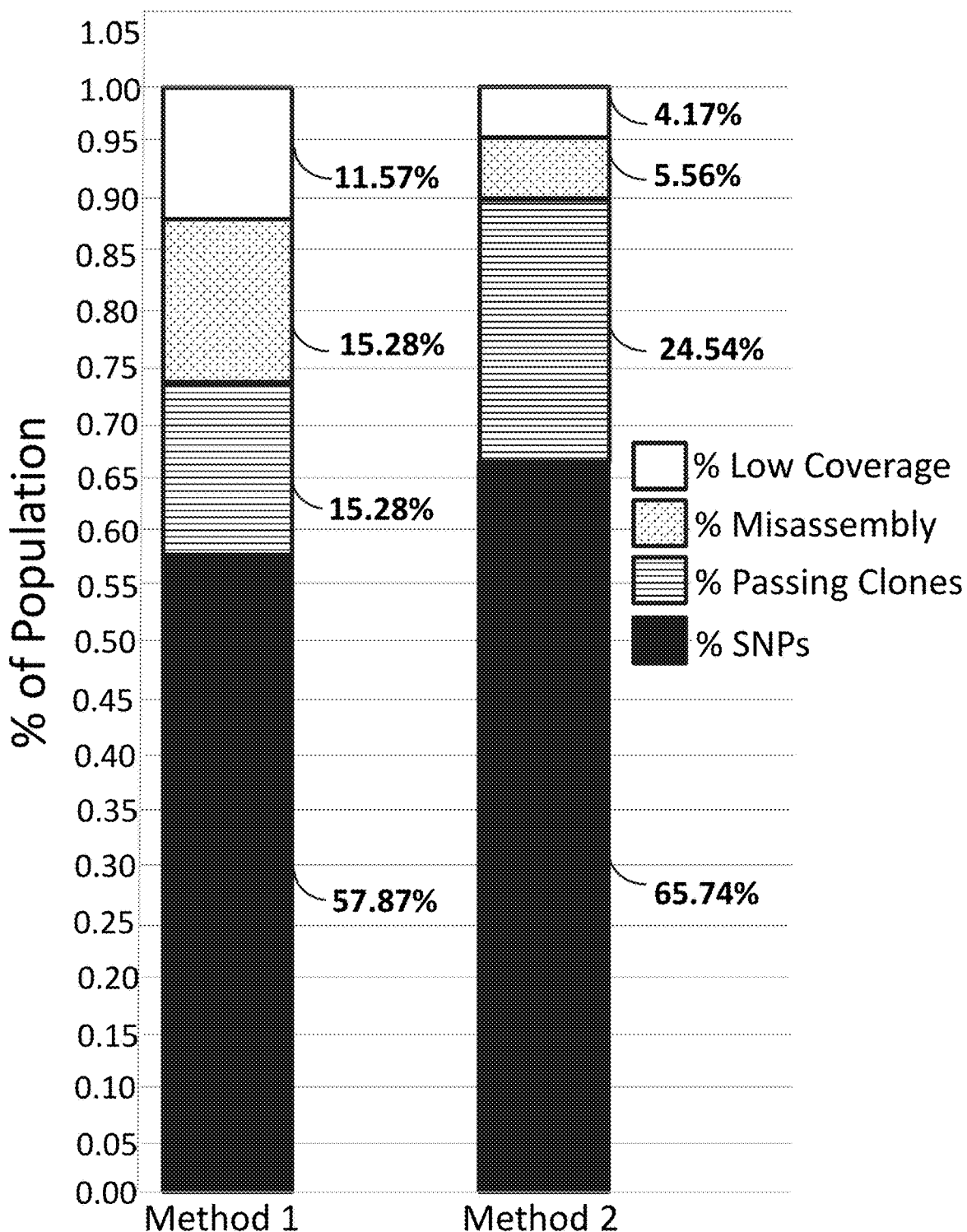
FIG. 14B is a plot of next generation sequence analysis of assembled genes.
Figure 14C:
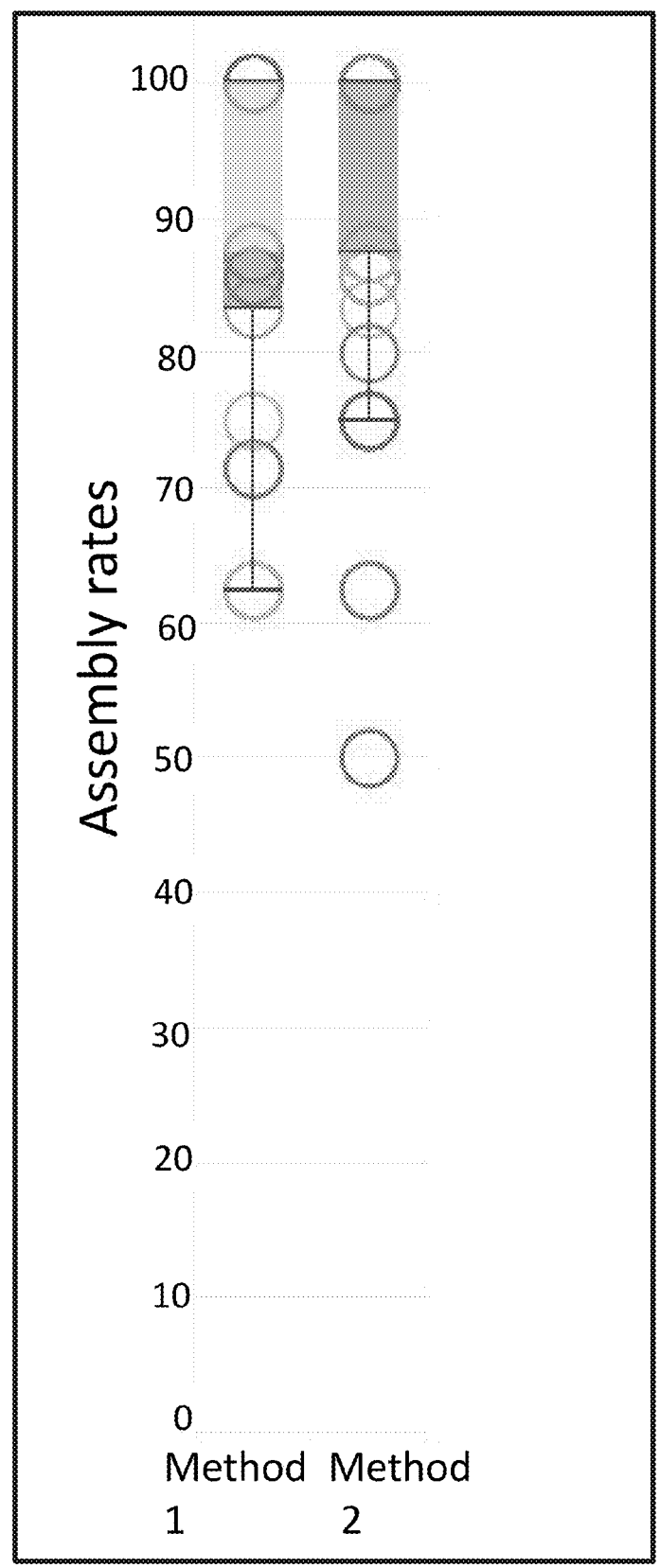
FIG. 14C is a plot of samples of assembly rate.

Next generation sequencing (NGS) was also performed. As seen in FIG. 14B, empty or low coverage (white bars), misassembly (dotted bars), passing clones (horizontal bars), and SNPs (black bars) were measured following flap endonuclease mediated nucleic acid assembly using reaction concentrations according to Method 1 (Table 14) and reaction concentrations according to Method 2 (Table 15). The NGS results showed similar results as FIG. 14A in that higher CFUs and improved assembly fidelity was observed using Method 2. Referring to FIG. 14C, assembly rate (y-axis) was compared using Method 1 and Method 2 (x-axis). Assembly fidelity rates were improved using Method 2 as compared to Method 1.

The example shows that the flap endonuclease mediated nucleic acid assembly reaction using the described reaction conditions resulted in higher colony forming units and improved assembly fidelity.

Example 12: Flap Endonuclease Mediated Nucleic Acid Assembly Using a Bridged Assembly Method A flap endonuclease mediated nucleic acid assembly reaction was prepared similarly to Example 4 and Example 10. The reaction conditions are seen in Table 14. In addition, 40 fmol of a DNA bridge was used.

The various samples included assembly with no bridge (negative control), fragments comprising a 40 base pair homology sequence (positive control), double stranded DNA bridge comprising a 40 base pair homology sequence to each fragment, and a double stranded DNA bridge comprising a 50 base pair homology sequence to each fragment. The reactions were prepared and transformed into E. coli. The number of correct assemblies and percentage of correct assemblies were then determined and are seen in Table 16.

TABLE 16

Bridged Assembly Method

| Sample Description | Clones Tested | Correct Assemblies | % Correct Assemblies |
| --- | --- | --- | --- |
| Negative Control (no bridge) | 12 | 0 | 0 |
| Positive Control (fragments have 40 bp homology) | 12 | 12 | 100 |
| dsDNA bridge with 40 bp homology to each insert. | 12 | 12 | 100 |
| dsDNA bridge with 50 bp homology to each insert | 12 | 12 | 100 |

Figure 15A:
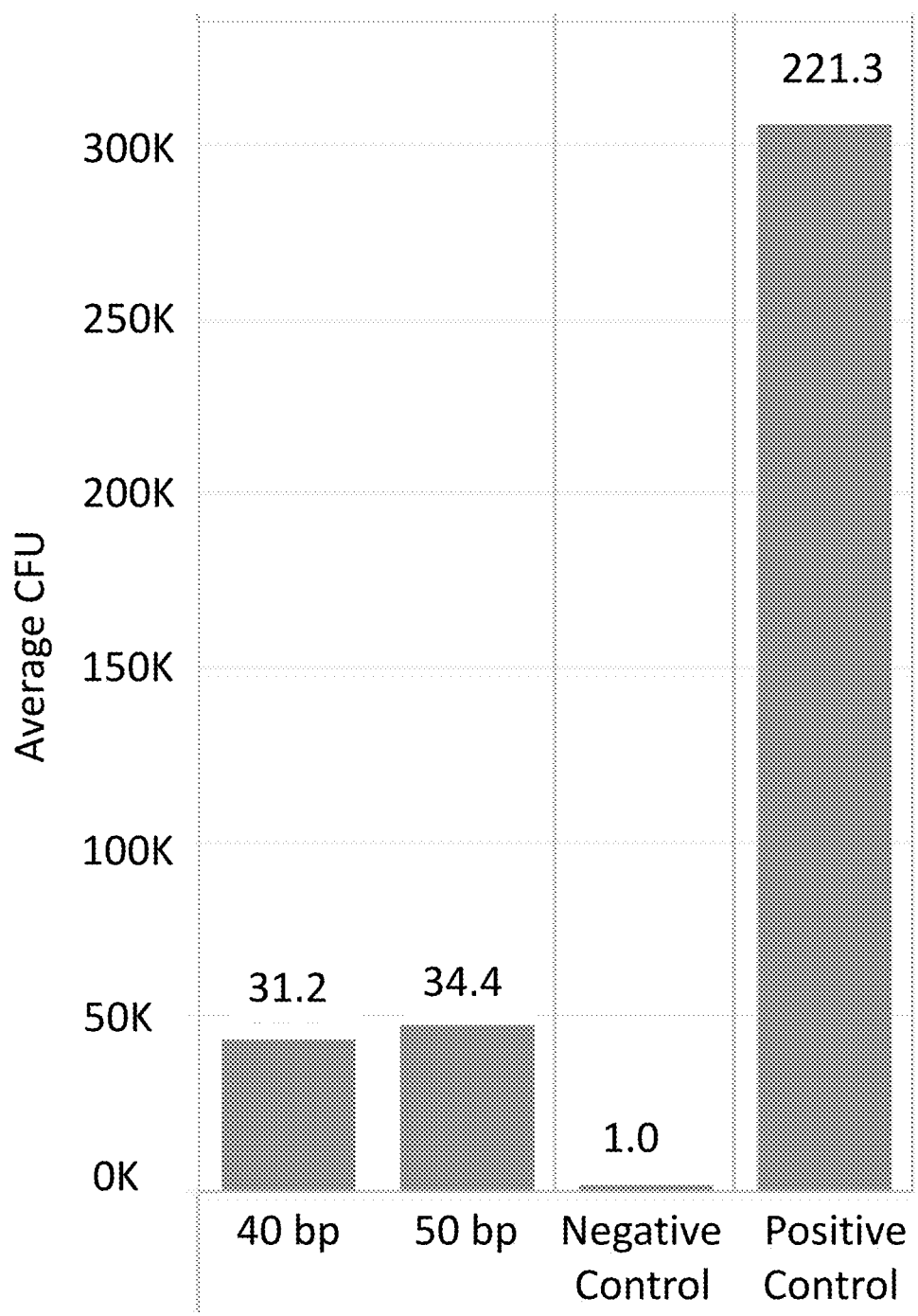
FIG. 15A is a plot of average colony forming units (CFU) (y-axis) of flap endonuclease mediated nucleic acid assembly using a nucleic acid bridge.

As seen in Table 16, flap endonuclease mediated nucleic acid assembly reaction using a double stranded DNA (dsDNA) bridge of 40 base pairs and 50 base pairs resulted in more than 90% correct assemblies. Further as seen in FIG. 15A, assembly using a dsDNA bridge of 40 base pairs and 50 base pairs resulted in higher levels of assembly as compared to the negative control.

Figure 15B:
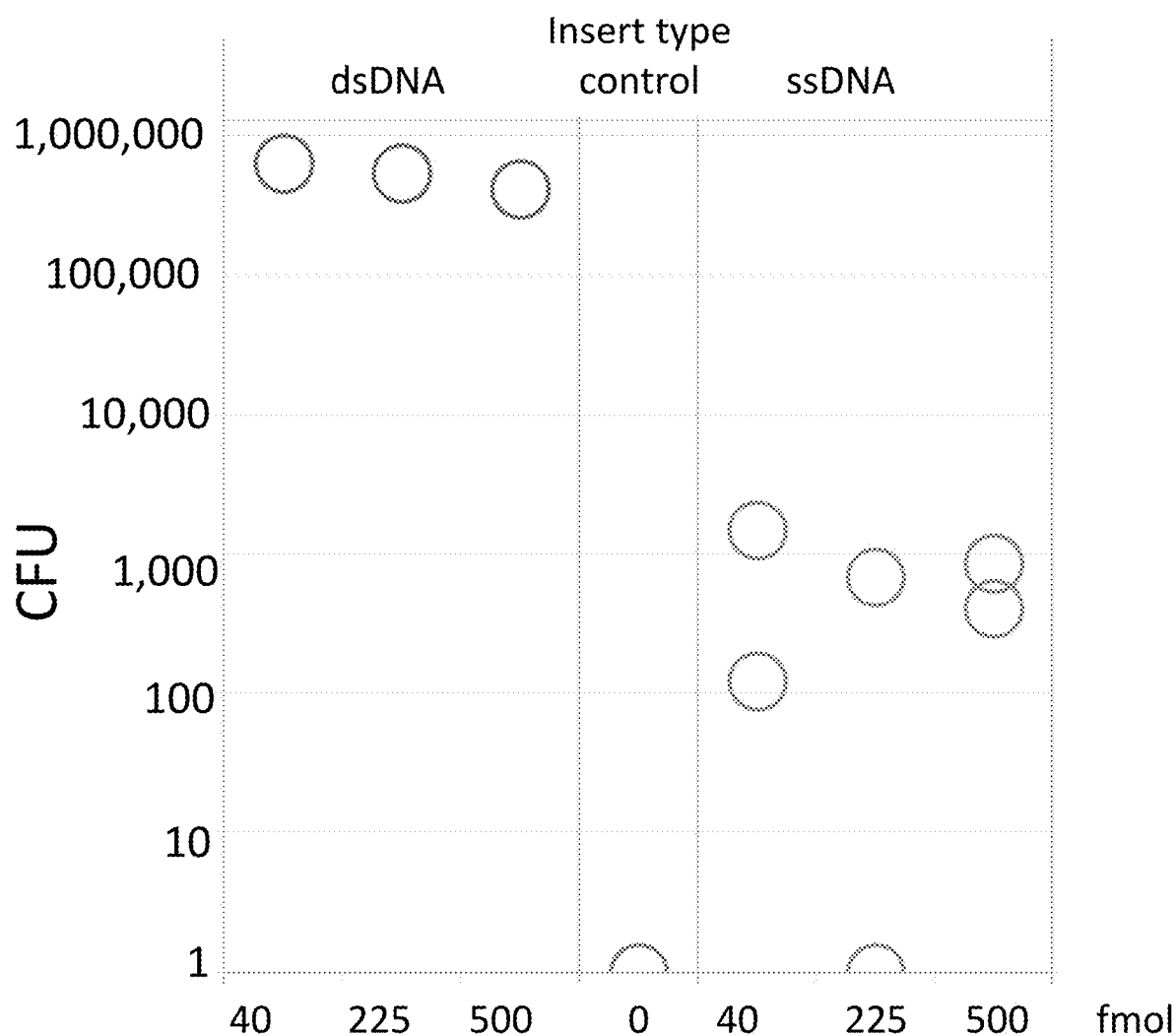
FIG. 15B is a plot of colony forming units (CFU) on a log scale (y-axis) of flap endonuclease mediated nucleic acid assembly using a nucleic acid bridge.

CFUs using the bridged assembly method were measured. As seen in FIG. 15B, colony forming units from assembly with single stranded DNA (ssDNA) at various amount of insert (40 fmol, 225 fmol, or 500 fmol) was higher than the negative control (control). As a positive control, ssDNA was PCR amplified to create a double stranded DNA (dsDNA) and was assembled.

The data indicates that assembly of ssDNA by flap endonuclease mediated nucleic acid assembly using a bridge nucleic acid results in a higher percentage of correct assemblies and higher number of colony forming units.

Figure 16A:
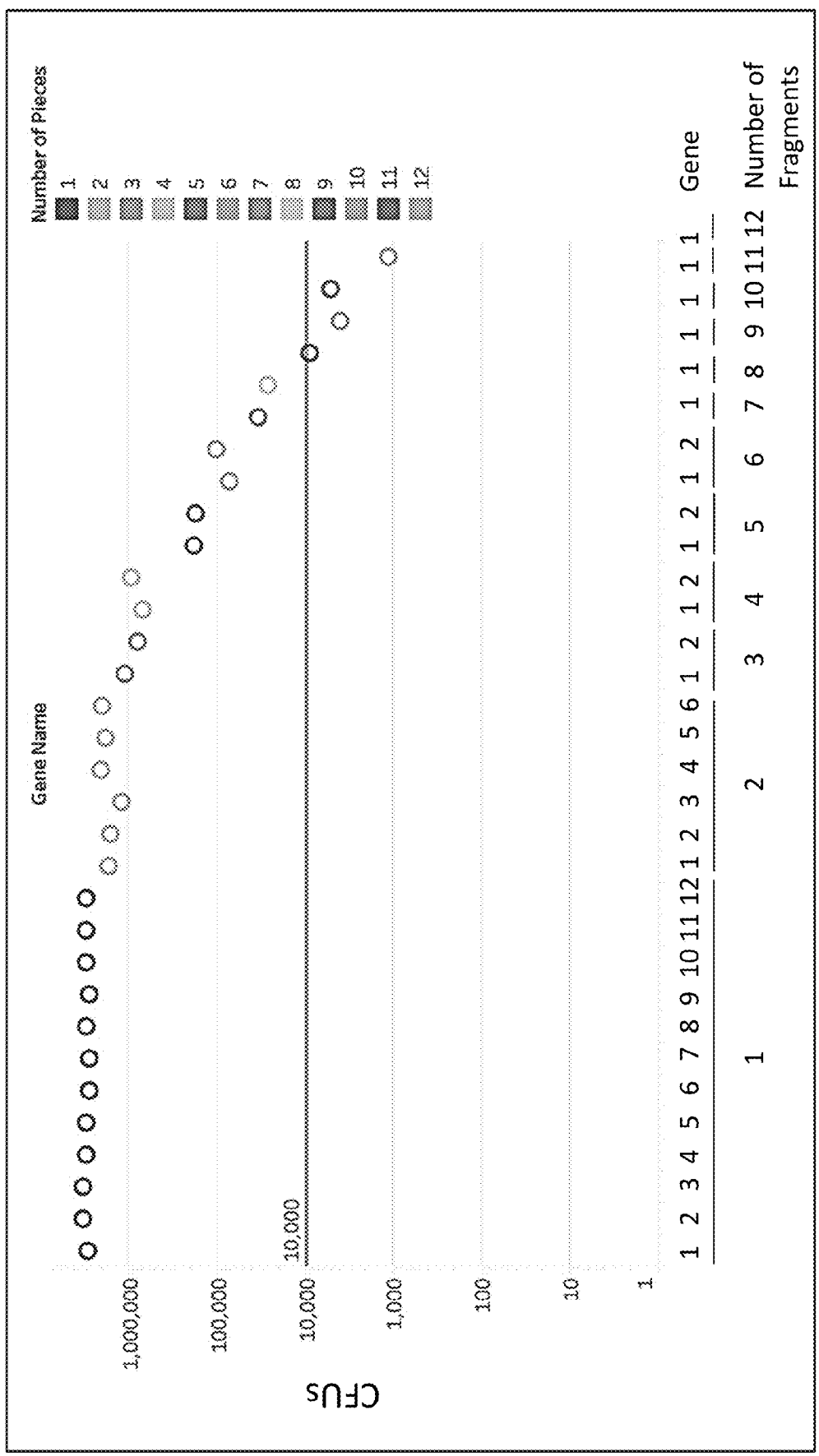
FIG. 16A is a plot of colony forming units (CFU, y-axis) of flap endonuclease mediated nucleic acid assembly of genes (x-axis) using 1, 2, 3, 4, 5, 6, 7, 8, 9, 10, 11, or 12 fragments.

Example 13: Flap Endonuclease Mediated Nucleic Acid Assembly of Twelve Fragments A flap endonuclease mediated nucleic acid assembly reaction was prepared similarly to Example 4 and Example 10. Multiple fragments were assembled into a vector including 1, 2, 3, 4, 5, 6, 7, 8, 9, 10, 11, and 12 fragments. Each DNA fragment was 500 base pairs. Following assembly reactions, the reactions were transformed into E. coli and colony forming units were measured. FIG. 16A illustrates a graph of colony forming units for assembly of 1, 2, 3, 4, 5, 6, 7, 8, 9, 10, 11, and 12 fragments.

Figure 16B:
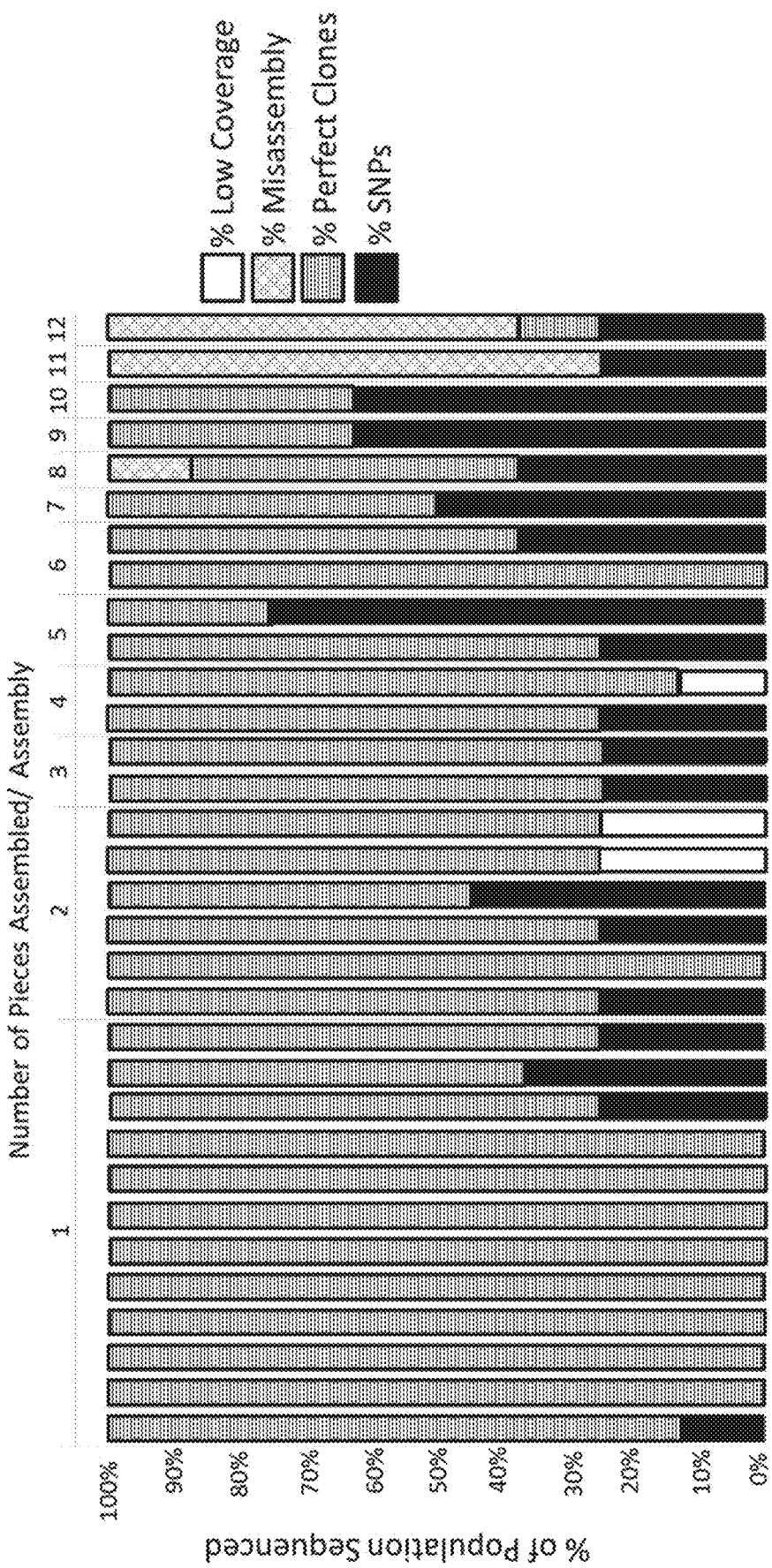
FIG. 16B is a plot of next generation sequence analysis of percent population sequenced (y-axis) and assembled genes (x-axis) using 1, 2, 3, 4, 5, 6, 7, 8, 9, 10, 11, or 12 fragments.
Figure 16C:
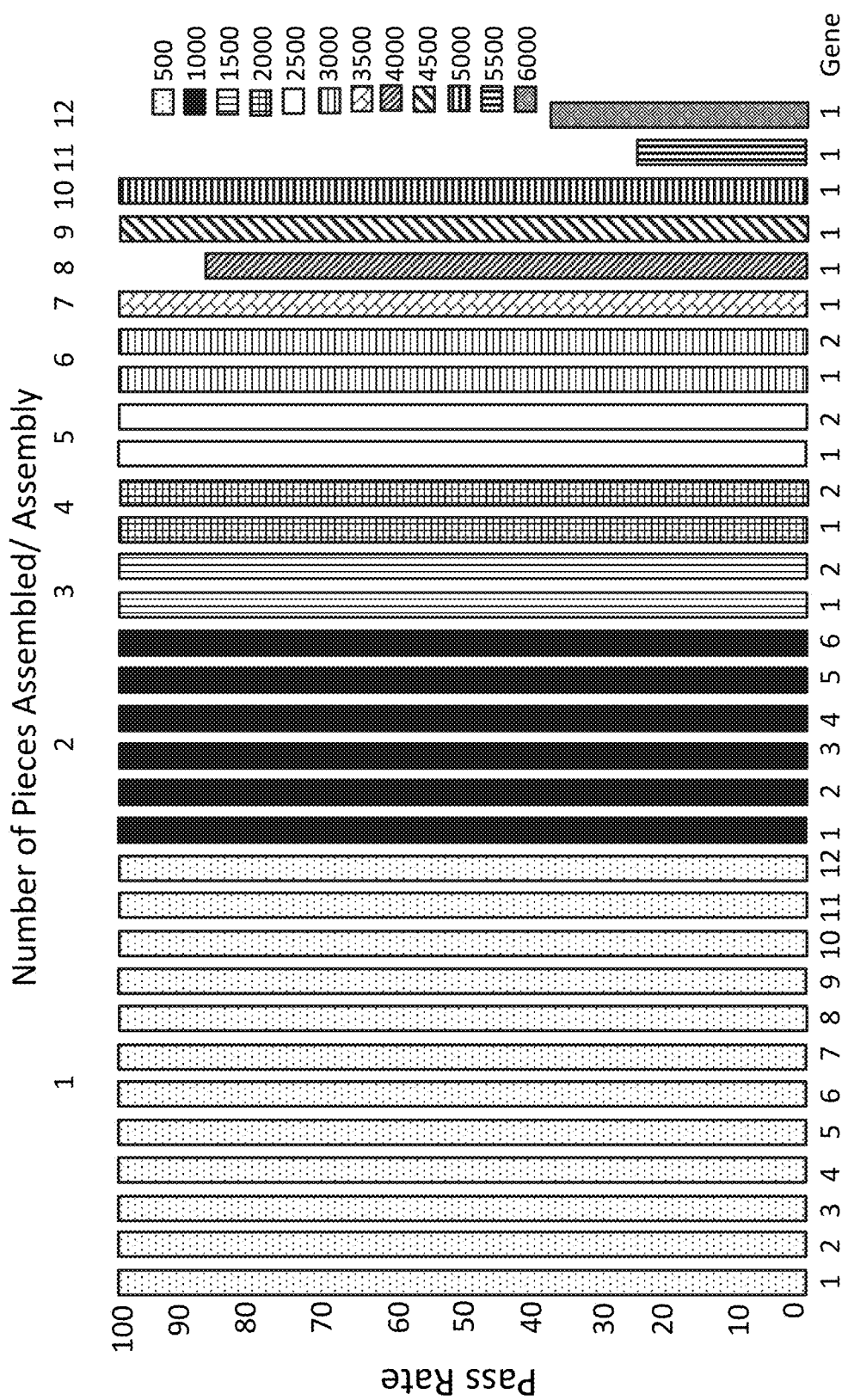
FIG. 16C is a plot of pass rate (y-axis) for genes (x-axis) using 1, 2, 3, 4, 5, 6, 7, 8, 9, 10, 11, or 12 fragments.

Next generation sequencing (NGS) was also performed. As seen in FIG. 16B, empty or low coverage (white bars), misassembly (dotted bars), passing clones (horizontal bars), and SNPs (black bars) were measured following flap endonuclease mediated nucleic acid assembly. Pass rates were also measured as seen in FIG. 16C. The data shows assembly of 12 fragments result in cloning success and high pass rates.

Figure 17:
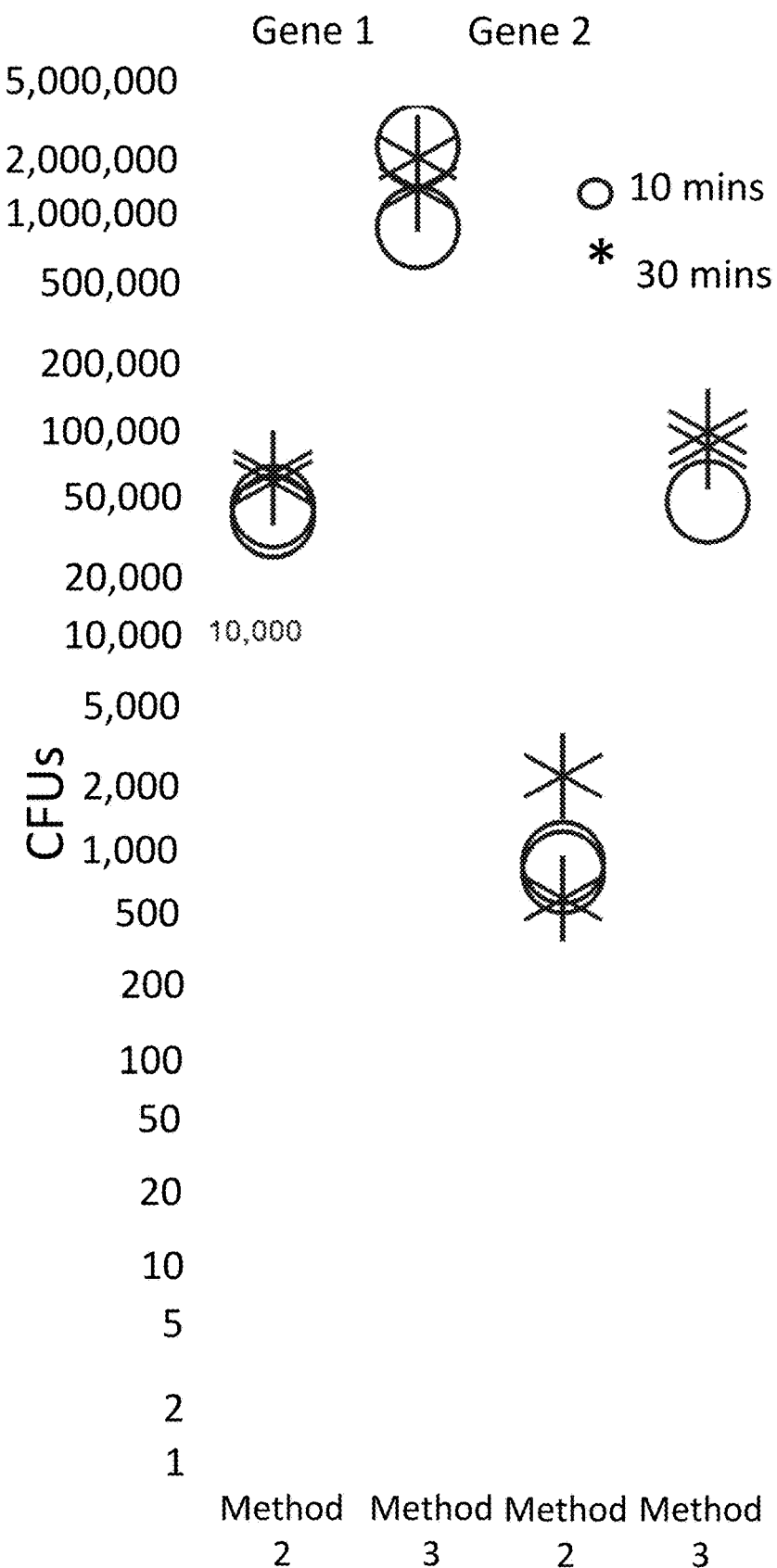
FIG. 17 is a plot of colony forming units (CFU, y-axis) of flap endonuclease mediated nucleic acid assembly using Method 2 and Method 3 for two genes using 10 minute and 30 minute incubation times.

Example 14: Flap Endonuclease Mediated Nucleic Acid Assembly Using Low Amount of Polymerase A flap endonuclease mediated nucleic acid assembly reaction was prepared similarly to Example 4 and Example 10. The concentration of Phusion polymerase was decreased 10 fold as compared to Example 10. The reaction concentrations are seen in Table 17. The reactions were prepared on ice, and following addition of the various reagents, the reactions were incubated at 65° C. for 10-30 minutes. The reactions comprising three fragments were cloned into a plasmid and transformed into E. coli. Colony forming units were measured following 10 minute incubation and 30 minute incubation as seen in FIG. 17. There was an increased number of CFUs using decreased Phusion polymerase according to the reaction concentrations in Table 17 as compared to the reaction concentrations described in Example 11 (Method 2). Similar CFUs were measured following 10 minute incubation or 30 minute incubation. Data shows that cloning efficiency was improved using a decreased amount of polymerase.

TABLE 17

Method 3 Reaction Conditions

| Master Mix | 5 uL reaction | Final Concentration |
|---|---|---|
| dNTP | 0.1 | .4 mM |
| 10x Ampligase buffer (Epicenter) | 0.5 | 2x |
| ExoIII 100 U/uL (NEB) | 0.08 | 1.6 U/uL |
| Phusion 2 U/uL (NEB) | 0.005 | 0.002 U/uL |
| Ampligase 5 U/uL (Epicenter) | 0.1 | 0.1 U/uL |
| Fen1 32 U/uL (NEB) | 0.005 | 0.032 U/uL |
| Water* | 1.695 | |

Figure 18A:
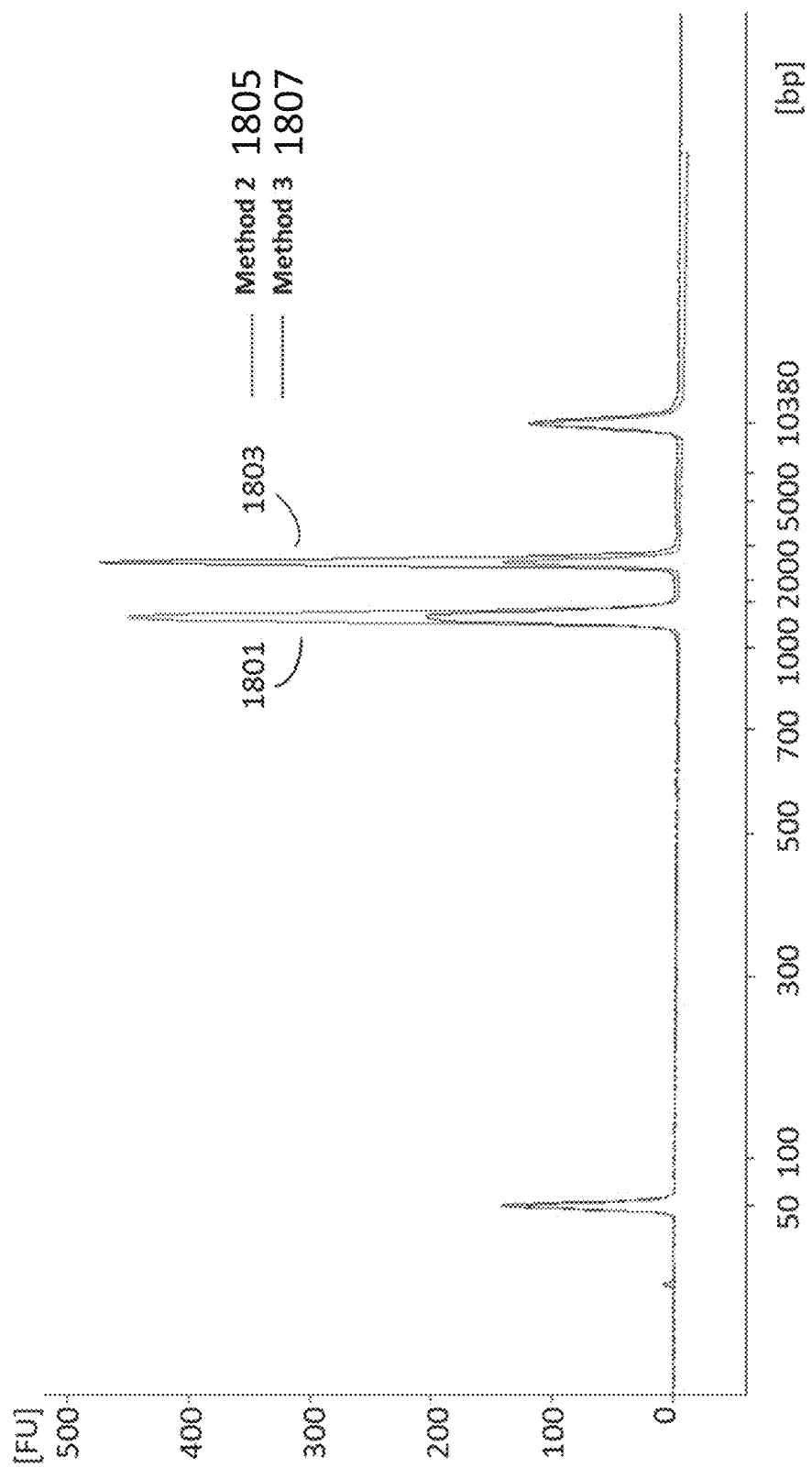
FIG. 18A is a plot from a BioAnalyzer reading with nucleotide bases on the x-axis and fluorescent units on the y-axis.

Example 15: Flap Endonuclease Mediated Nucleic Acid Assembly of Non-Clonal Fragments Reaction efficiency of assembly of non-clonal fragments was determined. Reactions were prepared for assembling 2 DNA fragments using Method 2 as seen in Table 15 and Method 3 as seen in Table 17. Reactions were then incubated at 65° C. for 10-30 minutes. Assembly PCR products were analyzed on a BioAnalyzer (FIG. 18A) with correctly assembled fragments being 3000 base pairs. Referring to FIG. 18A, 1801 is unassembled gene fragments and 1803 is assembled gene fragments using Method 2 (red line, 1805) and Method 3 (blue line, 1807).

Figure 18B:
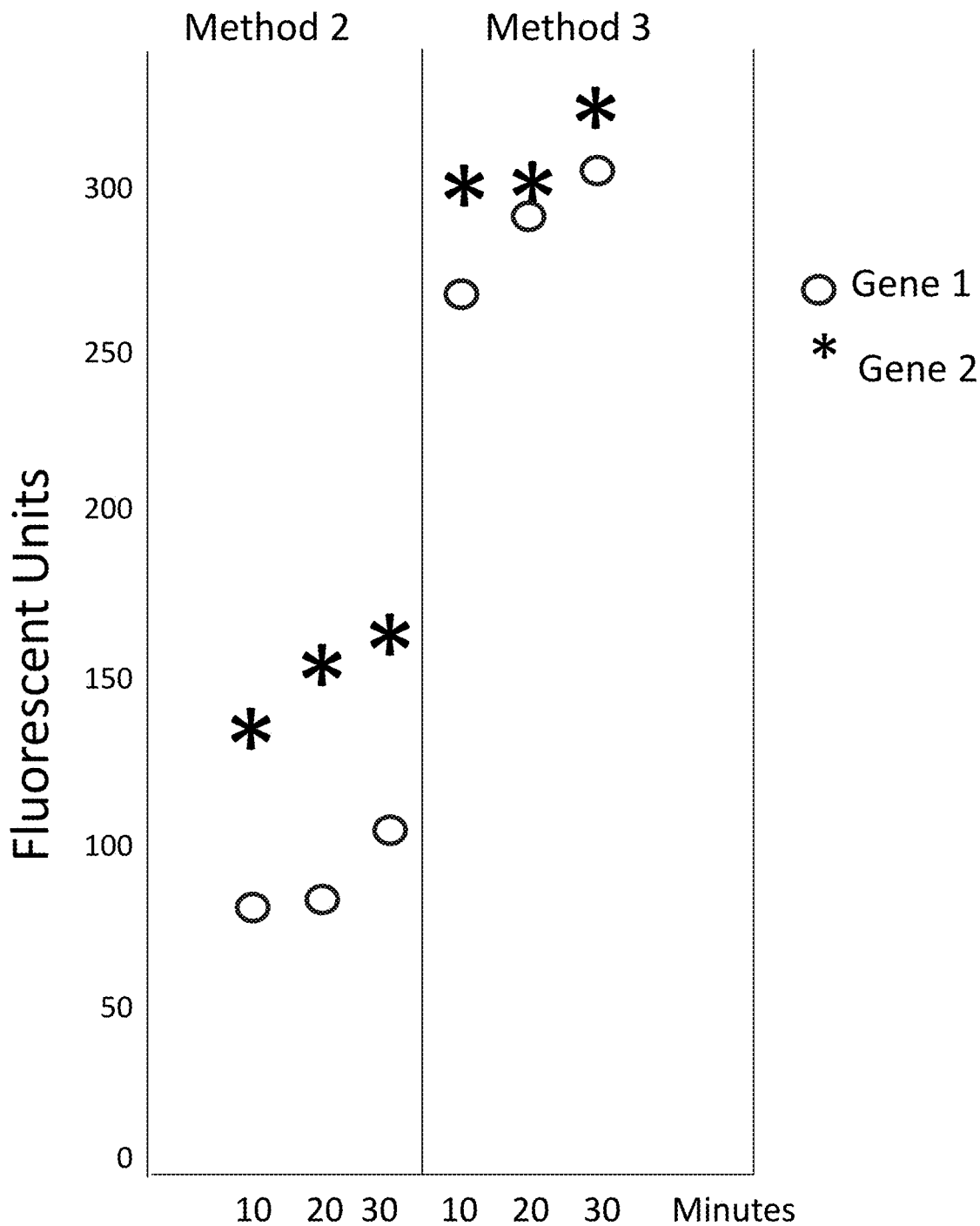
FIG. 18B is a plot from a BioAnalyzer reading with incubation time on the x-axis and fluorescent units on the y-axis.

Non-clonal assembly was also determined. Referring to FIG. 18B, fluorescent units (y-axis) was measured for 10 minutes, 20 minutes, or 30 minutes of incubation using Method 2 or Method 3 reaction conditions for Gene 1 and Gene 2. There was an increase in fluorescent units at 10 minutes, 20 minutes, or 30 minutes of incubation using Method 3 compared to Method 2. The data shows improved assembly of non-clonal fragments using Method 3.

Example 16: Improved Assembly with Flap Endonuclease Mediated Nucleic Acid Assembly Flap endonuclease mediated nucleic acid assembly using similar reaction conditions as described in Example 14 was compared to assembly by different comparators. Twelve 500 bp sequences were generated, and a series of constructs for assembly of one to ten DNA fragments into a vector were designed. DNA was assembled with homologous ends using the flap endonuclease mediated nucleic acid assembly method, Comparator 1 method, and Comparator 2 method. Comparator 1 assembly relies on homology at the ends of a construct that is quickly introduced by PCR or through DNA synthesis. Each fragment in Comparator 1 assembly requires a different pair of PCR primers. Comparator 2 method is an assembly method for nucleic acid fragments with varied overlap regions. Effects of multiple homology lengths and incubation times were determined.

Flap endonuclease mediated nucleic acid assembly was performed at 65° C. At 65° C. most secondary structures were eliminated and assembly fidelity was greatly improved (data not shown).

The efficiency and the accuracy of assembly using the flap endonuclease mediated nucleic acid assembly method, Comparator 1 method, and Comparator 2 method were determined. Efficiency was determined by colony forming units (CFUs), and accuracy was determined by next generation sequencing (NGS).

Figure 19A:
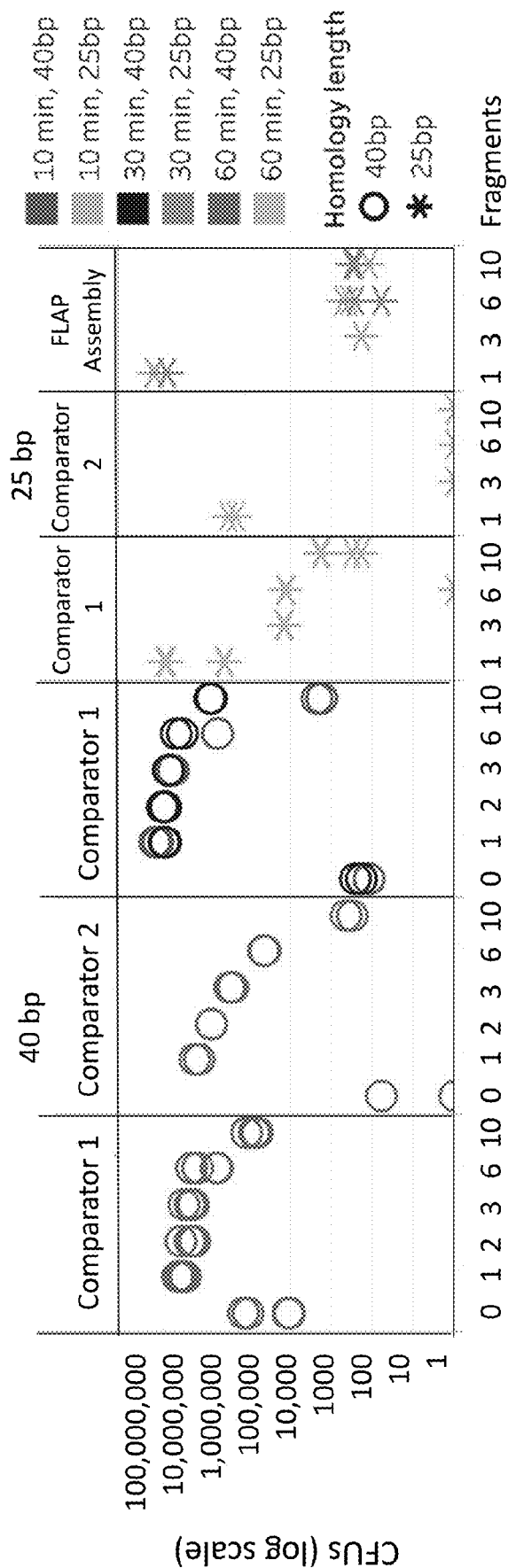
FIGS. 19A-19B are plots of colony forming units (y-axis) for different numbers of fragments (x-axis) using flap endonuclease mediated nucleic acid assembly, Comparator 1, and Comparator 2 methods.

Efficiency using the flap endonuclease mediated nucleic acid assembly method, Comparator 1 method, and Comparator 2 method was determined for double stranded DNA (dsDNA) non-clonal fragments comprising adaptor sequences. The adaptor sequences acted as universal primer pairs. dsDNA comprising homology ends was generated by amplifying dsDNA fragments with primers specific for each construct ("adaptors-off"). Each fragment contained 40 or 25 bp of overlapping homology to their intended destination. One to ten dsDNA fragments were assembled into a linearized plasmid and transformed the reaction into E. coli. For one fragment assemblies, flap endonuclease mediated nucleic acid assembly method, Comparator 1 method, and Comparator 2 method resulted in robust colony forming units. The flap endonuclease mediated nucleic acid assembly method resulted in higher colony forming units regardless of reaction time, homology lengths, and number of pieces assembled (FIG. 19A). Flap endonuclease mediated nucleic acid assembly method resulted in colony forming units higher than background for fragment assemblies for 6 or more fragments (FIG. 19A). When the number of fragments was increased, the flap endonuclease mediated nucleic acid assembly method was more efficient with a 30 minute reaction as compared to a 10 minute reaction (FIG. 19A). A 25 bp homology length was also tested using the flap endonuclease mediated nucleic acid assembly method, Comparator 1 method, and Comparator 2 method, and for all three methods was unsuccessful for assemblies of two or more fragments.

Figure 19B:
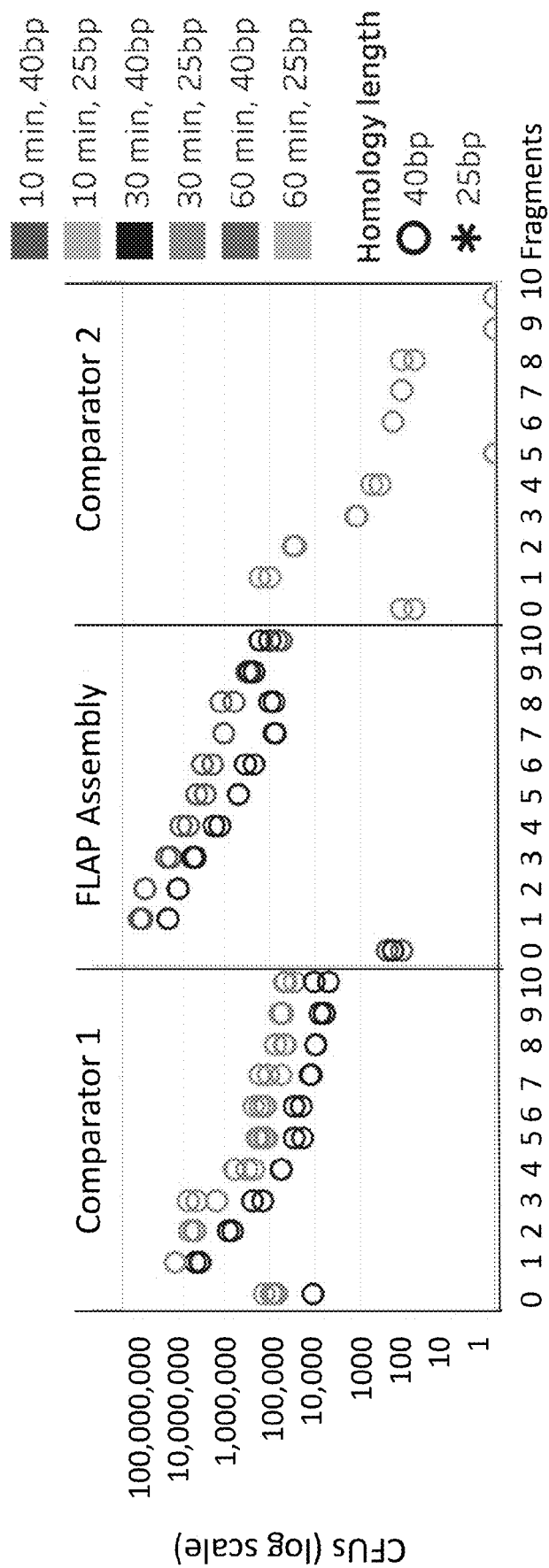

Efficiency for DNA with buried homology sequences ("adaptors-on") was determined using the flap endonuclease mediated nucleic acid assembly method, Comparator 1 method, and Comparator 2 method. Forty base pair homologies buried ~23 bp from the end of the DNA fragment were designed. All methods gave CFUs significantly higher than their respective backgrounds (FIG. 19B). Referring to FIG. 19B, one fragment flap endonuclease mediated nucleic acid assembly with a ten minute incubation resulted in 9-fold more colonies than assemblies using Comparator 1 method and 568-fold more colonies than assemblies using Comparator 2. When the number of inserts was increased, Comparator 1 method and Comparator 2 method failed to give colonies over background levels at four fragments (FIG. 19B). Flap endonuclease mediated nucleic acid assembly of ten fragments into a vector resulted in a 642-fold increase over background (FIG. 19B). Assembly of DNA with end homology sequences and buried homology sequences resulted in more efficient assemblies using the flap endonuclease mediated nucleic acid assembly as compared to assembly using Comparator 1 method or Comparator 2 method.

Figure 20A:
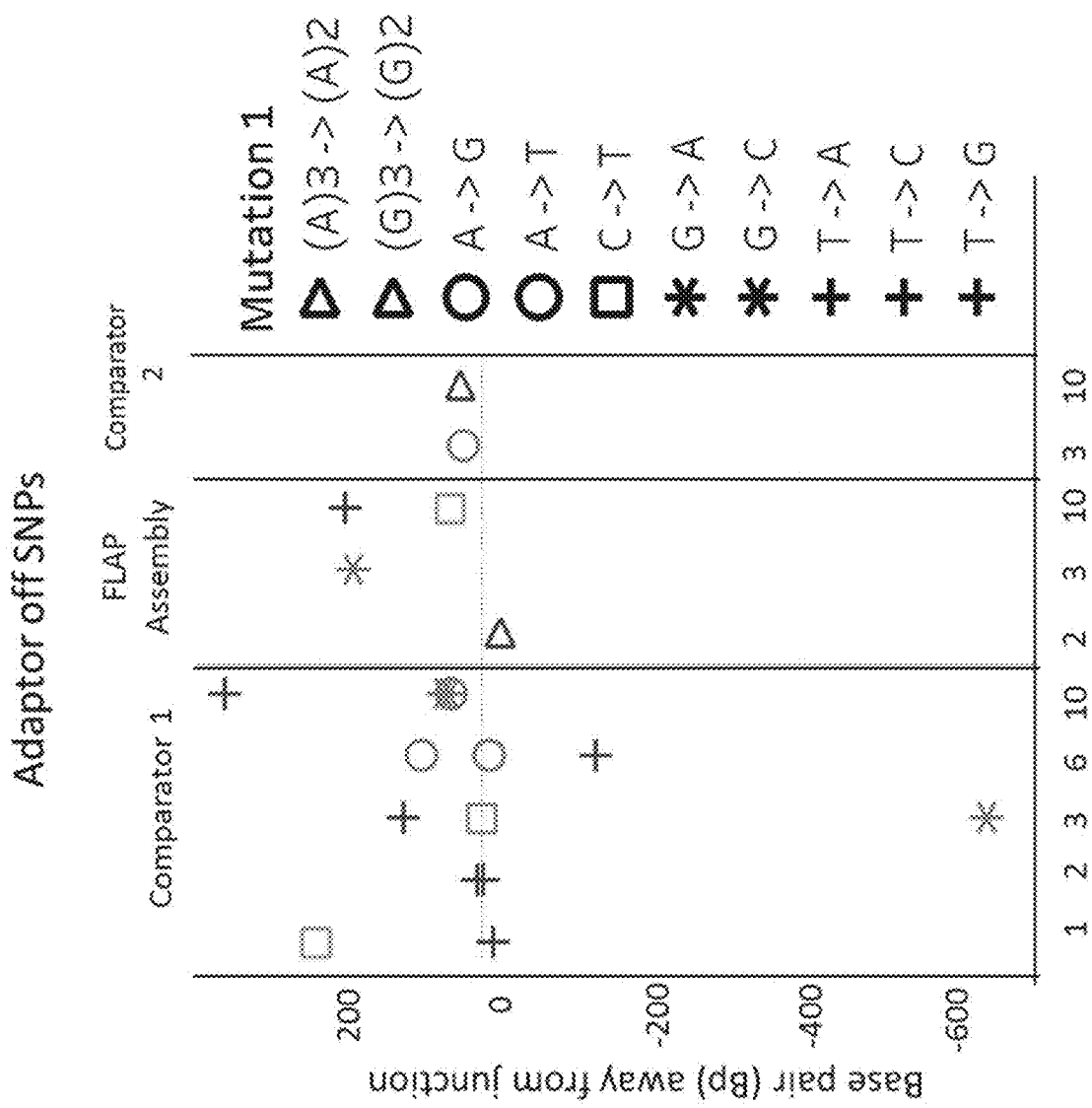
FIGS. 20A-20B are plots of assembly error for flap endonuclease mediated nucleic acid assembly, Comparator 1 assembly, and Comparator 2 assembly.
Figure 20B:
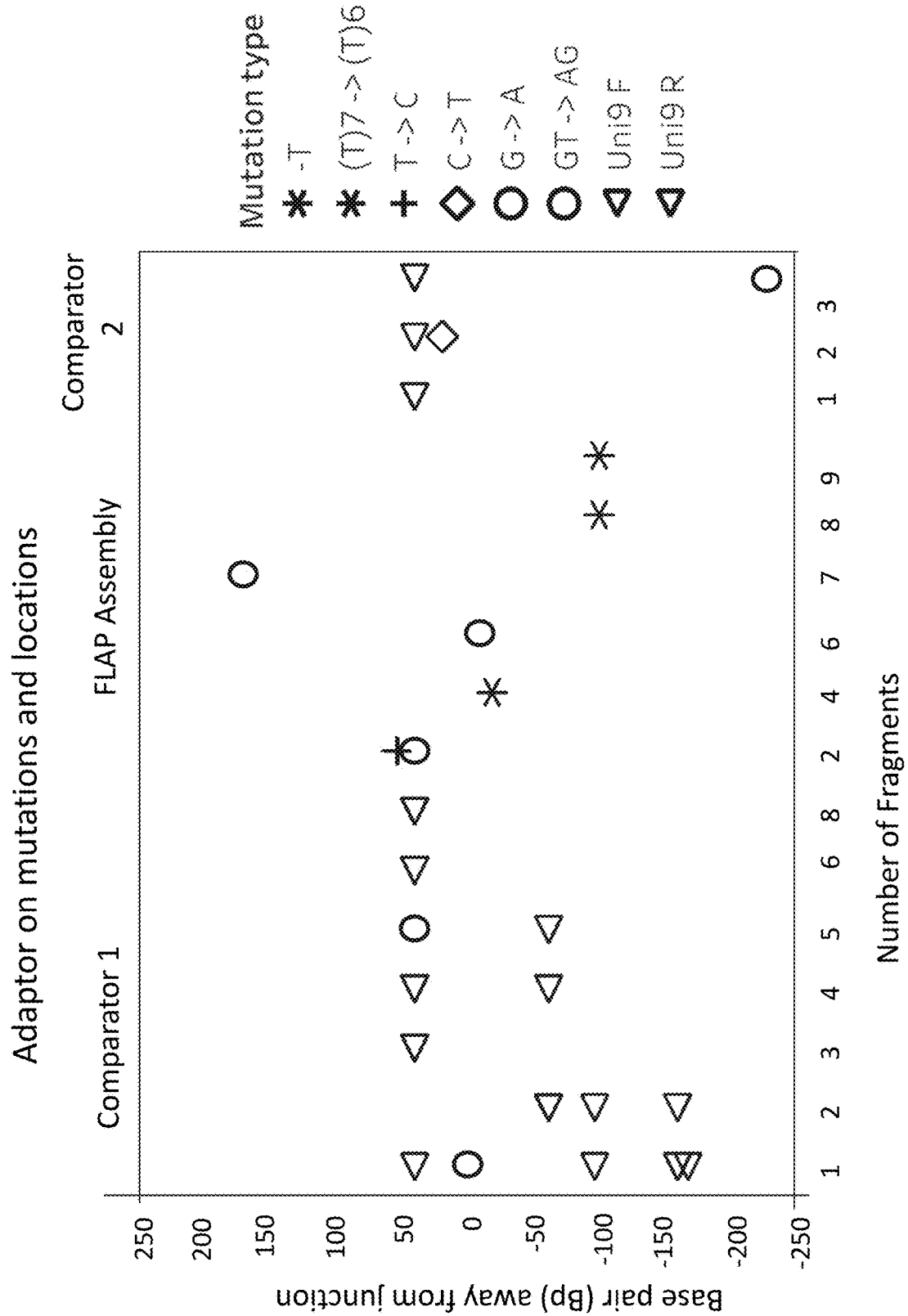
Figure 20C:
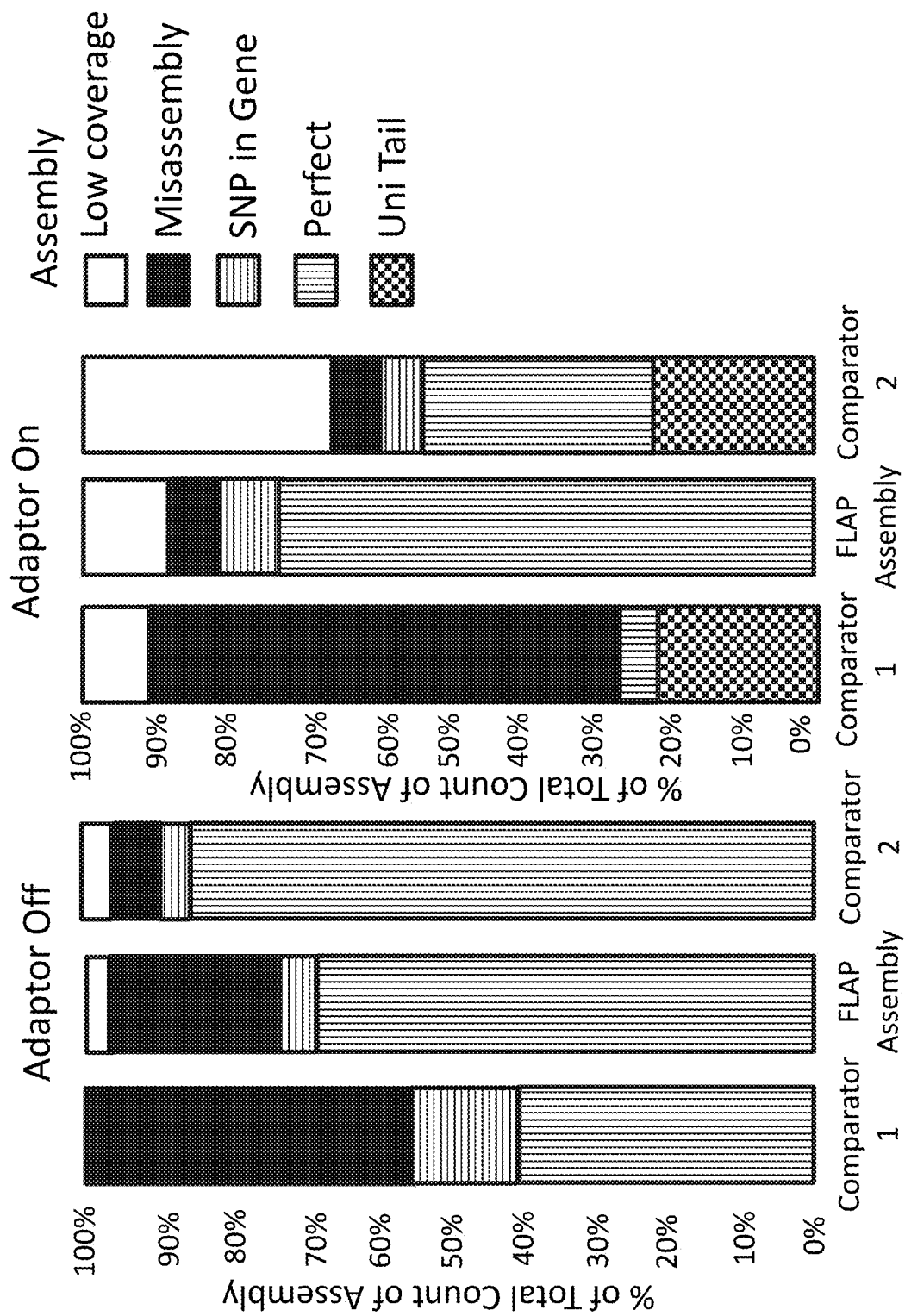
FIG. 20C is a plot of percentage of total count of assembly (y-axis) comparing endonuclease mediated nucleic acid assembly, Comparator 1 assembly, and Comparator 2 assembly (x-axis).

Next generation sequencing was performed using plasmids isolated from 8 colonies per reaction. The flap endonuclease mediated nucleic acid assembly and Comparator 2 method resulted in 84% and 86% correct assembly rates, respectively. Each method showed 8% of samples misassembled. Assemblies using Comparator 1 method resulted in 10% misassembly and a 25% SNP rate, resulting in an overall correct assembly rate of 65%. Analyzing the pass and failure rates dependent on the number of inserts assembled, Comparator 1 method resulted in a loss of fidelity at 10 inserts. Most errors were clustered within 25 bp of the fragment junctions for Comparator 1 assembly and Comparator 2 assembly (FIGS. 20A-20C).

Figure 21A:
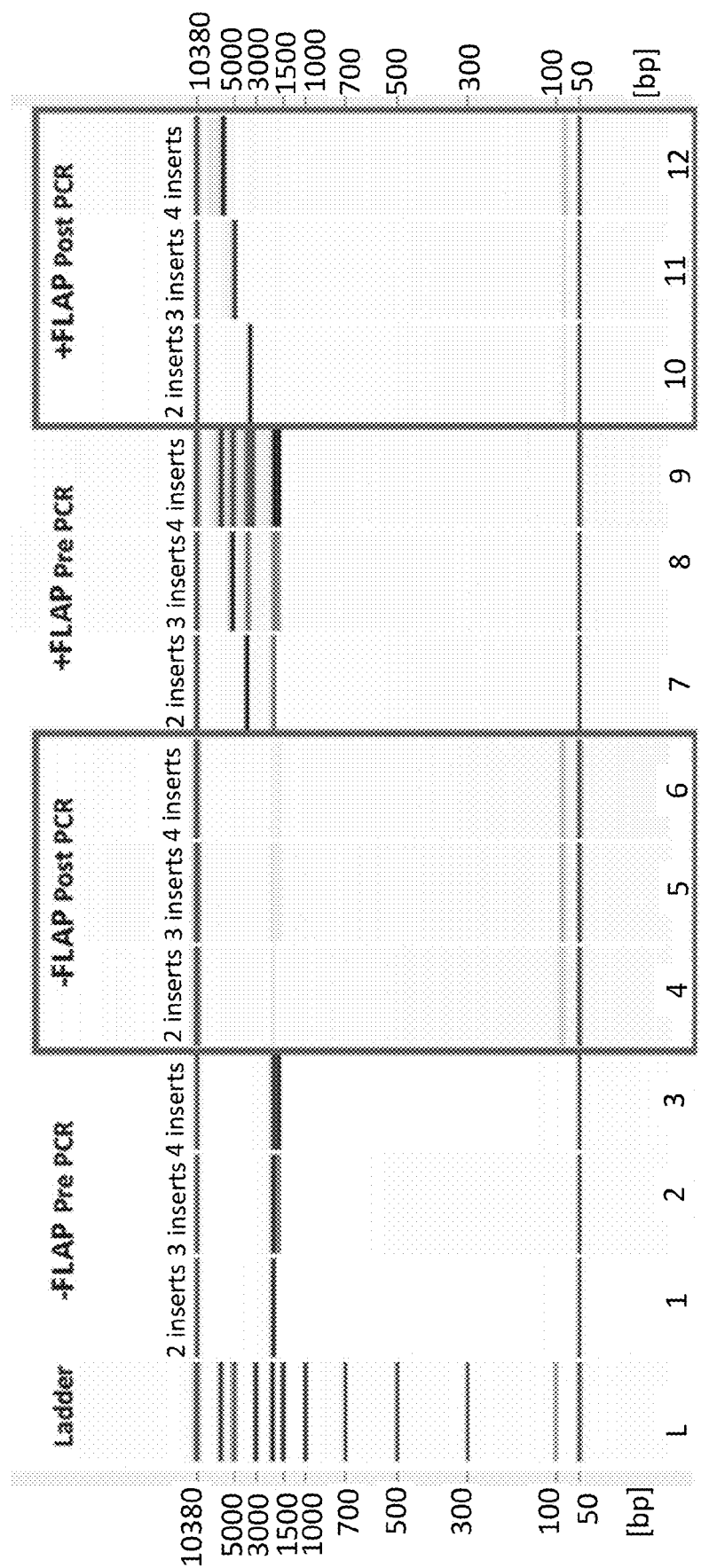
FIG. 21A is a plot of assembled constructs pre-PCR amplification and post-amplification for various numbers of inserts.
Figure 21B:
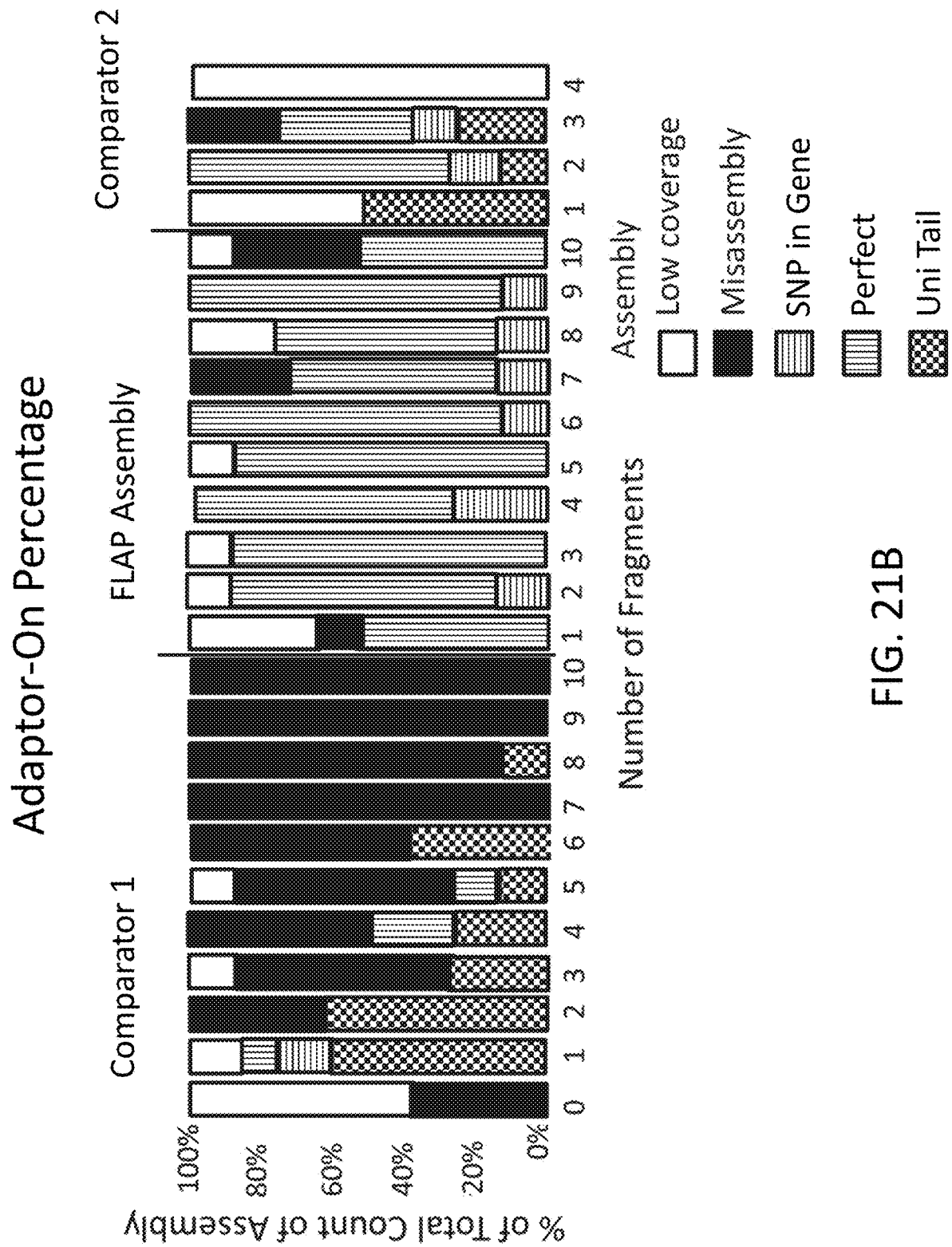
FIG. 21B is a graph of percentage of total count of assembly (y-axis) for different numbers of fragments (x-axis) using flap endonuclease mediated nucleic acid assembly, Comparator 1, and Comparator 2 methods.

Next generation sequencing was used to determine the presence of the 23 bp adaptor. Flap endonuclease mediated nucleic acid assembly resulted in higher correct assembly rates than Comparator 1 and Comparator 2 methods. Across all assembly reactions the average correct assembly rate was 72% for flap endonuclease mediated nucleic acid assembly reactions, compared to 4.5% for Comparator 1 assemblies and 31% for Comparator 2 assemblies. The adaptor sequence was never present in the flap endonuclease mediated nucleic acid assembly samples. In contrast, for full length constructs, 59% of Comparator 1 assemblies and 23% of Comparator 2 assemblies contain partial or full-length adaptor sequences. Constructs assembled by Comparator 1 assembly were more likely to misassembly, with an overall misassembly rate of 63% as compared to 7% for flap endonuclease mediated nucleic acid assembly and 6% for Comparator 2. The misassembly rates increased with the number of fragments in the Comparator 2 assemblies. Further, Comparator 1 assembly had high CFUs in the negative control reactions. Sequencing of the 24 Comparator 1 negative control samples (vector with no inserts) showed that each construct was the vector recombined to itself at various regions of the backbone. See FIG. 20C and FIG. 21B. FIG. 20C shows a graph of low coverage (white bars), misassembly (black bars), SNP in gene (horizontal hatched bars), perfect assembly (vertical hatched bars), and universal (uni) tail (checkered bars). Table 18 shows the data from FIG. 20C. Flap endonuclease mediated nucleic acid assembly resulted in more efficient and accurate assembly as compared to different assembly methods. FIG. 21B shows a graph of low coverage (white bars), misassembly (black bars), SNP in gene (horizontal hatched bars), perfect assembly (vertical hatched bars), and universal (uni) tail (checkered bars).

TABLE 18

Sequencing Data

| | Comparator 1 | | FLAP Assembly | | Comparator 2 | |
|---|---|---|---|---|---|---|
| | Adaptor Off | Adaptor On | Adaptor Off | Adaptor On | Adaptor Off | Adaptor On |
| Low Coverage | NA | 9.09% | 3.57% | 11.25% | 4.17% | 34.38% |
| Misassembly | 45.45% | 63.64% | 23.21% | 7.5% | 6.25% | 6.25% |
| SNP in Gene | 13.64% | NA | 5.36% | 8.75% | 4.17% | 6.25% |
| Perfect | 40.91% | 4.55% | 67.86% | 75.20% | 85.42% | 31.25% |
| Uni Tail | NA | 21.59% | NA | NA | NA | 21.88% |

Example 17: Improved Flexibility with Flap Endonuclease Mediated Nucleic Acid Assembly In Vitro Seamless Assembly Assembly of DNA fragments was determined using flap endonuclease mediated nucleic acid assembly. Flap endonuclease mediated nucleic acid assembly using similar reaction conditions as described in Example 14 was used to assemble 2, 3, and 4 linear dsDNA fragments together. In reactions comprising the flap endonuclease mediated nucleic acid assembly enzymatic cocktail, unincorporated starting material, partial and full-length constructs were detected (FIG. 21A, lanes 1-3, 7-9). In the absence of the flap endonuclease mediated nucleic acid assembly enzymatic cocktail after incubation at 65° C. for 30 minutes, there was starting material but not fully assembled constructs. To enrich for full length constructs, the reactions were PCR amplified using terminal primer sites specific for the full-length constructs. In the absence of the flap endonuclease mediated nucleic acid assembly enzymatic cocktail, no full length constructs were observed after PCR amplification (FIG. 21A, lanes 4-6). Products at the proper size for full length constructs were observed (FIG. 21A, lanes 10-12). Flap endonuclease mediated nucleic acid assembly resulted in properly assembled fragments in vitro.

One Pot Combinatorial Assembly

Figure 21C:
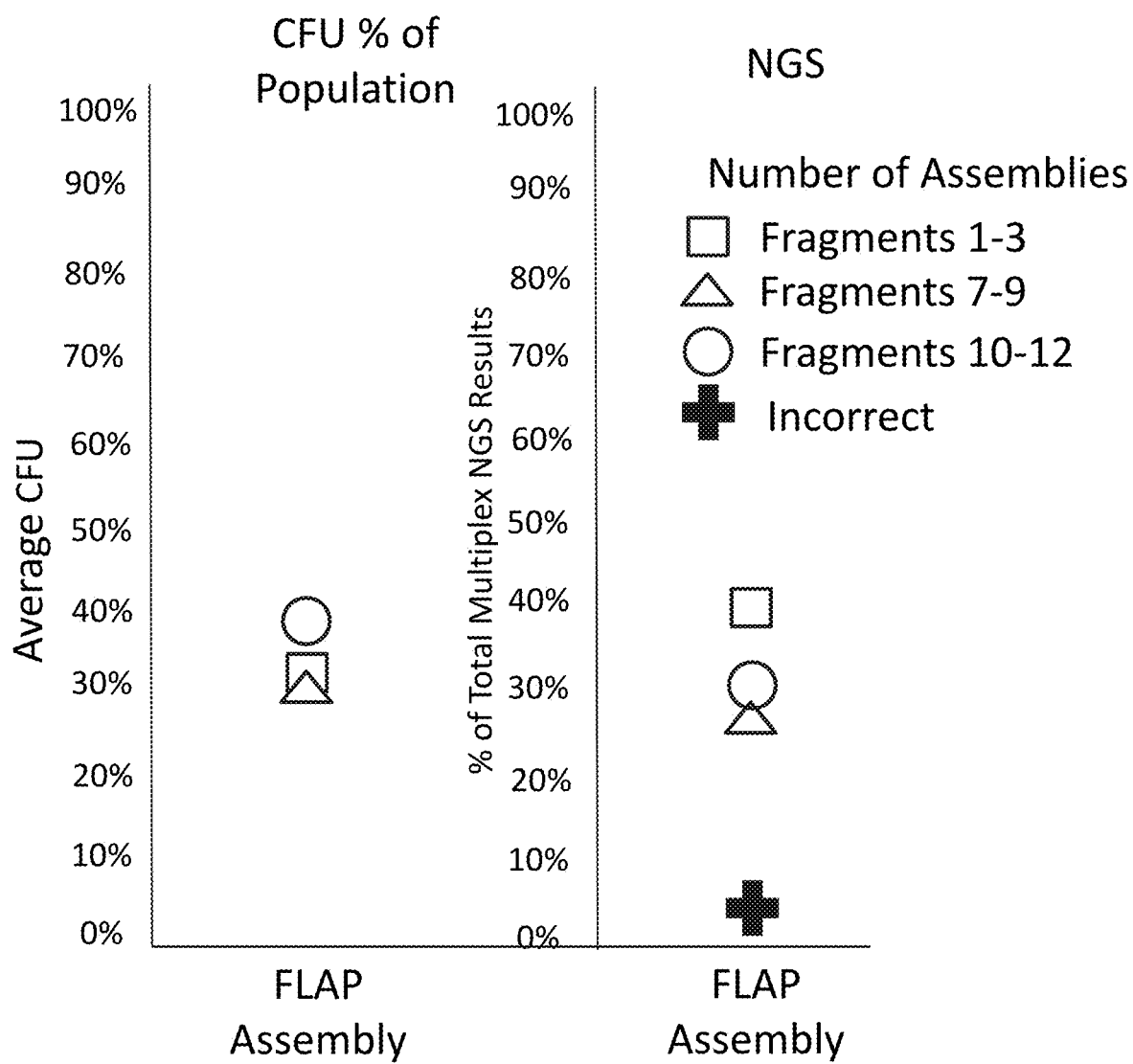
FIG. 21C is a plot of CFU percentage of population and NGS results using flap endonuclease mediated nucleic acid assembly.
Figure 21D:
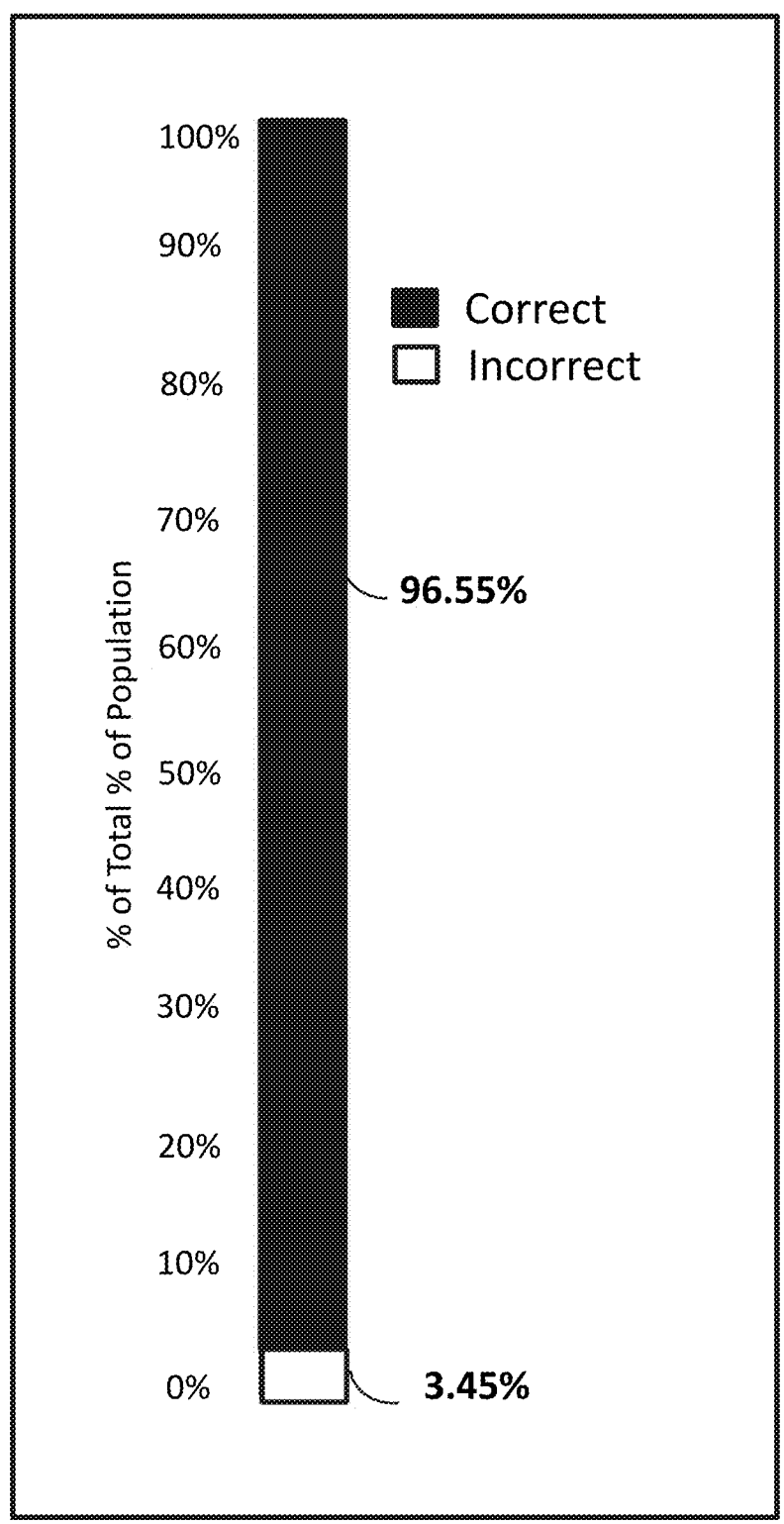
FIG. 21D is a plot of percentage of distribution of correctly assembled constructs and misassembled or incorrect constructs.

Specificity of the flap endonuclease mediated nucleic acid assembly was determined. Nine linear DNA fragments comprising the same universal primer tails were used. Forty bp homology sites directed to directionally assemble three different 3-piece constructs into the same vector were designed. The individual cloning efficiencies for each construct to screen for toxicity and establish an assembly baseline were determined. All nine DNA fragments and the destination vector were then used in a single in vitro assembly reaction. After cloning the reaction mixture into E. coli, 192 colonies were picked for mini-prep followed by NGS analysis. Referring to FIGS. 21A, 21C, and 21D, the expected median distributions, based on cloning individual constructs, was 31%±3% for each construct.

Referring to FIG. 21C, the average CFU was determined for assemblies comprising fragments 1-3 (squares), fragments 7-9 (triangles), fragments 10-12 (circles), and incorrect assembly (cross). After the combinatorial assembly the spread was increased to ±5% (FIG. 21C). Of the constructs tested, 96.5% contained properly assembled constructs (FIG. 21D). Failed assemblies consisted of full length genes of Fragments 7-8, Fragments 7-12, Fragments 9-12. Flap endonuclease mediated nucleic acid assembly resulted in specific, directional assembly.

Example 18. Cloning of Amplified Oligonucleotide Populations

Multiple fragments were assembled into genes. Cloning of amplified oligonucleotide populations was performed similar to Example 17. Overlap extension PCR was performed to generate double stranded DNA (dsDNA) fragments of more than 200 base pairs to assemble into a vector. Reactions were performed at 55° C. for 30 minutes and prepared according to a flap endonuclease mediated nucleic acid assembly method (Method 4) as seen in Table 19.

TABLE 19

Reaction Conditions (Method 4)

| Master Mix | 50 uL reaction | Final Concentration (for 2x MM) |
|---|---|---|
| ExoIII 100 U/uL | 0.05 | 0.2 U/uL |
| Phusion 2 U/uL | 0.05 | 0.004 U/uL |
| Fen1 32 U/uL | 0.05 | 0.064 U/uL |
| dNTP | 1 | .4 mM |
| Ampligase 5 U/uL | 1 | 0.2 U/uL |
| 10x Ampligase buffer | 5 | 2x |
| Water* | | |

Figure 22A:
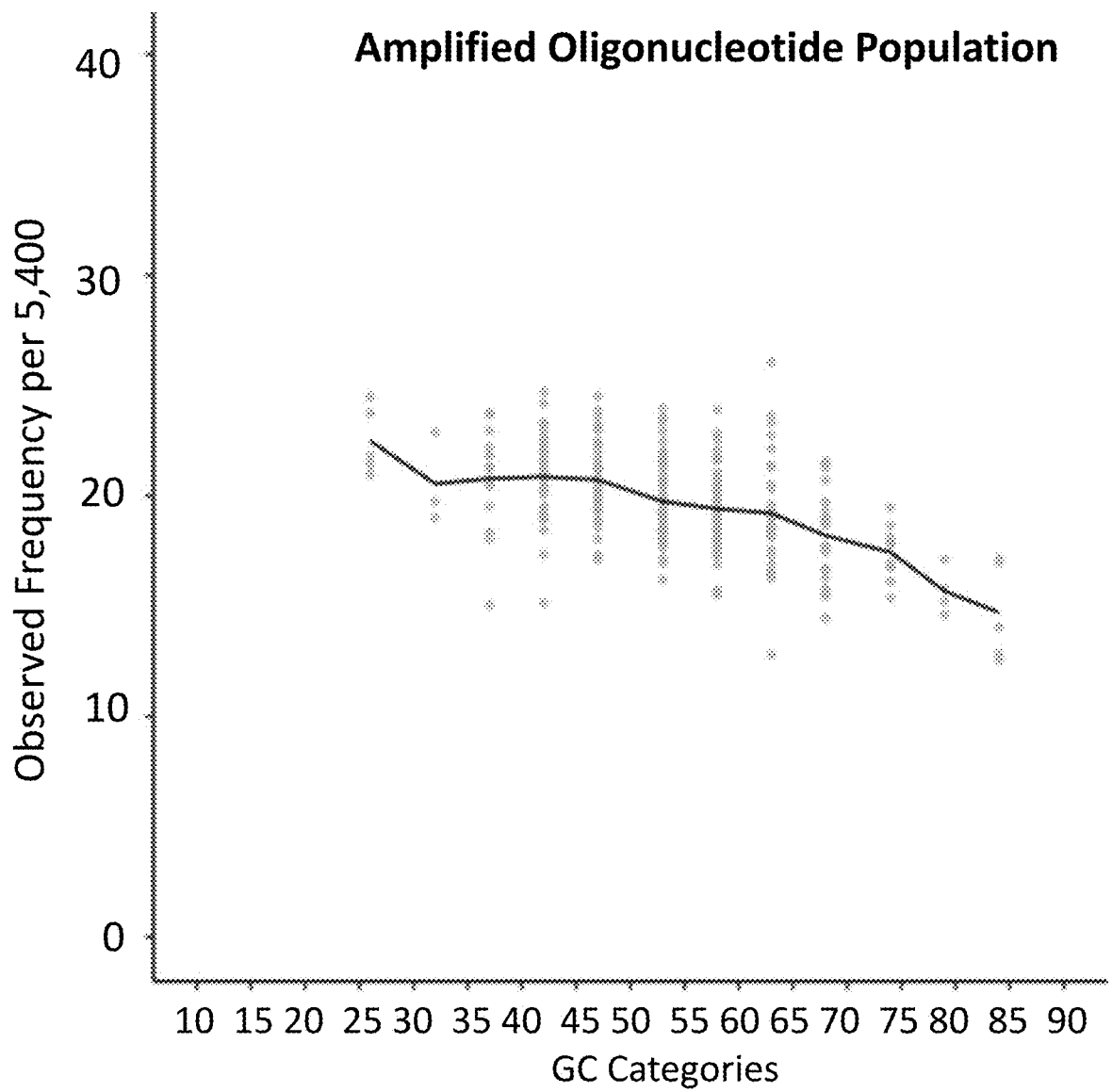
FIG. 22A is a graph of observed frequency per 5,400 (y-axis) compared to the various GC categories (x-axis) of an amplified oligonucleotide population prior to assembly.
Figure 22B:
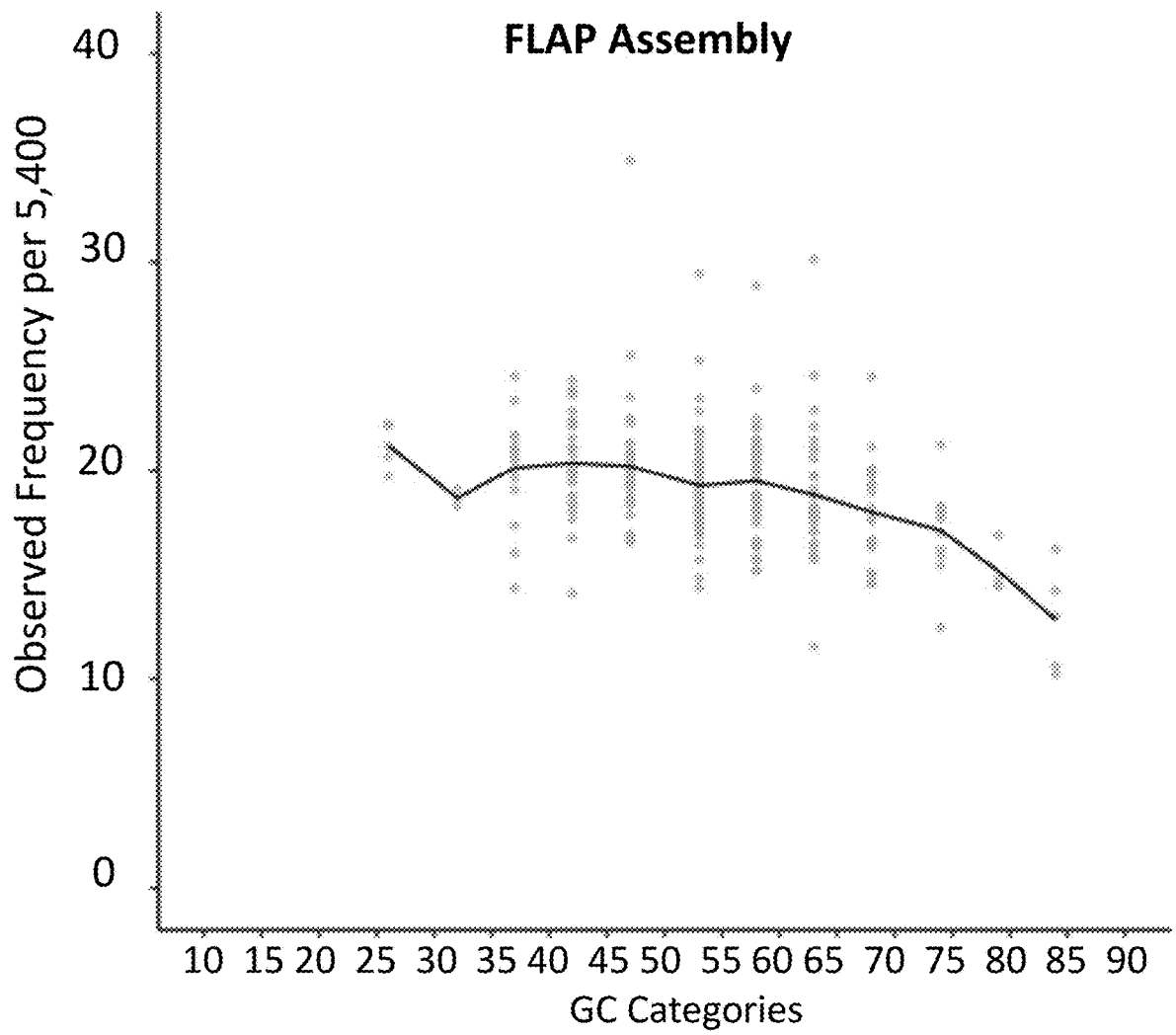
FIG. 22B is a graph of observed frequency per 5,400 (y-axis) compared to the various GC categories (x-axis) of oligonucleotide population assembled by flap endonuclease mediated nucleic acid assembly.

Next generation sequencing (NGS) was performed on the amplified oligonucleotide population prior to assembly (FIG. 22A) and following the flap endonuclease mediated nucleic acid assembly (FIG. 22B). FIGS. 22A-22B show that following flap endonuclease mediated nucleic acid assembly, there was no drop out of sequences and that samples were assembled without introducing significant sample bias as compared to the amplified oligonucleotide population prior to assembly.

Example 19. Multiplexed Gene Assembly

Figure 23:
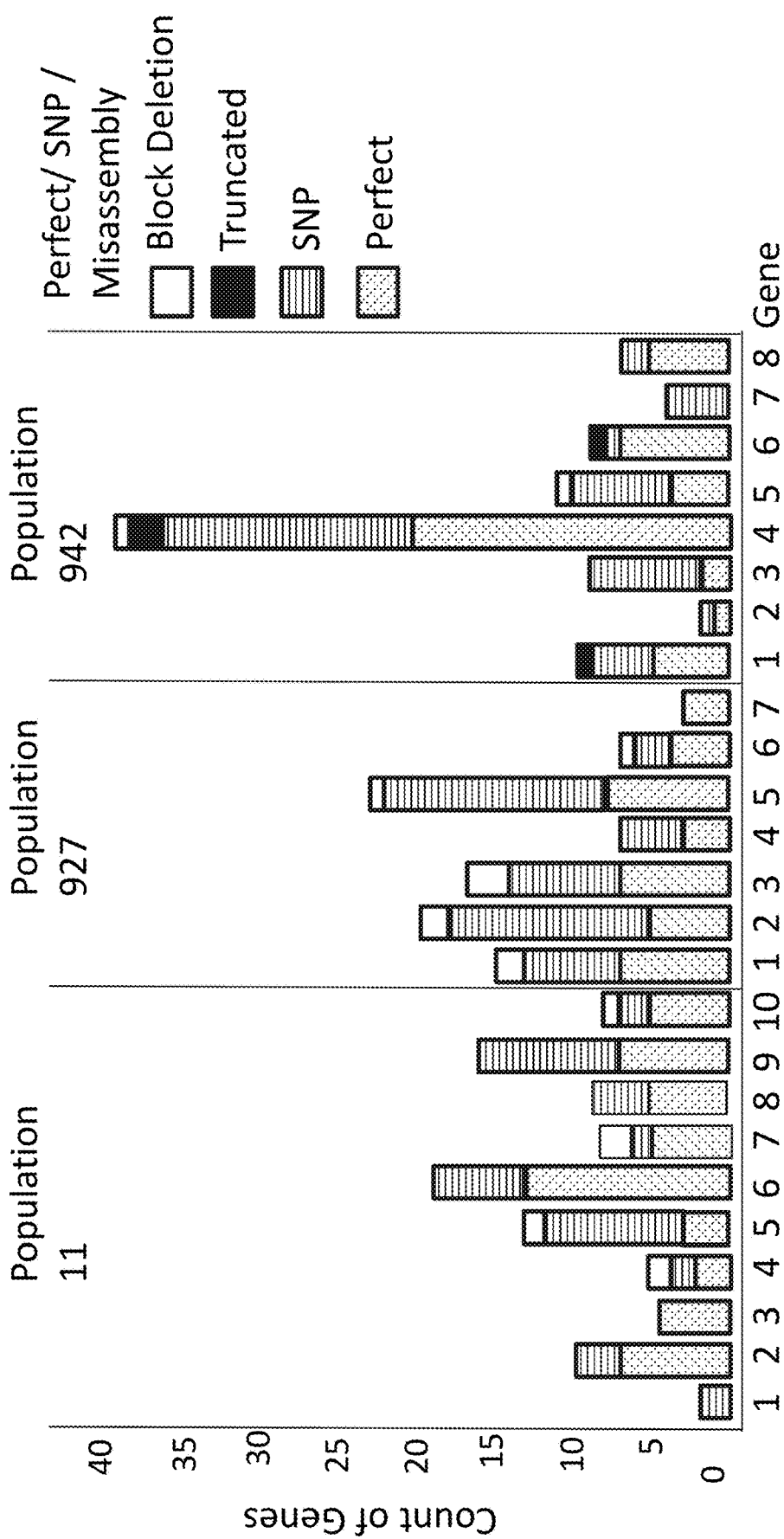
FIG. 23 is a graph of gene level results from multiplexed gene assembly reactions.

Multiplexed gene assembly was performed using a flap endonuclease mediated nucleic acid assembly method. Multiple sequences were assembled into 1 well. The sequences comprised two double stranded DNA (dsDNA) parts that are generated from overlap extension PCR. The reactions were prepared according to Method 4 as described in Table 19 and performed at 55° C. for 30 minutes. Samples were assembled and then cloned in a vector. Three populations were assembled: Population 11, Population 927, and Population 942. Each population comprised 96 individual clones that were Sanger sequenced to determine which gene was present. The quality of the starting DNA material was determined by measuring perfect sequences, sequences with SNPS, truncated material, or sequences with block deletions. As seen in FIG. 23, the accuracy of assembly was perfect (no chimeric genes) and uniformity/distribution was good.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What we claim is:

1. A method for nucleic acid assembly comprising:
    (a) providing at least 10 different nucleic acid fragments, wherein each of the at least 10 different nucleic acid fragments does not comprise a terminal region of sequence homology to another fragment of the at least 10 different nucleic acid fragments; and
    (b) mixing the at least 10 different nucleic acid fragments with a plurality of enzymes, wherein the plurality of enzymes is selected from an endonuclease, exonuclease, a polymerase, and a ligase to form a nucleic acid; and
wherein the endonuclease is a flap endonuclease.

2. The method of claim 1, wherein the exonuclease is exonuclease III.

3. The method of claim 2, wherein a concentration of the exonuclease III is in a range of about 0.1 U to about 10 U.

4. The method of claim 1, wherein the flap endonuclease is flap endonuclease 1, exonuclease 1, XPG, Dna2, or GEN1.

5. The method of claim 4, wherein a concentration of the flap endonuclease 1 provided is about 0.32 U to about 4.8 U.

6. The method of claim 4, wherein a concentration of the flap endonuclease 1 provided is less than about 5.0 U.

7. The method of claim 1, wherein the polymerase comprises 5' to 3' polymerase activity.

8. The method of claim 1, wherein the polymerase is a DNA polymerase.

9. The method of claim 1, wherein the ligase catalyzes joining of at least two nucleic acids.

10. The method of claim 1, wherein a concentration of the polymerase is in a range of about 0.01 U to about 2 U.

11. The method of claim 1, wherein a concentration of the ligase is up to about 2.0 U.

12. The method of claim 1, wherein a concentration of the ligase is in a range of about 4.0 U to about 8.0 U.

13. The method of claim 1, wherein step (b) occurs at a temperature of about 30° C. to about 60° C.

14. The method of claim 1, wherein mixing the at least 10 different fragments with the endonuclease results in a 5' overhang.

15. The method of claim 1, wherein the exonuclease is exonuclease III; the endonuclease is flap endonuclease 1, exonuclease 1, XPG, Dna2, or GEN1; and the polymerase is a DNA polymerase.

16. The method of claim 1, wherein a concentration of the exonuclease is in a range of about 0.1 U to about 10 U; a concentration of the endonuclease is in a range of about 0.32 U to about 4.8 U; a concentration of the polymerase is in a range of about 0.01 U to about 2 U; and a concentration of the ligase is in a range of about 4.0 U to about 8.0 U.

17. The method of claim 1, wherein a concentration of the exonuclease is in a range of about 0.1 U to about 10 U; a concentration of the endonuclease is in a range of about 0.32 U to about 4.8 U; a concentration of the polymerase is in a range of about 0.01 U to about 2 U; and a concentration of the ligase is up to about 2.0 U.

* * * * *

SEQUENCE LISTING

```
<160> NUMBER OF SEQ ID NOS: 4

<210> SEQ ID NO 1
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (51)..(52)
<223> OTHER INFORMATION: Thymidine-succinyl hexamide CED phosphoramidite

<400> SEQUENCE: 1
agacaatcaa ccatttgggg tggacagcct tgacctctag acttcggcat ttttttttt       60 tt                                                                    62

<210> SEQ ID NO 2
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (101)..(102)
<223> OTHER INFORMATION: Thymidine-succinyl hexamide CED phosphoramidite

<400> SEQUENCE: 2
cgggatcctt atcgtcatcg tcgtacagat cccgacccat ttgctgtcca ccagtcatgc       60
tagccatacc atgatgatga tgatgatgag aaccccgcat ttttttttt tt              112
```

```
<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atgcggggtt ctcatcatc                                                19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgggatcctt atcgtcatcg                                               20
```